US012625147B2

(12) United States Patent
Wu et al.

(10) Patent No.: US 12,625,147 B2
(45) Date of Patent: May 12, 2026

(54) MOLECULAR TOOLS TO VISUALIZE AND TARGET THE CARDIAC CONDUCTION SYSTEM (CCS)

(71) Applicant: The Board of Trustees of the Leland Stanford Junior University, Stanford, CA (US)

(72) Inventors: Sean M. Wu, Stanford, CA (US); William R. Goodyer, Stanford, CA (US); Benjamin Beyersdorf, Stanford, CA (US); Nynke Van Den Berg, Stanford, CA (US); Eben Rosenthal, Stanford, CA (US)

(73) Assignee: THE BOARD OF TRUSTEES OF THE LELAND STANFORD JUNIOR UNIVERSITY, Standford (CA)

( * ) Notice: Subject to any disclaimer, the term of this patent is extended or adjusted under 35 U.S.C. 154(b) by 1160 days.

(21) Appl. No.: 17/625,224

(22) PCT Filed: Jul. 7, 2020

(86) PCT No.: PCT/US2020/040965
§ 371 (c)(1),
(2) Date: Jan. 6, 2022

(87) PCT Pub. No.: WO2021/007193
PCT Pub. Date: Jan. 14, 2021

(65) Prior Publication Data
US 2022/0323616 A1      Oct. 13, 2022

Related U.S. Application Data

(60) Provisional application No. 62/950,428, filed on Dec. 19, 2019, provisional application No. 62/871,551, filed on Jul. 8, 2019.

(51) Int. Cl.
| | |
|---|---|
| *G01N 33/68* | (2006.01) |
| *A61K 39/00* | (2006.01) |
| *A61K 47/69* | (2017.01) |
| *A61K 49/00* | (2006.01) |
| *C07K 16/18* | (2006.01) |
| *C12N 5/077* | (2010.01) |
| *G01N 33/58* | (2006.01) |

(52) U.S. Cl.
CPC ..... *G01N 33/6893* (2013.01); *A61K 47/6913* (2017.08); *A61K 49/0013* (2013.01); *A61K 49/0058* (2013.01); *C07K 16/18* (2013.01); *C12N 5/0657* (2013.01); *G01N 33/582* (2013.01); *A61K 2039/505* (2013.01); *C07K 2317/31* (2013.01); *C07K 2317/54* (2013.01); *C07K 2317/55* (2013.01); *C07K 2317/622* (2013.01); *C07K 2317/626* (2013.01)

(58) Field of Classification Search
CPC ................ A61K 47/00; A61K 47/6913; A61K 49/0013; A61K 49/0058; A61K 2039/505; A61K 47/6843; A61K 49/00; A61K 49/0032; G01N 33/6893; G01N 33/582; G01N 2800/32; G01N 33/532; C07K 16/18; C07K 2317/54; C07K 2317/31; C07K 2317/55; C07K 2317/622; C07K 2317/626; C12N 5/0657
See application file for complete search history.

(56) References Cited

U.S. PATENT DOCUMENTS

| | | | |
|---|---|---|---|
| 2015/0164957 A1 | 6/2015 | Arnolds et al. | |
| 2017/0151339 A1* | 6/2017 | White | ..................... A61P 35/00 |
| 2019/0025329 A1 | 1/2019 | Goetzl et al. | |

OTHER PUBLICATIONS

Park et al., J. Cardiovasc. Dev. Dis., vol. 4, No. 7, pp. 1-16 (Year: 2017).*
Vedantham V. New Approaches to Biological Pacemakers: Links to Sinoatrial Node Development, Trends Mol Med. Dec. 2015, pp. 749-761, vol. 21, No. 12.
Christoffels, V., et al. "Moorman AFM. Development of the pacemaker tissues of the heart", Circulation Research, 2010, pp. 240-254, vol. 106.
CDC. Research | Congenital Heart Defects | NCBDDD | CDC [Internet]. Centers for Disease Control and Prevention. 2018 [cited Sep. 26, 2018];Available from: https://www.cdc.gov/ncbddd/heartdefects/research.html.
Peretto, G., et al., "Postoperative arrhythmias after cardiac surgery: incidence, risk factors, and therapeutic management", Cardiology Research and Practice, Jan. 6, 2014, pp. 1-15, vol. 2014.
Karyofillis, P., et al. "Conduction abnormalities after transcatheter aortic valve implantation", Journal of Geriatric Cardiology, Jan. 11, 2018, pp. 105-112, vol. 15.
Shekhar, A., et al. "Transcription factor ETV1 is essential for rapid conduction in the heart", The Journal of Clinical Investigation, Dec. 2016, pp. 4444-4459, vol. 126, No. 12.
Tranum-Jensen, J. et al., "Morphology of electrophysiologically identified junctions between Purkinje fibers and ventricular muscle in rabbit and pig hearts", Circulation Research, Apr. 26, 1991, pp. 429-437, vol. 69, No. 2.

(Continued)

*Primary Examiner* — D. L. Jones
(74) *Attorney, Agent, or Firm* — Greer, Burns & Crain, Ltd.

(57) ABSTRACT

Antibodies which bind selectively to cardiac conduction system (CCS) cells, imaging and/or diagnostic reagents and compositions visualizing the CCS cells and therapeutic products and compositions comprising one or more of the antibodies. Methods for delivering therapeutic agents to the CCS cells. The disclosure further provides methods for visualizing the CCS cells in vivo in real time, including in a subject undergoing a cardiothoracic surgery or other cardiac intervention. Compositions and methods for isolation, purification, analyses and/or transplantation of the CCS cells, including pluripotent stem cell (hiPSC)-derived or human embryonic stem cell (hESC)-derived CCS cells.

7 Claims, 107 Drawing Sheets

(56)         References Cited

OTHER PUBLICATIONS

Cho, YH, et al., "Residual and recurrent gradients after septal myectomy for hypertrophic cardiomyopathy-mechanisms of obstruction and outcomes of reoperation", The Journal of Thoracic Cardiovascular Surgery, Sep. 2014, pp. 909-915; discussion pp. 915-916, vol. 148, No. 3.

Harmsen, S., et al., "Teraphongphom N, Tweedle MF, Basilion JP, Rosenthal EL. Optical Surgical Navigation for Precision in Tumor Resections", Mol Imaging Biol., Jun. 2017, pp. 357-362, vol. 19, No. 3.

Butler, A., et al., "Integrating single-cell transcriptomic data across different conditions, technologies, and species", Nat Biotechnol, Jun. 2018, pp. 411-420, vol. 36, No. 5.

Macosko, EZ, et al., "Highly Parallel Genome-wide Expression Profiling of Individual Cells Using Nanoliter Droplets", Cell, May 21, 2015, pp. 1202-1214, vol. 161, No. 5.

Marshall, MV., et al., "Single-Dose Intravenous Toxicity Study of IRDye 800CW in Sprague-Dawley Rats", Mol Imaging Biol. Apr. 8, 2010, pp. 583-594, vol. 12.

Rosenthal, EL., et al., "Safety and Tumor Specificity of Cetuximab-IRDye800 for Surgical Navigation in Head and Neck Cancer", Clinical Cancer Research, Apr. 22, 2015, pp. 3658-3666, vol. 21, No. 16.

Goodyer, WR, et al., "Neonatal B cell development in mice and humans is regulated by calcineurin/NFAT", Dev Cell. Jul. 17, 2012, pp. 21-34, vol. 23, No. 1.

Pallante, B., et al., "Contactin-2 expression in the cardiac Purkinje fiber network", Circ Arrhythm Electrophysiol. Apr. 1, 2010, pp. 86-194, vol. 3, No. 2.

Shekhar, A., et al., "Transcription factor ETV1 is essential for rapid conduction in the heart", Dec. 2016, The Journal of Clinical Investigation, pp. 4444-4459, vol. 126, No. 12.

Prince, A., "Evaluation of optical imaging agents in a fluorescence-guided surgical model of head and neck cancer" Surg Oncol. Jun. 2018, pp. 225-230, vol. 27, No. 2.

Aanhaanen, WTJ, et al., "Developmental Origin, Growth, and Three-Dimensional Architecture of the Atrioventricular Conduction Axis of the Mouse Heart", Circulation Research, 2010, pp. 728-736, vol. 107.

Hoffman, JI. "The global burden of congenital heart disease", Cardiovascular Journal of Africa, May 2013, pp. 141-145, vol. 24. No. 4.

Csepe, TA., et al., "Human sinoatrial node structure: 3D microanatomy of sinoatrial conduction pathways", Progress In Biophysics and Molecular Biology. Jan. 2016, pp. 164-178, vol. 120, No. 1-3.

Ng, D, et al., "NIH Intramural Sequencing Center (NISC) Comparative Sequencing Program. Interpreting secondary cardiac disease variants in an exome cohort", Circ Cardiovasc Genet., Aug. 2013, 37-346, vol. 6, No. 4.

* cited by examiner

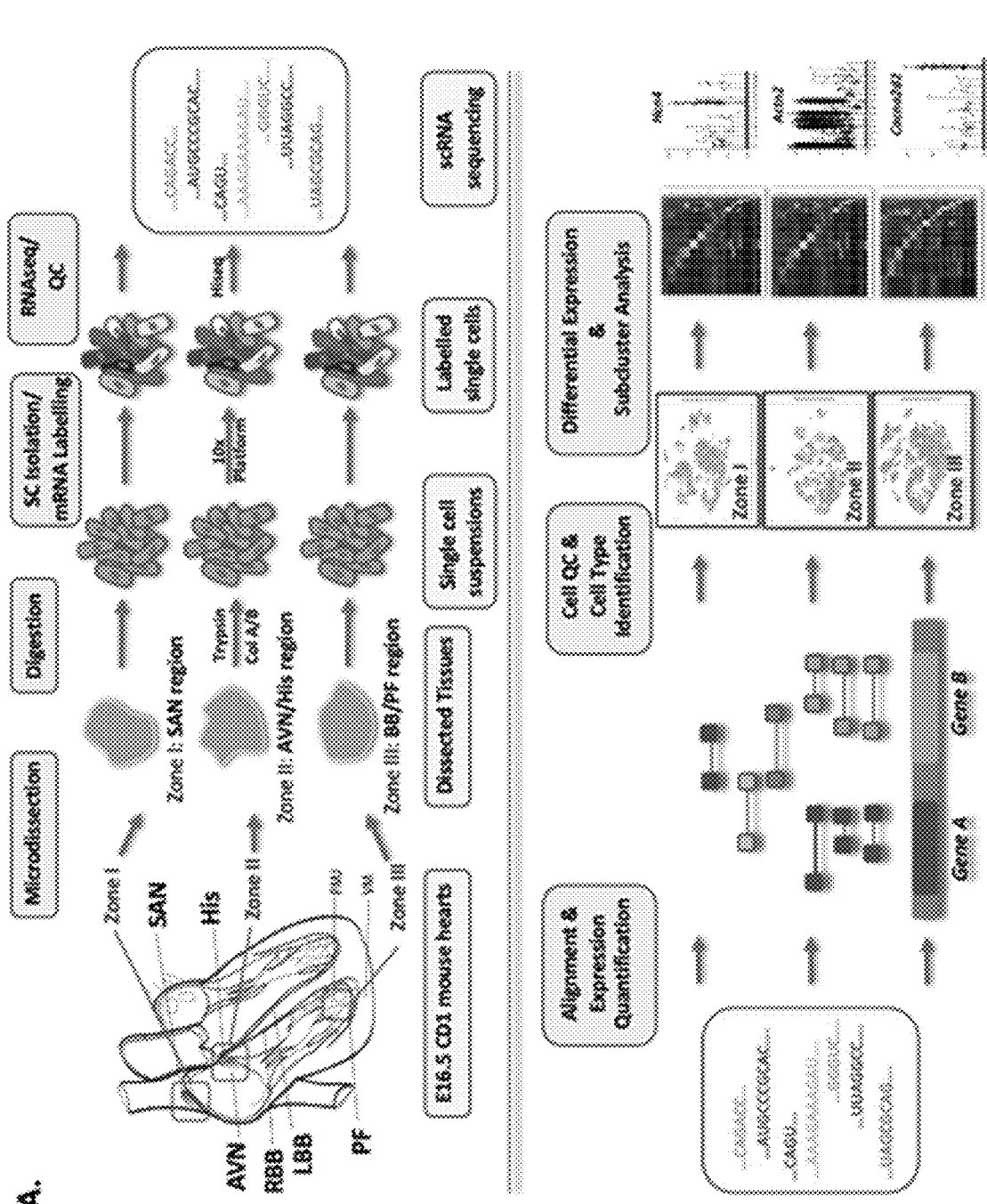
Figure 1. Single-Cell Isolation and Expression Profiling of Murine Cardiac Conduction System Components

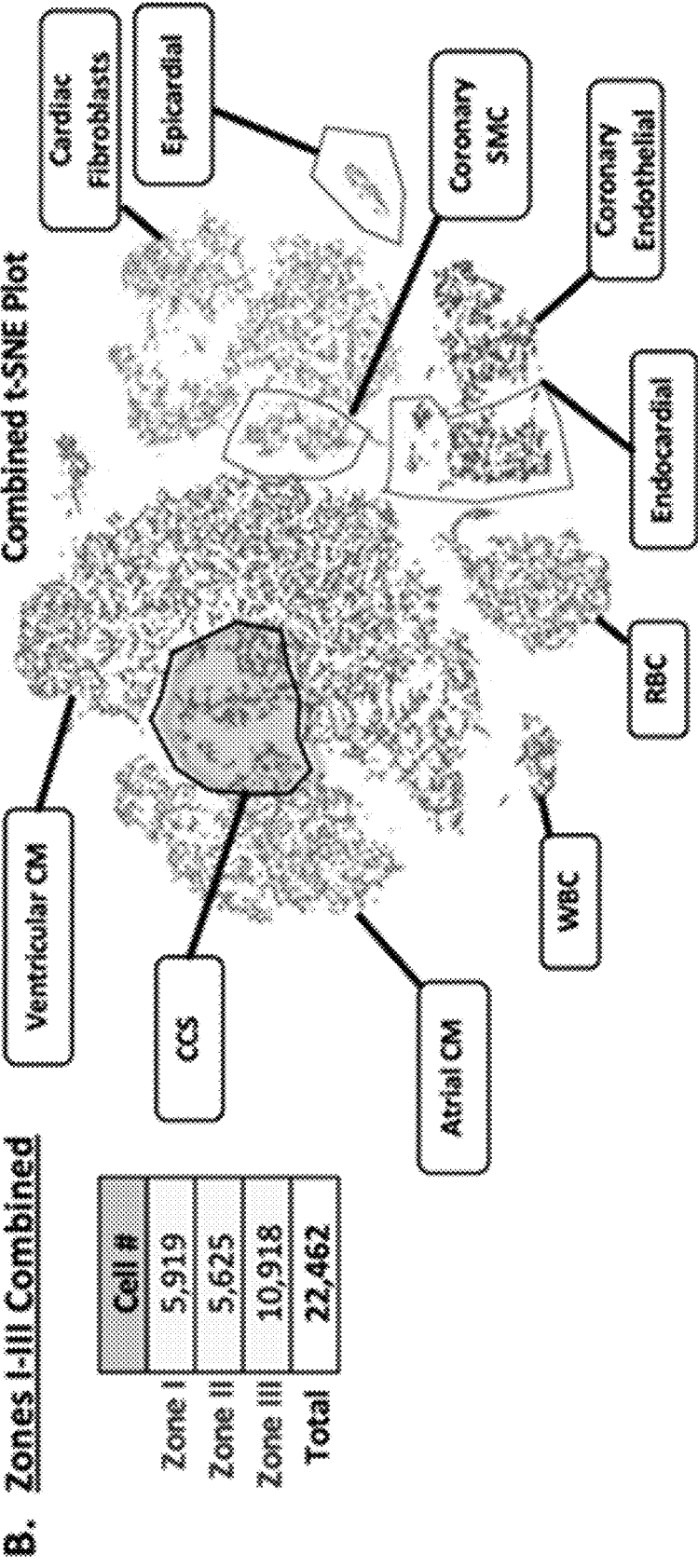
Figure 1 continued. Single-Cell Isolation and Expression Profiling of Murine Cardiac Conduction System Components

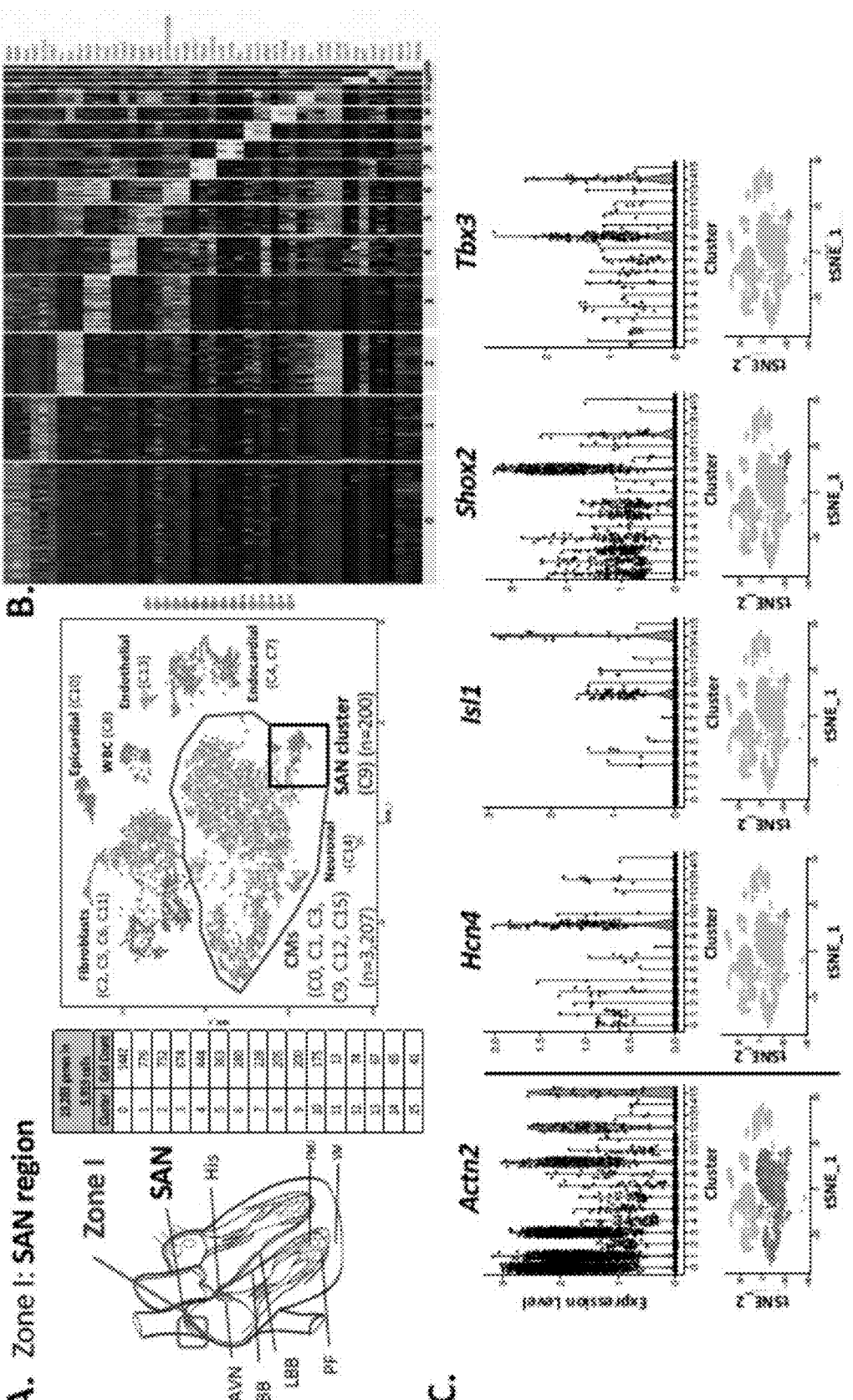
Figure 2. scRNA-seq Analysis of Zone I Revealed a Bona Fide Sino Atrial Node (SAN) Cell Cluster.

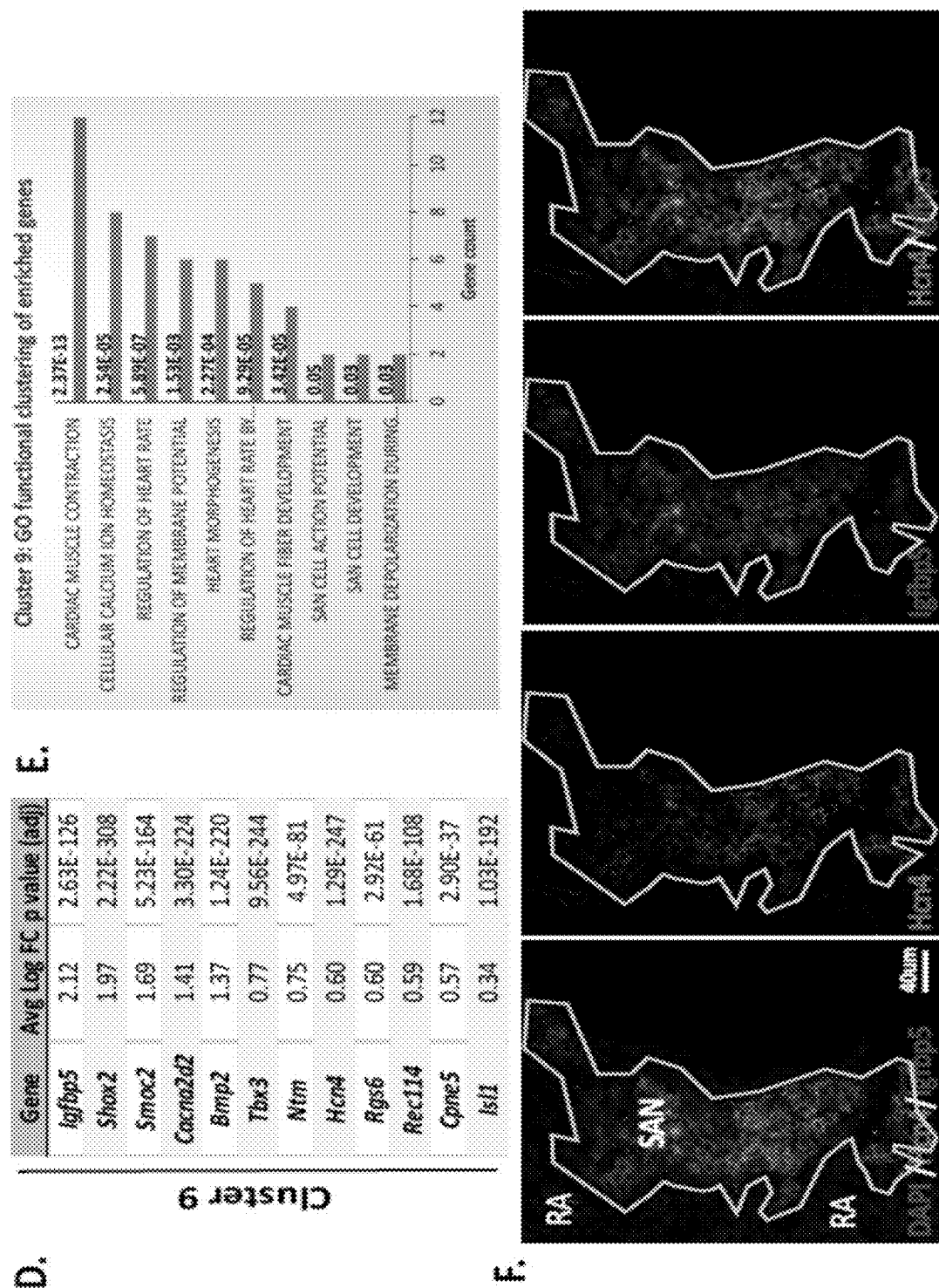
Figure 2 continued. scRNA-seq Analysis of Zone I Revealed a Bona Fide Sino Atrial Node (SAN) Cell Cluster.

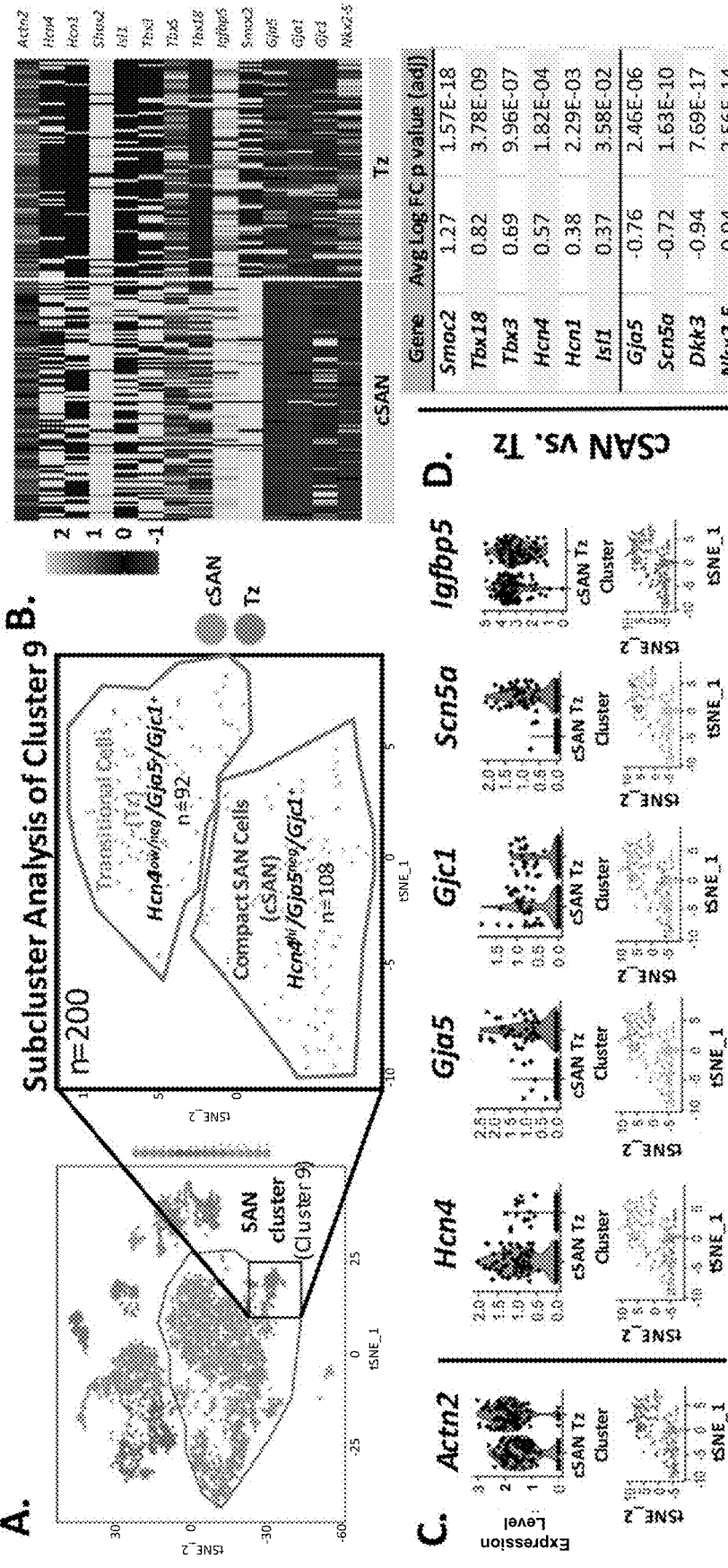
| Gene | Avg Log FC | p value (adj) |
|---|---|---|
| Smoc2 | 1.27 | 1.57E-18 |
| Tbx18 | 0.82 | 3.78E-09 |
| Tbx3 | 0.69 | 9.96E-07 |
| Hcn4 | 0.57 | 1.82E-04 |
| Hcn1 | 0.38 | 2.29E-03 |
| Isl1 | 0.37 | 3.58E-02 |
| Gja5 | -0.76 | 2.46E-06 |
| Scn5a | -0.72 | 1.63E-10 |
| Dkk3 | -0.94 | 7.69E-17 |
| Nkx2-5 | -0.94 | 2.56E-14 |
Figure 3. Analysis of Cluster 9 Revealed Unique SAN Subtypes.

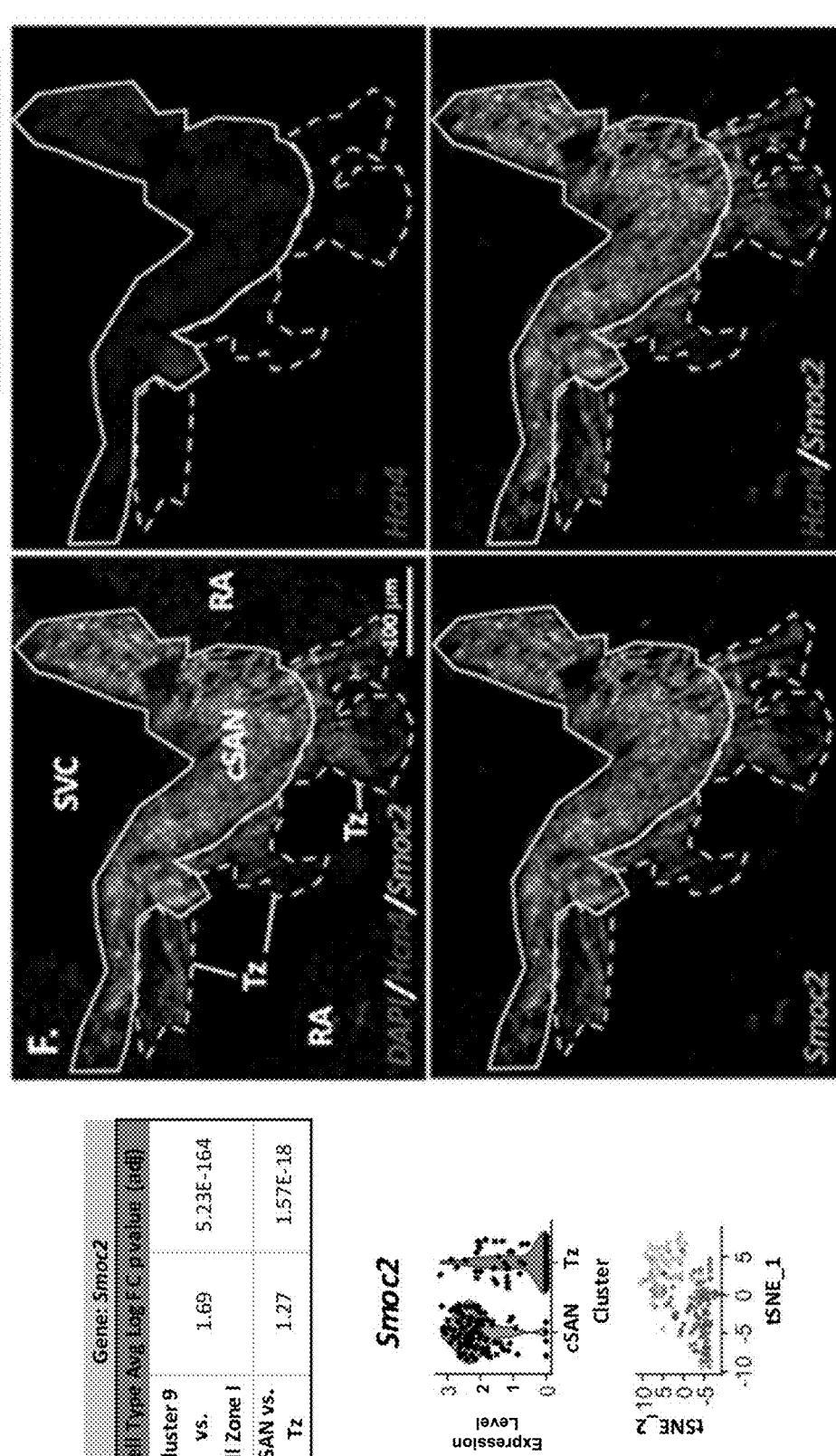
Figure 3 continued. Analysis of Cluster 9 Revealed Unique SAN Subtypes.

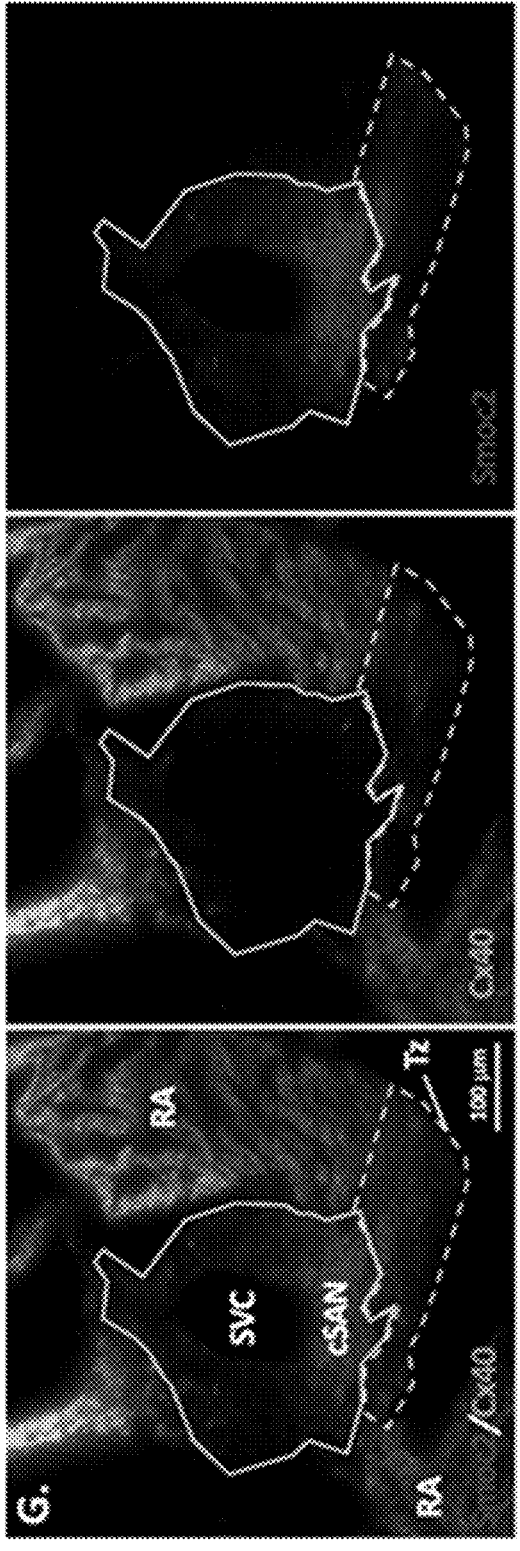
Figure 3 continued. Analysis of Cluster 9 Revealed Unique SAN Subtypes.

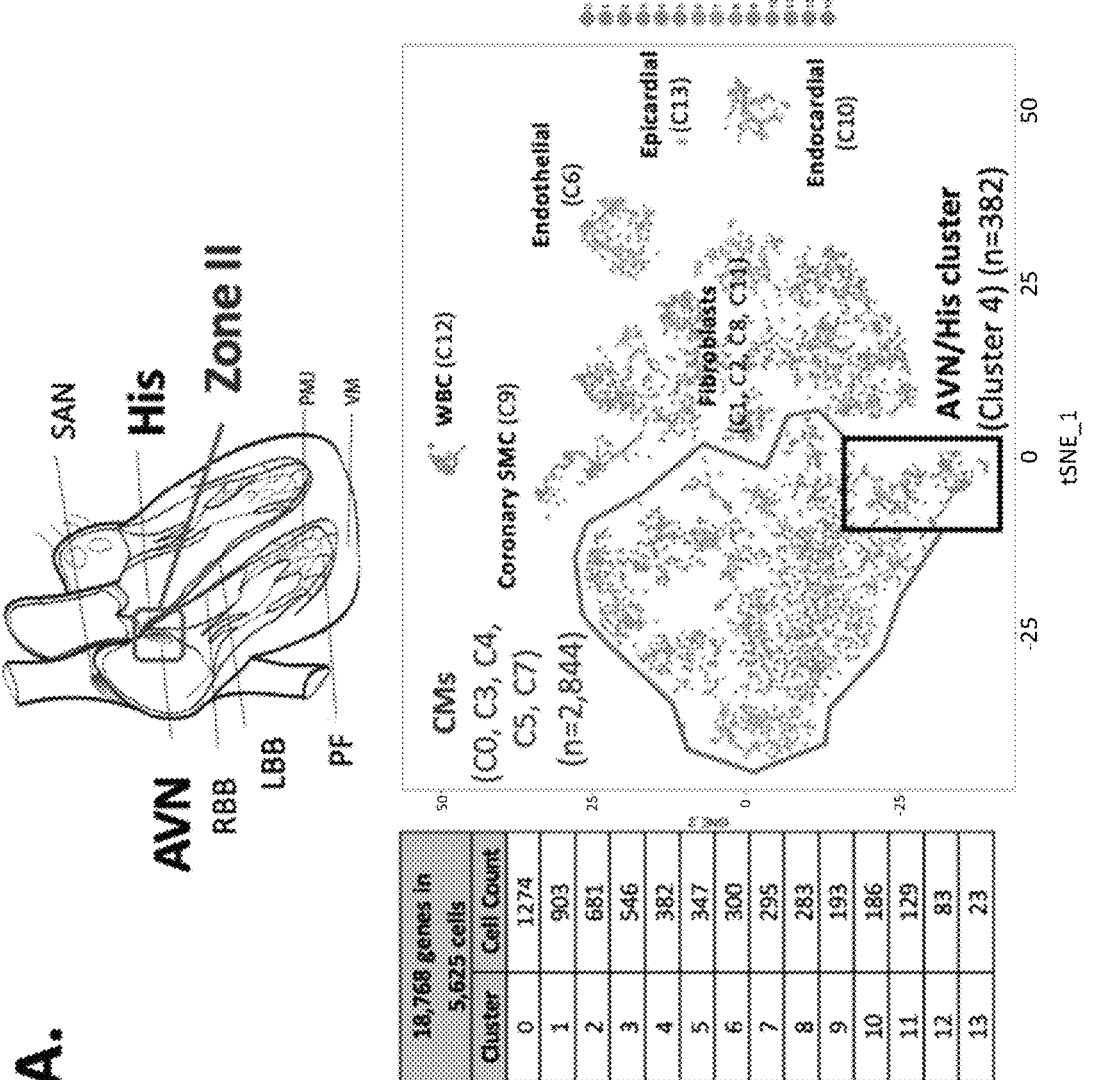
Figure 4. Identification of an AVN/His Cell Cluster Within Zone II.

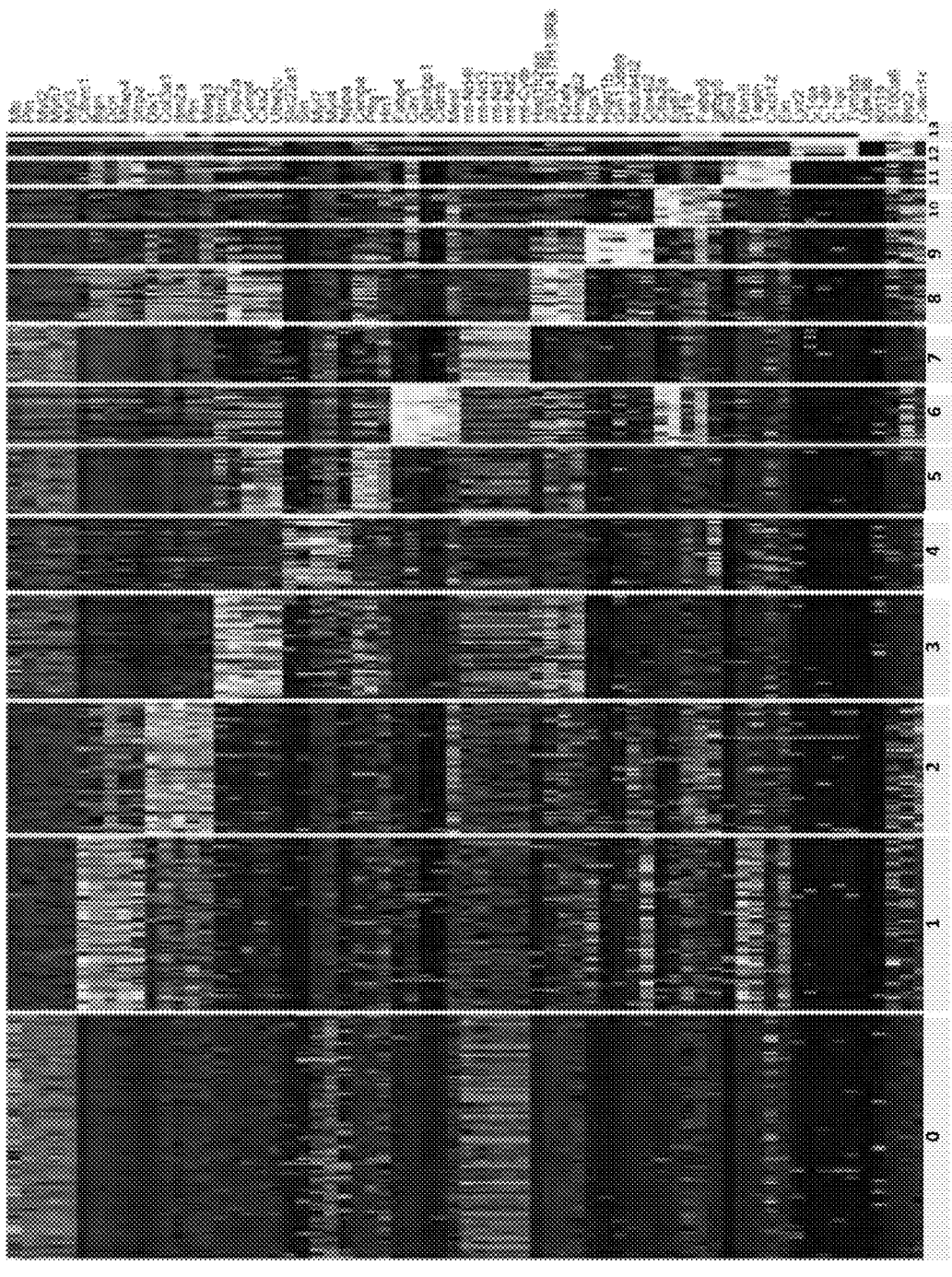
B.
Figure 4 continued. Identification of an AVN/His Cell Cluster Within Zone II.

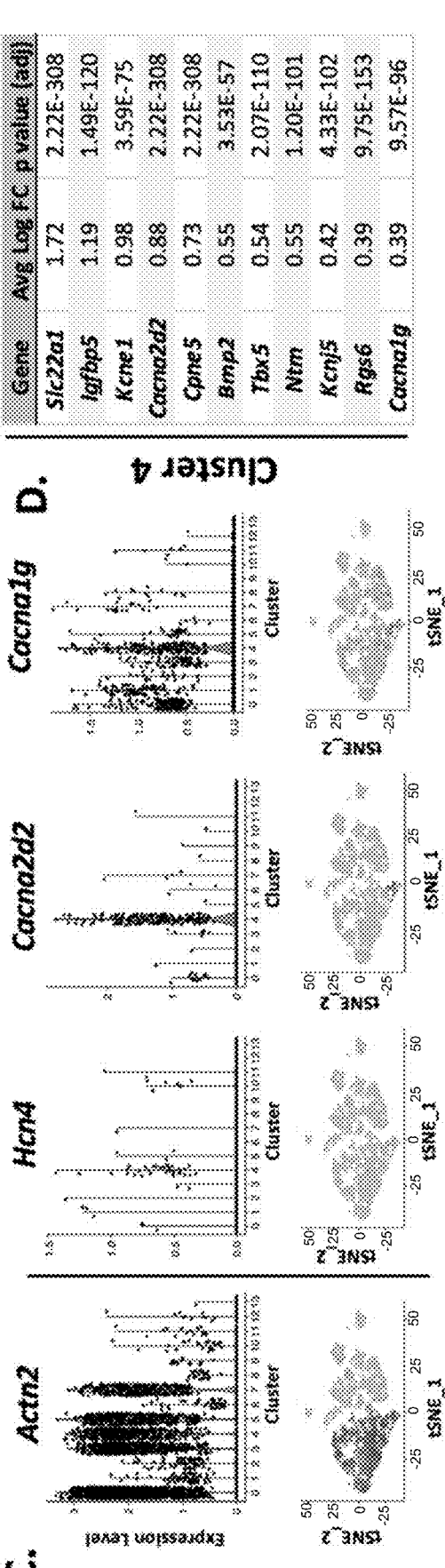
Figure 4 continued. Identification of an AVN/His Cell Cluster Within Zone II.

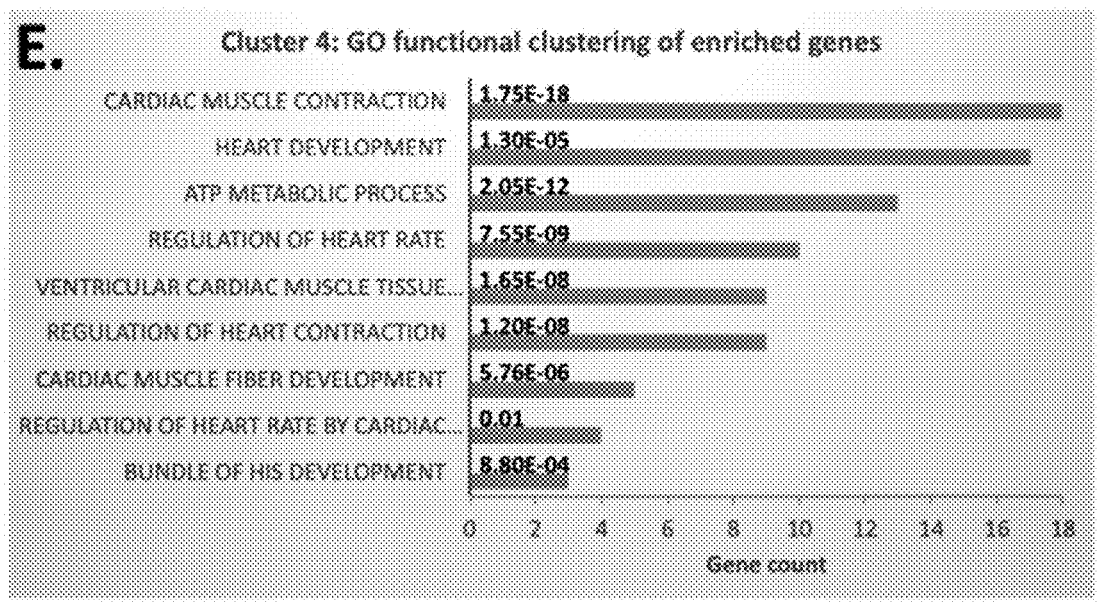
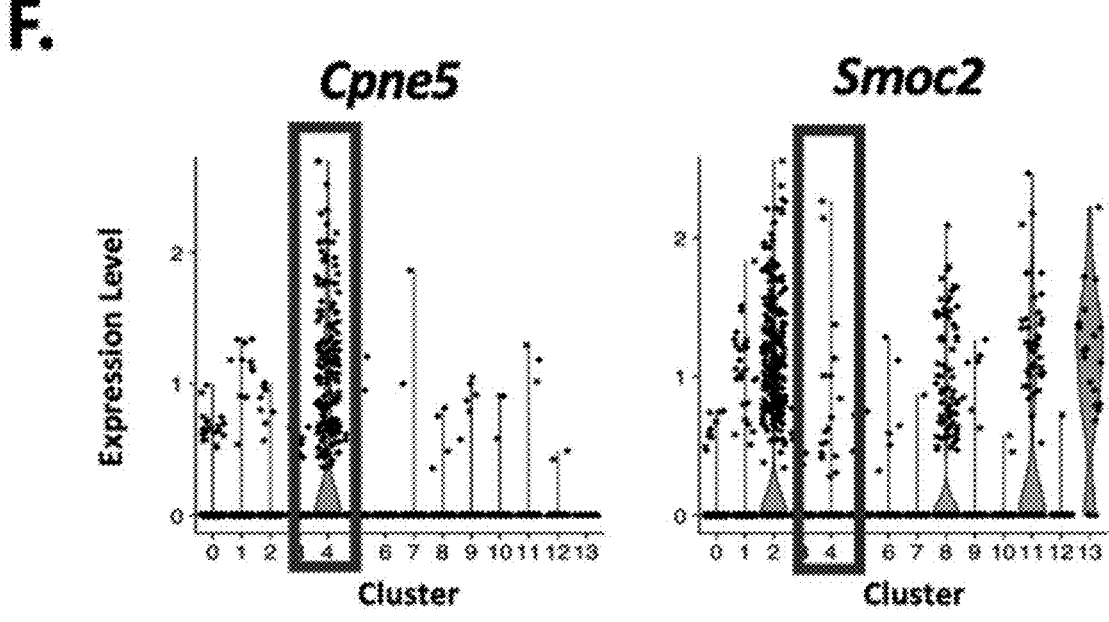
Figure 4 continued. Identification of an AVN/His Cell Cluster Within Zone II.

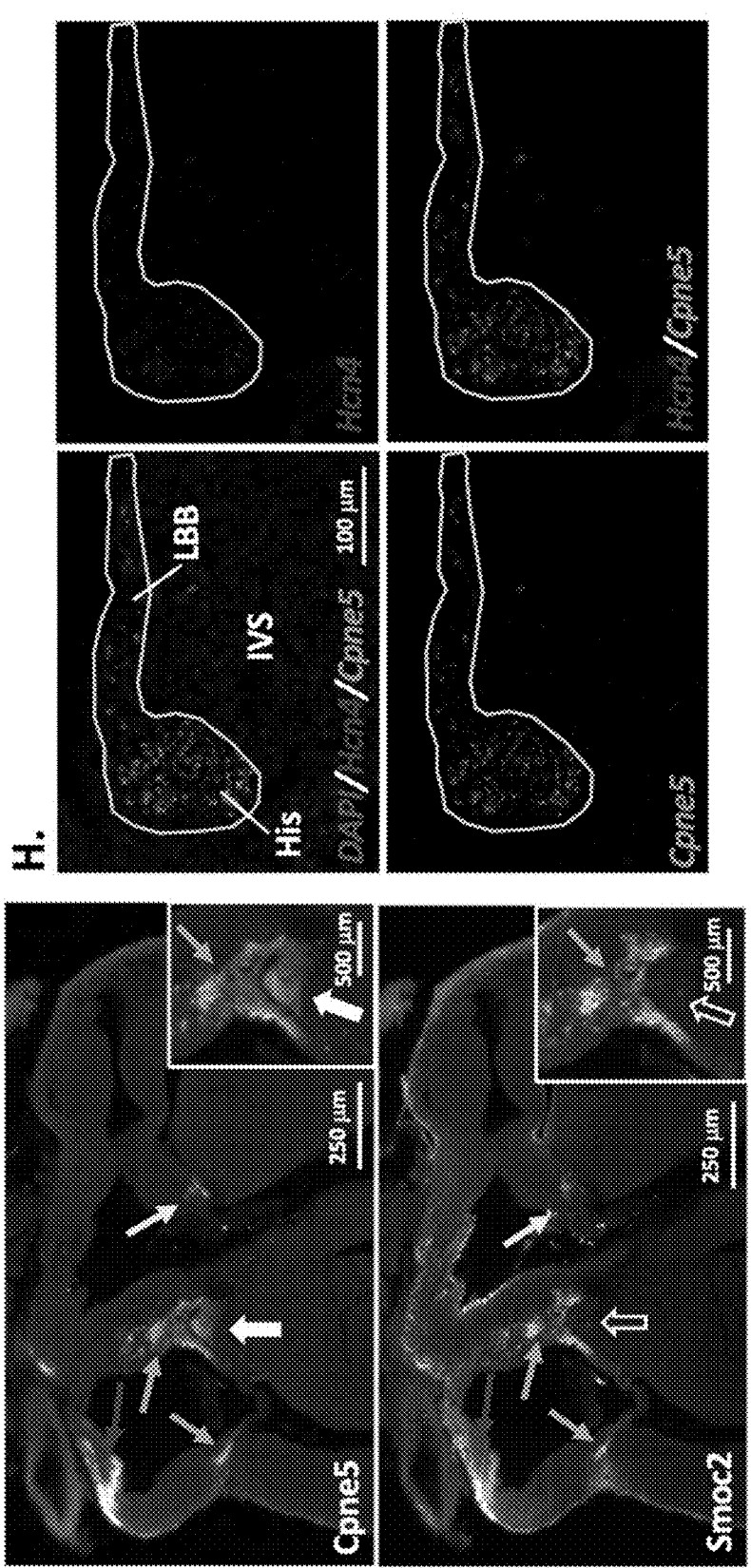
Figure 4 continued. Identification of an AVN/His Cell Cluster Within Zone II.

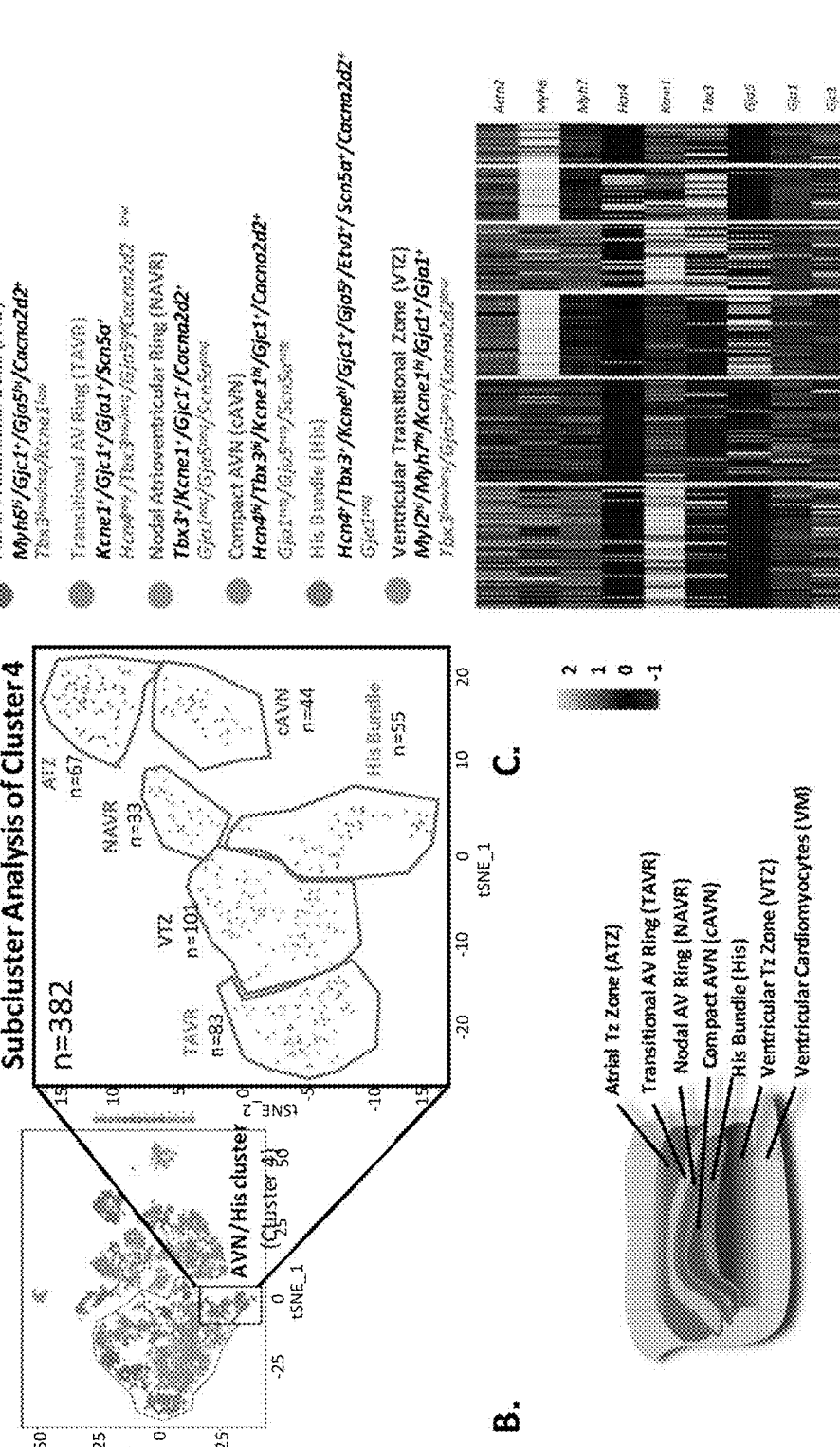
Figure 5. Analysis of Cluster 4 in Zone II Unveiled Distinct AVN and Transitional Cell Subtypes.

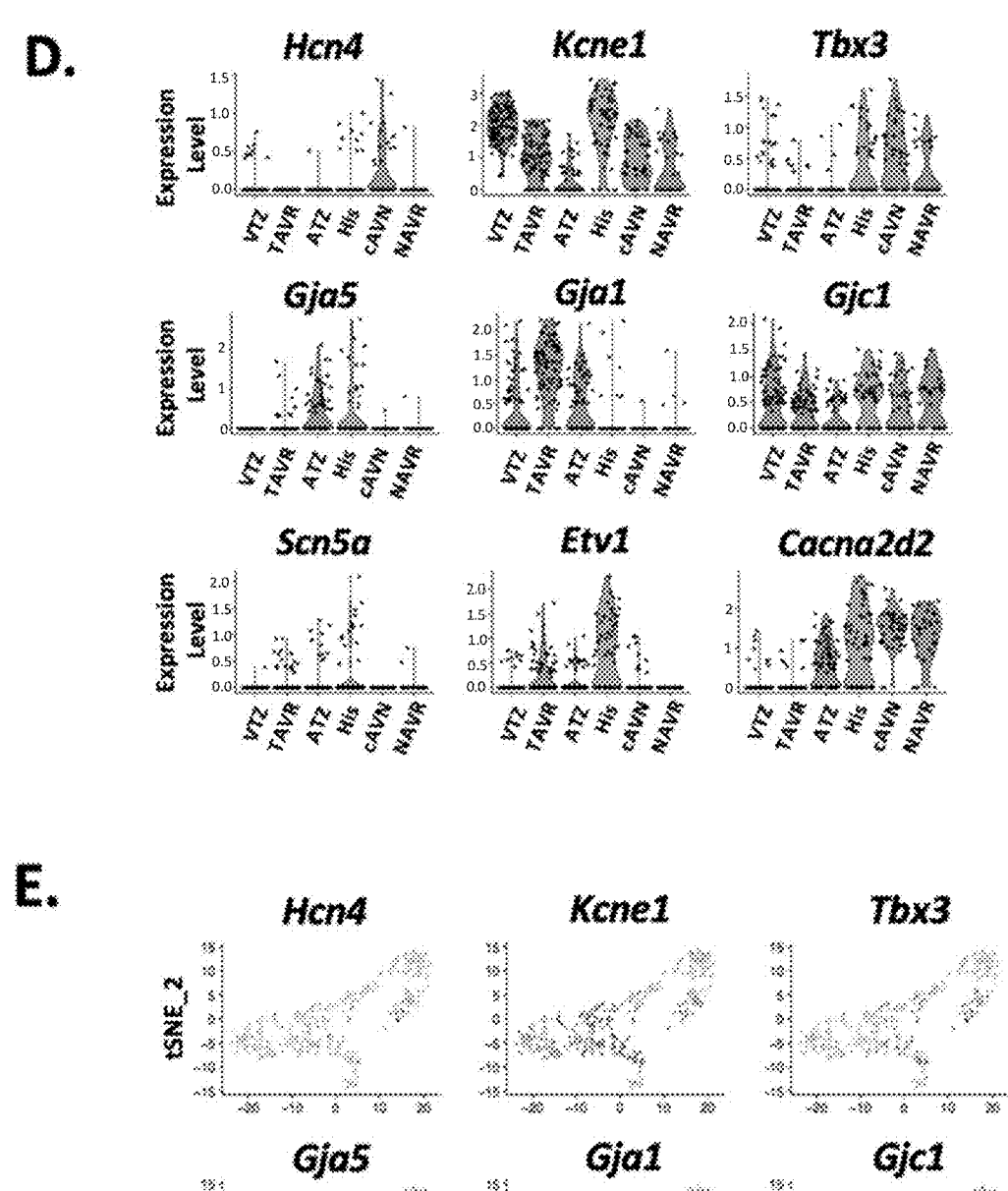
Figure 5 continued. Analysis of Cluster 4 in Zone II Unveiled Distinct AVN and Transitional Cell Subtypes.

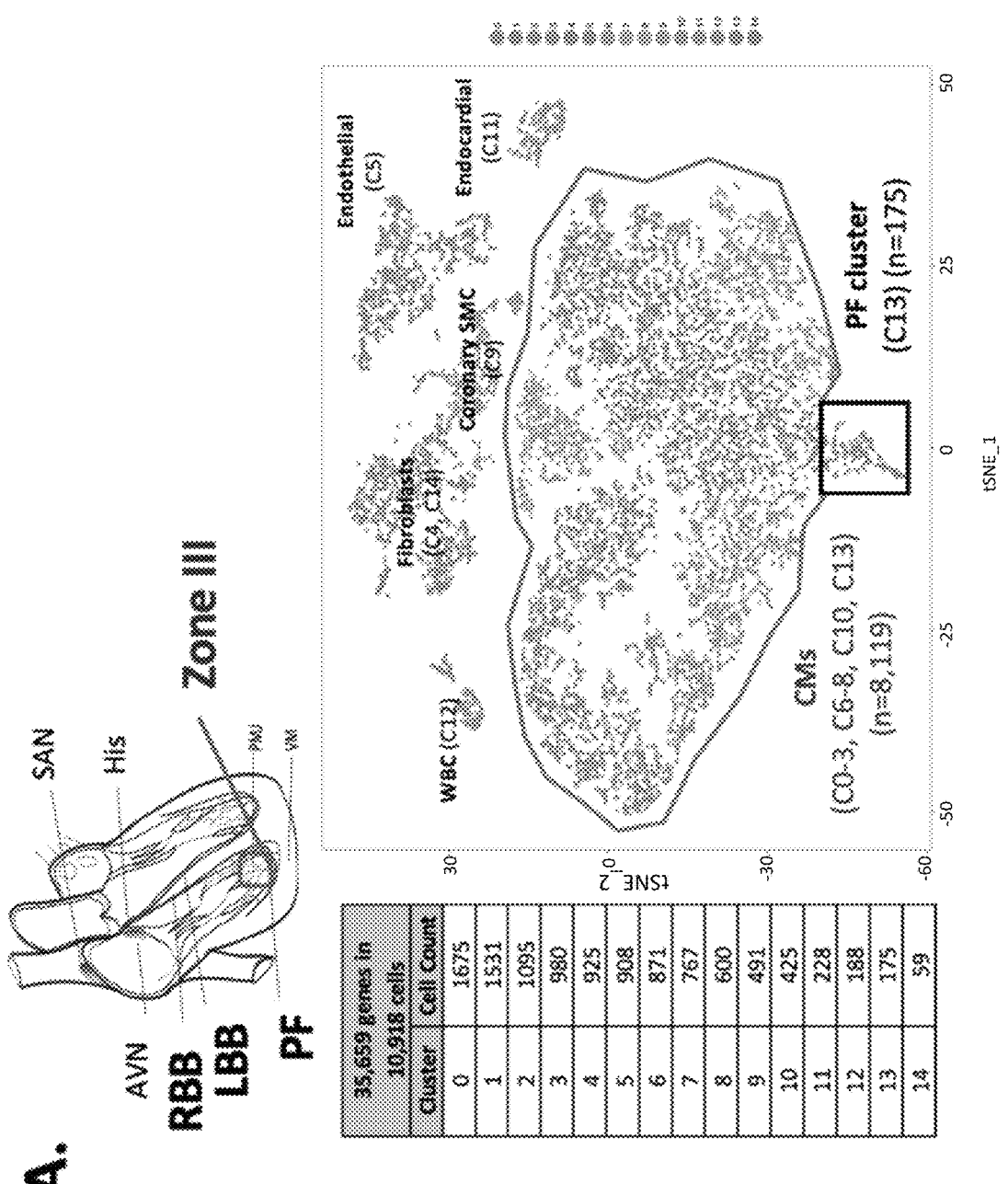
Figure 6. An Immature Purkinje Fiber (PF) Cell Cluster Was Detected Within Zone III.

B.
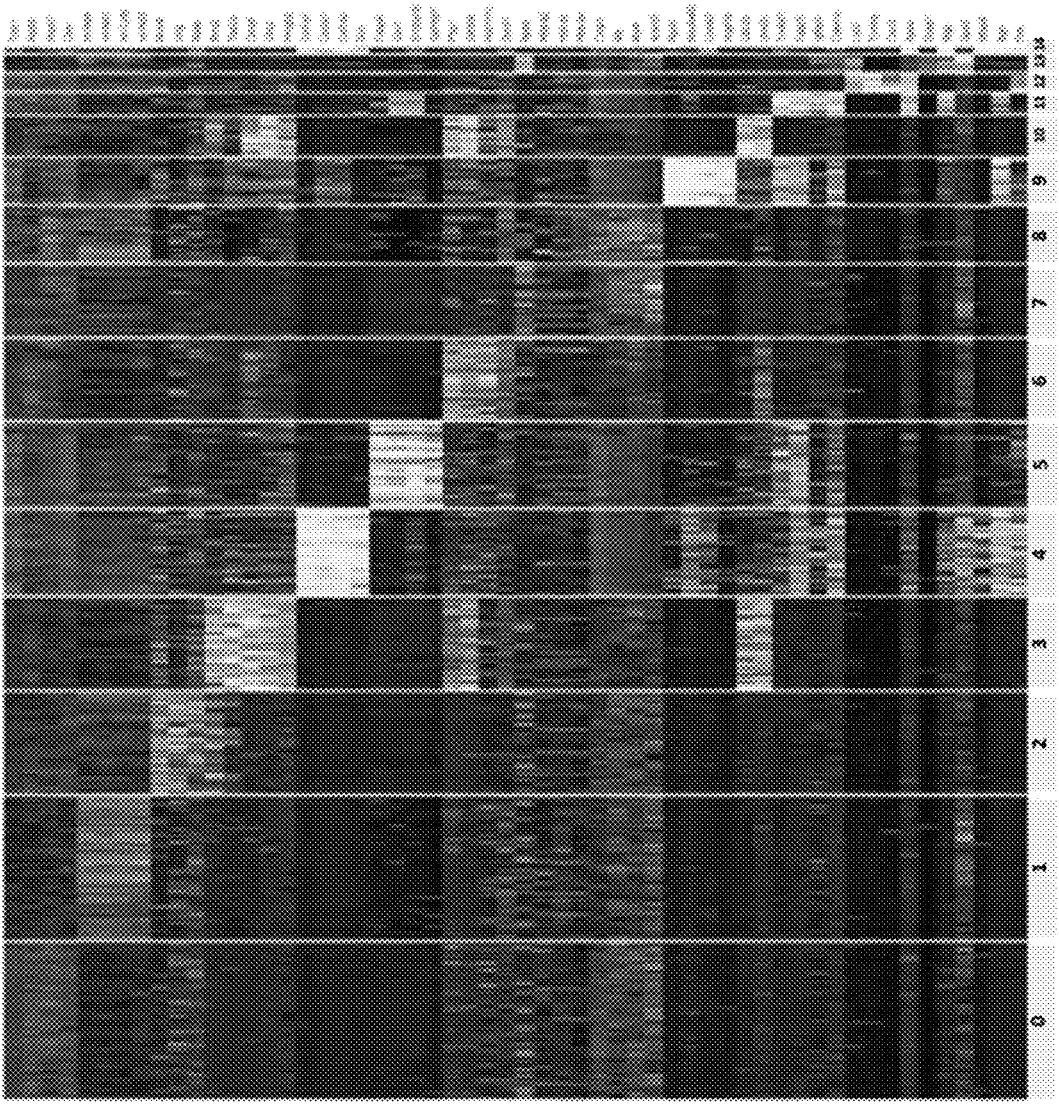
Figure 6 continued. An Immature Purkinje Fiber (PF) Cell Cluster Was Detected Within Zone III.

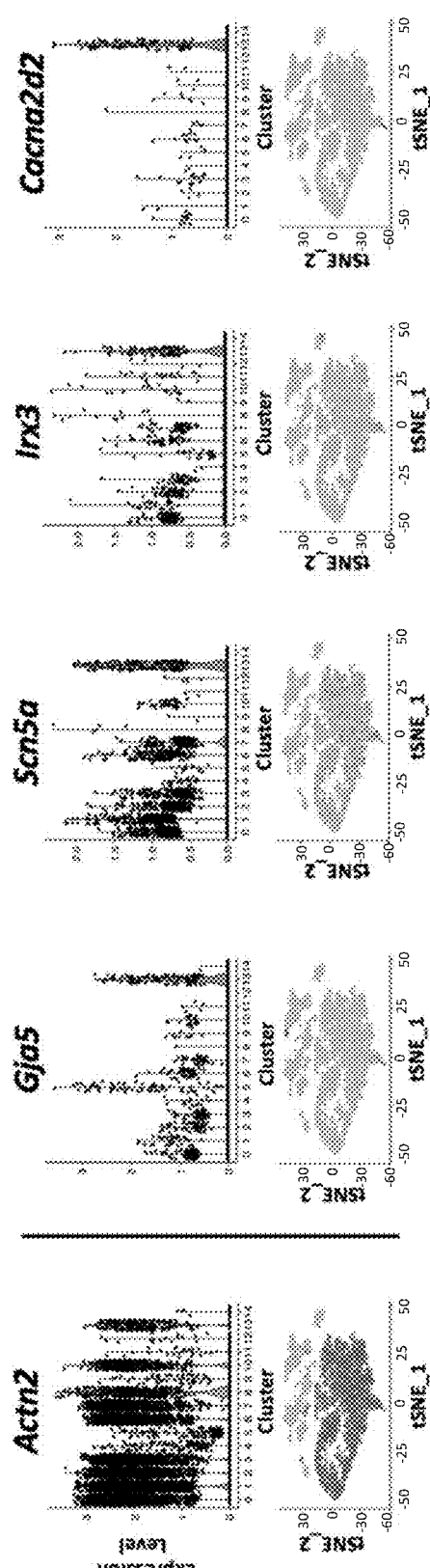
Figure 6 continued. An Immature Purkinje Fiber (PF) Cell Cluster Was Detected Within Zone III.

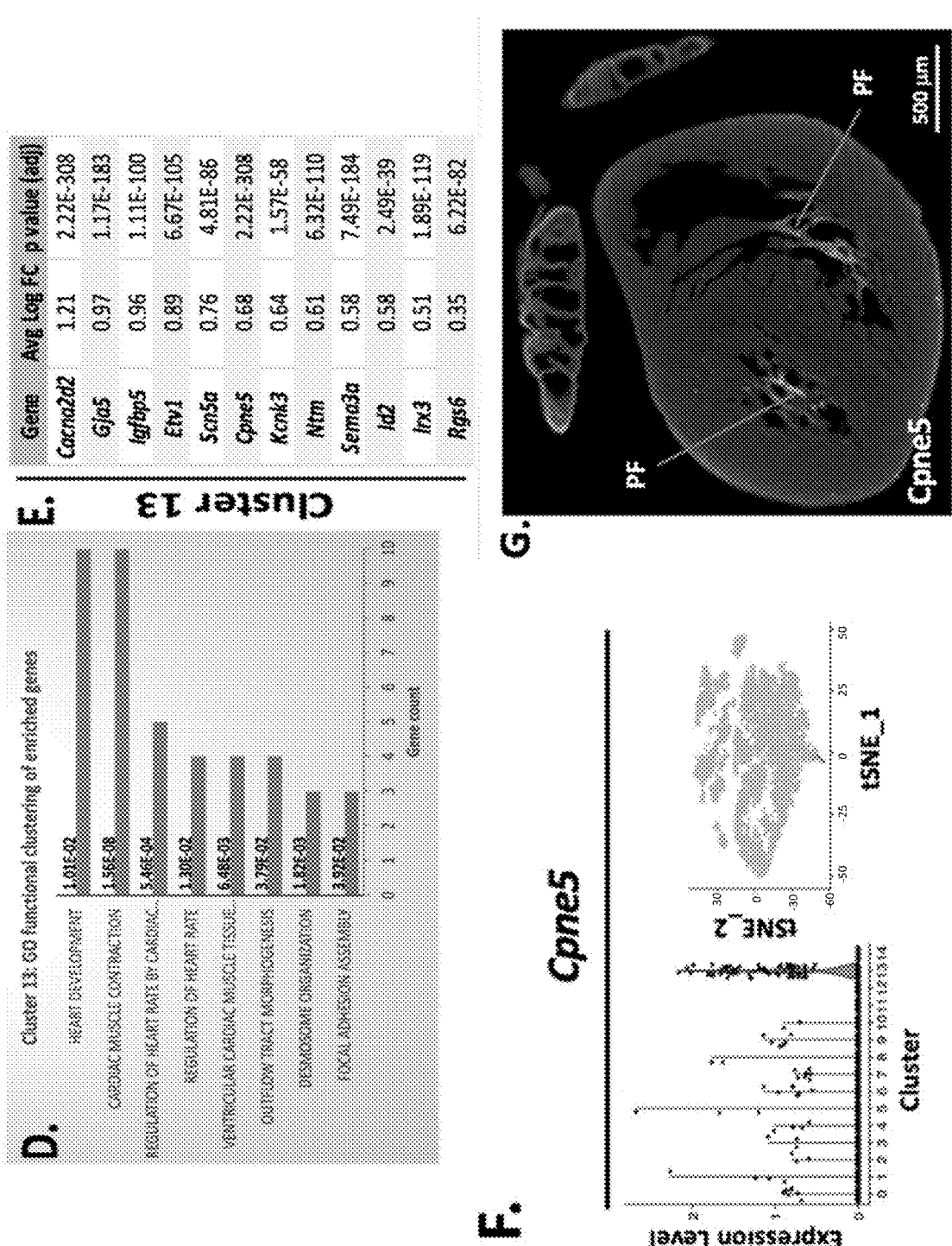
Cluster 13
| Gene | Avg Log FC | p value (adj) |
|---|---|---|
| Cacna2d2 | 1.21 | 2.22E-308 |
| Gja5 | 0.97 | 1.17E-183 |
| Igfbp5 | 0.96 | 1.11E-100 |
| Etv1 | 0.89 | 6.67E-105 |
| Scn5a | 0.76 | 4.81E-86 |
| Cpne5 | 0.68 | 2.22E-308 |
| Kcnk3 | 0.64 | 1.57E-58 |
| Ntm | 0.61 | 6.32E-110 |
| Sema3a | 0.58 | 7.49E-184 |
| Id2 | 0.58 | 2.49E-39 |
| Irx3 | 0.51 | 1.89E-119 |
| Rps6 | 0.35 | 6.22E-82 |
Figure 6 continued. An Immature Purkinje Fiber (PF) Cell Cluster Was Detected Within Zone III.

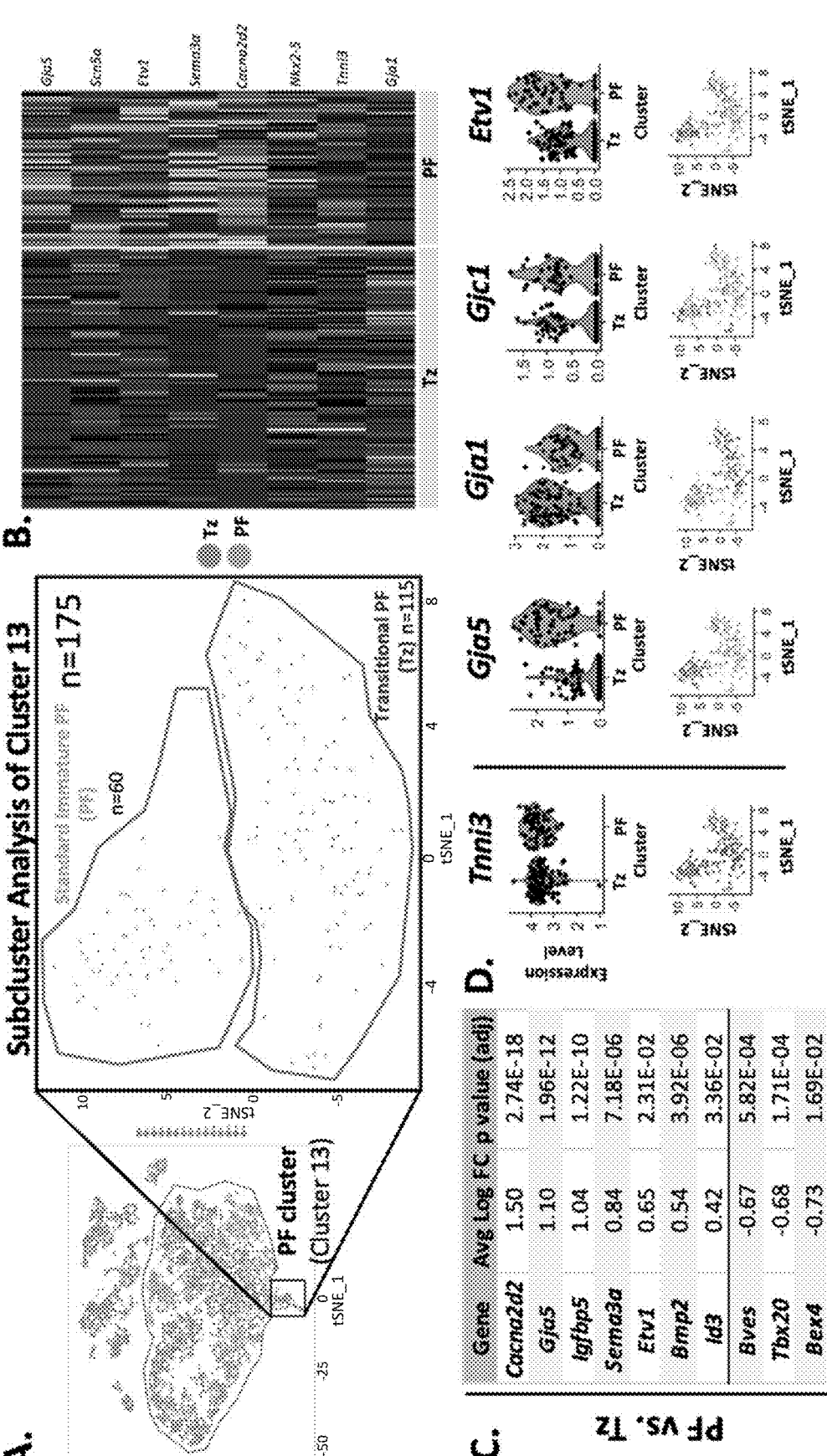
Figure 7. Analysis of Cluster 13 in Zone III Identified Unique Immature PF and Transitional PF Cell Subtypes

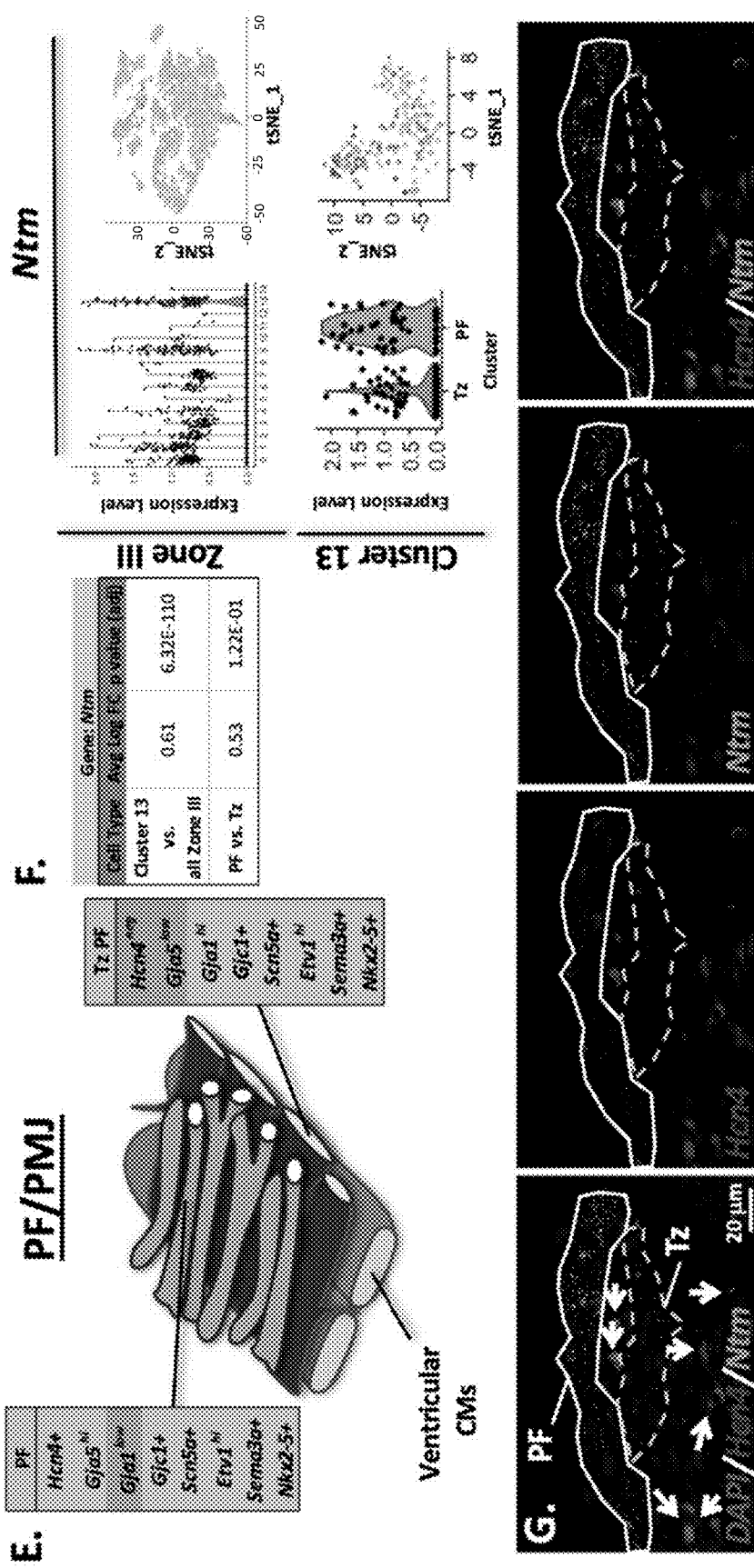
Figure 7 continued. Analysis of Cluster 13 in Zone III Identified Unique Immature PF and Transitional PF Cell Subtypes

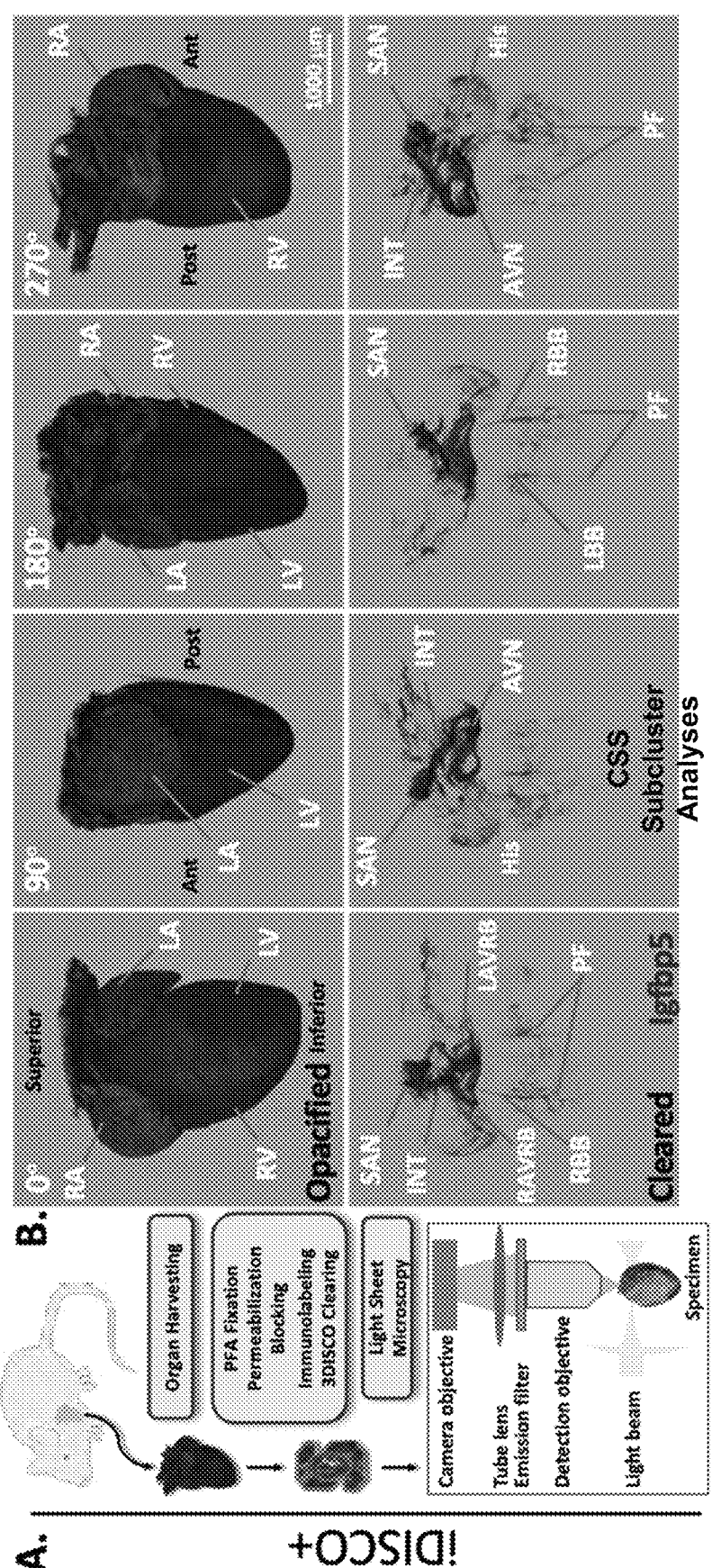
Figure 8. Optical Clearing and 3D Volumetric Analyses Delineate the Architecture of the Entire CCS and SA Nodal Substructure Within Intact Murine Hearts.

C.
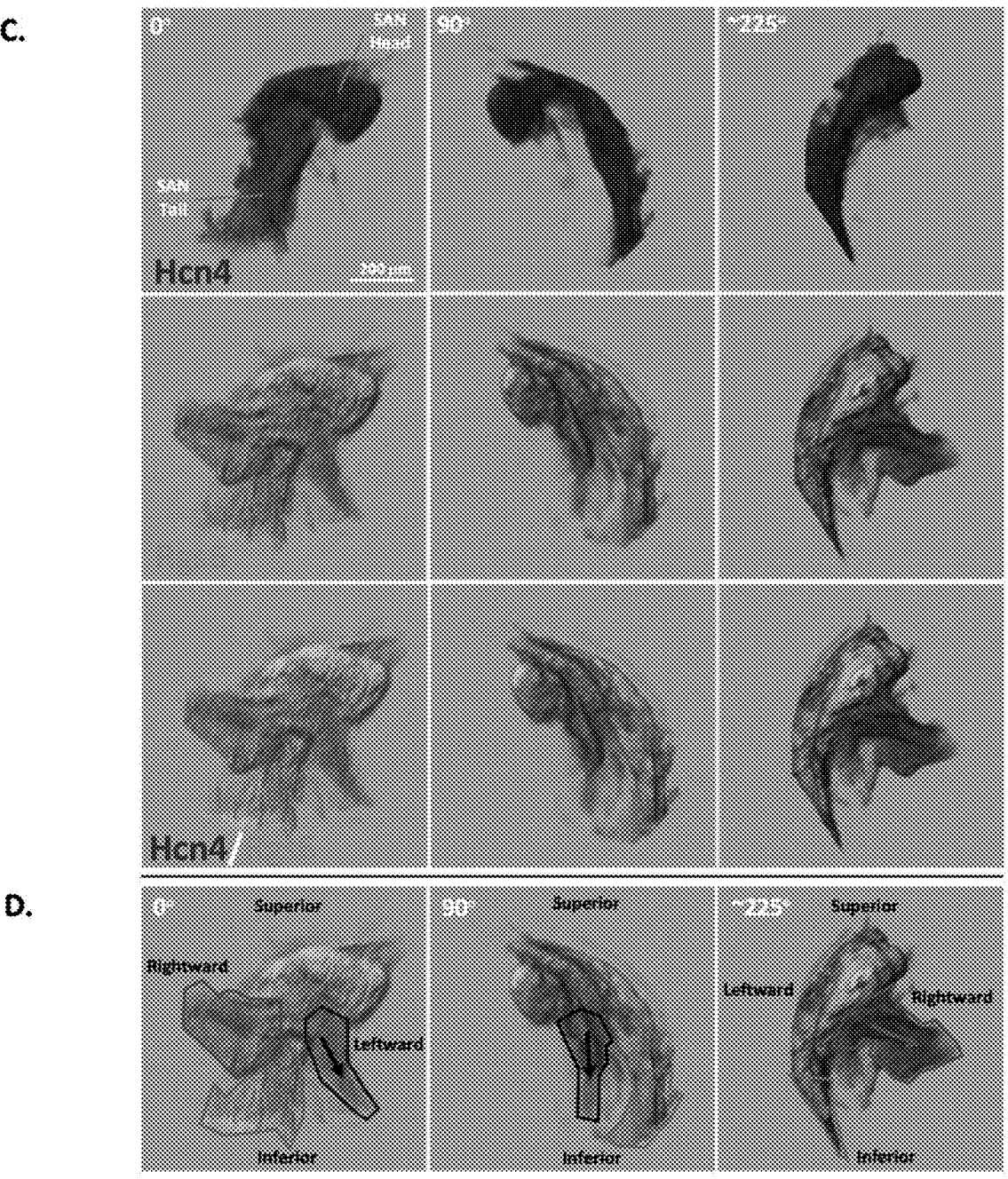
D.
Figure 8 continued. Optical Clearing and 3D Volumetric Analyses Delineate the Architecture of the Entire CCS and SA Nodal Substructure Within Intact Murine Hearts.

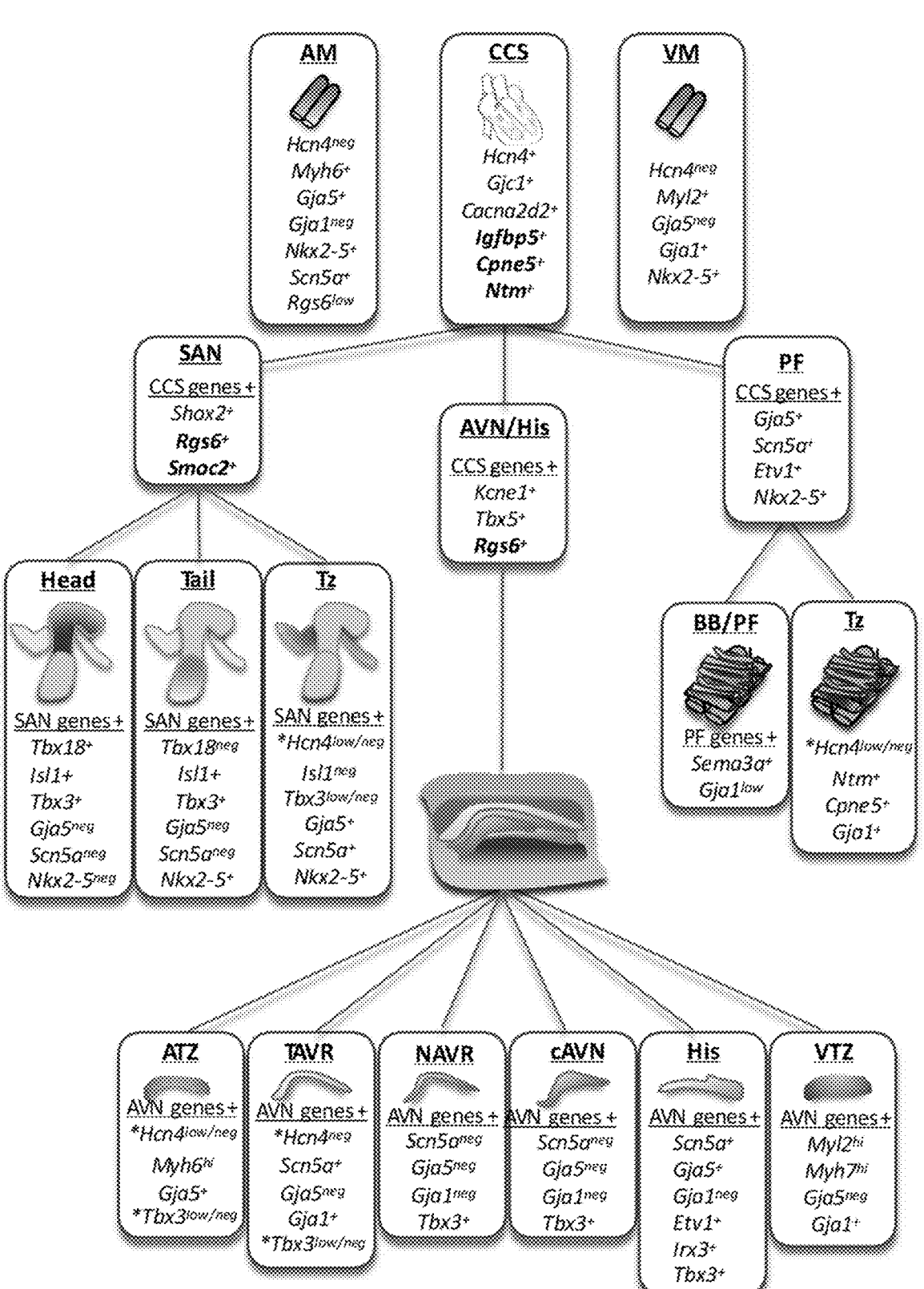
Figure 9. Transcriptional Landscape of the Cardiac Conduction System.

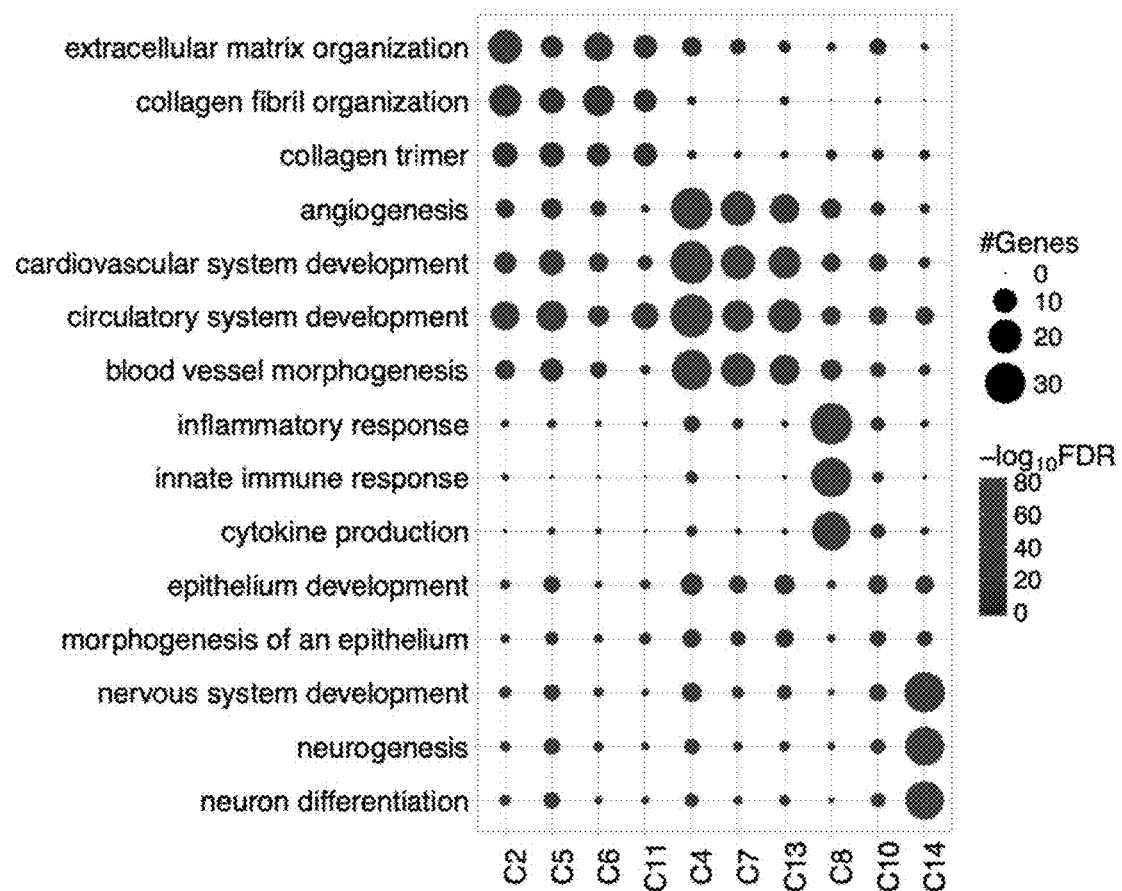
Figure 10. GO/KEGG Term Enrichment Analyses of Zone I Non-Cardiomyocyte Lineages.

A.

| Modified from Kedantham et al. 2035 | | | Current Study | |
|---|---|---|---|---|
| Gene | Log(2) Fold-Change RA vs SAN | p-value | Cluster Enrichment for Zone 1 | Associated Cluster Identities |
| Isl1 | -14.38835333 | 2.83E-75 | C9, C14 | SAN/Neuronal |
| Smoc2 | -7.385172368 | 1.62E-69 | | |
| | | | C9 | Neuronal |
| Hcn4 | -5.873773030 | 1.04E-43 | C9 | SAN |
| Tbx3 | -7.143232512 | 1.67E-39 | C9, C14 | SAN/Neuronal |
| Shox2 | -8.383438782 | 4.38E-37 | C5, C9, C12 | SAN/ Fibroblast/CM |
| Gm13423 | -3.106812377 | 4.53E-35 | Not detected | Not detected |
| Cck4 | -4.143877834 | 1.70E-33 | | |
| Camk1 | -6.368072298 | 1.53E-30 | | |
| Vsnl1 | -4.27327765 | 3.80E-28 | | |
| Smrt2 | -6.262581086 | 8.53E-28 | | |
| Tbx5 | -4.44115099 | 1.69E-27 | C9, C14 | SAN/Neuronal |
| Gabra3 | -4.825058638 | 1.17E-27 | | |
| Syt6 | -5.673823248 | 4.43E-27 | | |
| Gm3303 | -11.38561636 | 4.33E-26 | | |
| Kif1a | -4.730861185 | 7.00E-25 | | |
| Crhr | -6.363143611 | 1.96E-24 | | |
| | | | | SAN |
| Rgs6 | -3.10582387 | 1.00E-21 | | |
| Hcn1 | -5.343241944 | 1.13E-21 | C9 | SAN |
| Scrg1 | -4.815353764 | 7.50E-21 | | |
| Mfsd6 | -2.866743942 | 8.15E-21 | | |
| Gucy2e | -10.86679874 | 2.45E-20 | | |
| Uchl1 | -4.689855542 | 3.16E-20 | | |
| | | | C9 | Neuronal |
| | | | | Neuronal/ Neuronal |
| | | | | Neuronal |
| Fzd7 | -2.84976798 | 4.15E-18 | | |
| Rasrp1 | -3.794872111 | 5.78E-17 | | |

Figure 11. Comparison of SAN Gene Enrichment in Bulk vs. scRNA Sequencing.

B.
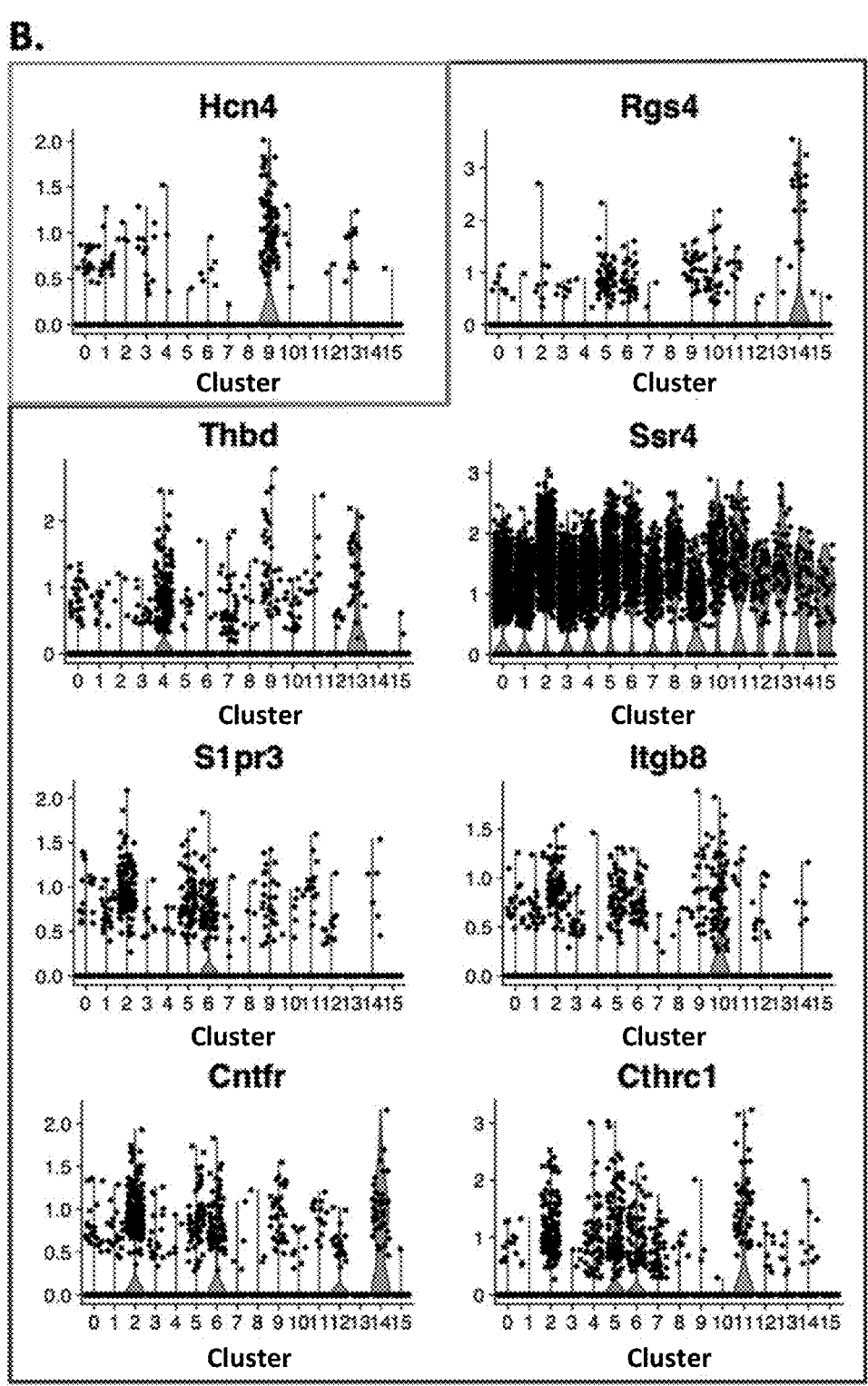
Figure 11 continued. Comparison of SAN Gene Enrichment in Bulk vs. scRNASequencing.

A.

| Gene | Modified from *Van Elf et al. 2019* | | Current Study | |
|------|------|------|------|------|
| | Log(2) Fold-Change RA (Katushka+) vs SAN (Venus+) | p-value | Cluster Enrichment for Zone I | Associated Cluster Identities |
| | | | C14 | Neuronal |
| | | | C11 | Fibroblast |
| | | | C5, C6 | Fibroblast |
| | | | C5, C6, C9, C10, C11, C12 | Fibroblast/Neuronal/CM |
| | | | C6, C9, C12 | Endocardial/SAN/Endothelial |
| Nfasc | -6.233067993 | 3.18E-35 | C9 | SAN |
| Sox18 | | | C6, C12 | Endothelial |
| Lbp1 | | | C4, C6, C9, C9, C7, C10, C11, C12 | Fibroblast/Endocardial/Neuronal |
| Hcn4 | -6.044298097 | 8.84E-19 | C9 | SAN |
| Adam12 | | | C5, C6, C9 | Fibroblast |
| Shox2 | -5.958663083 | 6.81E-28 | C6, C9, C12 | SAN/Fibroblast/CM |
| Cldn11 | | | C9, C7, C14 | Endocardial/Neuronal |
| Ngfr | | | C14 | Neuronal |
| Tnxb | | | C5, C6, C9, C10, C11, C14 | Fibroblast/Endocardial/CM |
| Plxn5 | | | C14 | Neuronal |
| Tbx3 | -5.77333563 | 3.30E-29 | C9, C14 | SAN/Neuronal |

B.

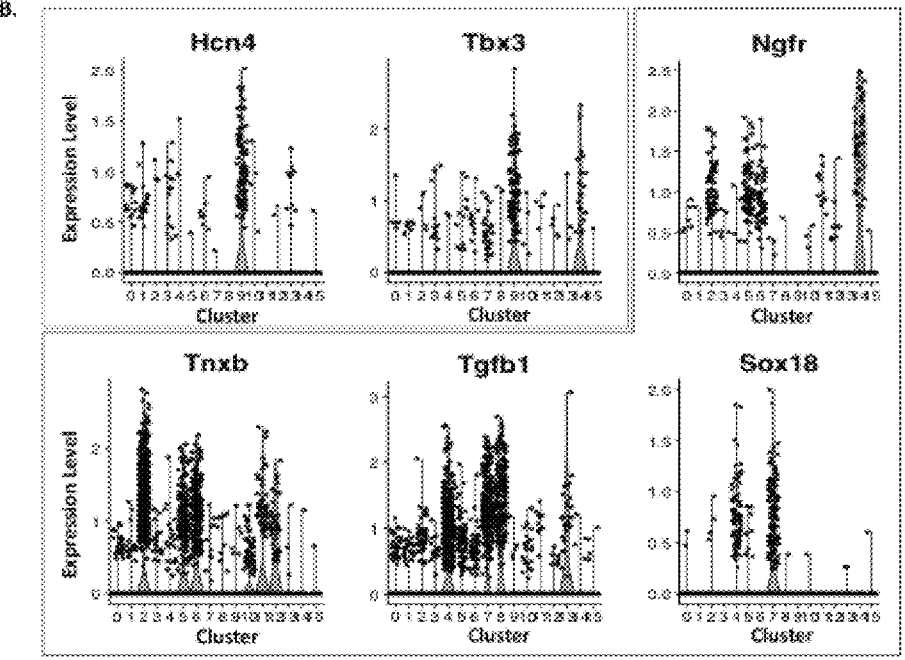

Figure 12. Comparison of SAN Gene Enrichment in Tbx3-sorted vs. scRNA Sequencing.

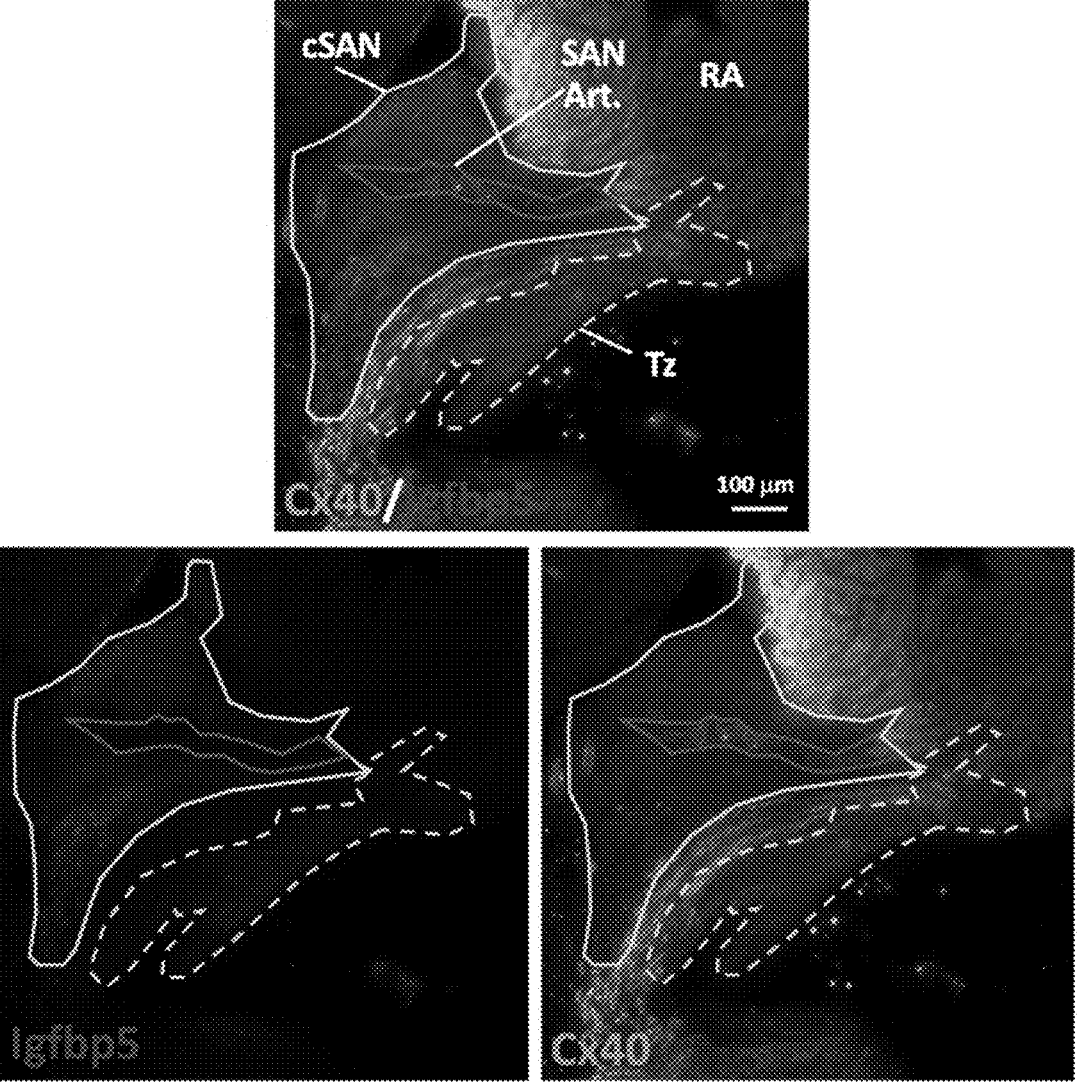
Figure 13. *Igfbp5* is Expressed Within the Compact SAN and Transitional Cells but NOT Within the SAN Artery.

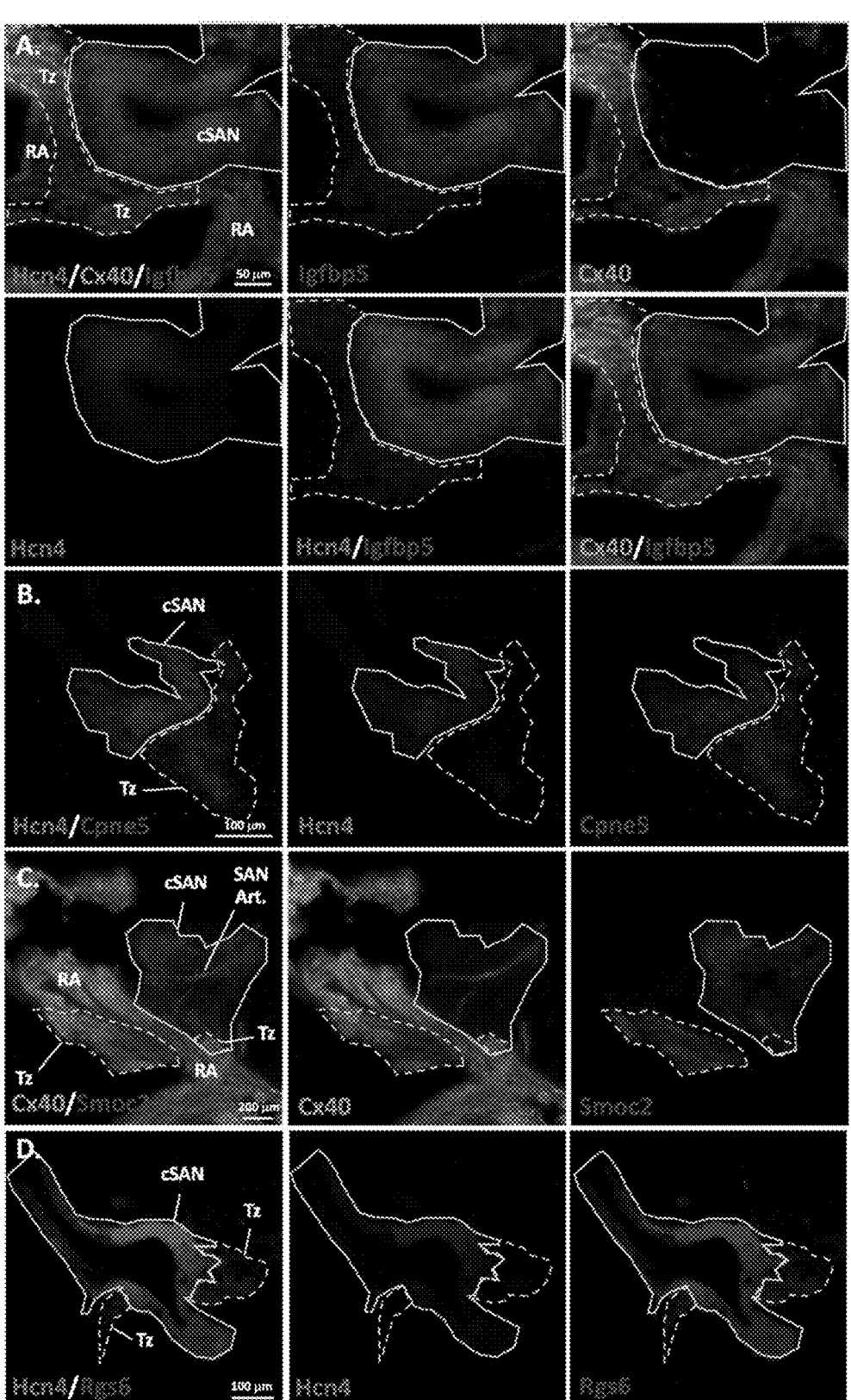
Figure 14. *Igfbp5, Cpne5, Smoc2, Rgs6* and *Ntm* are Enriched in the Compact SAN and Transitional Cells of the Mouse Heart.

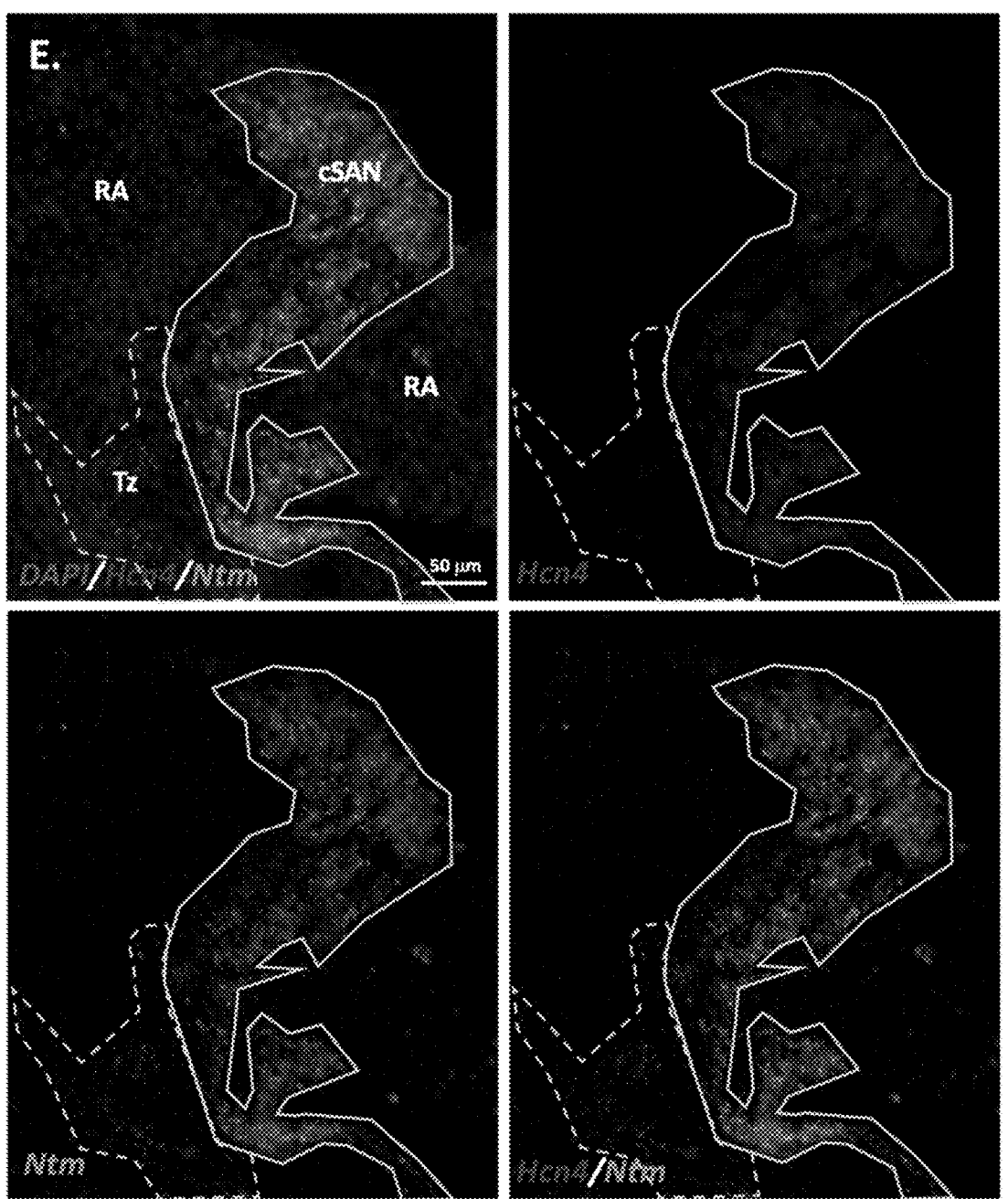
Figure 14 continued. *Igfbp5, Cpne5, Smoc2, Rgs6* and *Ntm* are Enriched in the Compact SAN and Transitional Cells of the Mouse Heart.

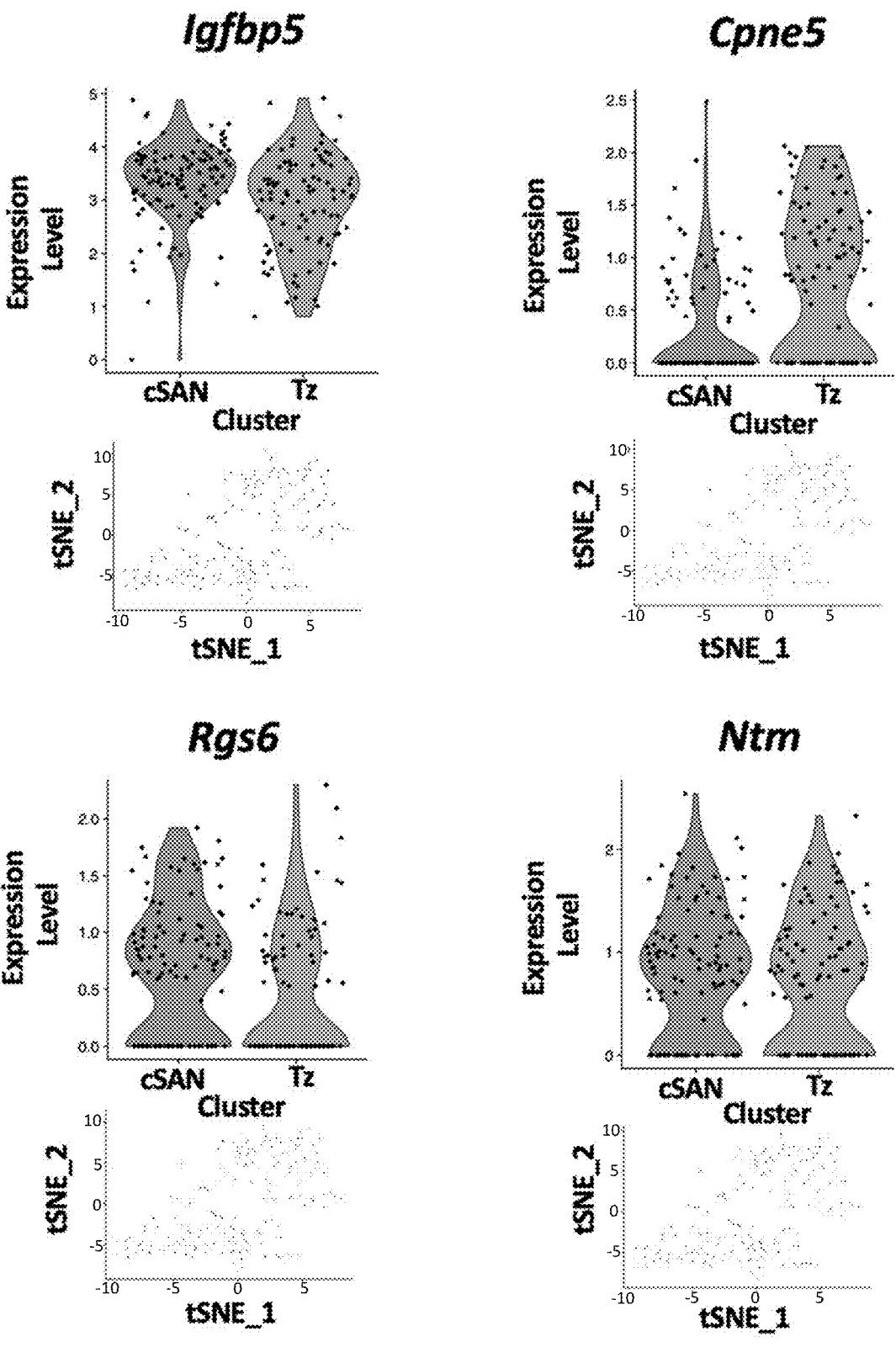
Figure 15. Expression of *Igfbp5, Cpne5, Rgs6* and *Ntm* Within cSAN and Transitional Cell Subclusters of Cluster 9.

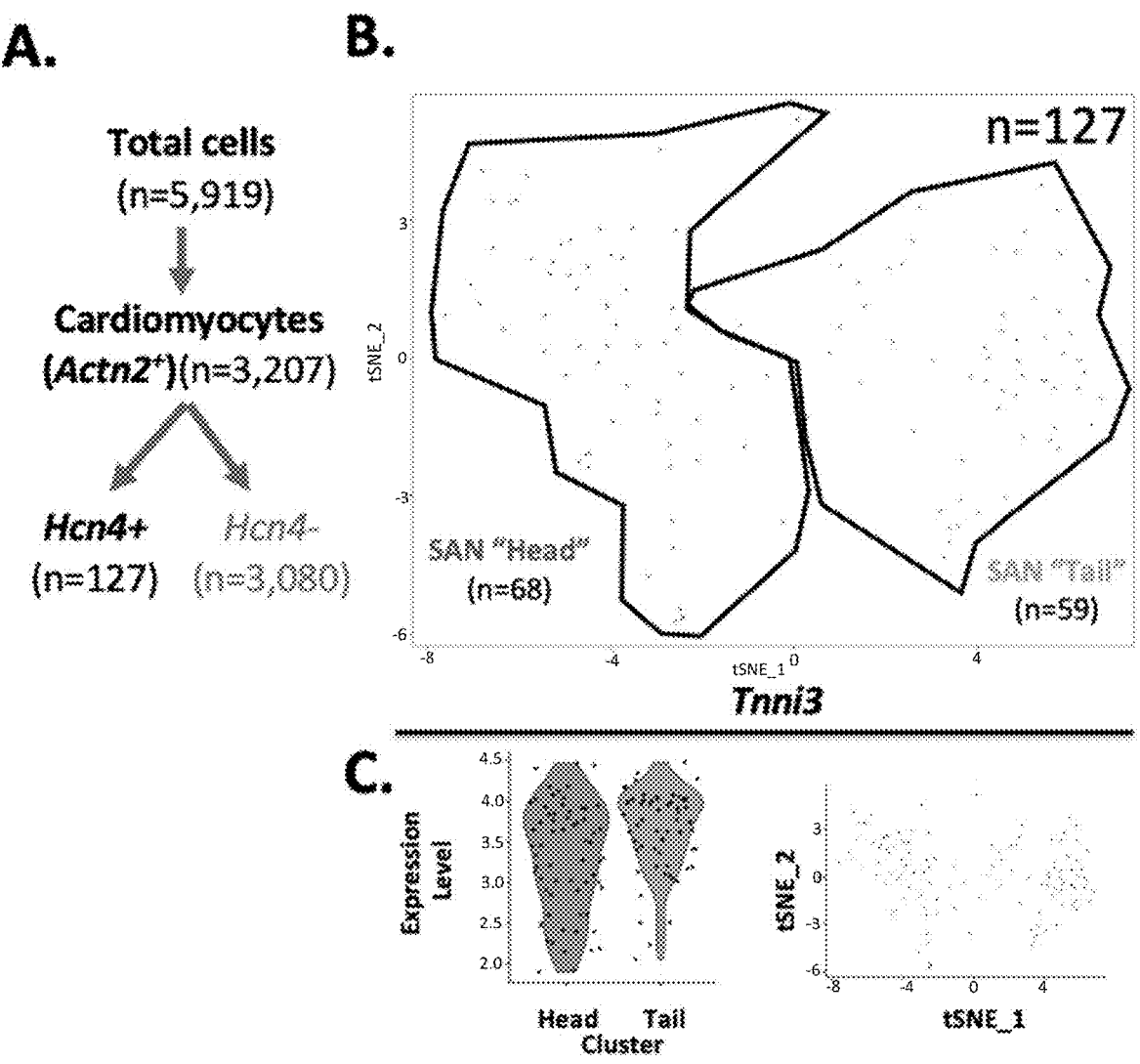
Figure 16. Analysis of _Hcn4+_ Cells in Zone I Reveal Compact SAN Subtypes Consistent with Head and Tail Regions.

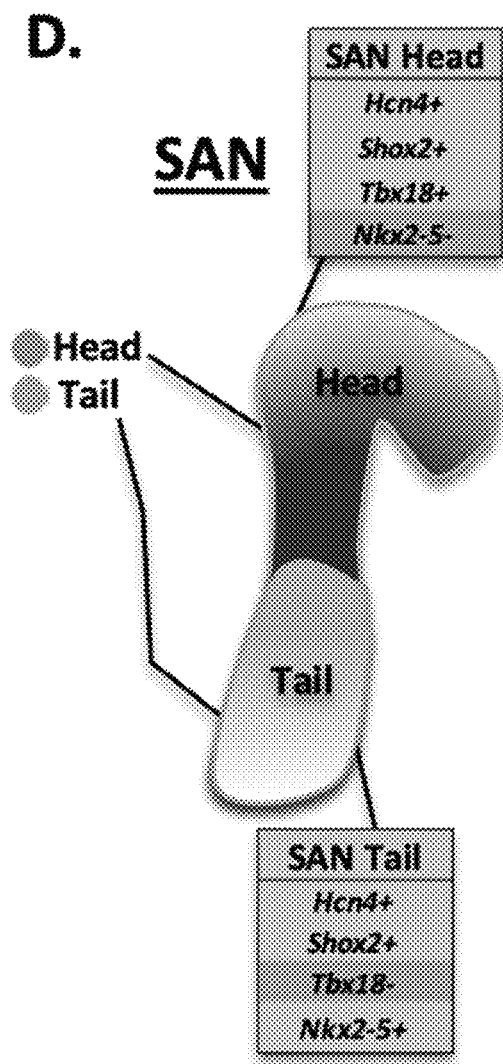
**Figure 16 continued. Analysis of *Hcn4*+ Cells in Zone I Reveal Compact SAN Subtypes Consistent with Head and Tail Regions.**

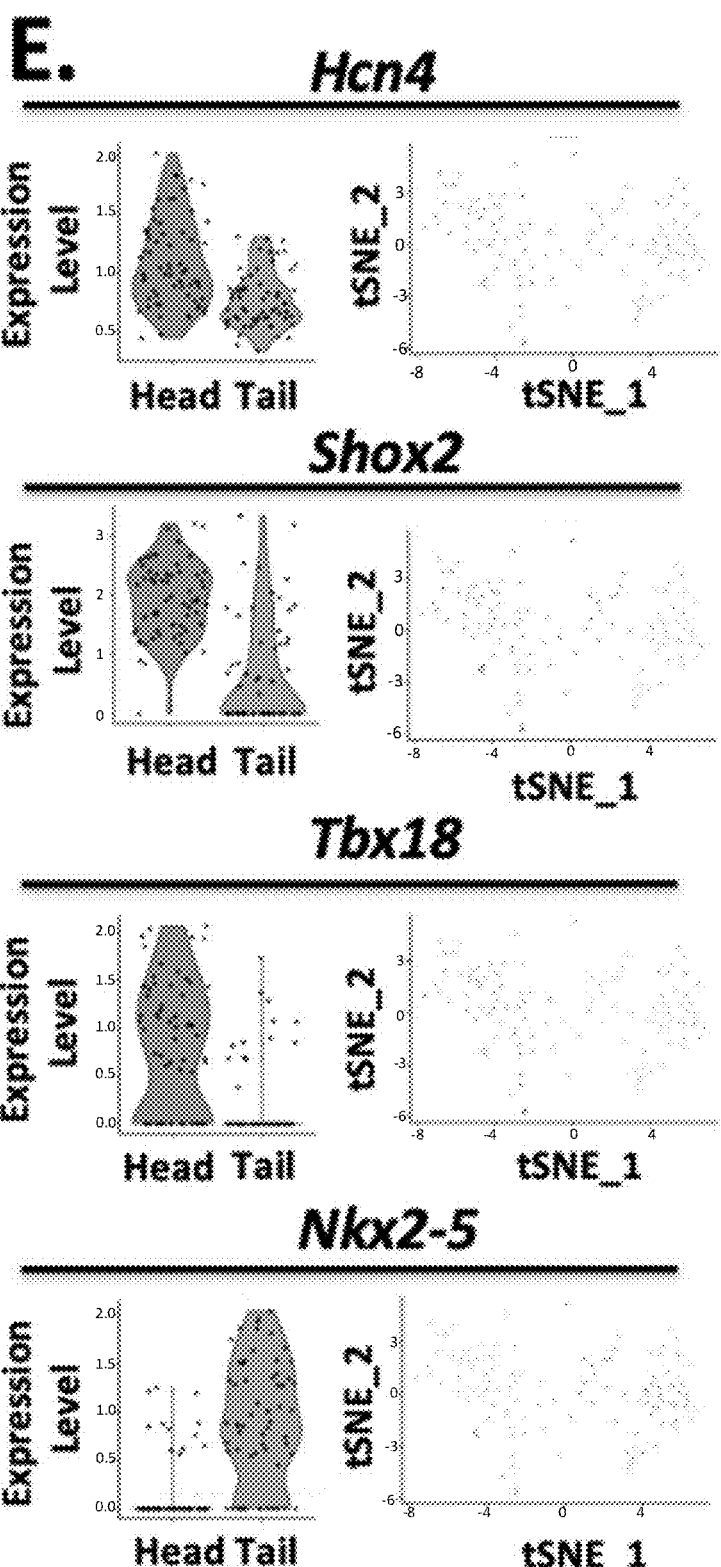
**Figure 16 continued. Analysis of *Hcn4*+ Cells in Zone I Reveal Compact SAN Subtypes Consistent with Head and Tail Regions.**

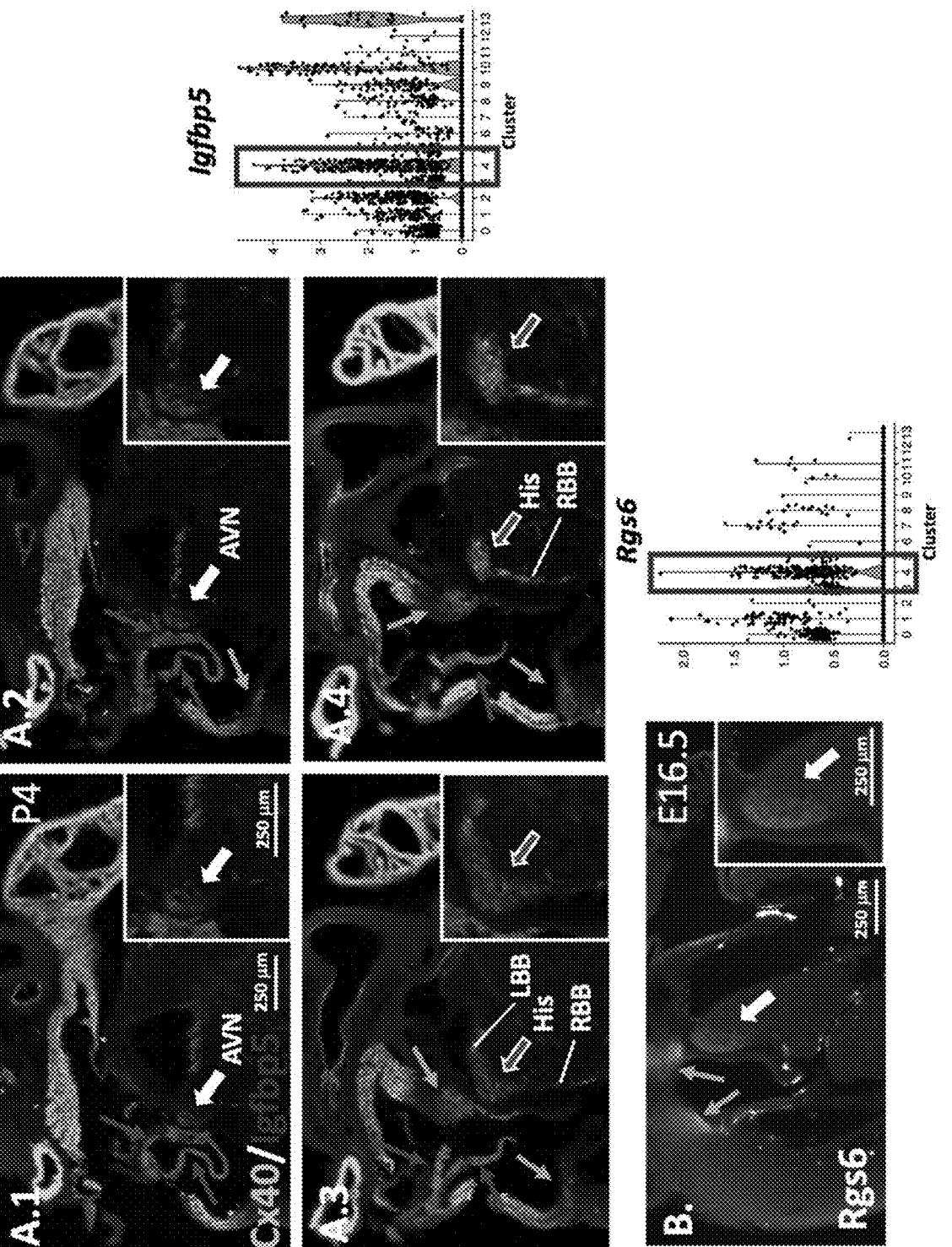
Figure 17. *Igfbp5*, *Rgs6* and *Ntm* are Enriched in the Murine AVN.

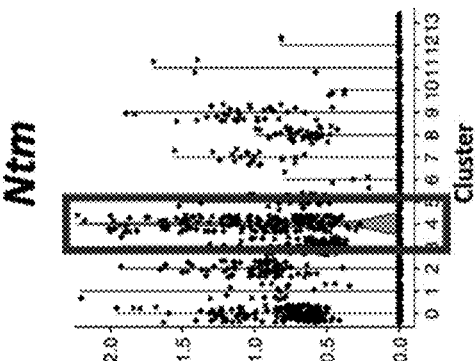
Figure 17 continued. *Igfbp5*, *Rgs6* and *Ntm* are Enriched in the Murine AVN.

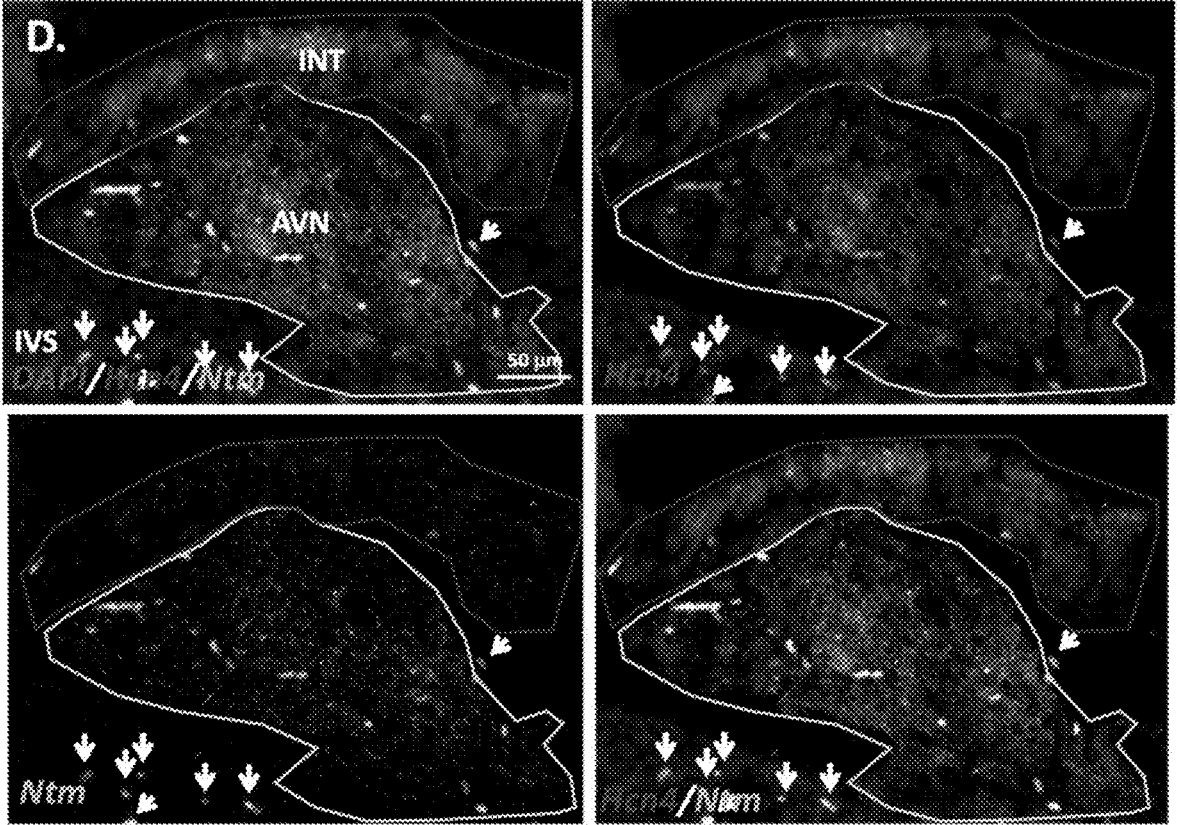
Figure 17 continued. *Igfbp5, Rgs6* and *Ntm* are Enriched in the Murine AVN.

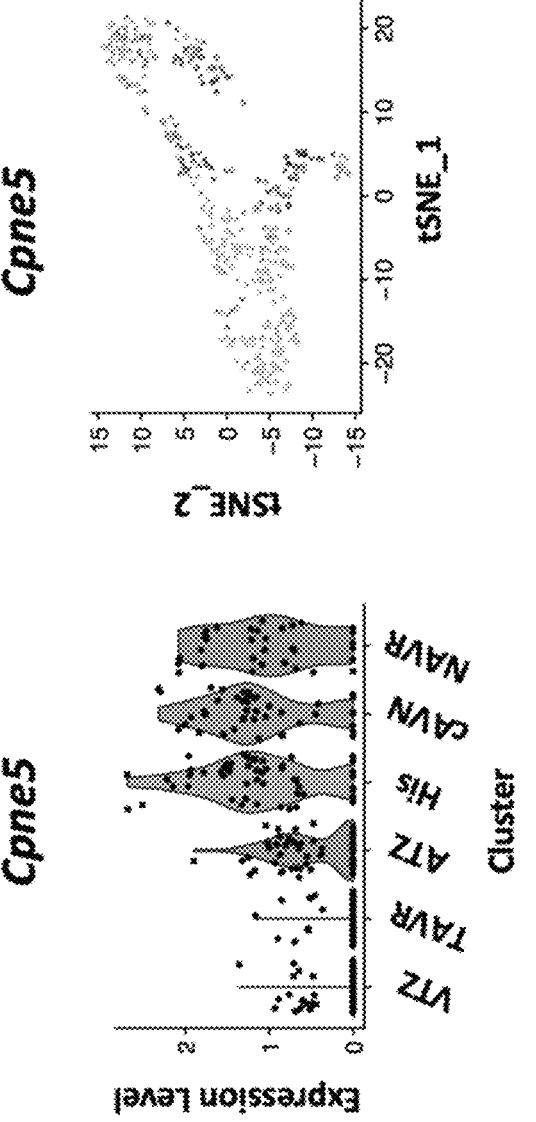
Figure 18. *Cpne5* Expression in Cluster 4 Cell Subtypes.

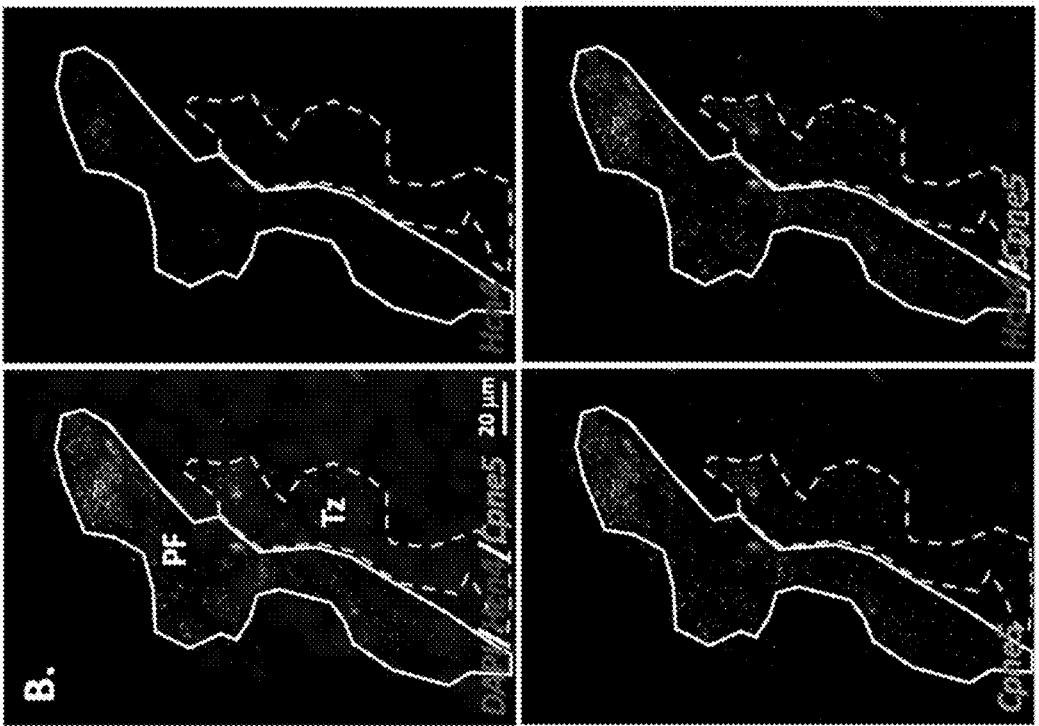
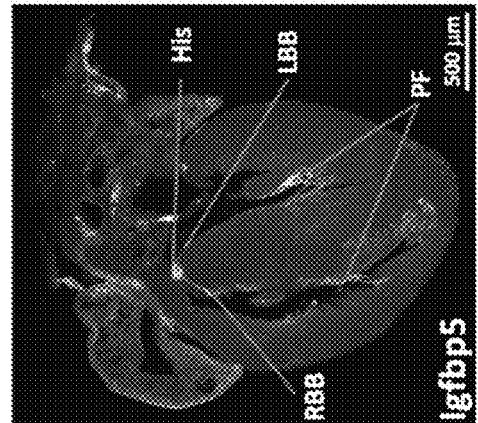
Figure 19. *Igfbp5*, and *Cpne5* Are Expressed in the Ventricular Conduction System.

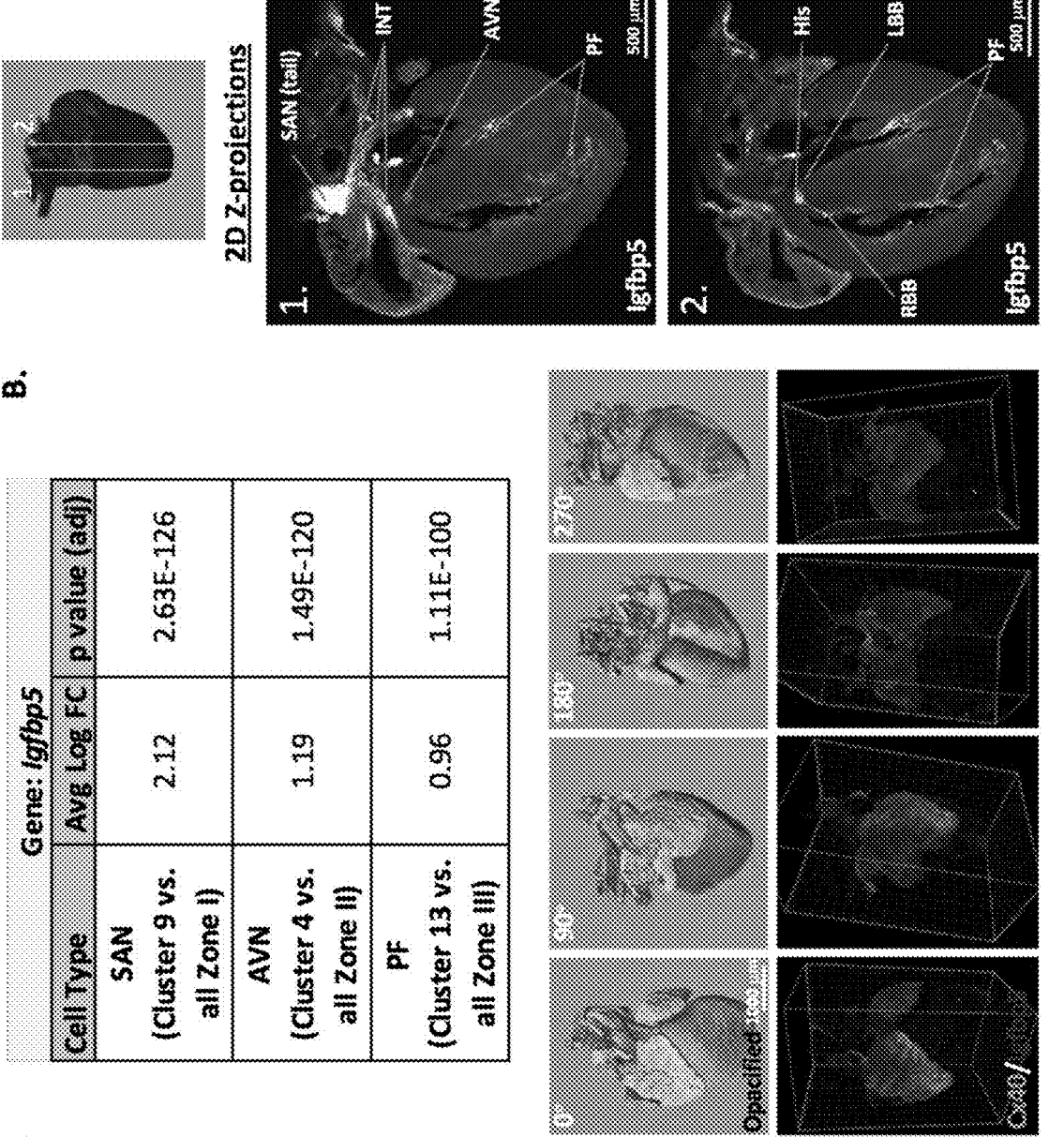
Figure 20. *Igfbp5* is Enriched Within the Entire Cardiac Conduction System.

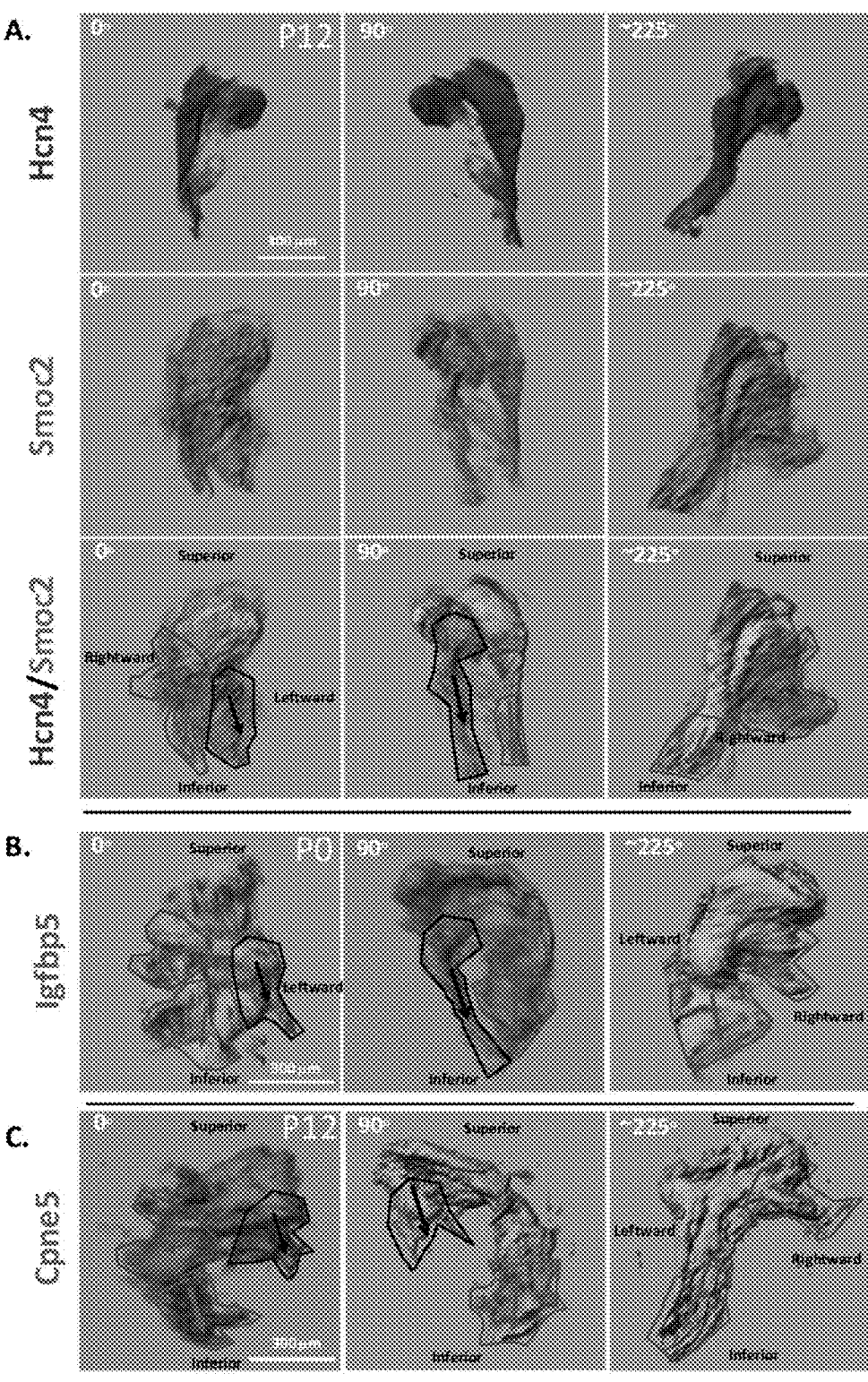
Figure 21. Optical Clearing and 3D Volumetric Analyses Illustrate Transitional Cell Populations Exiting the SAN.

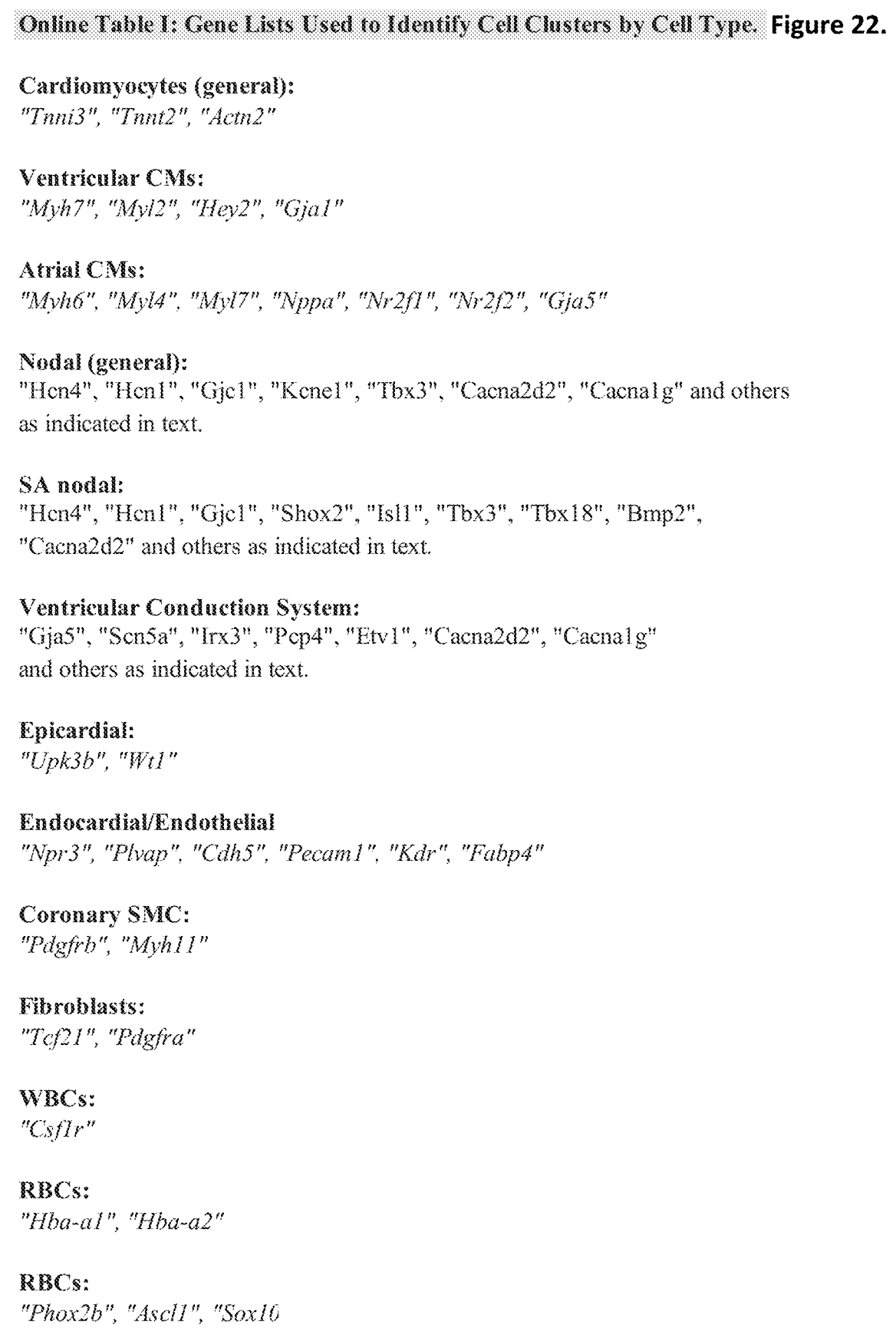

Online Table I: Gene Lists Used to Identify Cell Clusters by Cell Type. Figure 22.

Cardiomyocytes (general):
*"Tnni3", "Tnnt2", "Actn2"*

Ventricular CMs:
*"Myh7", "Myl2", "Hey2", "Gja1"*

Atrial CMs:
*"Myh6", "Myl4", "Myl7", "Nppa", "Nr2f1", "Nr2f2", "Gja5"*

Nodal (general):
"Hcn4", "Hcn1", "Gjc1", "Kcne1", "Tbx3", "Cacna2d2", "Cacna1g" and others
as indicated in text.

SA nodal:
"Hcn4", "Hcn1", "Gjc1", "Shox2", "Isl1", "Tbx3", "Tbx18", "Bmp2",
"Cacna2d2" and others as indicated in text.

Ventricular Conduction System:
"Gja5", "Scn5a", "Irx3", "Pcp4", "Etv1", "Cacna2d2", "Cacna1g"
and others as indicated in text.

Epicardial:
*"Upk3b", "Wt1"*

Endocardial/Endothelial
*"Npr3", "Plvap", "Cdh5", "Pecam1", "Kdr", "Fabp4"*

Coronary SMC:
*"Pdgfrb", "Myh11"*

Fibroblasts:
*"Tcf21", "Pdgfra"*

WBCs:
*"Csf1r"*

RBCs:
*"Hba-a1", "Hba-a2"*

RBCs:
*"Phox2b", "Ascl1", "Sox10*

Figure 23.

| Gene | p value | Average log Fold Change | Average value Cluster 9 | Average value other clusters | Adjusted p value |
|------|---------|------------------------|------------------------|------------------------------|------------------|
| Shox2 | 2.22E-308 | 1.974407 | 0.94 | 0.094 | 2.22E-308 |
| Hcn4 | 7.47E-252 | 0.5988952 | 0.405 | 0.014 | 1.29E-247 |
| Tbx3 | 5.54E-248 | 0.7670785 | 0.475 | 0.022 | 9.56E-244 |
| Cacna2d2 | 1.91E-228 | 1.41343 | 0.92 | 0.141 | 3.30E-224 |
| Bmp2 | 7.20E-225 | 1.369143 | 0.595 | 0.046 | 1.24E-220 |
| Isl1 | 5.99E-197 | 0.3403047 | 0.275 | 0.007 | 1.03E-192 |
| Smoc2 | 3.03E-168 | 1.6888529 | 0.675 | 0.093 | 5.23E-164 |
| Igfbp5 | 1.53E-130 | 2.1224393 | 0.995 | 0.406 | 2.63E-126 |
| Vsnl1 | 1.77E-115 | 1.3974063 | 0.88 | 0.292 | 3.05E-111 |
| Recl14 | 9.74E-113 | 0.5854624 | 0.405 | 0.042 | 1.68E-108 |
| Fbxo32 | 7.19E-106 | 0.9493654 | 0.79 | 0.208 | 1.24E-101 |
| Ntm | 2.88E-85 | 0.7501494 | 0.675 | 0.168 | 4.97E-81 |
| Sh2d4a | 1.98E-83 | 0.4308363 | 0.305 | 0.032 | 3.42E-79 |
| Atp1b1 | 3.33E-75 | 0.9616666 | 0.99 | 0.724 | 5.75E-71 |
| Atp1a1 | 1.11E-70 | 0.8579578 | 0.995 | 0.718 | 1.91E-66 |
| Tmod1 | 1.20E-69 | 0.860189 | 0.965 | 0.495 | 2.08E-65 |
| Tpm1 | 1.31E-66 | 0.9645624 | 1 | 0.934 | 2.27E-62 |
| Gfra2 | 8.09E-66 | 0.3189673 | 0.265 | 0.03 | 1.40E-61 |
| Rgs6 | 1.69E-65 | 0.5997764 | 0.57 | 0.148 | 2.92E-61 |
| Slc24a2 | 1.29E-62 | 0.3535928 | 0.365 | 0.06 | 2.23E-58 |
| Gnao1 | 9.83E-62 | 0.6984124 | 0.78 | 0.308 | 1.70E-57 |
| Aspscr1 | 1.44E-61 | 0.9752966 | 0.705 | 0.291 | 2.49E-57 |
| Ldb3 | 4.75E-61 | 0.8303587 | 0.98 | 0.555 | 8.21E-57 |
| Eef1a2 | 1.49E-58 | 0.7165284 | 0.785 | 0.325 | 2.57E-54 |
| Tcap | 1.90E-58 | 0.9604554 | 0.905 | 0.448 | 3.29E-54 |
| Plppr1 | 3.18E-58 | 0.33107 | 0.26 | 0.033 | 5.49E-54 |
| Rgs12 | 3.74E-58 | 0.6886888 | 0.695 | 0.262 | 6.46E-54 |
| Pcdh17 | 3.48E-57 | 0.6321118 | 0.335 | 0.056 | 6.01E-53 |
| Pln | 4.30E-57 | 1.2267752 | 0.87 | 0.47 | 7.42E-53 |
| Des | 4.66E-57 | 0.8110169 | 0.99 | 0.593 | 8.04E-53 |
| Ptp4a3 | 1.76E-56 | 0.7583342 | 0.88 | 0.492 | 3.04E-52 |
| Gde1 | 6.63E-56 | 0.7132635 | 0.75 | 0.333 | 1.15E-51 |
| mt-Nd2 | 1.12E-55 | 0.6354767 | 1 | 0.981 | 1.94E-51 |
| Kcnj5 | 1.13E-55 | 0.7139213 | 0.76 | 0.305 | 1.94E-51 |
| Mob1b | 5.56E-55 | 0.7374769 | 0.825 | 0.406 | 9.60E-51 |
| Sorbs2 | 1.79E-54 | 0.8375855 | 0.925 | 0.518 | 3.09E-50 |
| Snap91 | 5.59E-54 | 0.8867371 | 0.765 | 0.341 | 9.65E-50 |
| Cox8a | 9.16E-54 | 0.5444893 | 1 | 0.993 | 1.58E-49 |
| mt-Nd4 | 1.29E-53 | 0.6399511 | 1 | 0.992 | 2.22E-49 |
| Ndrg2 | 2.94E-53 | 0.6298521 | 0.97 | 0.613 | 5.08E-49 |
| Rpl10 | 3.86E-53 | -0.6451645 | 0.995 | 0.998 | 6.66E-49 |

Online Table II: Differentially Expressed Genes in Cluster 9 of Zone 1.

| | | | | | |
|---|---|---|---|---|---|
| Clic5 | 4.58E-52 | 0.5307451 | 0.545 | 0.16 | 7.90E-48 |
| Rpl32 | 8.75E-52 | -0.6955401 | 1 | 1 | 1.51E-47 |
| mt-Cytb | 1.94E-50 | 0.6022743 | 1 | 0.996 | 3.35E-46 |
| Rpl18a | 8.23E-50 | -0.7008656 | 0.995 | 0.999 | 1.42E-45 |
| Uchl1 | 9.88E-50 | 0.6520579 | 0.53 | 0.164 | 1.70E-45 |
| Myoz2 | 1.78E-49 | 0.7534594 | 0.94 | 0.523 | 3.07E-45 |
| Gm8113 | 3.51E-49 | 0.4218645 | 0.255 | 0.038 | 6.06E-45 |
| Lbh | 4.23E-49 | 1.0439915 | 0.72 | 0.335 | 7.31E-45 |
| Cryab | 5.18E-49 | 0.7045513 | 1 | 0.696 | 8.94E-45 |
| Hspb6 | 5.22E-49 | 0.6463397 | 0.72 | 0.294 | 9.02E-45 |
| Ank1 | 6.66E-49 | 0.7427694 | 0.84 | 0.417 | 1.15E-44 |
| Adora1 | 3.05E-48 | 0.4688747 | 0.465 | 0.123 | 5.27E-44 |
| Ttn | 1.85E-47 | 0.776609 | 1 | 0.624 | 3.20E-43 |
| Tenm4 | 4.50E-47 | 0.5478988 | 0.43 | 0.109 | 7.76E-43 |
| Smyd1 | 5.19E-47 | 0.6799102 | 0.855 | 0.446 | 8.97E-43 |
| mt-Nd1 | 1.05E-46 | 0.5531378 | 1 | 0.996 | 1.82E-42 |
| Cacna1h | 3.66E-46 | 0.3938078 | 0.415 | 0.102 | 6.31E-42 |
| Mfsd6 | 4.29E-46 | 0.4165877 | 0.33 | 0.068 | 7.41E-42 |
| Igf2 | 4.74E-46 | -1.0406318 | 0.825 | 0.942 | 8.18E-42 |
| Csrp2 | 1.58E-45 | 1.2091145 | 0.95 | 0.885 | 2.73E-41 |
| B2m | 2.25E-45 | -1.1096757 | 0.13 | 0.659 | 3.88E-41 |
| Chchd10 | 2.71E-45 | 0.6930042 | 0.995 | 0.613 | 4.67E-41 |
| Trabd2b | 1.06E-44 | 0.588442 | 0.53 | 0.168 | 1.82E-40 |
| Ramp1 | 1.18E-44 | 0.9100145 | 0.775 | 0.387 | 2.04E-40 |
| mt-Co3 | 1.31E-44 | 0.5141767 | 1 | 0.999 | 2.26E-40 |
| mt-Atp6 | 2.24E-43 | 0.5294369 | 1 | 0.999 | 3.87E-39 |
| Uqcrq | 3.27E-43 | 0.5381064 | 0.995 | 0.958 | 5.65E-39 |
| Lclat1 | 8.88E-43 | 0.4511478 | 0.42 | 0.115 | 1.53E-38 |
| Rpl23 | 1.83E-42 | -0.523306 | 1 | 0.999 | 3.16E-38 |
| Rpl39 | 2.91E-42 | -0.4838014 | 1 | 1 | 5.02E-38 |
| Fitm1 | 3.91E-42 | 0.624314 | 0.675 | 0.298 | 6.75E-38 |
| Gria1 | 5.92E-42 | 0.4073252 | 0.375 | 0.092 | 1.02E-37 |
| Strip2 | 7.49E-42 | 0.5472433 | 0.64 | 0.264 | 1.29E-37 |
| Dbh | 7.98E-42 | 0.3821388 | 0.305 | 0.063 | 1.38E-37 |
| Mmd | 9.05E-42 | 0.6630951 | 0.875 | 0.552 | 1.56E-37 |
| Cpne5 | 1.68E-41 | 0.5727294 | 0.465 | 0.138 | 2.90E-37 |
| Atp5e | 2.64E-41 | 0.4290129 | 0.995 | 0.99 | 4.57E-37 |
| Rpl7 | 2.65E-41 | -0.5763133 | 1 | 0.997 | 4.57E-37 |
| Pfn1 | 2.99E-41 | -0.6184949 | 0.945 | 0.985 | 5.16E-37 |
| Ccng1 | 3.99E-41 | 0.6316658 | 0.875 | 0.534 | 6.88E-37 |
| Atp2a2 | 5.40E-41 | 0.7340601 | 1 | 0.756 | 9.33E-37 |
| Nptn | 9.52E-41 | 0.6289068 | 0.83 | 0.492 | 1.64E-36 |
| Bmp7 | 1.47E-40 | 0.5619462 | 0.58 | 0.219 | 2.54E-36 |
| Rps5 | 1.72E-40 | -0.6882475 | 1 | 0.999 | 2.98E-36 |
| Mest | 2.08E-40 | -1.0769236 | 0.425 | 0.827 | 3.59E-36 |

Figure 23. continued

| | | | | | |
|---|---|---|---|---|---|
| Ftl1 | 2.14E-40 | -0.9581048 | 0.995 | 0.996 | 3.70E-36 |
| S100a11 | 2.83E-40 | -1.3813119 | 0.495 | 0.817 | 4.88E-36 |
| Uqcr11 | 3.01E-40 | 0.5409497 | 1 | 0.953 | 5.19E-36 |
| Rps8 | 5.47E-40 | -0.5706924 | 1 | 1 | 9.44E-36 |
| Myh7 | 8.40E-40 | 0.7781123 | 0.885 | 0.474 | 1.45E-35 |
| Enpep | 1.44E-39 | 0.3829946 | 0.415 | 0.115 | 2.48E-35 |
| Mybpc3 | 1.45E-39 | 0.5679654 | 0.96 | 0.541 | 2.51E-35 |
| Rps19 | 1.48E-39 | -0.7662552 | 1 | 1 | 2.55E-35 |
| Flnc | 1.65E-39 | 0.6614566 | 0.81 | 0.499 | 2.84E-35 |
| Nav2 | 1.93E-39 | 0.6354688 | 0.81 | 0.425 | 3.33E-35 |
| mt-Co1 | 3.75E-39 | 0.5352723 | 1 | 0.996 | 6.47E-35 |
| Rpl12 | 4.83E-39 | -0.6139497 | 0.97 | 0.991 | 8.34E-35 |
| Adcy5 | 5.54E-39 | 0.4740085 | 0.605 | 0.236 | 9.56E-35 |
| Rpl10a | 5.85E-39 | -0.5687525 | 1 | 0.998 | 1.01E-34 |
| Cdc14b | 6.68E-39 | 0.4794168 | 0.61 | 0.243 | 1.15E-34 |
| Mlf1 | 7.48E-39 | 0.6716834 | 0.965 | 0.595 | 1.29E-34 |
| mt-Co2 | 9.37E-39 | 0.4946668 | 1 | 0.995 | 1.62E-34 |
| Rps4x | 1.19E-38 | -0.5439918 | 1 | 1 | 2.05E-34 |
| Uqcrh | 2.41E-38 | 0.4197536 | 1 | 0.994 | 4.17E-34 |
| Atp5k | 2.45E-38 | 0.5147874 | 1 | 0.939 | 4.24E-34 |
| Rps27a | 3.16E-38 | -0.5594178 | 0.995 | 0.999 | 5.46E-34 |
| Cacna1g | 3.21E-38 | 0.3041655 | 0.255 | 0.048 | 5.54E-34 |
| Vim | 4.39E-38 | -1.8788667 | 0.715 | 0.881 | 7.58E-34 |
| Adprhl1 | 4.76E-38 | 0.5701442 | 0.81 | 0.41 | 8.21E-34 |
| H19 | 1.28E-37 | -1.2784657 | 0.775 | 0.932 | 2.21E-33 |
| Npm1 | 1.36E-37 | -0.7091247 | 0.94 | 0.978 | 2.36E-33 |
| Rps11 | 1.81E-37 | -0.5178609 | 1 | 0.999 | 3.12E-33 |
| Cox7c | 2.61E-37 | 0.4447016 | 1 | 0.994 | 4.50E-33 |
| Rps17 | 2.73E-37 | -0.4486691 | 0.995 | 1 | 4.71E-33 |
| Myl2 | 6.16E-37 | 0.8945793 | 0.26 | 0.052 | 1.06E-32 |
| Myom1 | 7.33E-37 | 0.5614666 | 0.83 | 0.442 | 1.27E-32 |
| Rpsa | 8.66E-37 | -0.5362583 | 0.985 | 0.997 | 1.50E-32 |
| Rps15a | 1.13E-36 | -0.5039319 | 1 | 1 | 1.96E-32 |
| Rnf207 | 2.22E-36 | 0.4927476 | 0.65 | 0.281 | 3.84E-32 |
| Rps3 | 3.76E-36 | -0.6121722 | 0.995 | 0.999 | 6.49E-32 |
| Ccdc141 | 5.20E-36 | 0.5917542 | 0.895 | 0.53 | 8.97E-32 |
| Slc38a2 | 6.93E-36 | 0.7000181 | 0.87 | 0.592 | 1.20E-31 |
| Ryr2 | 9.49E-36 | 0.6349469 | 0.89 | 0.499 | 1.64E-31 |
| Tns1 | 1.13E-35 | 0.6156813 | 0.81 | 0.52 | 1.95E-31 |
| Synpo2l | 1.33E-35 | 0.6474268 | 0.87 | 0.496 | 2.30E-31 |
| Ndrg4 | 1.53E-35 | 0.5853135 | 0.715 | 0.371 | 2.64E-31 |
| Cmya5 | 1.61E-35 | 0.5401716 | 0.535 | 0.207 | 2.78E-31 |
| Xirp1 | 2.30E-35 | 0.4758174 | 0.63 | 0.264 | 3.97E-31 |
| Adam33 | 4.39E-35 | 0.4877044 | 0.485 | 0.169 | 7.57E-31 |
| Pdlim7 | 5.15E-35 | 0.5953382 | 0.865 | 0.596 | 8.89E-31 |

Figure 23. continued

| | | | | | |
|---|---|---|---|---|---|
| Rps28 | 5.31E-35 | -0.5369851 | 1 | 0.998 | 9.16E-31 |
| Hlf | 7.17E-35 | 0.3997492 | 0.36 | 0.099 | 1.24E-30 |
| Rpl13 | 8.55E-35 | -0.5438669 | 1 | 0.999 | 1.48E-30 |
| Popdc2 | 1.06E-34 | 0.5687796 | 0.825 | 0.445 | 1.82E-30 |
| Cd63 | 1.12E-34 | -0.9307989 | 0.555 | 0.833 | 1.93E-30 |
| Rps16 | 1.30E-34 | -0.5492324 | 1 | 0.999 | 2.24E-30 |
| mt-Nd3 | 1.44E-34 | 0.4715661 | 1 | 0.92 | 2.49E-30 |
| Rpl13a | 1.74E-34 | -0.6024531 | 1 | 0.999 | 3.00E-30 |
| Enpp1 | 1.85E-34 | 0.314394 | 0.325 | 0.081 | 3.19E-30 |
| Crip2 | 2.64E-34 | 0.5527088 | 0.99 | 0.805 | 4.56E-30 |
| Rps26 | 4.58E-34 | -0.5602019 | 0.99 | 0.998 | 7.91E-30 |
| Rpl22l1 | 5.31E-34 | -0.5995867 | 0.965 | 0.99 | 9.17E-30 |
| Usmg5 | 8.62E-34 | 0.4581511 | 1 | 0.951 | 1.49E-29 |
| Pirt | 9.86E-34 | 0.385581 | 0.35 | 0.095 | 1.70E-29 |
| Rps15 | 1.33E-33 | -0.4923952 | 1 | 0.999 | 2.30E-29 |
| Prdx4 | 1.43E-33 | -0.9233495 | 0.405 | 0.747 | 2.47E-29 |
| Lrrn2 | 1.58E-33 | 0.3907484 | 0.41 | 0.127 | 2.73E-29 |
| Adgrb2 | 2.63E-33 | 0.2708076 | 0.255 | 0.053 | 4.53E-29 |
| Rpl35 | 3.13E-33 | -0.5232262 | 0.99 | 0.993 | 5.41E-29 |
| Cacna1d | 3.65E-33 | 0.290196 | 0.275 | 0.061 | 6.30E-29 |
| Slc25a4 | 3.67E-33 | 0.5319157 | 1 | 0.985 | 6.34E-29 |
| Ndufa1 | 3.72E-33 | 0.4940588 | 0.98 | 0.825 | 6.42E-29 |
| Rpl27a | 4.45E-33 | -0.4863245 | 0.995 | 0.999 | 7.68E-29 |
| Rps18 | 6.82E-33 | -0.5166595 | 1 | 0.998 | 1.18E-28 |
| Zdhhc2 | 8.74E-33 | 0.5316981 | 0.6 | 0.276 | 1.51E-28 |
| Naca | 9.24E-33 | -0.4891074 | 0.985 | 0.986 | 1.60E-28 |
| 700020I14Ri | 1.47E-32 | 0.5431571 | 0.895 | 0.658 | 2.54E-28 |
| Rps3a1 | 1.68E-32 | -0.480093 | 0.995 | 0.998 | 2.90E-28 |
| Unc45b | 1.97E-32 | 0.4575581 | 0.715 | 0.365 | 3.40E-28 |
| Chpt1 | 2.85E-32 | 0.5179783 | 0.64 | 0.314 | 4.92E-28 |
| Cav1 | 3.01E-32 | 0.5162639 | 0.965 | 0.672 | 5.19E-28 |
| Arpc1b | 3.17E-32 | -1.053535 | 0.12 | 0.55 | 5.46E-28 |
| mt-Nd4l | 3.45E-32 | 0.5087212 | 0.965 | 0.739 | 5.95E-28 |
| Enah | 3.61E-32 | 0.5591708 | 0.875 | 0.563 | 6.22E-28 |
| Atp1b2 | 3.71E-32 | 0.395875 | 0.465 | 0.163 | 6.41E-28 |
| Rps12 | 4.15E-32 | -0.6099358 | 1 | 0.998 | 7.17E-28 |
| Furin | 5.17E-32 | 0.6973162 | 0.595 | 0.299 | 8.93E-28 |
| Gata6 | 6.49E-32 | 0.5236352 | 0.925 | 0.743 | 1.12E-27 |
| Eef1b2 | 1.12E-31 | -0.5851041 | 0.91 | 0.968 | 1.93E-27 |
| Kcnh2 | 1.33E-31 | 0.3897399 | 0.465 | 0.165 | 2.29E-27 |
| Sptbn1 | 1.33E-31 | 0.4961229 | 0.955 | 0.84 | 2.30E-27 |
| Rbm24 | 1.48E-31 | 0.4788722 | 0.855 | 0.455 | 2.56E-27 |
| Srl | 1.50E-31 | 0.5352832 | 0.855 | 0.485 | 2.58E-27 |
| Atcayos | 2.11E-31 | 0.5179201 | 0.76 | 0.375 | 3.64E-27 |
| Nr2f1 | 2.15E-31 | 0.6567364 | 0.63 | 0.314 | 3.71E-27 |

**Figure 23.
continued**

| | | | | | |
|---|---|---|---|---|---|
| Rplp1 | 3.60E-31 | -0.3817615 | 1 | 1 | 6.21E-27 |
| Cox6c | 3.96E-31 | 0.4269553 | 1 | 0.991 | 6.84E-27 |
| Jph2 | 4.22E-31 | 0.4981324 | 0.73 | 0.38 | 7.29E-27 |
| Cfl2 | 4.54E-31 | 0.4775907 | 0.965 | 0.839 | 7.84E-27 |
| Actc1 | 4.97E-31 | 0.6224864 | 1 | 0.859 | 8.58E-27 |
| Ppia | 4.99E-31 | -0.4361828 | 1 | 0.998 | 8.62E-27 |
| Nexn | 6.68E-31 | 0.5046849 | 0.985 | 0.595 | 1.15E-26 |
| Myh6 | 7.67E-31 | 0.5958128 | 1 | 0.617 | 1.32E-26 |
| Rpl34 | 8.27E-31 | -0.52437 | 0.995 | 0.997 | 1.43E-26 |
| Rps9 | 1.11E-30 | -0.4415261 | 1 | 1 | 1.92E-26 |
| Fras1 | 1.11E-30 | 0.5470151 | 0.705 | 0.373 | 1.92E-26 |
| Unc5b | 1.56E-30 | 0.4932161 | 0.66 | 0.324 | 2.69E-26 |
| Pcp4l1 | 1.70E-30 | 0.4472797 | 0.65 | 0.294 | 2.94E-26 |
| Atp5l | 2.36E-30 | 0.4020454 | 1 | 0.99 | 4.07E-26 |
| Azin1 | 2.47E-30 | 0.5708274 | 0.765 | 0.466 | 4.26E-26 |
| Marcksl1 | 3.11E-30 | -0.9092608 | 0.44 | 0.759 | 5.37E-26 |
| Ppp1r14c | 3.51E-30 | 0.5172559 | 0.89 | 0.545 | 6.06E-26 |
| mt-Nd5 | 4.79E-30 | 0.4558497 | 0.995 | 0.891 | 8.26E-26 |
| Rpl22 | 5.57E-30 | -0.4744906 | 0.975 | 0.988 | 9.61E-26 |
| Spon1 | 1.16E-29 | 0.5233894 | 0.695 | 0.366 | 2.00E-25 |
| S100a10 | 1.35E-29 | -1.5965106 | 0.1 | 0.499 | 2.33E-25 |
| Ppp2r3a | 1.42E-29 | 0.4951703 | 0.845 | 0.533 | 2.44E-25 |
| Cox5b | 2.95E-29 | 0.4546289 | 1 | 0.949 | 5.09E-25 |
| Fry | 3.53E-29 | 0.5019208 | 0.66 | 0.341 | 6.10E-25 |
| Rpl6 | 3.72E-29 | -0.5055408 | 0.99 | 0.997 | 6.42E-25 |
| Mdk | 3.91E-29 | -1.1078479 | 0.495 | 0.776 | 6.75E-25 |
| Ndufa2 | 3.98E-29 | 0.3634994 | 0.995 | 0.972 | 6.86E-25 |
| Cdk4 | 5.33E-29 | -0.6530214 | 0.505 | 0.79 | 9.20E-25 |
| Tmsb10 | 5.43E-29 | -0.6117156 | 0.98 | 0.987 | 9.37E-25 |
| Rbp1 | 6.11E-29 | -1.6050392 | 0.105 | 0.494 | 1.05E-24 |
| Ank3 | 6.38E-29 | 0.4903755 | 0.735 | 0.397 | 1.10E-24 |
| Ptma | 7.47E-29 | -1.1385719 | 0.925 | 0.97 | 1.29E-24 |
| Rps6 | 8.51E-29 | -0.6564111 | 1 | 0.996 | 1.47E-24 |
| Rpl14 | 8.71E-29 | -0.4840244 | 0.995 | 0.999 | 1.50E-24 |
| Rps2 | 9.41E-29 | -0.4649503 | 0.99 | 0.993 | 1.63E-24 |
| Ppib | 9.52E-29 | -0.9828966 | 0.605 | 0.827 | 1.64E-24 |
| Rplp2 | 1.01E-28 | -0.4038252 | 1 | 1 | 1.74E-24 |
| Rpl17 | 1.17E-28 | -0.5612967 | 1 | 0.998 | 2.03E-24 |
| Myl6 | 1.22E-28 | -0.481622 | 0.93 | 0.987 | 2.10E-24 |
| Ndufc1 | 1.31E-28 | 0.4188309 | 1 | 0.91 | 2.27E-24 |
| Rrbp1 | 1.44E-28 | -0.7939808 | 0.405 | 0.723 | 2.49E-24 |
| Eif4a1 | 1.58E-28 | -0.6156759 | 0.75 | 0.901 | 2.72E-24 |
| Wbp5 | 1.73E-28 | -0.4851366 | 0.875 | 0.949 | 2.98E-24 |
| Pygm | 1.94E-28 | 0.4663478 | 0.69 | 0.358 | 3.35E-24 |
| Gnb2l1 | 1.97E-28 | -0.4851115 | 0.975 | 0.988 | 3.40E-24 |

Figure 23. continued

| | | | | | | |
|---|---|---|---|---|---|---|
| Rpl11 | 2.70E-28 | -0.4973886 | 1 | 0.999 | 4.66E-24 | Figure 23. |
| Gm8730 | 3.00E-28 | -0.6577553 | 0.815 | 0.94 | 5.18E-24 | continued |
| Lgals1 | 5.36E-28 | -1.4176915 | 0.805 | 0.909 | 9.26E-24 | |
| Klhl23 | 6.09E-28 | 0.4516765 | 0.655 | 0.334 | 1.05E-23 | |
| Rps13 | 7.09E-28 | -0.4213317 | 0.995 | 0.998 | 1.22E-23 | |
| Camta1 | 1.26E-27 | 0.4818235 | 0.82 | 0.59 | 2.18E-23 | |
| Rplp0 | 1.26E-27 | -0.5512346 | 0.995 | 0.998 | 2.18E-23 | |
| Cox7b | 1.44E-27 | 0.4414801 | 1 | 0.955 | 2.48E-23 | |
| Tbx5 | 1.50E-27 | 0.4935307 | 0.735 | 0.417 | 2.59E-23 | |
| Mfn2 | 1.58E-27 | 0.4330194 | 0.745 | 0.399 | 2.73E-23 | |
| Apoe | 1.74E-27 | -1.7772829 | 0.285 | 0.632 | 3.00E-23 | |
| Rpl19 | 1.76E-27 | -0.4375627 | 0.99 | 0.998 | 3.04E-23 | |
| Cox20 | 2.49E-27 | 0.5035664 | 0.9 | 0.693 | 4.29E-23 | |
| Ndufb9 | 2.90E-27 | 0.4608907 | 0.99 | 0.903 | 5.01E-23 | |
| Rpl28 | 3.41E-27 | -0.4620797 | 1 | 0.999 | 5.88E-23 | |
| Lmo7 | 4.51E-27 | 0.4658257 | 0.86 | 0.523 | 7.79E-23 | |
| Rps21 | 4.99E-27 | -0.4024322 | 1 | 0.997 | 8.61E-23 | |
| Ranbp1 | 1.04E-26 | -0.5989428 | 0.63 | 0.845 | 1.80E-22 | |
| Rpl36a | 1.11E-26 | -0.4859676 | 1 | 0.997 | 1.91E-22 | |
| Ostc | 1.37E-26 | -0.5964774 | 0.51 | 0.782 | 2.37E-22 | |
| Myl9 | 1.50E-26 | 0.530498 | 1 | 0.791 | 2.59E-22 | |
| Rbpms | 1.70E-26 | 0.5331467 | 0.94 | 0.745 | 2.94E-22 | |
| Rpl18 | 2.20E-26 | -0.4414863 | 0.995 | 0.997 | 3.79E-22 | |
| Fbn2 | 2.38E-26 | 0.4723575 | 0.85 | 0.608 | 4.11E-22 | |
| Fn1 | 2.69E-26 | -1.4073765 | 0.13 | 0.491 | 4.65E-22 | |
| Rps25 | 3.10E-26 | -0.3838882 | 1 | 0.997 | 5.35E-22 | |
| Ndufa5 | 4.06E-26 | 0.4480139 | 0.97 | 0.869 | 7.01E-22 | |
| Tagln2 | 4.34E-26 | -1.3373135 | 0.115 | 0.476 | 7.49E-22 | |
| Uqcr10 | 4.70E-26 | 0.4135439 | 0.995 | 0.953 | 8.11E-22 | |
| Aco2 | 5.16E-26 | 0.4416888 | 0.94 | 0.703 | 8.91E-22 | |
| Tpm4 | 5.28E-26 | -0.9278932 | 0.16 | 0.527 | 9.11E-22 | |
| Klhdc8b | 5.57E-26 | 0.4227544 | 0.625 | 0.322 | 9.62E-22 | |
| Efnb2 | 8.09E-26 | 0.3160209 | 0.35 | 0.11 | 1.40E-21 | |
| Chsy1 | 9.02E-26 | 0.4674052 | 0.575 | 0.287 | 1.56E-21 | |
| Adamts1 | 9.02E-26 | 0.5314553 | 0.625 | 0.315 | 1.56E-21 | |
| Slco3a1 | 9.38E-26 | 0.4103286 | 0.415 | 0.156 | 1.62E-21 | |
| Dusp27 | 9.42E-26 | 0.3378897 | 0.43 | 0.16 | 1.63E-21 | |
| Fabp3 | 1.03E-25 | 0.6061329 | 0.87 | 0.546 | 1.79E-21 | |
| Rps23 | 1.19E-25 | -0.505261 | 1 | 0.999 | 2.06E-21 | |
| Atp5g1 | 1.46E-25 | 0.4508151 | 1 | 0.953 | 2.52E-21 | |
| 15-Sep | 1.66E-25 | -0.5420712 | 0.65 | 0.847 | 2.87E-21 | |
| Camk2a | 1.88E-25 | 0.2765877 | 0.325 | 0.1 | 3.24E-21 | |
| Mif | 2.03E-25 | -0.5928031 | 0.92 | 0.965 | 3.51E-21 | |
| Ifitm2 | 2.21E-25 | -0.8277308 | 0.54 | 0.769 | 3.82E-21 | |
| Csrp3 | 3.08E-25 | 0.5867253 | 1 | 0.692 | 5.31E-21 | |

Figure 24.

| Gene | p value | Average log Fold Change | Average value cSAN | Average value Tz | Adjusted p value |
|------|---------|-------------------------|--------------------|--------------------|------------------|
| Smoc2 | 9.10E-23 | 1.2702341 | 0.954 | 0.341 | 1.57E-18 |
| Dkk3 | 4.45E-21 | -0.9445005 | 0.156 | 0.835 | 7.69E-17 |
| Tmsb4x | 2.11E-20 | 0.7929387 | 1 | 1 | 3.65E-16 |
| Smpx | 1.46E-18 | -1.0835793 | 0.716 | 0.978 | 2.52E-14 |
| Nkx2-5 | 1.48E-18 | -0.941359 | 0.239 | 0.824 | 2.56E-14 |
| Slc22a1 | 1.89E-18 | -1.6171893 | 0.202 | 0.791 | 3.27E-14 |
| Cited1 | 1.24E-17 | 1.1718603 | 0.78 | 0.231 | 2.13E-13 |
| Furin | 1.72E-17 | 0.9561301 | 0.826 | 0.319 | 2.97E-13 |
| Vsnl1 | 6.63E-17 | 0.8063162 | 0.982 | 0.758 | 1.14E-12 |
| Sh2d4a | 1.21E-15 | 0.6989496 | 0.55 | 0.011 | 2.08E-11 |
| Scn5a | 9.46E-15 | -0.722719 | 0.028 | 0.495 | 1.63E-10 |
| Arhgap31 | 1.94E-14 | -0.7926913 | 0.661 | 0.923 | 3.34E-10 |
| Hspb7 | 4.64E-14 | -0.7196078 | 0.972 | 0.978 | 8.01E-10 |
| Pde1a | 1.27E-13 | 0.6608881 | 0.523 | 0.033 | 2.19E-09 |
| Tbx18 | 2.19E-13 | 0.8221544 | 0.578 | 0.077 | 3.78E-09 |
| Epha4 | 3.05E-13 | -0.8530493 | 0.394 | 0.835 | 5.26E-09 |
| Aspscr1 | 5.69E-13 | 0.7675492 | 0.89 | 0.484 | 9.82E-09 |
| Bmp4 | 6.70E-13 | 0.7915019 | 0.523 | 0.055 | 1.16E-08 |
| Ryr2 | 2.55E-12 | -0.6305063 | 0.844 | 0.945 | 4.41E-08 |
| Tenm4 | 3.88E-12 | 0.6412648 | 0.651 | 0.165 | 6.70E-08 |
| Pvalb | 5.58E-12 | -1.3064089 | 0.028 | 0.418 | 9.62E-08 |
| Pln | 1.14E-11 | 0.8360227 | 0.972 | 0.747 | 1.97E-07 |
| Atp2a2 | 1.37E-11 | 0.4590049 | 1 | 1 | 2.36E-07 |
| Mfsd6 | 2.05E-11 | 0.6141172 | 0.532 | 0.088 | 3.54E-07 |
| Tnnt2 | 2.19E-11 | 0.5029115 | 1 | 1 | 3.78E-07 |
| Pam | 3.23E-11 | -0.7359268 | 0.89 | 0.956 | 5.58E-07 |
| Wisp1 | 4.89E-11 | -0.6541323 | 0.45 | 0.802 | 8.45E-07 |
| Tbx3 | 5.77E-11 | 0.6888049 | 0.679 | 0.231 | 9.96E-07 |
| Acta2 | 8.44E-11 | 1.2887068 | 0.789 | 0.44 | 1.46E-06 |
| Cox6a1 | 1.03E-10 | 0.4833699 | 0.982 | 0.967 | 1.78E-06 |
| Gja5 | 1.42E-10 | -0.7578481 | 0.064 | 0.451 | 2.46E-06 |
| Camk1d | 1.56E-10 | -0.6226252 | 0.055 | 0.429 | 2.70E-06 |
| Murc | 2.00E-10 | -0.5093891 | 0.018 | 0.363 | 3.45E-06 |
| Cox8a | 3.32E-10 | 0.3078921 | 1 | 1 | 5.73E-06 |
| Obscn | 1.18E-09 | -0.542549 | 0.817 | 0.945 | 2.04E-05 |
| Thbs4 | 1.29E-09 | -0.4784863 | 0.018 | 0.341 | 2.22E-05 |
| Lbh | 1.96E-09 | 0.8695399 | 0.817 | 0.604 | 3.39E-05 |
| Gpx3 | 2.12E-09 | 0.6096092 | 1 | 0.967 | 3.65E-05 |
| Kdr | 2.22E-09 | -0.6286521 | 0.037 | 0.363 | 3.83E-05 |
| Recl14 | 2.45E-09 | 0.5896212 | 0.596 | 0.176 | 4.24E-05 |

Online Table III: Differentially Expressed Genes in cSAN versus Transitional Subclusters within Cluster 9 of Zone I.

| | | | | | | |
|---|---|---|---|---|---|---|
| Tmem163 | 2.48E-09 | -0.4194326 | 0.037 | 0.363 | 4.28E-05 | Figure 24. |
| Adm | 2.64E-09 | -0.7303558 | 0.11 | 0.462 | 4.56E-05 | continued |
| Adam33 | 6.82E-09 | 0.5644022 | 0.67 | 0.264 | 1.18E-04 | |
| Sspn | 1.04E-08 | -0.5199126 | 0.688 | 0.879 | 1.79E-04 | |
| Hcn4 | 1.06E-08 | 0.5719565 | 0.578 | 0.198 | 1.82E-04 | |
| Slitrk5 | 1.37E-08 | -0.4852517 | 0.018 | 0.308 | 2.36E-04 | |
| Cdkn1a | 1.40E-08 | -0.5119402 | 0.138 | 0.484 | 2.41E-04 | |
| Nrk | 1.69E-08 | 0.7800582 | 0.606 | 0.264 | 2.91E-04 | |
| Gsta4 | 1.86E-08 | 0.5514922 | 0.523 | 0.154 | 3.21E-04 | |
| Cox6b1 | 2.10E-08 | 0.302742 | 1 | 1 | 3.63E-04 | |
| 2610204G07Rik | 2.41E-08 | -0.3748703 | 0.009 | 0.275 | 4.17E-04 | |
| Aldh1b1 | 2.62E-08 | -0.498102 | 0.202 | 0.571 | 4.52E-04 | |
| Egln3 | 2.64E-08 | 0.4173723 | 0.587 | 0.165 | 4.56E-04 | |
| Fitm1 | 3.59E-08 | 0.4787359 | 0.817 | 0.505 | 6.20E-04 | |
| Nebl | 3.62E-08 | -0.6553419 | 0.624 | 0.769 | 6.26E-04 | |
| Pcdh17 | 4.31E-08 | 0.7594191 | 0.495 | 0.143 | 7.43E-04 | |
| Zfp579 | 4.50E-08 | -0.4351514 | 0.073 | 0.385 | 7.77E-04 | |
| Ndufc1 | 4.54E-08 | 0.296284 | 1 | 1 | 7.84E-04 | |
| Slc17a7 | 5.35E-08 | -0.3799678 | 0.018 | 0.286 | 9.24E-04 | |
| Ramp1 | 5.53E-08 | 0.6172185 | 0.899 | 0.626 | 9.55E-04 | |
| Cdh2 | 6.15E-08 | -0.4779358 | 0.495 | 0.769 | 1.06E-03 | |
| Uchl1 | 7.55E-08 | 0.6326587 | 0.688 | 0.341 | 1.30E-03 | |
| Tubb2a | 8.90E-08 | 0.392342 | 0.376 | 0.055 | 1.54E-03 | |
| Mdk | 9.38E-08 | 0.566093 | 0.642 | 0.319 | 1.62E-03 | |
| Actn2 | 1.13E-07 | -0.4728491 | 0.826 | 0.934 | 1.95E-03 | |
| Hcn1 | 1.33E-07 | 0.381375 | 0.385 | 0.055 | 2.29E-03 | |
| Zyx | 1.54E-07 | 0.42054 | 0.881 | 0.527 | 2.66E-03 | |
| Thbd | 1.74E-07 | 0.6346547 | 0.349 | 0.044 | 3.00E-03 | |
| Ttn | 2.45E-07 | -0.3253016 | 1 | 1 | 4.22E-03 | |
| Pcdh7 | 2.50E-07 | -0.4644992 | 0.156 | 0.473 | 4.32E-03 | |
| Cpne5 | 3.12E-07 | -0.5661463 | 0.339 | 0.615 | 5.39E-03 | |
| Gipr | 3.14E-07 | -0.3774564 | 0.064 | 0.352 | 5.41E-03 | |
| Trim11 | 3.54E-07 | -0.5162972 | 0.211 | 0.505 | 6.11E-03 | |
| Hs6st2 | 3.62E-07 | 0.3831832 | 0.541 | 0.176 | 6.25E-03 | |
| Id2 | 4.06E-07 | -1.0309643 | 0.468 | 0.67 | 7.02E-03 | |
| Fhl2 | 4.35E-07 | -0.6393803 | 0.477 | 0.692 | 7.51E-03 | |
| Rpl32 | 4.98E-07 | -0.3181376 | 1 | 1 | 8.61E-03 | |
| Uqcr11 | 5.59E-07 | 0.2597402 | 1 | 1 | 9.65E-03 | |
| 1300080G10Rik | 5.93E-07 | -0.5506099 | 0.239 | 0.56 | 1.02E-02 | |
| Amotl1 | 6.24E-07 | -0.5104833 | 0.459 | 0.692 | 1.08E-02 | |
| Col1a2 | 7.30E-07 | 0.4541268 | 0.606 | 0.297 | 1.26E-02 | |
| Ppp1r14c | 7.64E-07 | 0.3814031 | 0.963 | 0.802 | 1.32E-02 | |
| Calca | 8.31E-07 | -0.6047494 | 0.064 | 0.341 | 1.43E-02 | |
| Gdel | 8.68E-07 | 0.3969567 | 0.881 | 0.593 | 1.50E-02 | |
| Xist | 9.02E-07 | -1.1715588 | 0.037 | 0.275 | 1.56E-02 | |

| | | | | | | |
|---|---|---|---|---|---|---|
| Kank3 | 1.02E-06 | 0.3431447 | 0.394 | 0.088 | 1.75E-02 | Figure 24. |
| Shisa2 | 1.02E-06 | -0.457706 | 0.128 | 0.418 | 1.76E-02 | continued |
| Cacna1g | 1.10E-06 | 0.3902864 | 0.394 | 0.088 | 1.90E-02 | |
| Mt3 | 1.15E-06 | 0.4162818 | 0.642 | 0.297 | 1.99E-02 | |
| Xirp2 | 1.16E-06 | -0.3884712 | 0.028 | 0.264 | 2.01E-02 | |
| Arl5a | 1.25E-06 | -0.4260652 | 0.394 | 0.681 | 2.16E-02 | |
| Dpy19l1 | 1.40E-06 | 0.3371649 | 0.394 | 0.088 | 2.42E-02 | |
| Vash2 | 1.65E-06 | -0.4484544 | 0.239 | 0.527 | 2.85E-02 | |
| Lnx1 | 1.69E-06 | 0.2949138 | 0.275 | 0.022 | 2.91E-02 | |
| Azin1 | 1.88E-06 | 0.433839 | 0.862 | 0.648 | 3.24E-02 | |
| Nr2f2 | 1.89E-06 | -0.4032374 | 0.367 | 0.681 | 3.26E-02 | |
| Eif3h | 1.99E-06 | -0.8870246 | 0.963 | 0.945 | 3.43E-02 | |
| Isl1 | 2.07E-06 | 0.3685163 | 0.413 | 0.11 | 3.58E-02 | |
| Stox2 | 2.36E-06 | -0.3040244 | 0.083 | 0.352 | 4.08E-02 | |
| Inpp4a | 2.58E-06 | 0.32699 | 0.339 | 0.066 | 4.45E-02 | |
| Sparc | 2.80E-06 | 0.3500881 | 0.991 | 0.967 | 4.84E-02 | |
| Alpk2 | 2.80E-06 | -0.4295858 | 0.239 | 0.549 | 4.84E-02 | |

Figure 25.

| Gene | p value | Average log Fold Change | Average value Head | Average value Tail | Adjusted p value |
|---|---|---|---|---|---|
| Smoc2 | 3.99E-23 | 2.0210488 | 1 | 0.097 | 6.89E-19 |
| Smpx | 4.01E-16 | -1.4461303 | 0.708 | 0.984 | 6.93E-12 |
| Vsnl1 | 8.50E-16 | 1.0844099 | 0.985 | 0.726 | 1.47E-11 |
| Tmsb4x | 3.57E-15 | 0.7305554 | 1 | 1 | 6.17E-11 |
| Igfbp5 | 6.56E-15 | 1.4065294 | 1 | 0.597 | 1.13E-10 |
| Lbh | 2.08E-14 | 1.4512027 | 0.877 | 0.403 | 3.60E-10 |
| Furin | 2.09E-14 | 1.0520747 | 0.892 | 0.371 | 3.60E-10 |
| Aspscr1 | 7.45E-14 | 0.9569721 | 0.954 | 0.452 | 1.29E-09 |
| Slc22a1 | 6.26E-13 | -1.3823951 | 0.185 | 0.823 | 1.08E-08 |
| Shox2 | 9.77E-13 | 0.9185817 | 0.985 | 0.452 | 1.69E-08 |
| Gja1 | 1.16E-12 | -1.0369533 | 0.062 | 0.677 | 2.01E-08 |
| Aldh1b1 | 1.56E-12 | -0.856844 | 0.169 | 0.774 | 2.69E-08 |
| Pln | 6.19E-12 | 1.0805279 | 1 | 0.774 | 1.07E-07 |
| Hspb7 | 9.90E-12 | -0.7522063 | 0.954 | 1 | 1.71E-07 |
| Nkx2-5 | 1.04E-11 | -0.8466996 | 0.185 | 0.774 | 1.79E-07 |
| Myl4 | 2.96E-11 | -0.4831099 | 1 | 1 | 5.10E-07 |
| Tenm4 | 4.57E-11 | 0.7183494 | 0.708 | 0.097 | 7.88E-07 |
| Tbx3 | 1.21E-10 | 0.8838392 | 0.708 | 0.177 | 2.09E-06 |
| Gja5 | 1.47E-10 | -0.8774501 | 0.062 | 0.581 | 2.54E-06 |
| Nppa | 1.48E-10 | -3.6080284 | 0.815 | 0.968 | 2.56E-06 |
| Pam | 1.56E-10 | -1.6212711 | 0.877 | 0.968 | 2.69E-06 |
| Fgf12 | 1.61E-10 | -0.8167953 | 0.154 | 0.677 | 2.77E-06 |
| Fbxo32 | 1.76E-10 | 0.6187558 | 0.892 | 0.452 | 3.04E-06 |
| Meg3 | 1.97E-10 | 1.0444162 | 0.831 | 0.323 | 3.41E-06 |
| Fhl2 | 2.63E-10 | -0.8914635 | 0.492 | 0.839 | 4.54E-06 |
| Pde1a | 3.94E-10 | 0.7433082 | 0.569 | 0.048 | 6.81E-06 |
| Camk1d | 4.94E-10 | -0.6685789 | 0.046 | 0.532 | 8.53E-06 |
| Sh2d4a | 5.84E-10 | 0.6570215 | 0.615 | 0.081 | 1.01E-05 |
| Pcdh7 | 1.01E-09 | -0.7544212 | 0.154 | 0.645 | 1.74E-05 |
| Bmp4 | 1.24E-09 | 0.9236329 | 0.615 | 0.129 | 2.14E-05 |
| Tbx20 | 2.46E-09 | -0.9250756 | 0.585 | 0.871 | 4.25E-05 |
| Bmp2 | 3.03E-09 | 1.2595518 | 0.708 | 0.242 | 5.22E-05 |
| Dkk3 | 3.35E-09 | -0.6753413 | 0.169 | 0.694 | 5.79E-05 |
| Nrk | 4.52E-09 | 0.9683507 | 0.662 | 0.194 | 7.80E-05 |
| Zdhhc2 | 4.75E-09 | 0.7414815 | 0.785 | 0.355 | 8.20E-05 |
| Ckm | 6.45E-09 | -1.0962088 | 0.769 | 0.935 | 1.11E-04 |
| Pcdh17 | 9.87E-09 | 0.8448644 | 0.554 | 0.081 | 1.70E-04 |
| Epha4 | 1.85E-08 | -0.8385607 | 0.415 | 0.855 | 3.19E-04 |
| Snap91 | 2.69E-08 | 0.7286084 | 0.908 | 0.597 | 4.64E-04 |
| Egln3 | 2.87E-08 | 0.498703 | 0.662 | 0.177 | 4.96E-04 |

Online Table IV: Differentially Expressed Genes in SA nodal "Head" versus "Tail" Subclusters of Hcn4+ Cardiomyocytes of Zone I.

| | | | | | |
|---|---|---|---|---|---|
| Hspa1a | 4.07E-08 | 0.9801878 | 0.723 | 0.258 | 7.03E-04 |
| Mest | 4.71E-08 | -1.2787494 | 0.4 | 0.742 | 8.13E-04 |
| Tmem163 | 5.58E-08 | -0.5207137 | 0.031 | 0.435 | 9.63E-04 |
| Zyx | 7.07E-08 | 0.555396 | 0.862 | 0.548 | 1.22E-03 |
| Nptn | 7.69E-08 | 0.5595338 | 0.969 | 0.645 | 1.33E-03 |
| Fitm1 | 1.06E-07 | 0.6452094 | 0.862 | 0.5 | 1.82E-03 |
| Idh2 | 1.17E-07 | -0.5786791 | 0.923 | 0.968 | 2.01E-03 |
| Nfia | 1.19E-07 | 0.6590945 | 0.938 | 0.79 | 2.06E-03 |
| Gata6 | 1.31E-07 | 0.4700119 | 0.985 | 0.855 | 2.26E-03 |
| Hs6st2 | 1.70E-07 | 0.5010007 | 0.677 | 0.226 | 2.94E-03 |
| Tbx18 | 1.94E-07 | 0.7049733 | 0.646 | 0.21 | 3.34E-03 |
| Mfsd6 | 2.03E-07 | 0.5879635 | 0.492 | 0.097 | 3.51E-03 |
| Id3 | 2.21E-07 | 0.6761465 | 0.677 | 0.274 | 3.81E-03 |
| Nppb | 2.39E-07 | -1.6227745 | 0.108 | 0.5 | 4.12E-03 |
| Hcn4 | 2.49E-07 | 0.3663406 | 1 | 1 | 4.30E-03 |
| Adam33 | 3.24E-07 | 0.5542818 | 0.723 | 0.274 | 5.59E-03 |
| Gde1 | 3.35E-07 | 0.5205572 | 0.892 | 0.629 | 5.78E-03 |
| Obscn | 3.85E-07 | -0.5243878 | 0.769 | 0.952 | 6.64E-03 |
| Atp1b1 | 3.90E-07 | 0.4723052 | 0.985 | 0.984 | 6.73E-03 |
| Cav1 | 4.19E-07 | 0.5090996 | 0.985 | 0.903 | 7.24E-03 |
| Atp2a2 | 4.37E-07 | 0.3832822 | 1 | 0.968 | 7.54E-03 |
| Perp | 4.67E-07 | -0.8668969 | 0.431 | 0.71 | 8.06E-03 |
| Bmp7 | 5.16E-07 | 0.6191281 | 0.754 | 0.419 | 8.91E-03 |
| Uchl1 | 5.33E-07 | 0.6253868 | 0.754 | 0.371 | 9.19E-03 |
| Angpt1 | 6.01E-07 | -0.8780265 | 0.031 | 0.387 | 1.04E-02 |
| Jag1 | 7.77E-07 | -0.363514 | 0 | 0.323 | 1.34E-02 |
| Ryr3 | 8.48E-07 | -0.3937169 | 0.015 | 0.355 | 1.46E-02 |
| Lclat1 | 8.57E-07 | 0.5234249 | 0.615 | 0.21 | 1.48E-02 |
| Marcks | 9.54E-07 | 0.6033005 | 0.769 | 0.452 | 1.65E-02 |
| Flrt3 | 9.65E-07 | 0.4526881 | 0.477 | 0.081 | 1.67E-02 |
| Cacna1g | 9.84E-07 | 0.4528278 | 0.446 | 0.065 | 1.70E-02 |
| Ntm | 1.06E-06 | 0.5630099 | 0.754 | 0.355 | 1.83E-02 |
| Eid1 | 1.38E-06 | 0.549116 | 0.938 | 0.774 | 2.39E-02 |
| Spats2l | 1.39E-06 | 0.6839366 | 0.738 | 0.484 | 2.40E-02 |
| Thbd | 1.67E-06 | 0.7437631 | 0.385 | 0.032 | 2.88E-02 |
| Cacna2d2 | 1.93E-06 | 0.4506011 | 0.938 | 0.516 | 3.33E-02 |
| Isl1 | 1.97E-06 | 0.4246025 | 0.4 | 0.048 | 3.41E-02 |
| Thbs4 | 2.20E-06 | -0.4588322 | 0.031 | 0.355 | 3.79E-02 |
| Mif | 2.38E-06 | -0.6851869 | 0.892 | 0.952 | 4.11E-02 |
| Gnao1 | 2.41E-06 | 0.4692505 | 0.892 | 0.613 | 4.17E-02 |
| Lnx1 | 2.44E-06 | 0.3661533 | 0.308 | 0 | 4.22E-02 |
| Fam69c | 2.44E-06 | 0.3141518 | 0.308 | 0 | 4.22E-02 |
| Foxp1 | 2.59E-06 | 0.4508698 | 0.723 | 0.339 | 4.47E-02 |
| Chsy1 | 2.84E-06 | 0.5645569 | 0.692 | 0.323 | 4.91E-02 |
| Cdh2 | 2.87E-06 | -0.4367481 | 0.492 | 0.887 | 4.96E-02 |

| Gene | p value | Average log Fold Change | Average value Cluster 4 | Average value Other Clusters | Adjusted p value |
|---|---|---|---|---|---|
| Slc22a1 | 2.22E-308 | 1.717583 | 0.534 | 0.036 | 2.22E-308 |
| Cacna2d2 | 2.22E-308 | 0.8803632 | 0.424 | 0.006 | 2.22E-308 |
| Cpne5 | 2.22E-308 | 0.7281356 | 0.429 | 0.014 | 2.22E-308 |
| Myl1 | 7.49E-233 | 1.0020598 | 0.469 | 0.04 | 1.26E-228 |
| Mybphl | 2.61E-214 | 0.5619241 | 0.267 | 0.008 | 4.40E-210 |
| Sln | 6.27E-170 | 2.7591749 | 0.432 | 0.053 | 1.06E-165 |
| Rgs6 | 5.78E-157 | 0.390851 | 0.437 | 0.054 | 9.75E-153 |
| Atp1b1 | 1.68E-149 | 1.2873591 | 0.997 | 0.618 | 2.83E-145 |
| Stard10 | 4.68E-144 | 0.5374945 | 0.398 | 0.051 | 7.89E-140 |
| Myl7 | 6.15E-142 | 3.5171953 | 0.945 | 0.512 | 1.04E-137 |
| Myl4 | 1.21E-139 | 1.8079154 | 0.987 | 0.632 | 2.04E-135 |
| Csrp3 | 2.48E-136 | 1.2306797 | 1 | 0.617 | 4.18E-132 |
| Tpm1 | 1.43E-131 | 1.0145874 | 1 | 0.934 | 2.41E-127 |
| Ramp1 | 4.27E-130 | 1.0187293 | 0.88 | 0.333 | 7.20E-126 |
| Myh6 | 5.34E-128 | 1.713184 | 0.935 | 0.415 | 9.01E-124 |
| Gpx3 | 6.09E-128 | 1.5083443 | 0.966 | 0.569 | 1.03E-123 |
| Casq1 | 7.11E-127 | 1.1581711 | 0.717 | 0.22 | 1.20E-122 |
| Igfbp5 | 8.86E-125 | 1.1872976 | 0.649 | 0.171 | 1.49E-120 |
| Atp1a1 | 4.05E-124 | 1.0011281 | 0.979 | 0.616 | 6.83E-120 |
| Cnn1 | 5.99E-119 | 0.8751006 | 0.715 | 0.22 | 1.01E-114 |
| P23-455C13 | 3.43E-118 | 0.8214517 | 0.919 | 0.377 | 5.78E-114 |
| Pirt | 6.95E-116 | 0.2988842 | 0.291 | 0.031 | 1.17E-111 |
| Recl14 | 2.67E-115 | 0.2841933 | 0.277 | 0.028 | 4.50E-111 |
| Tbx5 | 1.23E-114 | 0.5441783 | 0.474 | 0.093 | 2.07E-110 |
| Perp | 4.01E-114 | 0.8737594 | 0.901 | 0.393 | 6.77E-110 |
| Fam78a | 6.12E-113 | 0.4641781 | 0.508 | 0.109 | 1.03E-108 |
| Myl9 | 1.21E-112 | 1.1040838 | 0.992 | 0.719 | 2.05E-108 |
| Tcap | 3.40E-112 | 1.0007091 | 0.924 | 0.419 | 5.73E-108 |
| Des | 7.53E-111 | 0.8854541 | 0.992 | 0.55 | 1.27E-106 |
| Gnao1 | 7.01E-109 | 0.3970358 | 0.393 | 0.064 | 1.18E-104 |
| Cryab | 7.38E-107 | 0.8130457 | 1 | 0.693 | 1.24E-102 |
| Kcnj5 | 2.57E-106 | 0.4200146 | 0.432 | 0.081 | 4.33E-102 |
| Ntm | 7.15E-106 | 0.5547082 | 0.466 | 0.097 | 1.20E-101 |
| Hspb7 | 2.08E-104 | 0.8239858 | 0.997 | 0.601 | 3.50E-100 |
| Adamtsl2 | 2.14E-104 | 0.2539012 | 0.306 | 0.038 | 3.61E-100 |
| Eef1a2 | 1.71E-102 | 0.6391691 | 0.864 | 0.355 | 2.89E-98 |
| Nkx2-5 | 2.05E-102 | 0.6666748 | 0.911 | 0.389 | 3.46E-98 |
| Casq2 | 9.63E-102 | 0.8351158 | 0.961 | 0.46 | 1.62E-97 |
| Trdn | 1.45E-101 | 0.7132955 | 0.948 | 0.427 | 2.44E-97 |
| Ankrd1 | 1.50E-101 | 1.2838897 | 0.906 | 0.449 | 2.53E-97 |
| Cacna1g | 5.68E-100 | 0.3851945 | 0.421 | 0.08 | 9.57E-96 |

Online Table V: Differentially Expressed Genes in Cluster 4 of Zone II.

| | | | | | |
|---|---|---|---|---|---|
| Actc1 | 1.35E-99 | 0.9450009 | 1 | 0.822 | 2.28E-95 |
| Pgam2 | 3.78E-99 | 0.8768539 | 0.995 | 0.527 | 6.37E-95 |
| Serpinb6b | 4.45E-99 | 0.4865127 | 0.584 | 0.154 | 7.50E-95 |
| Adprhl1 | 9.12E-98 | 0.7343854 | 0.895 | 0.408 | 1.54E-93 |
| Smyd1 | 5.76E-97 | 0.5712566 | 0.872 | 0.359 | 9.70E-93 |
| Clu | 5.32E-96 | 0.9069356 | 0.707 | 0.249 | 8.96E-92 |
| Fras1 | 1.70E-94 | 0.3530212 | 0.369 | 0.065 | 2.87E-90 |
| Mlip | 6.87E-94 | 0.6361488 | 0.887 | 0.381 | 1.16E-89 |
| Parm1 | 2.40E-93 | 0.508829 | 0.694 | 0.229 | 4.05E-89 |
| Aspscr1 | 1.45E-92 | 0.8382208 | 0.762 | 0.314 | 2.45E-88 |
| Wisp1 | 8.99E-89 | 0.5131696 | 0.618 | 0.189 | 1.51E-84 |
| Tnnc1 | 1.86E-87 | 0.8102697 | 1 | 0.738 | 3.13E-83 |
| Tom1l1 | 3.66E-86 | 0.330663 | 0.411 | 0.087 | 6.18E-82 |
| Epha4 | 6.05E-86 | 0.4528144 | 0.435 | 0.1 | 1.02E-81 |
| Sorbs2 | 7.88E-86 | 0.722372 | 0.984 | 0.543 | 1.33E-81 |
| Rbpms | 2.51E-85 | 0.6566869 | 0.979 | 0.66 | 4.23E-81 |
| Hspb2 | 1.55E-83 | 0.5886721 | 0.924 | 0.458 | 2.61E-79 |
| Sh3bgr | 2.36E-83 | 0.6777172 | 0.984 | 0.514 | 3.98E-79 |
| Hspb1 | 3.17E-83 | 0.7606519 | 0.984 | 0.674 | 5.35E-79 |
| Synpo2l | 9.54E-83 | 0.5750529 | 0.895 | 0.418 | 1.61E-78 |
| Fxyd1 | 1.14E-82 | 0.6419029 | 1 | 0.737 | 1.92E-78 |
| Tmod1 | 2.30E-82 | 0.5875172 | 0.95 | 0.475 | 3.88E-78 |
| Rrad | 3.35E-82 | 0.6632153 | 0.906 | 0.451 | 5.64E-78 |
| Rxfp1 | 2.87E-81 | 0.3784357 | 0.372 | 0.076 | 4.84E-77 |
| Hspb3 | 1.18E-80 | 0.3565626 | 0.531 | 0.149 | 2.00E-76 |
| Hist3h2ba | 1.92E-80 | 0.3008039 | 0.296 | 0.048 | 3.24E-76 |
| Adora1 | 4.29E-80 | 0.2762405 | 0.34 | 0.064 | 7.23E-76 |
| Kcne1 | 2.13E-79 | 0.9821127 | 0.762 | 0.35 | 3.59E-75 |
| Fitm1 | 3.29E-78 | 0.5997174 | 0.767 | 0.312 | 5.54E-74 |
| Ldb3 | 8.45E-78 | 0.5941579 | 0.982 | 0.499 | 1.42E-73 |
| Col4a5 | 3.09E-77 | 0.4045018 | 0.644 | 0.215 | 5.21E-73 |
| Pygm | 7.09E-76 | 0.4772138 | 0.832 | 0.349 | 1.20E-71 |
| Tmem51 | 5.09E-75 | 0.3666991 | 0.508 | 0.146 | 8.58E-71 |
| Apobec2 | 7.40E-75 | 0.5636228 | 0.916 | 0.439 | 1.25E-70 |
| Alpk2 | 2.47E-74 | 0.3973565 | 0.579 | 0.187 | 4.17E-70 |
| Chrm2 | 2.98E-74 | 0.3183513 | 0.497 | 0.136 | 5.02E-70 |
| Nrtn | 4.44E-74 | 0.478254 | 0.599 | 0.204 | 7.48E-70 |
| Ank1 | 6.35E-74 | 0.450655 | 0.429 | 0.111 | 1.07E-69 |
| Gpc1 | 4.83E-73 | 0.4195219 | 0.599 | 0.201 | 8.14E-69 |
| Fbxo32 | 1.01E-72 | 0.3813748 | 0.492 | 0.138 | 1.70E-68 |
| Nav2 | 1.20E-72 | 0.459084 | 0.728 | 0.301 | 2.03E-68 |
| Clip4 | 3.32E-72 | 0.3527554 | 0.552 | 0.17 | 5.60E-68 |
| Cap2 | 5.80E-72 | 0.4379385 | 0.835 | 0.36 | 9.78E-68 |
| Actn2 | 1.09E-71 | 0.6302471 | 0.966 | 0.501 | 1.84E-67 |
| Bcam | 1.41E-71 | 0.4940838 | 0.916 | 0.448 | 2.38E-67 |

Figure 26. continued

| | | | | | |
|---|---|---|---|---|---|
| Lmod2 | 2.13E-71 | 0.44638 | 0.66 | 0.237 | 3.59E-67 |
| Bex4 | 4.92E-69 | 0.6656097 | 0.887 | 0.483 | 8.29E-65 |
| Trim63 | 1.32E-68 | 0.4660741 | 0.859 | 0.385 | 2.22E-64 |
| Tnnt1 | 2.40E-68 | 1.1956817 | 0.704 | 0.295 | 4.04E-64 |
| Ndufa11 | 2.47E-68 | 0.5197993 | 0.997 | 0.88 | 4.16E-64 |
| Rnf207 | 1.60E-66 | 0.3684651 | 0.675 | 0.248 | 2.69E-62 |
| Rps8 | 8.51E-66 | -0.4618739 | 1 | 1 | 1.43E-61 |
| Gpi1 | 1.41E-65 | 0.4957534 | 0.979 | 0.74 | 2.37E-61 |
| Rbm24 | 1.90E-65 | 0.4573813 | 0.877 | 0.408 | 3.20E-61 |
| Zbtb20 | 6.96E-65 | 0.6005708 | 0.921 | 0.594 | 1.17E-60 |
| Myom1 | 1.02E-64 | 0.4445716 | 0.877 | 0.401 | 1.72E-60 |
| Slitrk5 | 1.28E-64 | 0.2730861 | 0.277 | 0.053 | 2.16E-60 |
| Asb2 | 1.72E-64 | 0.4782099 | 0.853 | 0.395 | 2.91E-60 |
| Myoz2 | 6.56E-64 | 0.5633839 | 0.932 | 0.472 | 1.10E-59 |
| Tnni3 | 2.10E-63 | 0.6864531 | 0.995 | 0.658 | 3.53E-59 |
| Pfkp | 4.14E-63 | 0.4297134 | 0.738 | 0.321 | 6.97E-59 |
| Rpl18a | 1.53E-62 | -0.4707537 | 1 | 0.999 | 2.58E-58 |
| Rpl32 | 2.03E-62 | -0.431278 | 1 | 1 | 3.42E-58 |
| Trp53inp2 | 2.62E-62 | 0.4203955 | 0.762 | 0.352 | 4.41E-58 |
| Eno3 | 7.72E-62 | 0.5224304 | 0.969 | 0.499 | 1.30E-57 |
| Ppp1r1a | 8.44E-62 | 0.41571 | 0.715 | 0.297 | 1.42E-57 |
| Rpl28 | 1.40E-61 | -0.4242848 | 1 | 0.999 | 2.36E-57 |
| Bmp2 | 2.09E-61 | 0.5543899 | 0.319 | 0.071 | 3.53E-57 |
| Rps19 | 7.33E-61 | -0.6096073 | 1 | 0.999 | 1.23E-56 |
| Rgs12 | 5.61E-60 | 0.3656596 | 0.476 | 0.154 | 9.45E-56 |
| Kcnk3 | 5.91E-60 | 0.3058292 | 0.369 | 0.094 | 9.97E-56 |
| Aldoa | 1.24E-59 | 0.4977768 | 0.997 | 0.912 | 2.08E-55 |
| 130080G10R | 1.38E-59 | 0.4356417 | 0.767 | 0.328 | 2.33E-55 |
| Hspb6 | 2.35E-59 | 0.4879715 | 0.814 | 0.403 | 3.96E-55 |
| Ttn | 4.75E-59 | 0.6229877 | 1 | 0.527 | 8.01E-55 |
| Nebl | 4.93E-59 | 0.4530723 | 0.882 | 0.421 | 8.30E-55 |
| Smarcd3 | 5.64E-59 | 0.3891715 | 0.728 | 0.314 | 9.50E-55 |
| Ddr1 | 6.39E-59 | 0.3443631 | 0.647 | 0.248 | 1.08E-54 |
| Furin | 1.03E-58 | 0.3569637 | 0.579 | 0.213 | 1.74E-54 |
| Kif26b | 2.02E-58 | 0.3094961 | 0.479 | 0.15 | 3.40E-54 |
| Cst3 | 4.33E-58 | 0.6071662 | 0.992 | 0.923 | 7.31E-54 |
| Rplp2 | 5.71E-58 | -0.3278109 | 0.997 | 0.999 | 9.62E-54 |
| Rpsa | 8.74E-58 | -0.4471307 | 0.997 | 0.996 | 1.47E-53 |
| Srl | 8.78E-58 | 0.4580454 | 0.856 | 0.43 | 1.48E-53 |
| Acadl | 1.02E-57 | 0.5021953 | 0.966 | 0.654 | 1.72E-53 |
| Ank3 | 1.16E-57 | 0.4125177 | 0.749 | 0.343 | 1.96E-53 |
| Rpl13a | 1.23E-57 | -0.4971239 | 1 | 0.999 | 2.08E-53 |
| Map1lc3a | 3.09E-57 | 0.4978542 | 0.99 | 0.845 | 5.21E-53 |
| Fuca2 | 3.80E-57 | 0.3700527 | 0.516 | 0.179 | 6.40E-53 |
| Mgst3 | 5.81E-57 | 0.4596381 | 0.937 | 0.547 | 9.80E-53 |

Figure 26. continued

| | | | | | |
|---|---|---|---|---|---|
| Gas6 | 7.55E-57 | 0.4243843 | 0.83 | 0.414 | 1.27E-52 |
| Popdc2 | 9.39E-57 | 0.4700631 | 0.88 | 0.457 | 1.58E-52 |
| Rpl39 | 1.73E-56 | -0.3231857 | 0.997 | 0.999 | 2.91E-52 |
| Pgam1 | 2.10E-56 | 0.4848561 | 0.976 | 0.845 | 3.54E-52 |
| Chchd10 | 2.31E-56 | 0.591405 | 1 | 0.558 | 3.89E-52 |
| Rpl17 | 2.54E-56 | -0.5260071 | 1 | 0.999 | 4.28E-52 |
| Gmpr | 2.75E-56 | 0.3912156 | 0.746 | 0.342 | 4.63E-52 |
| Cox6a2 | 3.89E-56 | 0.5919 | 0.982 | 0.559 | 6.56E-52 |
| Rps16 | 9.55E-56 | -0.4413657 | 1 | 0.999 | 1.61E-51 |
| Atp2a2 | 9.67E-56 | 0.6312578 | 0.987 | 0.659 | 1.63E-51 |
| Rpl23 | 1.27E-55 | -0.3763087 | 1 | 1 | 2.14E-51 |
| Cav3 | 2.08E-55 | 0.4440366 | 0.895 | 0.446 | 3.51E-51 |
| Rps26 | 2.22E-55 | -0.4575054 | 1 | 0.998 | 3.74E-51 |
| Kif13a | 2.64E-55 | 0.3123595 | 0.584 | 0.22 | 4.46E-51 |
| Rps29 | 2.69E-55 | -0.3016444 | 1 | 1 | 4.53E-51 |
| Slc25a4 | 3.01E-55 | 0.5076602 | 1 | 0.984 | 5.07E-51 |
| Rps12 | 3.36E-55 | -0.5662884 | 0.995 | 0.998 | 5.66E-51 |
| Rpl13 | 4.30E-55 | -0.4067322 | 1 | 1 | 7.24E-51 |
| Rps4x | 1.23E-54 | -0.4202762 | 0.995 | 0.997 | 2.08E-50 |
| Rps5 | 1.27E-54 | -0.5087628 | 1 | 0.998 | 2.15E-50 |
| Tnni1 | 1.46E-54 | 0.6231671 | 1 | 0.682 | 2.46E-50 |
| Ckm | 1.55E-54 | 0.5995933 | 0.979 | 0.609 | 2.61E-50 |
| Ldhb | 1.67E-54 | 0.4986917 | 0.987 | 0.7 | 2.81E-50 |
| Mybpc3 | 4.44E-54 | 0.471538 | 0.974 | 0.514 | 7.49E-50 |
| Kcng2 | 5.40E-54 | 0.3233737 | 0.628 | 0.25 | 9.10E-50 |
| Bex1 | 6.58E-54 | 0.5112087 | 0.856 | 0.455 | 1.11E-49 |
| Rplp1 | 7.18E-54 | -0.3266809 | 1 | 1 | 1.21E-49 |
| Dstn | 9.40E-54 | 0.4312267 | 0.99 | 0.918 | 1.58E-49 |
| Rpl19 | 1.03E-53 | -0.3683774 | 1 | 0.999 | 1.74E-49 |
| Fabp3 | 1.25E-53 | 0.5451934 | 0.971 | 0.553 | 2.10E-49 |
| Ppp1r3c | 1.47E-53 | 0.3776787 | 0.777 | 0.356 | 2.49E-49 |
| Tgm2 | 1.76E-53 | 0.4737716 | 0.785 | 0.412 | 2.97E-49 |
| Ccdc141 | 2.15E-53 | 0.4379902 | 0.801 | 0.387 | 3.62E-49 |
| Mmd | 3.14E-53 | 0.420136 | 0.921 | 0.541 | 5.28E-49 |
| Obscn | 3.73E-53 | 0.5657296 | 0.785 | 0.391 | 6.28E-49 |
| Klhdc8b | 5.28E-53 | 0.4114766 | 0.691 | 0.312 | 8.90E-49 |
| Pbxip1 | 5.99E-53 | 0.3954375 | 0.733 | 0.354 | 1.01E-48 |
| Rpl23a | 7.10E-53 | -0.4302224 | 0.995 | 0.997 | 1.20E-48 |
| Rps15 | 1.15E-52 | -0.3784755 | 1 | 0.999 | 1.93E-48 |
| Rps20 | 1.21E-52 | -0.5497503 | 0.997 | 0.998 | 2.04E-48 |
| Homer2 | 1.43E-52 | 0.3174552 | 0.644 | 0.258 | 2.41E-48 |
| Mlf1 | 3.20E-52 | 0.4760866 | 0.948 | 0.525 | 5.39E-48 |
| Mylk3 | 3.76E-52 | 0.3751267 | 0.764 | 0.347 | 6.33E-48 |
| Rpl14 | 3.76E-52 | -0.4366467 | 1 | 0.998 | 6.34E-48 |
| Tox3 | 7.88E-52 | 0.3087649 | 0.51 | 0.18 | 1.33E-47 |

Figure 26.
continued

| | | | | | |
|---|---|---|---|---|---|
| Ppp1r14c | 1.15E-51 | 0.4469762 | 0.966 | 0.584 | 1.94E-47 |
| Flnc | 1.48E-51 | 0.4172285 | 0.798 | 0.405 | 2.50E-47 |
| Tnnt2 | 1.55E-51 | 0.6074491 | 1 | 0.8 | 2.61E-47 |
| H19 | 1.73E-51 | -0.8992891 | 0.783 | 0.941 | 2.91E-47 |
| Bves | 3.33E-51 | 0.5302741 | 0.822 | 0.416 | 5.61E-47 |
| Sgcg | 6.19E-51 | 0.3780823 | 0.534 | 0.203 | 1.04E-46 |
| Rpl41 | 6.27E-51 | -0.2964997 | 1 | 0.999 | 1.06E-46 |
| Jph2 | 7.92E-51 | 0.3442737 | 0.723 | 0.326 | 1.34E-46 |
| Gyg | 1.43E-50 | 0.5924324 | 0.971 | 0.684 | 2.42E-46 |
| Cxadr | 1.90E-50 | 0.3025121 | 0.592 | 0.231 | 3.20E-46 |
| Pdlim7 | 2.07E-50 | 0.5049774 | 0.851 | 0.516 | 3.49E-46 |
| Mdh1 | 3.05E-50 | 0.4820481 | 0.992 | 0.841 | 5.15E-46 |
| Rplp0 | 6.18E-50 | -0.4542254 | 0.997 | 0.997 | 1.04E-45 |
| Ndufa1 | 1.04E-49 | 0.4126917 | 0.99 | 0.834 | 1.75E-45 |
| Rps28 | 2.48E-49 | -0.432673 | 0.997 | 0.999 | 4.18E-45 |
| Hrc | 2.58E-49 | 0.3354643 | 0.547 | 0.211 | 4.35E-45 |
| Sspn | 3.63E-49 | 0.3607074 | 0.78 | 0.391 | 6.12E-45 |
| Crip2 | 5.79E-49 | 0.4606568 | 0.997 | 0.898 | 9.76E-45 |
| Itgb1bp2 | 5.80E-49 | 0.3001095 | 0.602 | 0.239 | 9.77E-45 |
| Rps24 | 6.74E-49 | -0.3492156 | 1 | 0.999 | 1.14E-44 |
| Rpl31 | 7.74E-49 | -0.361111 | 1 | 0.999 | 1.31E-44 |
| Rpl12 | 7.84E-49 | -0.4333515 | 0.992 | 0.994 | 1.32E-44 |
| Gapdh | 1.21E-48 | 0.4504155 | 1 | 0.959 | 2.03E-44 |
| Rpl21 | 1.42E-48 | -0.3916026 | 0.995 | 0.996 | 2.39E-44 |
| Casz1 | 1.60E-48 | 0.2736784 | 0.728 | 0.314 | 2.69E-44 |
| Unc45b | 2.02E-48 | 0.3483042 | 0.741 | 0.353 | 3.40E-44 |
| Vldlr | 4.28E-47 | 0.3924854 | 0.678 | 0.309 | 7.22E-43 |
| Rpl8 | 5.23E-46 | -0.3634515 | 1 | 0.997 | 8.81E-42 |
| Vim | 7.54E-46 | -1.5373533 | 0.869 | 0.914 | 1.27E-41 |
| Mical3 | 1.34E-45 | 0.2937486 | 0.56 | 0.225 | 2.26E-41 |
| Rpl27a | 1.52E-45 | -0.3519406 | 0.997 | 1 | 2.57E-41 |
| Fhl2 | 1.81E-45 | 0.5220327 | 0.872 | 0.558 | 3.05E-41 |
| Hk1 | 2.48E-45 | 0.3639559 | 0.783 | 0.42 | 4.18E-41 |
| Trim55 | 3.34E-45 | 0.3297179 | 0.785 | 0.375 | 5.63E-41 |
| Rps3 | 4.16E-45 | -0.407379 | 0.997 | 0.998 | 7.00E-41 |
| Got1 | 1.01E-44 | 0.3606197 | 0.835 | 0.445 | 1.70E-40 |
| Tpi1 | 3.54E-44 | 0.4009821 | 0.992 | 0.897 | 5.96E-40 |
| Pfkm | 3.85E-44 | 0.3100938 | 0.639 | 0.282 | 6.49E-40 |
| Igf2 | 4.10E-44 | -0.8295822 | 0.825 | 0.933 | 6.91E-40 |
| Pkp2 | 4.14E-44 | 0.3528918 | 0.746 | 0.37 | 6.97E-40 |
| Mob1b | 4.96E-44 | 0.3736352 | 0.699 | 0.335 | 8.36E-40 |
| Atp5b | 5.85E-44 | 0.4027933 | 1 | 0.964 | 9.87E-40 |
| Rps25 | 5.91E-44 | -0.3078729 | 1 | 0.998 | 9.97E-40 |
| Cdh13 | 7.51E-44 | 0.3628228 | 0.662 | 0.315 | 1.27E-39 |
| Phyh | 8.40E-44 | 0.3239611 | 0.793 | 0.406 | 1.42E-39 |

Figure 26. continued

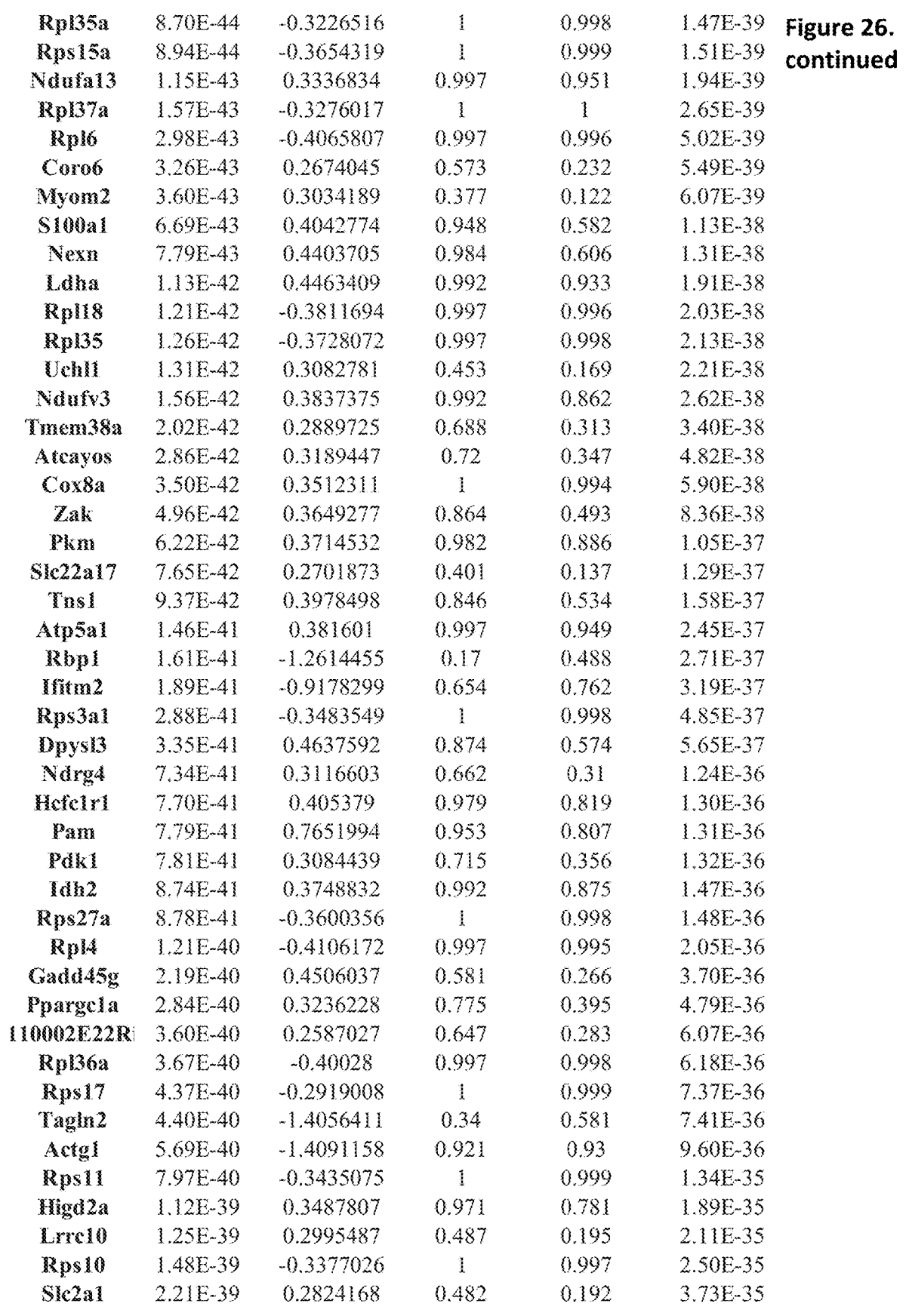

| | | | | | |
|---|---|---|---|---|---|
| Rpl35a | 8.70E-44 | -0.3226516 | 1 | 0.998 | 1.47E-39 |
| Rps15a | 8.94E-44 | -0.3654319 | 1 | 0.999 | 1.51E-39 |
| Ndufa13 | 1.15E-43 | 0.3336834 | 0.997 | 0.951 | 1.94E-39 |
| Rpl37a | 1.57E-43 | -0.3276017 | 1 | 1 | 2.65E-39 |
| Rpl6 | 2.98E-43 | -0.4065807 | 0.997 | 0.996 | 5.02E-39 |
| Coro6 | 3.26E-43 | 0.2674045 | 0.573 | 0.232 | 5.49E-39 |
| Myom2 | 3.60E-43 | 0.3034189 | 0.377 | 0.122 | 6.07E-39 |
| S100a1 | 6.69E-43 | 0.4042774 | 0.948 | 0.582 | 1.13E-38 |
| Nexn | 7.79E-43 | 0.4403705 | 0.984 | 0.606 | 1.31E-38 |
| Ldha | 1.13E-42 | 0.4463409 | 0.992 | 0.933 | 1.91E-38 |
| Rpl18 | 1.21E-42 | -0.3811694 | 0.997 | 0.996 | 2.03E-38 |
| Rpl35 | 1.26E-42 | -0.3728072 | 0.997 | 0.998 | 2.13E-38 |
| Uchl1 | 1.31E-42 | 0.3082781 | 0.453 | 0.169 | 2.21E-38 |
| Ndufv3 | 1.56E-42 | 0.3837375 | 0.992 | 0.862 | 2.62E-38 |
| Tmem38a | 2.02E-42 | 0.2889725 | 0.688 | 0.313 | 3.40E-38 |
| Atcayos | 2.86E-42 | 0.3189447 | 0.72 | 0.347 | 4.82E-38 |
| Cox8a | 3.50E-42 | 0.3512311 | 1 | 0.994 | 5.90E-38 |
| Zak | 4.96E-42 | 0.3649277 | 0.864 | 0.493 | 8.36E-38 |
| Pkm | 6.22E-42 | 0.3714532 | 0.982 | 0.886 | 1.05E-37 |
| Slc22a17 | 7.65E-42 | 0.2701873 | 0.401 | 0.137 | 1.29E-37 |
| Tns1 | 9.37E-42 | 0.3978498 | 0.846 | 0.534 | 1.58E-37 |
| Atp5a1 | 1.46E-41 | 0.381601 | 0.997 | 0.949 | 2.45E-37 |
| Rbp1 | 1.61E-41 | -1.2614455 | 0.17 | 0.488 | 2.71E-37 |
| Ifitm2 | 1.89E-41 | -0.9178299 | 0.654 | 0.762 | 3.19E-37 |
| Rps3a1 | 2.88E-41 | -0.3483549 | 1 | 0.998 | 4.85E-37 |
| Dpysl3 | 3.35E-41 | 0.4637592 | 0.874 | 0.574 | 5.65E-37 |
| Ndrg4 | 7.34E-41 | 0.3116603 | 0.662 | 0.31 | 1.24E-36 |
| Hcfc1r1 | 7.70E-41 | 0.405379 | 0.979 | 0.819 | 1.30E-36 |
| Pam | 7.79E-41 | 0.7651994 | 0.953 | 0.807 | 1.31E-36 |
| Pdk1 | 7.81E-41 | 0.3084439 | 0.715 | 0.356 | 1.32E-36 |
| Idh2 | 8.74E-41 | 0.3748832 | 0.992 | 0.875 | 1.47E-36 |
| Rps27a | 8.78E-41 | -0.3600356 | 1 | 0.998 | 1.48E-36 |
| Rpl4 | 1.21E-40 | -0.4106172 | 0.997 | 0.995 | 2.05E-36 |
| Gadd45g | 2.19E-40 | 0.4506037 | 0.581 | 0.266 | 3.70E-36 |
| Ppargc1a | 2.84E-40 | 0.3236228 | 0.775 | 0.395 | 4.79E-36 |
| 1110002E22Ri | 3.60E-40 | 0.2587027 | 0.647 | 0.283 | 6.07E-36 |
| Rpl36a | 3.67E-40 | -0.40028 | 0.997 | 0.998 | 6.18E-36 |
| Rps17 | 4.37E-40 | -0.2919008 | 1 | 0.999 | 7.37E-36 |
| Tagln2 | 4.40E-40 | -1.4056411 | 0.34 | 0.581 | 7.41E-36 |
| Actg1 | 5.69E-40 | -1.4091158 | 0.921 | 0.93 | 9.60E-36 |
| Rps11 | 7.97E-40 | -0.3435075 | 1 | 0.999 | 1.34E-35 |
| Higd2a | 1.12E-39 | 0.3487807 | 0.971 | 0.781 | 1.89E-35 |
| Lrrc10 | 1.25E-39 | 0.2995487 | 0.487 | 0.195 | 2.11E-35 |
| Rps10 | 1.48E-39 | -0.3377026 | 1 | 0.997 | 2.50E-35 |
| Slc2a1 | 2.21E-39 | 0.2824168 | 0.482 | 0.192 | 3.73E-35 |

Figure 26. continued

| | | | | | |
|---|---|---|---|---|---|
| Arhgap31 | 2.27E-39 | 0.4685492 | 0.848 | 0.513 | 3.83E-35 |
| Nppa | 2.35E-39 | 2.9326319 | 0.366 | 0.138 | 3.95E-35 |
| Ramp2 | 4.42E-39 | -1.3072609 | 0.144 | 0.464 | 7.46E-35 |
| Ndufb9 | 4.71E-39 | 0.372792 | 0.997 | 0.905 | 7.94E-35 |
| Lgals1 | 6.03E-39 | -1.3369159 | 0.919 | 0.945 | 1.02E-34 |
| Asph | 7.00E-39 | 0.3282814 | 0.827 | 0.502 | 1.18E-34 |
| Itga9 | 8.55E-39 | 0.3039495 | 0.393 | 0.142 | 1.44E-34 |
| S100a10 | 9.59E-39 | -1.2488845 | 0.275 | 0.547 | 1.62E-34 |
| Rps13 | 1.26E-38 | -0.324465 | 0.997 | 0.998 | 2.13E-34 |
| Rps2 | 1.99E-38 | -0.3464538 | 0.997 | 0.996 | 3.36E-34 |
| Ndufa12 | 2.54E-38 | 0.3346108 | 0.995 | 0.876 | 4.28E-34 |
| Ifitm3 | 8.91E-38 | -1.1114637 | 0.123 | 0.434 | 1.50E-33 |
| Rpl24 | 9.38E-38 | -0.2765679 | 1 | 0.999 | 1.58E-33 |
| Dsp | 1.00E-37 | 0.3235901 | 0.887 | 0.483 | 1.69E-33 |
| Smim5 | 1.06E-37 | 0.2657224 | 0.573 | 0.25 | 1.79E-33 |
| Rps6 | 1.78E-37 | -0.4885221 | 0.997 | 0.997 | 2.99E-33 |
| Glrx | 2.05E-37 | 0.3194622 | 0.736 | 0.384 | 3.46E-33 |
| Atp1a2 | 2.09E-37 | 0.3040155 | 0.49 | 0.205 | 3.52E-33 |
| Atp5o | 2.23E-37 | 0.3922606 | 1 | 0.957 | 3.76E-33 |
| Cdh2 | 3.54E-37 | 0.3548011 | 0.929 | 0.594 | 5.97E-33 |
| Vdac1 | 4.02E-37 | 0.3165798 | 0.982 | 0.863 | 6.78E-33 |
| Rbm20 | 4.09E-37 | 0.2604055 | 0.641 | 0.298 | 6.90E-33 |
| Atp5l | 5.25E-37 | 0.3260761 | 1 | 0.989 | 8.84E-33 |
| Ndufb2 | 6.94E-37 | 0.3202447 | 0.992 | 0.864 | 1.17E-32 |
| Ndrg2 | 9.87E-37 | 0.3624224 | 0.95 | 0.68 | 1.66E-32 |
| Idh3a | 1.09E-36 | 0.3167519 | 0.963 | 0.61 | 1.84E-32 |
| Aco2 | 1.38E-36 | 0.3202266 | 0.987 | 0.689 | 2.33E-32 |
| Rps18 | 1.48E-36 | -0.3657375 | 0.997 | 0.995 | 2.49E-32 |
| Emp3 | 1.95E-36 | -0.8197517 | 0.113 | 0.416 | 3.28E-32 |
| Sfrp1 | 2.06E-36 | 0.6325691 | 0.767 | 0.471 | 3.48E-32 |
| Cdc14b | 2.72E-36 | 0.2637532 | 0.387 | 0.143 | 4.58E-32 |
| Rpl37 | 2.72E-36 | -0.3173145 | 1 | 1 | 4.58E-32 |
| Tpm4 | 3.52E-36 | -1.0537152 | 0.406 | 0.594 | 5.93E-32 |
| Atp5c1 | 3.63E-36 | 0.3432703 | 0.995 | 0.948 | 6.11E-32 |
| Cers4 | 4.18E-36 | 0.3003216 | 0.681 | 0.342 | 7.04E-32 |
| Slc25a3 | 4.33E-36 | 0.3173438 | 0.995 | 0.954 | 7.29E-32 |
| Ptma | 4.99E-36 | -0.8749073 | 0.992 | 0.991 | 8.41E-32 |
| B2m | 5.02E-36 | -1.0058402 | 0.521 | 0.669 | 8.46E-32 |
| Eif4ebp1 | 5.03E-36 | 0.3220711 | 0.969 | 0.784 | 8.48E-32 |
| Svil | 7.64E-36 | 0.3351465 | 0.848 | 0.505 | 1.29E-31 |
| Bri3 | 9.37E-36 | 0.3491925 | 0.961 | 0.865 | 1.58E-31 |
| Rpl22 | 1.08E-35 | -0.3398559 | 0.982 | 0.992 | 1.81E-31 |
| Rpl9 | 1.36E-35 | -0.3254217 | 1 | 0.996 | 2.30E-31 |
| Ehbp1l1 | 1.65E-35 | 0.2605121 | 0.647 | 0.313 | 2.77E-31 |
| Tmx4 | 1.69E-35 | 0.3284541 | 0.662 | 0.337 | 2.85E-31 |

Figure 26. continued

| | | | | | |
|---|---|---|---|---|---|
| Sod2 | 2.47E-35 | 0.3181 | 0.976 | 0.678 | 4.17E-31 |
| Mtss1 | 2.50E-35 | 0.3022557 | 0.639 | 0.317 | 4.22E-31 |
| Hif1a | 4.24E-35 | 0.3595731 | 0.806 | 0.481 | 7.15E-31 |
| Fry | 4.49E-35 | 0.2578585 | 0.565 | 0.253 | 7.56E-31 |
| Rps23 | 5.30E-35 | -0.3997718 | 1 | 1 | 8.93E-31 |
| Ppa2 | 7.02E-35 | 0.3061653 | 0.798 | 0.449 | 1.18E-30 |
| Ndufa4 | 8.93E-35 | 0.3377904 | 1 | 0.973 | 1.51E-30 |
| Ppp2r3a | 1.03E-34 | 0.3060679 | 0.835 | 0.487 | 1.73E-30 |
| Ryr2 | 1.39E-34 | 0.3018278 | 0.817 | 0.418 | 2.35E-30 |
| Clasp1 | 1.57E-34 | 0.3125178 | 0.814 | 0.487 | 2.64E-30 |
| Rbm38 | 1.72E-34 | 0.252403 | 0.586 | 0.276 | 2.91E-30 |
| Usmg5 | 2.08E-34 | 0.3361647 | 1 | 0.96 | 3.50E-30 |
| Ndufa3 | 2.25E-34 | 0.2936244 | 0.997 | 0.923 | 3.78E-30 |
| Hacd1 | 2.51E-34 | 0.3465608 | 0.945 | 0.668 | 4.23E-30 |
| H3f3b | 2.79E-34 | -0.8647759 | 0.969 | 0.965 | 4.71E-30 |
| Gng5 | 4.15E-34 | 0.2540297 | 0.997 | 0.982 | 7.00E-30 |
| Rps27 | 6.25E-34 | -0.3660365 | 1 | 0.999 | 1.05E-29 |
| Rps7 | 6.34E-34 | -0.3720275 | 0.997 | 0.996 | 1.07E-29 |
| Atp5h | 1.76E-33 | 0.284184 | 1 | 0.983 | 2.96E-29 |
| Rpl34 | 2.05E-33 | -0.3632387 | 0.995 | 0.999 | 3.45E-29 |
| Mef2a | 3.14E-33 | 0.3267014 | 0.927 | 0.677 | 5.29E-29 |
| Gnb2l1 | 3.40E-33 | -0.3706824 | 0.982 | 0.99 | 5.73E-29 |
| Rpl7 | 4.70E-33 | -0.3457314 | 1 | 0.996 | 7.92E-29 |
| Actb | 5.98E-33 | -1.5588621 | 0.838 | 0.856 | 1.01E-28 |
| Spon1 | 6.13E-33 | 0.3158369 | 0.445 | 0.189 | 1.03E-28 |
| Mapkapk2 | 7.43E-33 | 0.2620493 | 0.67 | 0.343 | 1.25E-28 |
| Mdh2 | 9.75E-33 | 0.3034465 | 0.982 | 0.878 | 1.64E-28 |
| Rpl11 | 1.01E-32 | -0.3468524 | 0.997 | 0.998 | 1.71E-28 |
| Arpc1b | 1.23E-32 | -0.9816466 | 0.398 | 0.574 | 2.08E-28 |
| Dag1 | 1.81E-32 | 0.3131466 | 0.814 | 0.506 | 3.06E-28 |
| Ak1 | 1.97E-32 | 0.3033831 | 0.945 | 0.622 | 3.31E-28 |
| Cox6c | 2.12E-32 | 0.3523739 | 1 | 0.995 | 3.57E-28 |
| Ndufb4 | 2.66E-32 | 0.296309 | 0.99 | 0.868 | 4.48E-28 |
| Rps9 | 2.73E-32 | -0.2840834 | 1 | 0.999 | 4.60E-28 |
| Rpl22l1 | 2.87E-32 | -0.4209701 | 0.987 | 0.985 | 4.84E-28 |
| Eef1b2 | 2.88E-32 | -0.3979698 | 0.963 | 0.969 | 4.85E-28 |
| Rps21 | 3.01E-32 | -0.3262524 | 0.992 | 0.995 | 5.07E-28 |
| Snap91 | 3.36E-32 | 0.2617745 | 0.668 | 0.33 | 5.66E-28 |
| Bgn | 3.59E-32 | -1.6597358 | 0.259 | 0.508 | 6.05E-28 |
| Cfl2 | 7.15E-32 | 0.3103598 | 0.974 | 0.784 | 1.21E-27 |
| Rbm3 | 1.36E-31 | -0.3993657 | 0.924 | 0.949 | 2.29E-27 |
| Cox7c | 1.57E-31 | 0.3279437 | 1 | 0.995 | 2.65E-27 |
| Uqcrb | 1.71E-31 | 0.3015553 | 0.997 | 0.979 | 2.88E-27 |
| Dcn | 1.96E-31 | -2.1531799 | 0.194 | 0.459 | 3.31E-27 |
| Col3a1 | 2.45E-31 | -1.5347367 | 0.27 | 0.525 | 4.12E-27 |

Figure 26. continued

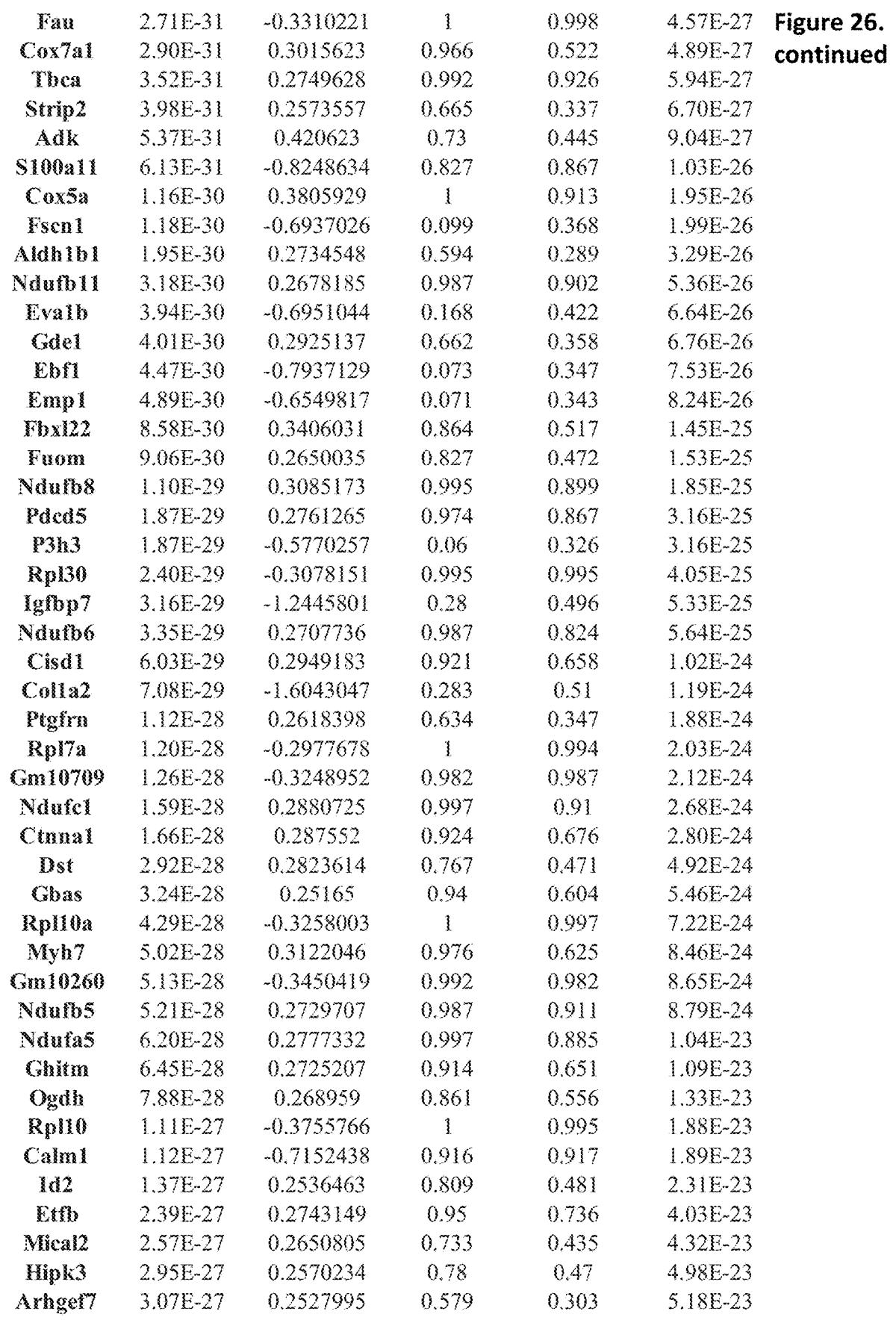

| | | | | | |
|---|---|---|---|---|---|
| Fau | 2.71E-31 | -0.3310221 | 1 | 0.998 | 4.57E-27 |
| Cox7a1 | 2.90E-31 | 0.3015623 | 0.966 | 0.522 | 4.89E-27 |
| Tbca | 3.52E-31 | 0.2749628 | 0.992 | 0.926 | 5.94E-27 |
| Strip2 | 3.98E-31 | 0.2573557 | 0.665 | 0.337 | 6.70E-27 |
| Adk | 5.37E-31 | 0.420623 | 0.73 | 0.445 | 9.04E-27 |
| S100a11 | 6.13E-31 | -0.8248634 | 0.827 | 0.867 | 1.03E-26 |
| Cox5a | 1.16E-30 | 0.3805929 | 1 | 0.913 | 1.95E-26 |
| Fscn1 | 1.18E-30 | -0.6937026 | 0.099 | 0.368 | 1.99E-26 |
| Aldh1b1 | 1.95E-30 | 0.2734548 | 0.594 | 0.289 | 3.29E-26 |
| Ndufb11 | 3.18E-30 | 0.2678185 | 0.987 | 0.902 | 5.36E-26 |
| Eva1b | 3.94E-30 | -0.6951044 | 0.168 | 0.422 | 6.64E-26 |
| Gde1 | 4.01E-30 | 0.2925137 | 0.662 | 0.358 | 6.76E-26 |
| Ebf1 | 4.47E-30 | -0.7937129 | 0.073 | 0.347 | 7.53E-26 |
| Emp1 | 4.89E-30 | -0.6549817 | 0.071 | 0.343 | 8.24E-26 |
| Fbxl22 | 8.58E-30 | 0.3406031 | 0.864 | 0.517 | 1.45E-25 |
| Fuom | 9.06E-30 | 0.2650035 | 0.827 | 0.472 | 1.53E-25 |
| Ndufb8 | 1.10E-29 | 0.3085173 | 0.995 | 0.899 | 1.85E-25 |
| Pdcd5 | 1.87E-29 | 0.2761265 | 0.974 | 0.867 | 3.16E-25 |
| P3h3 | 1.87E-29 | -0.5770257 | 0.06 | 0.326 | 3.16E-25 |
| Rpl30 | 2.40E-29 | -0.3078151 | 0.995 | 0.995 | 4.05E-25 |
| Igfbp7 | 3.16E-29 | -1.2445801 | 0.28 | 0.496 | 5.33E-25 |
| Ndufb6 | 3.35E-29 | 0.2707736 | 0.987 | 0.824 | 5.64E-25 |
| Cisd1 | 6.03E-29 | 0.2949183 | 0.921 | 0.658 | 1.02E-24 |
| Col1a2 | 7.08E-29 | -1.6043047 | 0.283 | 0.51 | 1.19E-24 |
| Ptgfrn | 1.12E-28 | 0.2618398 | 0.634 | 0.347 | 1.88E-24 |
| Rpl7a | 1.20E-28 | -0.2977678 | 1 | 0.994 | 2.03E-24 |
| Gm10709 | 1.26E-28 | -0.3248952 | 0.982 | 0.987 | 2.12E-24 |
| Ndufc1 | 1.59E-28 | 0.2880725 | 0.997 | 0.91 | 2.68E-24 |
| Ctnna1 | 1.66E-28 | 0.287552 | 0.924 | 0.676 | 2.80E-24 |
| Dst | 2.92E-28 | 0.2823614 | 0.767 | 0.471 | 4.92E-24 |
| Gbas | 3.24E-28 | 0.25165 | 0.94 | 0.604 | 5.46E-24 |
| Rpl10a | 4.29E-28 | -0.3258003 | 1 | 0.997 | 7.22E-24 |
| Myh7 | 5.02E-28 | 0.3122046 | 0.976 | 0.625 | 8.46E-24 |
| Gm10260 | 5.13E-28 | -0.3450419 | 0.992 | 0.982 | 8.65E-24 |
| Ndufb5 | 5.21E-28 | 0.2729707 | 0.987 | 0.911 | 8.79E-24 |
| Ndufa5 | 6.20E-28 | 0.2777332 | 0.997 | 0.885 | 1.04E-23 |
| Ghitm | 6.45E-28 | 0.2725207 | 0.914 | 0.651 | 1.09E-23 |
| Ogdh | 7.88E-28 | 0.268959 | 0.861 | 0.556 | 1.33E-23 |
| Rpl10 | 1.11E-27 | -0.3755766 | 1 | 0.995 | 1.88E-23 |
| Calm1 | 1.12E-27 | -0.7152438 | 0.916 | 0.917 | 1.89E-23 |
| Id2 | 1.37E-27 | 0.2536463 | 0.809 | 0.481 | 2.31E-23 |
| Etfb | 2.39E-27 | 0.2743149 | 0.95 | 0.736 | 4.03E-23 |
| Mical2 | 2.57E-27 | 0.2650805 | 0.733 | 0.435 | 4.32E-23 |
| Hipk3 | 2.95E-27 | 0.2570234 | 0.78 | 0.47 | 4.98E-23 |
| Arhgef7 | 3.07E-27 | 0.2527995 | 0.579 | 0.303 | 5.18E-23 |

**Figure 26.
continued**

| | | | | | |
|---|---|---|---|---|---|
| Postn | 3.33E-27 | -1.5210651 | 0.319 | 0.533 | 5.61E-23 |
| Prnp | 3.63E-27 | 0.4167748 | 0.749 | 0.476 | 6.12E-23 |
| Cox5b | 5.27E-27 | 0.2955831 | 1 | 0.956 | 8.87E-23 |
| Hmgb1 | 5.33E-27 | -0.4912243 | 0.969 | 0.952 | 8.99E-23 |
| Acaa2 | 5.41E-27 | 0.3236147 | 0.882 | 0.586 | 9.11E-23 |
| Dnajc15 | 6.71E-27 | 0.268826 | 0.882 | 0.607 | 1.13E-22 |
| Cd34 | 8.42E-27 | -0.7676609 | 0.073 | 0.32 | 1.42E-22 |
| Qk | 9.10E-27 | 0.276149 | 0.924 | 0.685 | 1.53E-22 |
| Mmp2 | 9.37E-27 | -0.7763399 | 0.102 | 0.354 | 1.58E-22 |
| Emilin1 | 1.42E-26 | -0.6119098 | 0.126 | 0.377 | 2.40E-22 |
| Marcks | 2.12E-26 | -0.6616836 | 0.707 | 0.758 | 3.57E-22 |
| Uqcrc1 | 5.49E-26 | 0.2651521 | 0.969 | 0.806 | 9.26E-22 |
| Rhoj | 6.50E-26 | -0.5140743 | 0.065 | 0.312 | 1.10E-21 |
| Fibp | 6.77E-26 | 0.2788782 | 0.613 | 0.333 | 1.14E-21 |
| Eef1g | 6.89E-26 | -0.3819405 | 0.987 | 0.976 | 1.16E-21 |
| Pdhb | 7.37E-26 | 0.25296 | 0.937 | 0.619 | 1.24E-21 |
| Ptn | 1.01E-25 | -1.7768914 | 0.348 | 0.531 | 1.71E-21 |
| Sh3bgrl3 | 1.12E-25 | -0.8064627 | 0.432 | 0.561 | 1.89E-21 |
| Rcan1 | 1.21E-25 | 0.3072217 | 0.516 | 0.267 | 2.04E-21 |
| Tm4sf1 | 1.76E-25 | -0.9375165 | 0.076 | 0.321 | 2.97E-21 |
| Ndufs3 | 2.10E-25 | 0.2599219 | 0.942 | 0.746 | 3.53E-21 |
| Tmsb10 | 2.47E-25 | -0.4732073 | 0.997 | 0.994 | 4.16E-21 |
| Cox7b | 2.52E-25 | 0.2979801 | 1 | 0.955 | 4.25E-21 |
| Eef1a1 | 3.23E-25 | -0.2609895 | 1 | 1 | 5.45E-21 |
| Lum | 3.77E-25 | -1.4210308 | 0.165 | 0.397 | 6.35E-21 |
| Celf2 | 4.07E-25 | 0.292855 | 0.812 | 0.55 | 6.86E-21 |
| Camta1 | 6.14E-25 | 0.2502048 | 0.885 | 0.599 | 1.03E-20 |
| Eng | 7.01E-25 | -0.6390612 | 0.113 | 0.346 | 1.18E-20 |
| Ndufb7 | 7.04E-25 | 0.2508975 | 0.995 | 0.885 | 1.19E-20 |
| Prkar1a | 7.30E-25 | 0.272577 | 0.955 | 0.83 | 1.23E-20 |
| Npm1 | 8.89E-25 | -0.3667139 | 0.984 | 0.979 | 1.50E-20 |
| Pkig | 9.14E-25 | 0.2565542 | 0.961 | 0.773 | 1.54E-20 |
| Pabpc1 | 1.38E-24 | -0.3461338 | 0.911 | 0.938 | 2.33E-20 |
| Suclg1 | 3.02E-24 | 0.2509816 | 0.937 | 0.705 | 5.09E-20 |
| Eno1 | 3.60E-24 | 0.3090698 | 0.929 | 0.768 | 6.08E-20 |
| Rps14 | 4.02E-24 | -0.2702911 | 1 | 0.999 | 6.78E-20 |
| Uqcr10 | 5.22E-24 | 0.2960588 | 1 | 0.957 | 8.79E-20 |
| Fbln2 | 6.65E-24 | -0.6137145 | 0.076 | 0.31 | 1.12E-19 |
| Dhrs7 | 7.77E-24 | 0.284787 | 0.547 | 0.291 | 1.31E-19 |
| Uqcrh | 9.26E-24 | 0.2524154 | 1 | 0.993 | 1.56E-19 |
| Arf4 | 1.37E-23 | -0.5766357 | 0.838 | 0.825 | 2.30E-19 |
| Rps12-ps3 | 1.52E-23 | -0.4080811 | 0.694 | 0.771 | 2.56E-19 |
| Smpx | 1.69E-23 | 0.3147271 | 0.935 | 0.536 | 2.85E-19 |
| Bnip3 | 2.10E-23 | 0.2824445 | 0.709 | 0.422 | 3.53E-19 |
| Uqcr11 | 2.13E-23 | 0.3019861 | 1 | 0.947 | 3.60E-19 |

Figure 26. continued

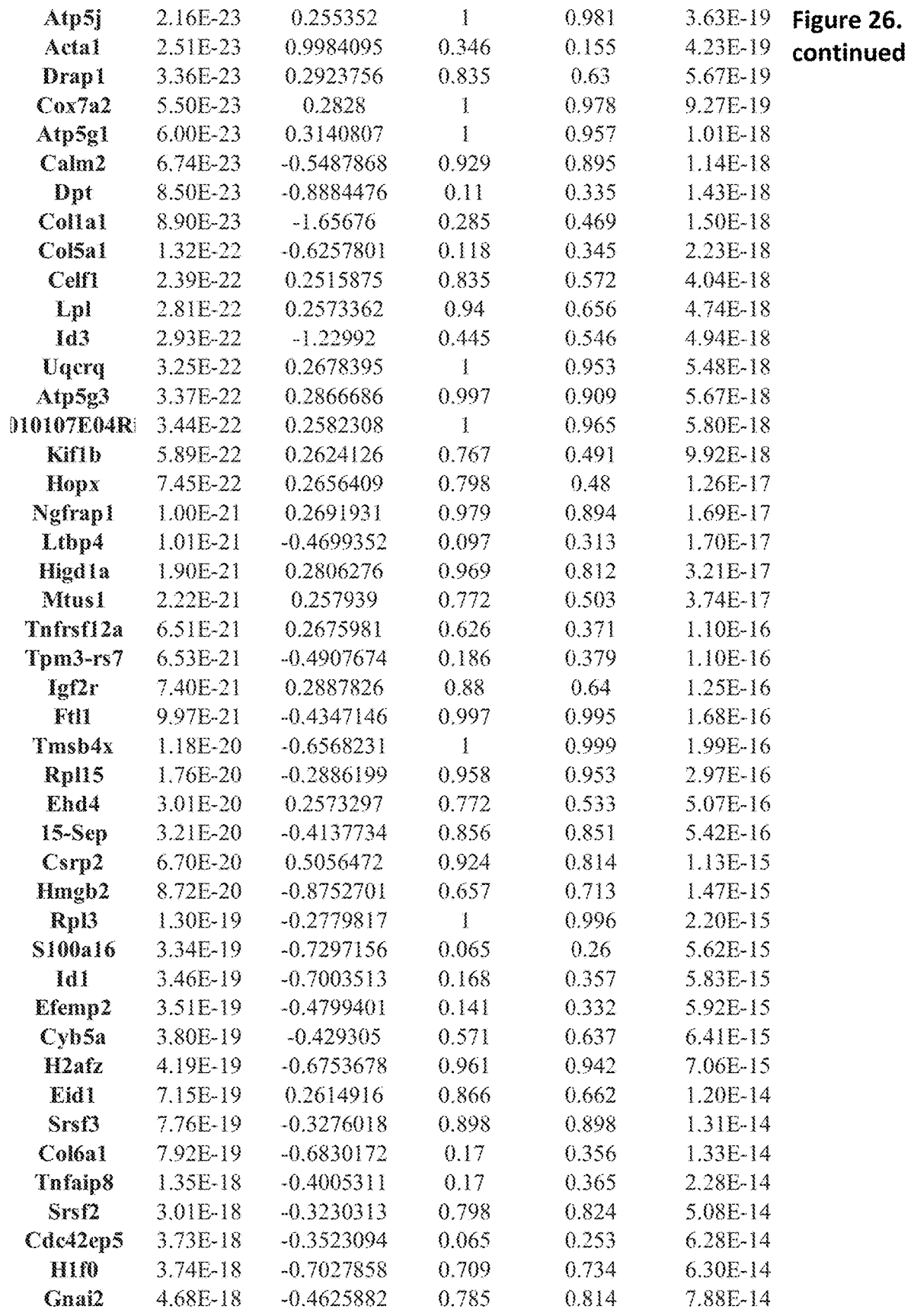

| | | | | | | |
|---|---|---|---|---|---|---|
| Atp5j | 2.16E-23 | 0.255352 | 1 | 0.981 | 3.63E-19 | Figure 26. |
| Acta1 | 2.51E-23 | 0.9984095 | 0.346 | 0.155 | 4.23E-19 | continued |
| Drap1 | 3.36E-23 | 0.2923756 | 0.835 | 0.63 | 5.67E-19 | |
| Cox7a2 | 5.50E-23 | 0.2828 | 1 | 0.978 | 9.27E-19 | |
| Atp5g1 | 6.00E-23 | 0.3140807 | 1 | 0.957 | 1.01E-18 | |
| Calm2 | 6.74E-23 | -0.5487868 | 0.929 | 0.895 | 1.14E-18 | |
| Dpt | 8.50E-23 | -0.8884476 | 0.11 | 0.335 | 1.43E-18 | |
| Col1a1 | 8.90E-23 | -1.65676 | 0.285 | 0.469 | 1.50E-18 | |
| Col5a1 | 1.32E-22 | -0.6257801 | 0.118 | 0.345 | 2.23E-18 | |
| Celf1 | 2.39E-22 | 0.2515875 | 0.835 | 0.572 | 4.04E-18 | |
| Lpl | 2.81E-22 | 0.2573362 | 0.94 | 0.656 | 4.74E-18 | |
| Id3 | 2.93E-22 | -1.22992 | 0.445 | 0.546 | 4.94E-18 | |
| Uqcrq | 3.25E-22 | 0.2678395 | 1 | 0.953 | 5.48E-18 | |
| Atp5g3 | 3.37E-22 | 0.2866686 | 0.997 | 0.909 | 5.67E-18 | |
| 010107E04Ri | 3.44E-22 | 0.2582308 | 1 | 0.965 | 5.80E-18 | |
| Kif1b | 5.89E-22 | 0.2624126 | 0.767 | 0.491 | 9.92E-18 | |
| Hopx | 7.45E-22 | 0.2656409 | 0.798 | 0.48 | 1.26E-17 | |
| Ngfrap1 | 1.00E-21 | 0.2691931 | 0.979 | 0.894 | 1.69E-17 | |
| Ltbp4 | 1.01E-21 | -0.4699352 | 0.097 | 0.313 | 1.70E-17 | |
| Higd1a | 1.90E-21 | 0.2806276 | 0.969 | 0.812 | 3.21E-17 | |
| Mtus1 | 2.22E-21 | 0.257939 | 0.772 | 0.503 | 3.74E-17 | |
| Tnfrsf12a | 6.51E-21 | 0.2675981 | 0.626 | 0.371 | 1.10E-16 | |
| Tpm3-rs7 | 6.53E-21 | -0.4907674 | 0.186 | 0.379 | 1.10E-16 | |
| Igf2r | 7.40E-21 | 0.2887826 | 0.88 | 0.64 | 1.25E-16 | |
| Ftl1 | 9.97E-21 | -0.4347146 | 0.997 | 0.995 | 1.68E-16 | |
| Tmsb4x | 1.18E-20 | -0.6568231 | 1 | 0.999 | 1.99E-16 | |
| Rpl15 | 1.76E-20 | -0.2886199 | 0.958 | 0.953 | 2.97E-16 | |
| Ehd4 | 3.01E-20 | 0.2573297 | 0.772 | 0.533 | 5.07E-16 | |
| 15-Sep | 3.21E-20 | -0.4137734 | 0.856 | 0.851 | 5.42E-16 | |
| Csrp2 | 6.70E-20 | 0.5056472 | 0.924 | 0.814 | 1.13E-15 | |
| Hmgb2 | 8.72E-20 | -0.8752701 | 0.657 | 0.713 | 1.47E-15 | |
| Rpl3 | 1.30E-19 | -0.2779817 | 1 | 0.996 | 2.20E-15 | |
| S100a16 | 3.34E-19 | -0.7297156 | 0.065 | 0.26 | 5.62E-15 | |
| Id1 | 3.46E-19 | -0.7003513 | 0.168 | 0.357 | 5.83E-15 | |
| Efemp2 | 3.51E-19 | -0.4799401 | 0.141 | 0.332 | 5.92E-15 | |
| Cyb5a | 3.80E-19 | -0.429305 | 0.571 | 0.637 | 6.41E-15 | |
| H2afz | 4.19E-19 | -0.6753678 | 0.961 | 0.942 | 7.06E-15 | |
| Eid1 | 7.15E-19 | 0.2614916 | 0.866 | 0.662 | 1.20E-14 | |
| Srsf3 | 7.76E-19 | -0.3276018 | 0.898 | 0.898 | 1.31E-14 | |
| Col6a1 | 7.92E-19 | -0.6830172 | 0.17 | 0.356 | 1.33E-14 | |
| Tnfaip8 | 1.35E-18 | -0.4005311 | 0.17 | 0.365 | 2.28E-14 | |
| Srsf2 | 3.01E-18 | -0.3230313 | 0.798 | 0.824 | 5.08E-14 | |
| Cdc42ep5 | 3.73E-18 | -0.3523094 | 0.065 | 0.253 | 6.28E-14 | |
| H1f0 | 3.74E-18 | -0.7027858 | 0.709 | 0.734 | 6.30E-14 | |
| Gnai2 | 4.68E-18 | -0.4625882 | 0.785 | 0.814 | 7.88E-14 | |

| | | | | | |
|---|---|---|---|---|---|
| Aspn | 5.15E-18 | -0.8989459 | 0.102 | 0.291 | 8.68E-14 |
| Ranbp1 | 5.26E-18 | -0.3378249 | 0.916 | 0.893 | 8.86E-14 |
| Fxyd6 | 5.48E-18 | -0.8653786 | 0.162 | 0.345 | 9.24E-14 |
| Igfbp4 | 6.95E-18 | -0.8073876 | 0.298 | 0.455 | 1.17E-13 |
| Cotl1 | 7.48E-18 | -0.4644166 | 0.094 | 0.28 | 1.26E-13 |
| Hmgn1 | 7.58E-18 | -0.3806694 | 0.961 | 0.945 | 1.28E-13 |
| Klf2 | 7.83E-18 | -0.7833847 | 0.071 | 0.257 | 1.32E-13 |
| Sptssa | 8.89E-18 | -0.3122263 | 0.694 | 0.747 | 1.50E-13 |
| Naca | 1.11E-17 | -0.2813725 | 0.987 | 0.99 | 1.87E-13 |
| Sox9 | 1.27E-17 | -0.5917339 | 0.097 | 0.294 | 2.13E-13 |
| Lsp1 | 1.39E-17 | -0.619098 | 0.115 | 0.303 | 2.34E-13 |
| Col5a2 | 1.64E-17 | -0.6178865 | 0.259 | 0.435 | 2.77E-13 |
| Fbn1 | 2.03E-17 | -0.4788697 | 0.157 | 0.339 | 3.42E-13 |
| Loxl1 | 3.05E-17 | -0.5457609 | 0.139 | 0.317 | 5.15E-13 |
| Rpl23a-ps3 | 3.52E-17 | -0.3113505 | 0.791 | 0.813 | 5.93E-13 |
| Tkt | 4.19E-17 | -0.4005855 | 0.181 | 0.357 | 7.06E-13 |
| Mpzl1 | 5.71E-17 | -0.5613006 | 0.419 | 0.521 | 9.63E-13 |
| Nid1 | 6.10E-17 | -0.4795247 | 0.199 | 0.37 | 1.03E-12 |
| Cdk4 | 1.06E-16 | -0.3329976 | 0.859 | 0.85 | 1.78E-12 |
| Anp32b | 1.22E-16 | -0.3623402 | 0.872 | 0.859 | 2.05E-12 |
| Sec61b | 1.30E-16 | -0.4947877 | 0.72 | 0.715 | 2.19E-12 |
| Mfap4 | 2.69E-16 | -1.3773314 | 0.254 | 0.412 | 4.53E-12 |

| Online Table VI: Differentially Expressed Genes in Six Subclusters of Cluster 4. | | | | | |
|---|---|---|---|---|---|
| VTZ Cluster | | | | | |
| Gene | p value | Average log Fold Change | Average value VTZ | Average value Others | Adjusted p value |
| Myl3 | 8.48E-30 | 0.8881216 | 1 | 0.875 | 1.43E-25 |
| Fabp3 | 2.52E-23 | 0.5882898 | 1 | 0.961 | 4.24E-19 |
| Kcne1 | 2.58E-21 | 0.6884415 | 1 | 0.676 | 4.35E-17 |
| Bves | 2.82E-21 | 0.7603043 | 0.96 | 0.772 | 4.75E-17 |
| Myl2 | 1.02E-19 | 0.8253032 | 0.99 | 0.918 | 1.72E-15 |
| Cnn1 | 5.57E-18 | 0.7942641 | 0.911 | 0.644 | 9.39E-14 |
| Myh7 | 7.54E-18 | 0.6855811 | 1 | 0.968 | 1.27E-13 |
| Hcfc1r1 | 2.04E-17 | 0.4763867 | 1 | 0.972 | 3.43E-13 |
| Pdlim1 | 9.46E-17 | 0.5015756 | 0.703 | 0.288 | 1.59E-12 |
| Csrp1 | 1.84E-16 | 0.8175626 | 0.901 | 0.676 | 3.10E-12 |
| Tnnc1 | 4.47E-16 | 0.3790124 | 1 | 1 | 7.54E-12 |
| Cav1 | 6.21E-16 | -0.8334744 | 0.079 | 0.544 | 1.05E-11 |
| Cacna2d2 | 1.61E-15 | -0.9334504 | 0.089 | 0.544 | 2.72E-11 |
| Cda | 1.88E-15 | 0.463235 | 0.446 | 0.089 | 3.17E-11 |
| Itga9 | 2.31E-15 | 0.5012242 | 0.683 | 0.288 | 3.89E-11 |
| Krt18 | 5.96E-15 | 0.3542824 | 0.376 | 0.06 | 1.01E-10 |
| Tagln | 1.01E-14 | 1.0970512 | 0.683 | 0.288 | 1.71E-10 |
| Ucp2 | 2.09E-14 | 0.522271 | 0.653 | 0.263 | 3.52E-10 |
| Sorbs2 | 3.14E-14 | 0.4789474 | 1 | 0.979 | 5.30E-10 |
| Acta1 | 4.21E-14 | 1.7152264 | 0.614 | 0.249 | 7.10E-10 |
| Obscn | 7.24E-14 | -0.7310741 | 0.644 | 0.836 | 1.22E-09 |
| Grb10 | 1.62E-13 | 0.3981255 | 1 | 0.979 | 2.73E-09 |
| Actc1 | 1.73E-13 | 0.3868457 | 1 | 1 | 2.91E-09 |
| Mif | 1.96E-13 | 0.4223122 | 1 | 0.982 | 3.30E-09 |
| Fstl3 | 6.74E-13 | 0.3825237 | 0.594 | 0.217 | 1.14E-08 |
| Higd1a | 7.19E-13 | 0.4049906 | 0.99 | 0.961 | 1.21E-08 |
| Clu | 1.01E-12 | 0.845084 | 0.921 | 0.63 | 1.70E-08 |
| Dkk3 | 2.47E-12 | -0.636721 | 0.069 | 0.456 | 4.16E-08 |
| Tbx5 | 2.73E-12 | -0.5872823 | 0.188 | 0.577 | 4.60E-08 |
| Loxl2 | 2.75E-12 | 0.4524261 | 0.703 | 0.335 | 4.64E-08 |
| Pdlim3 | 2.99E-12 | 0.5950575 | 0.861 | 0.637 | 5.03E-08 |
| Mybphl | 3.64E-12 | -0.7158041 | 0 | 0.363 | 6.13E-08 |
| Wbp5 | 3.66E-12 | 0.4420065 | 0.99 | 0.982 | 6.16E-08 |
| Tmsb4x | 3.81E-12 | 0.4805278 | 1 | 1 | 6.42E-08 |
| Tnnt2 | 6.74E-12 | 0.2610935 | 1 | 1 | 1.14E-07 |
| Crip1 | 9.57E-12 | 0.5492857 | 0.921 | 0.722 | 1.61E-07 |
| Casq1 | 9.67E-12 | 0.7072578 | 0.901 | 0.651 | 1.63E-07 |
| Rhoc | 1.01E-11 | 0.4668145 | 0.921 | 0.762 | 1.70E-07 |
| Hspb1 | 1.17E-11 | 0.4786866 | 1 | 0.979 | 1.97E-07 |

| | | | | | |
|---|---|---|---|---|---|
| Cpne5 | 1.38E-11 | -0.7359129 | 0.168 | 0.523 | 2.33E-07 |
| Myl6 | 1.83E-11 | 0.4008596 | 1 | 0.989 | 3.08E-07 |
| Ank1 | 1.86E-11 | -0.5762634 | 0.168 | 0.523 | 3.13E-07 |
| Smyd2 | 2.10E-11 | 0.4164914 | 0.762 | 0.406 | 3.54E-07 |
| Prnp | 2.96E-11 | 0.6304625 | 0.891 | 0.698 | 4.98E-07 |
| Stard10 | 3.31E-11 | -0.6108752 | 0.149 | 0.488 | 5.57E-07 |
| Trim11 | 3.41E-11 | -0.3713915 | 0.059 | 0.413 | 5.75E-07 |
| Hspb6 | 4.59E-11 | 0.4979433 | 0.931 | 0.772 | 7.73E-07 |
| Sln | 5.61E-11 | -1.8990856 | 0.188 | 0.52 | 9.45E-07 |
| Cd63 | 1.25E-10 | 0.3295953 | 1 | 0.915 | 2.11E-06 |
| Hsp90aa1 | 1.80E-10 | 0.3502468 | 1 | 0.975 | 3.04E-06 |
| Myl1 | 2.18E-10 | -0.9636496 | 0.228 | 0.555 | 3.68E-06 |
| Shisa2 | 2.22E-10 | -0.4173553 | 0.02 | 0.345 | 3.74E-06 |
| Actn2 | 3.31E-10 | 0.4067013 | 1 | 0.954 | 5.59E-06 |
| Epha4 | 5.40E-10 | -0.5263321 | 0.188 | 0.523 | 9.10E-06 |
| Myh6 | 7.67E-10 | -1.1803489 | 0.911 | 0.943 | 1.29E-05 |
| Ldha | 7.71E-10 | 0.3575052 | 0.99 | 0.993 | 1.30E-05 |
| Atp2a2 | 1.01E-09 | -0.5392888 | 0.98 | 0.989 | 1.70E-05 |
| Cxcl12 | 1.04E-09 | 0.5520274 | 0.653 | 0.345 | 1.75E-05 |
| Spon1 | 1.20E-09 | -0.4791291 | 0.198 | 0.534 | 2.02E-05 |
| Kcnj3 | 1.78E-09 | -0.31306 | 0.02 | 0.331 | 2.99E-05 |
| Tceal7 | 2.46E-09 | 0.5147489 | 0.505 | 0.224 | 4.14E-05 |
| Cox6a2 | 2.75E-09 | -0.3743555 | 0.97 | 0.986 | 4.63E-05 |
| Cox6a1 | 3.19E-09 | 0.2522616 | 1 | 1 | 5.37E-05 |
| Fzd2 | 5.30E-09 | 0.3261453 | 0.693 | 0.416 | 8.94E-05 |
| Ilk | 5.31E-09 | 0.3742772 | 0.931 | 0.765 | 8.96E-05 |
| Dync1li1 | 8.88E-09 | 0.3326834 | 0.723 | 0.484 | 1.50E-04 |
| Slc22a1 | 9.33E-09 | -1.3112179 | 0.376 | 0.591 | 1.57E-04 |
| Perp | 1.06E-08 | -0.4856662 | 0.802 | 0.936 | 1.79E-04 |
| Bag2 | 1.17E-08 | 0.269631 | 0.743 | 0.459 | 1.97E-04 |
| Lbh | 1.42E-08 | 0.3962142 | 0.96 | 0.719 | 2.39E-04 |
| Pkp2 | 1.70E-08 | 0.3533328 | 0.891 | 0.694 | 2.86E-04 |
| Vsnl1 | 1.76E-08 | -0.4760659 | 0.02 | 0.295 | 2.96E-04 |
| Prkar1a | 2.06E-08 | 0.2988694 | 0.99 | 0.943 | 3.47E-04 |
| Trim47 | 2.72E-08 | 0.3389803 | 0.574 | 0.288 | 4.58E-04 |
| Otulin | 3.25E-08 | 0.2598989 | 0.545 | 0.263 | 5.48E-04 |
| Hspb7 | 3.26E-08 | 0.3056798 | 1 | 0.996 | 5.50E-04 |
| Gpx3 | 4.02E-08 | -0.8507088 | 0.96 | 0.968 | 6.77E-04 |
| Spats2l | 4.39E-08 | -0.3396964 | 0.109 | 0.413 | 7.41E-04 |
| Bsg | 5.16E-08 | 0.2517276 | 1 | 0.986 | 8.69E-04 |
| Tnfrsf12a | 5.52E-08 | 0.5026721 | 0.792 | 0.566 | 9.31E-04 |
| Nr2f2 | 5.82E-08 | -0.3132114 | 0.02 | 0.274 | 9.81E-04 |
| Aldoa | 5.84E-08 | 0.2664807 | 1 | 0.996 | 9.84E-04 |
| S100a11 | 6.24E-08 | 0.3482339 | 0.931 | 0.79 | 1.05E-03 |
| Nudt4 | 6.34E-08 | -0.3314348 | 0.317 | 0.598 | 1.07E-03 |

Figure 27. continued

| | | | | | |
|---|---|---|---|---|---|
| Gnao1 | 6.70E-08 | -0.4014 | 0.178 | 0.47 | 1.13E-03 |
| St3gal4 | 6.91E-08 | 0.280347 | 0.564 | 0.288 | 1.16E-03 |
| Slitrk4 | 7.28E-08 | 0.3003889 | 0.426 | 0.164 | 1.23E-03 |
| Csrp3 | 7.51E-08 | 0.3861928 | 1 | 1 | 1.27E-03 |
| Anxa2 | 8.59E-08 | 0.3129747 | 0.911 | 0.779 | 1.45E-03 |
| Mapre2 | 8.63E-08 | 0.3284087 | 0.901 | 0.733 | 1.45E-03 |
| Mest | 8.72E-08 | -1.0836392 | 0.228 | 0.512 | 1.47E-03 |
| Eno1 | 1.06E-07 | 0.3431877 | 0.99 | 0.907 | 1.78E-03 |
| Kcnj5 | 1.10E-07 | -0.4201844 | 0.228 | 0.505 | 1.85E-03 |
| Azin1 | 1.17E-07 | 0.3439342 | 0.901 | 0.751 | 1.98E-03 |
| Myoz2 | 1.29E-07 | 0.3852017 | 0.96 | 0.922 | 2.18E-03 |
| Prkcdbp | 1.51E-07 | 0.3491486 | 0.772 | 0.555 | 2.54E-03 |
| Nexn | 1.63E-07 | 0.2914978 | 1 | 0.979 | 2.74E-03 |
| Actn1 | 2.09E-07 | 0.3295066 | 0.663 | 0.427 | 3.53E-03 |
| Cyba | 2.10E-07 | 0.2998689 | 0.842 | 0.633 | 3.54E-03 |
| Smim1 | 2.43E-07 | -0.3565036 | 0.079 | 0.342 | 4.09E-03 |
| Acadl | 2.73E-07 | 0.2697279 | 0.99 | 0.957 | 4.60E-03 |
| Actr3 | 3.08E-07 | 0.3131481 | 0.96 | 0.826 | 5.19E-03 |
| Nrap | 3.24E-07 | 0.301697 | 0.762 | 0.552 | 5.46E-03 |
| AW551984 | 3.42E-07 | 0.30098 | 0.277 | 0.085 | 5.77E-03 |
| Mlf1 | 3.56E-07 | -0.3540878 | 0.95 | 0.947 | 6.00E-03 |
| Eln | 3.64E-07 | 0.6439887 | 0.525 | 0.267 | 6.14E-03 |
| Col12a1 | 3.78E-07 | 0.2926078 | 0.426 | 0.189 | 6.37E-03 |
| Lmod3 | 3.97E-07 | 0.2855678 | 0.564 | 0.331 | 6.69E-03 |
| Cald1 | 4.22E-07 | 0.4822677 | 0.792 | 0.555 | 7.11E-03 |
| Myl12a | 4.99E-07 | 0.3057381 | 1 | 0.964 | 8.42E-03 |
| Rxfp1 | 5.19E-07 | -0.3645931 | 0.178 | 0.441 | 8.75E-03 |
| Vcam1 | 5.20E-07 | -0.2534057 | 0.119 | 0.391 | 8.76E-03 |
| Dbi | 5.88E-07 | -0.3232175 | 0.97 | 0.982 | 9.91E-03 |
| Adam33 | 6.45E-07 | -0.2837261 | 0.04 | 0.278 | 1.09E-02 |
| Limk2 | 7.96E-07 | 0.2674435 | 0.564 | 0.313 | 1.34E-02 |
| Mfge8 | 8.14E-07 | 0.4032821 | 0.782 | 0.58 | 1.37E-02 |
| Trappc6a | 8.17E-07 | 0.2705239 | 0.733 | 0.502 | 1.38E-02 |
| Sgcg | 8.20E-07 | 0.3183618 | 0.703 | 0.473 | 1.38E-02 |
| Gng2 | 9.73E-07 | -0.3285623 | 0.267 | 0.523 | 1.64E-02 |
| Corin | 1.46E-06 | -0.3278278 | 0.168 | 0.456 | 2.45E-02 |
| Fbxl22 | 1.63E-06 | 0.3629031 | 0.95 | 0.833 | 2.75E-02 |
| Meis2 | 1.66E-06 | 0.4033354 | 0.663 | 0.448 | 2.79E-02 |
| Csrp2 | 1.66E-06 | 0.4041998 | 0.99 | 0.9 | 2.79E-02 |
| 6-Sep | 1.67E-06 | 0.3218408 | 0.683 | 0.459 | 2.82E-02 |
| Gyg | 1.68E-06 | 0.3811358 | 0.99 | 0.964 | 2.82E-02 |
| P23-455C13 | 1.80E-06 | 0.2960327 | 0.99 | 0.893 | 3.04E-02 |
| Etv1 | 2.03E-06 | -0.355084 | 0.089 | 0.331 | 3.42E-02 |
| Ngfrap1 | 2.38E-06 | 0.2830928 | 0.99 | 0.975 | 4.01E-02 |
| Ppp3ca | 2.49E-06 | -0.3453533 | 0.554 | 0.719 | 4.20E-02 |

Figure 27. continued

| Cdc14b | 2.62E-06 | -0.3201186 | 0.198 | 0.456 | 4.41E-02 |
|---|---|---|---|---|---|

Figure 27. continued

| | | TAVR Cluster | | | |
|---|---|---|---|---|---|
| Gene | p value | Average log Fold Change | Average value TAVR | Average value Others | Adjusted p value |
| Gja1 | 3.73E-27 | 0.8742722 | 0.867 | 0.268 | 6.29E-23 |
| Gpx3 | 1.10E-26 | -1.4822157 | 0.904 | 0.983 | 1.86E-22 |
| Atp1a1 | 3.40E-24 | -0.8435281 | 0.964 | 0.983 | 5.74E-20 |
| Myl7 | 8.25E-24 | -3.1707002 | 0.904 | 0.957 | 1.39E-19 |
| Hey2 | 1.50E-23 | 0.4773099 | 0.747 | 0.171 | 2.52E-19 |
| Mb | 1.02E-22 | 1.2923422 | 0.94 | 0.522 | 1.71E-18 |
| Myl9 | 3.40E-21 | -0.928786 | 1 | 0.99 | 5.73E-17 |
| Tuba1a | 5.61E-21 | -0.9217527 | 0.916 | 0.973 | 9.46E-17 |
| Myl4 | 1.17E-20 | -1.3434072 | 0.988 | 0.987 | 1.97E-16 |
| Cst3 | 1.25E-20 | -0.7343775 | 0.988 | 0.993 | 2.10E-16 |
| Sox9 | 1.28E-20 | 0.6312107 | 0.361 | 0.023 | 2.15E-16 |
| Atp1b1 | 2.75E-20 | -0.8872522 | 1 | 0.997 | 4.64E-16 |
| Tpt1 | 6.47E-20 | 0.3458798 | 1 | 1 | 1.09E-15 |
| Csrp3 | 1.44E-19 | -0.7742254 | 1 | 1 | 2.42E-15 |
| Col1a2 | 3.08E-19 | 1.3643388 | 0.627 | 0.187 | 5.18E-15 |
| Slc22a1 | 4.10E-19 | -1.8230054 | 0.096 | 0.656 | 6.90E-15 |
| Bgn | 8.03E-19 | 1.0669867 | 0.602 | 0.164 | 1.35E-14 |
| Clu | 1.77E-18 | -1.2854454 | 0.373 | 0.799 | 2.99E-14 |
| Sh3kbp1 | 5.74E-18 | 0.5633899 | 0.88 | 0.495 | 9.68E-14 |
| Pln | 1.09E-17 | 0.6244932 | 1 | 0.94 | 1.85E-13 |
| Igfbp5 | 2.23E-17 | -1.5623443 | 0.289 | 0.749 | 3.76E-13 |
| Abcc9 | 2.58E-17 | 0.3179199 | 0.627 | 0.14 | 4.35E-13 |
| Ppip5k2 | 3.24E-17 | 0.3714452 | 0.747 | 0.227 | 5.46E-13 |
| Tnfaip8 | 3.91E-17 | 0.2894052 | 0.482 | 0.084 | 6.59E-13 |
| Ramp2 | 3.95E-17 | 0.6257669 | 0.422 | 0.067 | 6.66E-13 |
| Dpt | 4.90E-17 | 0.5024972 | 0.361 | 0.04 | 8.26E-13 |
| Mmp2 | 5.46E-17 | 0.3619499 | 0.349 | 0.033 | 9.20E-13 |
| Igf2 | 6.11E-17 | 0.6796281 | 1 | 0.776 | 1.03E-12 |
| Cryab | 6.75E-17 | -0.4464053 | 1 | 1 | 1.14E-12 |
| Tpm1 | 2.81E-16 | -0.4310459 | 1 | 1 | 4.74E-12 |
| Lum | 3.42E-16 | 0.7491928 | 0.446 | 0.087 | 5.76E-12 |
| Aspscr1 | 3.45E-16 | -0.9139475 | 0.554 | 0.819 | 5.81E-12 |
| Dcn | 4.05E-16 | 1.2985043 | 0.482 | 0.114 | 6.83E-12 |
| Fibin | 9.79E-16 | 0.3931671 | 0.277 | 0.017 | 1.65E-11 |
| Itih5 | 1.05E-15 | 0.2637767 | 0.265 | 0.013 | 1.77E-11 |
| Tnnc1 | 1.91E-15 | -0.4706173 | 1 | 1 | 3.21E-11 |
| Tcap | 2.25E-15 | -0.8773648 | 0.88 | 0.936 | 3.80E-11 |
| Ramp1 | 5.31E-15 | -0.8747956 | 0.831 | 0.893 | 8.95E-11 |
| Rps15a | 6.76E-15 | 0.3347131 | 1 | 1 | 1.14E-10 |

| | | | | | |
|---|---|---|---|---|---|
| Rps27a | 7.93E-15 | 0.2935912 | 1 | 1 | 1.34E-10 |
| Rpl39 | 1.08E-14 | 0.2819523 | 1 | 0.997 | 1.82E-10 |
| Rpl32 | 1.91E-14 | 0.3343278 | 1 | 1 | 3.21E-10 |
| Cthrc1 | 2.31E-14 | 0.5082993 | 0.289 | 0.027 | 3.90E-10 |
| Mt2 | 2.62E-14 | 0.3263139 | 0.53 | 0.13 | 4.41E-10 |
| Postn | 2.79E-14 | 1.3159744 | 0.627 | 0.234 | 4.71E-10 |
| Ebf1 | 3.64E-14 | 0.3220781 | 0.265 | 0.02 | 6.14E-10 |
| Tgfbi | 6.17E-14 | 0.4116364 | 0.349 | 0.054 | 1.04E-09 |
| Col1a1 | 7.18E-14 | 1.185278 | 0.578 | 0.204 | 1.21E-09 |
| mt-Co2 | 9.29E-14 | 0.4498445 | 1 | 0.997 | 1.57E-09 |
| Rps4x | 9.37E-14 | 0.3151746 | 1 | 0.993 | 1.58E-09 |
| Hspb7 | 1.05E-13 | -0.4500056 | 1 | 0.997 | 1.76E-09 |
| Rps5 | 1.22E-13 | 0.2921647 | 1 | 1 | 2.05E-09 |
| Col6a3 | 1.38E-13 | 0.2546827 | 0.349 | 0.05 | 2.32E-09 |
| Tbx5 | 2.96E-13 | -0.6904229 | 0.157 | 0.562 | 4.99E-09 |
| Sln | 3.44E-13 | -2.6493055 | 0.096 | 0.525 | 5.80E-09 |
| H19 | 4.25E-13 | 0.6042401 | 1 | 0.722 | 7.16E-09 |
| Col6a1 | 6.32E-13 | 0.3317666 | 0.434 | 0.097 | 1.06E-08 |
| Cacna2d2 | 9.12E-13 | -0.9238713 | 0.084 | 0.518 | 1.54E-08 |
| Pdlim7 | 9.64E-13 | -0.5889799 | 0.795 | 0.866 | 1.62E-08 |
| Col3a1 | 1.22E-12 | 1.3556943 | 0.53 | 0.197 | 2.06E-08 |
| Nid1 | 1.30E-12 | 0.2965704 | 0.482 | 0.12 | 2.19E-08 |
| Hspb1 | 1.30E-12 | -0.5327019 | 0.988 | 0.983 | 2.20E-08 |
| mt-Nd1 | 1.49E-12 | 0.4893615 | 1 | 1 | 2.51E-08 |
| Atp5g3 | 1.98E-12 | 0.3537953 | 1 | 0.997 | 3.33E-08 |
| Col5a1 | 2.11E-12 | 0.3575973 | 0.337 | 0.057 | 3.56E-08 |
| Acsl1 | 2.16E-12 | 0.3053605 | 0.795 | 0.308 | 3.64E-08 |
| Smyd2 | 4.33E-12 | 0.3744746 | 0.88 | 0.395 | 7.29E-08 |
| Map1lc3a | 4.63E-12 | -0.450262 | 1 | 0.987 | 7.81E-08 |
| Aspn | 5.83E-12 | 0.4182583 | 0.301 | 0.047 | 9.83E-08 |
| Fbln2 | 6.63E-12 | 0.268029 | 0.253 | 0.027 | 1.12E-07 |
| Myh6 | 7.19E-12 | -1.448186 | 0.94 | 0.933 | 1.21E-07 |
| Cpne5 | 7.50E-12 | -0.7656262 | 0.108 | 0.518 | 1.26E-07 |
| Ptn | 7.66E-12 | 1.2147831 | 0.627 | 0.271 | 1.29E-07 |
| Rpl13 | 9.98E-12 | 0.2536602 | 1 | 1 | 1.68E-07 |
| Mt1 | 2.36E-11 | 0.4528754 | 0.976 | 0.709 | 3.98E-07 |
| Mpc2 | 2.95E-11 | 0.374532 | 1 | 0.963 | 4.97E-07 |
| Ubb | 3.56E-11 | -0.4303798 | 1 | 0.98 | 5.99E-07 |
| Slc25a13 | 4.71E-11 | 0.2753888 | 0.651 | 0.247 | 7.94E-07 |
| Lclat1 | 5.29E-11 | 0.3250579 | 0.759 | 0.338 | 8.91E-07 |
| Fbn1 | 5.95E-11 | 0.2968508 | 0.398 | 0.09 | 1.00E-06 |
| Stard10 | 6.09E-11 | -0.6161322 | 0.096 | 0.482 | 1.03E-06 |
| Atp5f1 | 1.01E-10 | 0.3323998 | 1 | 0.997 | 1.70E-06 |
| Nkx2-5 | 1.11E-10 | -0.4755291 | 0.928 | 0.906 | 1.86E-06 |
| Rpsa | 1.11E-10 | 0.3049104 | 1 | 0.997 | 1.87E-06 |

Figure 27. continued

| | | | | | |
|---|---|---|---|---|---|
| mt–Atp6 | 1.21E-10 | 0.3670055 | 1 | 1 | 2.04E-06 |
| Lmo7 | 1.27E-10 | 0.3937692 | 0.976 | 0.853 | 2.14E-06 |
| Hspb2 | 1.45E-10 | -0.4305865 | 0.916 | 0.926 | 2.44E-06 |
| Col5a2 | 1.55E-10 | 0.4542545 | 0.53 | 0.184 | 2.61E-06 |
| Rps25 | 1.83E-10 | 0.253548 | 1 | 1 | 3.08E-06 |
| Cnn1 | 1.94E-10 | -0.780457 | 0.542 | 0.763 | 3.27E-06 |
| Rplp0 | 1.99E-10 | 0.3200605 | 1 | 0.997 | 3.36E-06 |
| Smpx | 2.08E-10 | 0.4236365 | 1 | 0.916 | 3.50E-06 |
| Eef1a1 | 2.31E-10 | 0.268669 | 1 | 1 | 3.89E-06 |
| Ammecr1 | 2.43E-10 | 0.3378338 | 0.843 | 0.428 | 4.10E-06 |
| Ptgds | 2.52E-10 | 0.5200913 | 0.867 | 0.548 | 4.25E-06 |
| Sfrp2 | 3.23E-10 | 0.7411864 | 0.337 | 0.08 | 5.44E-06 |
| Hspd1 | 4.04E-10 | 0.338728 | 0.988 | 0.91 | 6.81E-06 |
| Mfap4 | 4.12E-10 | 0.6899754 | 0.506 | 0.184 | 6.94E-06 |
| Meox1 | 4.82E-10 | 0.3873257 | 0.301 | 0.06 | 8.13E-06 |
| Ivns1abp | 5.84E-10 | 0.3913094 | 0.952 | 0.676 | 9.84E-06 |
| Ndufa3 | 6.02E-10 | -0.3189676 | 0.988 | 1 | 1.01E-05 |
| Rps19 | 8.95E-10 | 0.2870915 | 1 | 1 | 1.51E-05 |
| Htra1 | 9.63E-10 | -0.657337 | 0.41 | 0.686 | 1.62E-05 |
| Myl1 | 9.83E-10 | -0.906666 | 0.205 | 0.542 | 1.66E-05 |
| Fbln5 | 1.09E-09 | 0.4732958 | 0.337 | 0.08 | 1.84E-05 |
| Meis2 | 1.12E-09 | 0.317973 | 0.855 | 0.408 | 1.89E-05 |
| Fxyd1 | 1.17E-09 | -0.3053659 | 1 | 1 | 1.97E-05 |
| Tagln2 | 1.24E-09 | 0.6756638 | 0.59 | 0.271 | 2.08E-05 |
| Uqcrfs1 | 1.52E-09 | 0.3212259 | 1 | 0.97 | 2.57E-05 |
| Rbp1 | 1.93E-09 | 0.4253558 | 0.386 | 0.11 | 3.24E-05 |
| Rps12 | 2.10E-09 | 0.3030898 | 1 | 0.993 | 3.54E-05 |
| Vim | 2.25E-09 | 0.8122612 | 1 | 0.833 | 3.79E-05 |
| Atp5g1 | 2.30E-09 | 0.2520168 | 1 | 1 | 3.87E-05 |
| Ifitm3 | 2.51E-09 | 0.3315311 | 0.313 | 0.07 | 4.23E-05 |
| Myl2 | 2.93E-09 | 0.5397332 | 1 | 0.92 | 4.93E-05 |
| Fam198b | 3.25E-09 | 0.2745672 | 0.675 | 0.291 | 5.48E-05 |
| Mybph1 | 3.77E-09 | -0.6723145 | 0.012 | 0.338 | 6.36E-05 |
| Ddc | 3.91E-09 | 0.4423069 | 0.59 | 0.251 | 6.58E-05 |
| Npm1 | 3.94E-09 | 0.284272 | 1 | 0.98 | 6.64E-05 |
| Tmem176b | 5.18E-09 | -0.4425305 | 0.807 | 0.843 | 8.73E-05 |
| Lbh | 5.50E-09 | 0.3647519 | 0.976 | 0.729 | 9.28E-05 |
| Emilin1 | 7.61E-09 | 0.2696628 | 0.313 | 0.074 | 1.28E-04 |
| Cs | 7.93E-09 | 0.3225489 | 0.964 | 0.866 | 1.34E-04 |
| Arhgap31 | 8.46E-09 | -0.5686239 | 0.843 | 0.849 | 1.43E-04 |
| Fxyd6 | 1.13E-08 | 0.3220087 | 0.361 | 0.107 | 1.90E-04 |
| mt–Nd2 | 1.24E-08 | 0.2943004 | 1 | 1 | 2.09E-04 |
| Trdn | 1.36E-08 | -0.4028084 | 0.952 | 0.946 | 2.30E-04 |
| Gpc1 | 1.42E-08 | -0.4624288 | 0.446 | 0.642 | 2.40E-04 |
| Ctsl | 1.50E-08 | -0.409605 | 0.916 | 0.883 | 2.53E-04 |

Figure 27. continued

| | | | | | |
|---|---|---|---|---|---|
| Csrp2 | 1.87E-08 | -0.8386267 | 0.94 | 0.92 | 3.15E-04 |
| Pabpc1 | 1.94E-08 | 0.3279608 | 0.988 | 0.89 | 3.27E-04 |
| Smarcd3 | 1.95E-08 | -0.4038013 | 0.651 | 0.749 | 3.29E-04 |
| Des | 2.09E-08 | -0.3905642 | 0.976 | 0.997 | 3.52E-04 |
| Gadd45g | 2.11E-08 | -0.69967 | 0.41 | 0.629 | 3.56E-04 |
| Ndufa11 | 2.25E-08 | -0.2733752 | 1 | 0.997 | 3.79E-04 |
| Hspe1 | 2.36E-08 | 0.2674596 | 1 | 0.97 | 3.98E-04 |
| Pgam2 | 2.39E-08 | -0.4745614 | 1 | 0.993 | 4.03E-04 |
| Rbpms | 2.61E-08 | -0.3802963 | 1 | 0.973 | 4.40E-04 |
| Zbtb20 | 2.99E-08 | -0.454395 | 0.904 | 0.926 | 5.04E-04 |
| Vcan | 3.07E-08 | 0.2618419 | 0.723 | 0.321 | 5.17E-04 |
| Ybx1 | 3.45E-08 | 0.2757943 | 1 | 0.997 | 5.81E-04 |
| Mrpl42 | 3.68E-08 | 0.3452667 | 1 | 0.977 | 6.20E-04 |
| Myl6 | 3.70E-08 | -0.398012 | 1 | 0.99 | 6.24E-04 |
| Nedd8 | 4.55E-08 | -0.2691624 | 0.988 | 0.98 | 7.67E-04 |
| Mlip | 5.30E-08 | -0.4516999 | 0.916 | 0.88 | 8.93E-04 |
| Tpi1 | 5.57E-08 | -0.3295772 | 1 | 0.99 | 9.39E-04 |
| Ndufa1 | 6.79E-08 | -0.3132225 | 0.988 | 0.99 | 1.14E-03 |
| Lgals1 | 7.40E-08 | 0.6345023 | 0.988 | 0.9 | 1.25E-03 |
| Hopx | 8.21E-08 | 0.2878327 | 0.964 | 0.753 | 1.38E-03 |
| Tnni3 | 8.93E-08 | -0.2940228 | 0.976 | 1 | 1.50E-03 |
| Nnt | 1.01E-07 | 0.3335089 | 0.892 | 0.682 | 1.71E-03 |
| Dpysl3 | 1.09E-07 | -0.4613995 | 0.867 | 0.876 | 1.83E-03 |
| Acadm | 1.18E-07 | 0.2660391 | 0.988 | 0.87 | 2.00E-03 |
| Pgam1 | 1.19E-07 | -0.3469662 | 0.976 | 0.977 | 2.00E-03 |
| Fam78a | 1.19E-07 | -0.4479163 | 0.325 | 0.559 | 2.00E-03 |
| Hspa9 | 1.31E-07 | 0.2857245 | 0.988 | 0.876 | 2.20E-03 |
| P23-455C13 | 1.43E-07 | -0.521012 | 0.88 | 0.93 | 2.41E-03 |
| Pfkp | 1.45E-07 | -0.404847 | 0.687 | 0.753 | 2.45E-03 |
| Sfrp1 | 1.46E-07 | -0.8520582 | 0.723 | 0.779 | 2.45E-03 |
| Stk39 | 1.56E-07 | 0.3009448 | 0.855 | 0.538 | 2.63E-03 |
| Adprhl1 | 1.65E-07 | -0.4450706 | 0.904 | 0.893 | 2.79E-03 |
| Wisp1 | 1.83E-07 | -0.4733104 | 0.47 | 0.659 | 3.08E-03 |
| Vsnl1 | 1.90E-07 | -0.492652 | 0.012 | 0.281 | 3.20E-03 |
| Perp | 2.03E-07 | -0.5255122 | 0.94 | 0.89 | 3.42E-03 |
| Chchd3 | 2.43E-07 | 0.2688653 | 0.964 | 0.846 | 4.09E-03 |
| Rgs6 | 2.48E-07 | -0.3854022 | 0.241 | 0.492 | 4.19E-03 |
| Tnnt1 | 2.94E-07 | -1.2892015 | 0.614 | 0.729 | 4.95E-03 |
| Oxct1 | 2.98E-07 | 0.2703002 | 0.964 | 0.746 | 5.03E-03 |
| Prnp | 3.07E-07 | -0.57589 | 0.699 | 0.763 | 5.18E-03 |
| Rpl12 | 3.24E-07 | 0.255163 | 1 | 0.99 | 5.46E-03 |
| Acta2 | 3.50E-07 | 0.4823699 | 0.892 | 0.605 | 5.89E-03 |
| Prkaa2 | 3.63E-07 | 0.2740184 | 0.892 | 0.595 | 6.12E-03 |
| Rrad | 3.69E-07 | -0.425156 | 0.855 | 0.92 | 6.22E-03 |
| 11-Sep | 3.98E-07 | 0.2607788 | 0.542 | 0.231 | 6.70E-03 |

**Figure 27.
continued**

| Gene | | | | | |
|---|---|---|---|---|---|
| Ntm | 4.53E-07 | -0.5418883 | 0.277 | 0.518 | 7.64E-03 Figure 27. |
| Cav1 | 4.78E-07 | -0.6289092 | 0.217 | 0.478 | 8.05E-03 continued |
| Epha4 | 4.95E-07 | -0.4993685 | 0.241 | 0.488 | 8.34E-03 |
| Tomm5 | 5.10E-07 | 0.2929507 | 0.976 | 0.86 | 8.60E-03 |
| Dynlrb1 | 5.72E-07 | -0.2900791 | 0.988 | 0.936 | 9.64E-03 |
| Fam162a | 6.84E-07 | 0.2534339 | 0.976 | 0.933 | 1.15E-02 |
| Kcnj5 | 8.07E-07 | -0.4490729 | 0.265 | 0.478 | 1.36E-02 |
| Rpl22l1 | 8.62E-07 | 0.2678107 | 1 | 0.983 | 1.45E-02 |
| Gas6 | 9.99E-07 | -0.3564337 | 0.819 | 0.833 | 1.68E-02 |
| Casq1 | 1.22E-06 | -0.8542752 | 0.675 | 0.729 | 2.06E-02 |
| Pkm | 1.44E-06 | -0.2736811 | 1 | 0.977 | 2.43E-02 |
| Igfbp7 | 1.49E-06 | 0.2729761 | 0.494 | 0.221 | 2.52E-02 |
| C1qbp | 1.54E-06 | 0.305309 | 0.976 | 0.776 | 2.59E-02 |
| Ankrd1 | 1.58E-06 | -0.8372374 | 0.928 | 0.9 | 2.66E-02 |
| mt-Nd3 | 1.66E-06 | 0.2909843 | 1 | 0.997 | 2.80E-02 |
| Actn2 | 1.74E-06 | -0.3318136 | 0.976 | 0.963 | 2.94E-02 |
| Atp6v1f | 1.77E-06 | -0.2980792 | 0.892 | 0.906 | 2.99E-02 |
| Arhgef7 | 1.82E-06 | -0.3632949 | 0.47 | 0.609 | 3.07E-02 |
| Sdhd | 2.02E-06 | 0.2581014 | 0.976 | 0.933 | 3.41E-02 |
| Id2 | 2.22E-06 | -0.5485623 | 0.771 | 0.819 | 3.74E-02 |
| Tmem51 | 2.52E-06 | -0.3578754 | 0.349 | 0.552 | 4.25E-02 |
| Tpm4 | 2.72E-06 | 0.3718828 | 0.639 | 0.341 | 4.59E-02 |
| Rgs12 | 2.93E-06 | -0.4036889 | 0.325 | 0.518 | 4.94E-02 |

| ATZ Cluster | | | | | |
|---|---|---|---|---|---|
| Gene | p value | Average log Fold Change | Average value ATZ | Average value Others | Adjusted p value |
| Fgf12 | 1.03E-47 | 1.0460367 | 0.701 | 0.025 | 1.74E-43 |
| Nppa | 1.74E-37 | 3.6383132 | 0.91 | 0.251 | 2.93E-33 |
| Mybph1 | 1.32E-32 | 0.9911819 | 0.836 | 0.146 | 2.22E-28 |
| Sln | 4.41E-30 | 1.4978235 | 1 | 0.311 | 7.43E-26 |
| Myl7 | 1.13E-26 | 1.3718916 | 1 | 0.933 | 1.91E-22 |
| Myl4 | 2.23E-26 | 0.9792574 | 1 | 0.984 | 3.76E-22 |
| Pln | 1.34E-24 | -1.6335118 | 0.866 | 0.971 | 2.25E-20 |
| Pam | 2.46E-23 | 1.1471012 | 1 | 0.943 | 4.14E-19 |
| Aif1l | 7.84E-23 | 0.6417681 | 0.776 | 0.241 | 1.32E-18 |
| Myh7 | 7.85E-23 | -1.5262137 | 0.955 | 0.981 | 1.32E-18 |
| Gpx3 | 1.26E-22 | 0.9041634 | 1 | 0.959 | 2.12E-18 |
| Lbh | 1.94E-22 | -1.2390256 | 0.388 | 0.867 | 3.26E-18 |
| Myl2 | 8.59E-22 | -2.7909581 | 0.881 | 0.949 | 1.45E-17 |
| Kcne1 | 2.34E-21 | -1.4654571 | 0.313 | 0.857 | 3.94E-17 |
| Dkk3 | 1.33E-20 | 0.7393445 | 0.791 | 0.26 | 2.24E-16 |
| Myh6 | 6.35E-20 | 0.9932658 | 1 | 0.921 | 1.07E-15 |
| Cav1 | 1.50E-19 | 0.6840497 | 0.91 | 0.317 | 2.53E-15 |

| | | | | | |
|---|---|---|---|---|---|
| Pgam2 | 1.99E-19 | 0.6294304 | 1 | 0.994 | 3.35E-15 |
| Grb10 | 1.49E-18 | -0.6553537 | 0.955 | 0.99 | 2.51E-14 |
| Stard10 | 1.54E-17 | 0.5886779 | 0.836 | 0.305 | 2.60E-13 |
| Epha4 | 1.59E-17 | 0.5627403 | 0.866 | 0.343 | 2.68E-13 |
| Sepw1 | 4.54E-17 | -0.6003899 | 0.985 | 0.99 | 7.66E-13 |
| Obscn | 7.31E-17 | 0.6912277 | 0.94 | 0.752 | 1.23E-12 |
| Camk1d | 2.55E-16 | 0.4354765 | 0.493 | 0.092 | 4.29E-12 |
| Adam33 | 9.68E-16 | 0.4322256 | 0.582 | 0.137 | 1.63E-11 |
| Kcnh7 | 2.31E-15 | 0.2712808 | 0.269 | 0.016 | 3.90E-11 |
| Gm15543 | 2.44E-15 | 0.4421681 | 0.552 | 0.13 | 4.11E-11 |
| Trim11 | 1.08E-14 | 0.4959845 | 0.672 | 0.244 | 1.83E-10 |
| H19 | 1.27E-14 | 0.8265658 | 0.97 | 0.743 | 2.15E-10 |
| Myl3 | 1.38E-14 | -1.1908077 | 0.821 | 0.927 | 2.32E-10 |
| Reep5 | 1.76E-14 | 0.4466617 | 0.985 | 0.943 | 2.97E-10 |
| Vsnl1 | 1.76E-14 | 0.2929932 | 0.612 | 0.14 | 2.97E-10 |
| Smyd2 | 2.46E-14 | -0.669464 | 0.06 | 0.594 | 4.15E-10 |
| Gja5 | 3.79E-14 | 0.3730891 | 0.463 | 0.089 | 6.40E-10 |
| Ankrd1 | 6.35E-14 | 0.8495606 | 0.985 | 0.889 | 1.07E-09 |
| Pvalb | 6.91E-14 | 0.522515 | 0.373 | 0.057 | 1.17E-09 |
| Igf2 | 1.37E-13 | 0.5769702 | 0.985 | 0.79 | 2.32E-09 |
| Aebp1 | 1.86E-13 | 0.3491065 | 0.478 | 0.108 | 3.13E-09 |
| P23-378D16. | 2.81E-13 | 0.2824661 | 0.388 | 0.067 | 4.74E-09 |
| Trim54 | 3.30E-13 | 0.3044472 | 0.373 | 0.067 | 5.56E-09 |
| Myl9 | 9.17E-13 | 0.5091758 | 1 | 0.99 | 1.55E-08 |
| Nppb | 1.23E-12 | 1.3524643 | 0.672 | 0.308 | 2.07E-08 |
| Slc22a1 | 3.27E-12 | 0.7044713 | 0.881 | 0.46 | 5.51E-08 |
| Tmem163 | 3.78E-12 | 0.3001842 | 0.418 | 0.086 | 6.37E-08 |
| Aldh1b1 | 6.30E-12 | 0.5573107 | 0.836 | 0.543 | 1.06E-07 |
| Myom2 | 8.74E-12 | 0.451558 | 0.731 | 0.302 | 1.47E-07 |
| Fras1 | 1.91E-11 | 0.4041305 | 0.716 | 0.295 | 3.21E-07 |
| Ahnak | 1.94E-11 | -0.5016114 | 0.358 | 0.778 | 3.26E-07 |
| Mpped2 | 2.81E-11 | -0.5751969 | 0.015 | 0.467 | 4.74E-07 |
| Meg3 | 3.81E-11 | -1.1944276 | 0.224 | 0.644 | 6.42E-07 |
| Ckm | 7.70E-11 | 0.4498846 | 1 | 0.975 | 1.30E-06 |
| Cdh2 | 1.20E-10 | -0.4376325 | 0.791 | 0.959 | 2.02E-06 |
| Atp2a2 | 1.92E-10 | 0.4823464 | 1 | 0.984 | 3.24E-06 |
| Nr2f1 | 1.92E-10 | 0.2932607 | 0.448 | 0.111 | 3.24E-06 |
| Nfib | 5.13E-10 | -0.4655429 | 0.881 | 0.937 | 8.64E-06 |
| Ybx1 | 5.45E-10 | 0.3131318 | 1 | 0.997 | 9.19E-06 |
| Crip1 | 5.82E-10 | -0.8751033 | 0.627 | 0.806 | 9.81E-06 |
| Tbx5 | 7.36E-10 | 0.4135111 | 0.806 | 0.403 | 1.24E-05 |
| Gng2 | 8.76E-10 | 0.4424192 | 0.716 | 0.4 | 1.48E-05 |
| Rsrp1 | 1.01E-09 | -0.4679817 | 0.791 | 0.937 | 1.70E-05 |
| Kcnj3 | 1.05E-09 | 0.3067799 | 0.552 | 0.184 | 1.78E-05 |
| Cd24a | 1.08E-09 | 0.4654658 | 0.672 | 0.33 | 1.82E-05 |

Figure 27. continued

| | | | | | |
|---|---|---|---|---|---|
| Nr2f2 | 1.29E-09 | 0.2617109 | 0.493 | 0.146 | 2.18E-05 |
| Meis2 | 1.40E-09 | -0.5517023 | 0.164 | 0.578 | 2.36E-05 |
| Loxl2 | 2.31E-09 | -0.454992 | 0.09 | 0.505 | 3.90E-05 |
| Tmsb10 | 2.81E-09 | 0.2979717 | 1 | 0.997 | 4.74E-05 |
| Cdkn1c | 4.23E-09 | -1.0742778 | 0.463 | 0.743 | 7.13E-05 |
| Bves | 4.64E-09 | -0.5876609 | 0.716 | 0.844 | 7.83E-05 |
| Chchd10 | 5.18E-09 | 0.2555925 | 1 | 1 | 8.74E-05 |
| Fstl1 | 5.70E-09 | -0.4973816 | 0.791 | 0.93 | 9.61E-05 |
| Hey2 | 1.09E-08 | -0.3719691 | 0 | 0.359 | 1.83E-04 |
| Dok4 | 1.16E-08 | 0.3362289 | 0.537 | 0.21 | 1.96E-04 |
| Hint1 | 1.84E-08 | 0.2538916 | 1 | 0.997 | 3.11E-04 |
| Krt19 | 2.11E-08 | 0.2764966 | 0.284 | 0.06 | 3.56E-04 |
| Gsn | 2.36E-08 | -0.4355649 | 0.552 | 0.829 | 3.98E-04 |
| Vcan | 2.73E-08 | -0.5657729 | 0.104 | 0.473 | 4.60E-04 |
| Acaa2 | 2.79E-08 | 0.4218552 | 0.97 | 0.863 | 4.71E-04 |
| Nr2c2ap | 3.72E-08 | 0.3900386 | 0.746 | 0.46 | 6.26E-04 |
| Tnni3 | 4.21E-08 | 0.2640321 | 1 | 0.994 | 7.10E-04 |
| Lclat1 | 4.74E-08 | -0.3756496 | 0.134 | 0.492 | 7.99E-04 |
| Ptma | 5.05E-08 | -0.3931543 | 0.985 | 0.994 | 8.52E-04 |
| Nt5dc2 | 5.22E-08 | 0.3756266 | 0.851 | 0.651 | 8.80E-04 |
| Dbi | 5.47E-08 | 0.3197299 | 1 | 0.975 | 9.21E-04 |
| Bambi | 5.96E-08 | -0.5102231 | 0.552 | 0.822 | 1.00E-03 |
| Mfap2 | 6.33E-08 | -0.5457412 | 0.239 | 0.6 | 1.07E-03 |
| Pdlim1 | 6.44E-08 | -0.4020846 | 0.104 | 0.46 | 1.09E-03 |
| Myh10 | 6.98E-08 | -0.3787927 | 0.493 | 0.787 | 1.18E-03 |
| Hn1 | 7.85E-08 | 0.4098032 | 0.955 | 0.924 | 1.32E-03 |
| St3gal4 | 8.18E-08 | -0.3866854 | 0.075 | 0.422 | 1.38E-03 |
| Irx4 | 8.86E-08 | -0.3320642 | 0.03 | 0.371 | 1.49E-03 |
| Cyba | 9.20E-08 | -0.4147019 | 0.448 | 0.74 | 1.55E-03 |
| Mest | 9.35E-08 | 0.8875193 | 0.672 | 0.387 | 1.58E-03 |
| Tnni1 | 1.01E-07 | -0.2535875 | 1 | 1 | 1.69E-03 |
| Tsc22d3 | 1.09E-07 | -0.5060589 | 0.552 | 0.803 | 1.83E-03 |
| Cox6a2 | 1.10E-07 | 0.320458 | 1 | 0.978 | 1.86E-03 |
| Asb11 | 1.12E-07 | -0.2876254 | 0.06 | 0.419 | 1.88E-03 |
| Smtnl2 | 1.13E-07 | -0.4366065 | 0.194 | 0.552 | 1.90E-03 |
| Tmsb4x | 1.32E-07 | -0.4851596 | 1 | 1 | 2.23E-03 |
| Eif4a2 | 1.35E-07 | -0.3885233 | 0.836 | 0.905 | 2.28E-03 |
| Eln | 1.57E-07 | -0.8790379 | 0.06 | 0.394 | 2.65E-03 |
| Pde4dip | 2.07E-07 | -0.3879516 | 0.328 | 0.648 | 3.48E-03 |
| Lpar3 | 2.56E-07 | -0.3461991 | 0.119 | 0.451 | 4.32E-03 |
| Gnai2 | 2.75E-07 | -0.3840481 | 0.627 | 0.819 | 4.64E-03 |
| Rxfp1 | 3.38E-07 | 0.3079711 | 0.627 | 0.317 | 5.70E-03 |
| Asph | 3.70E-07 | -0.3337545 | 0.657 | 0.863 | 6.24E-03 |
| Doc2g | 3.72E-07 | 0.4066659 | 0.627 | 0.378 | 6.27E-03 |
| Cd81 | 4.05E-07 | -0.3477704 | 0.955 | 0.997 | 6.82E-03 |

Figure 27. continued

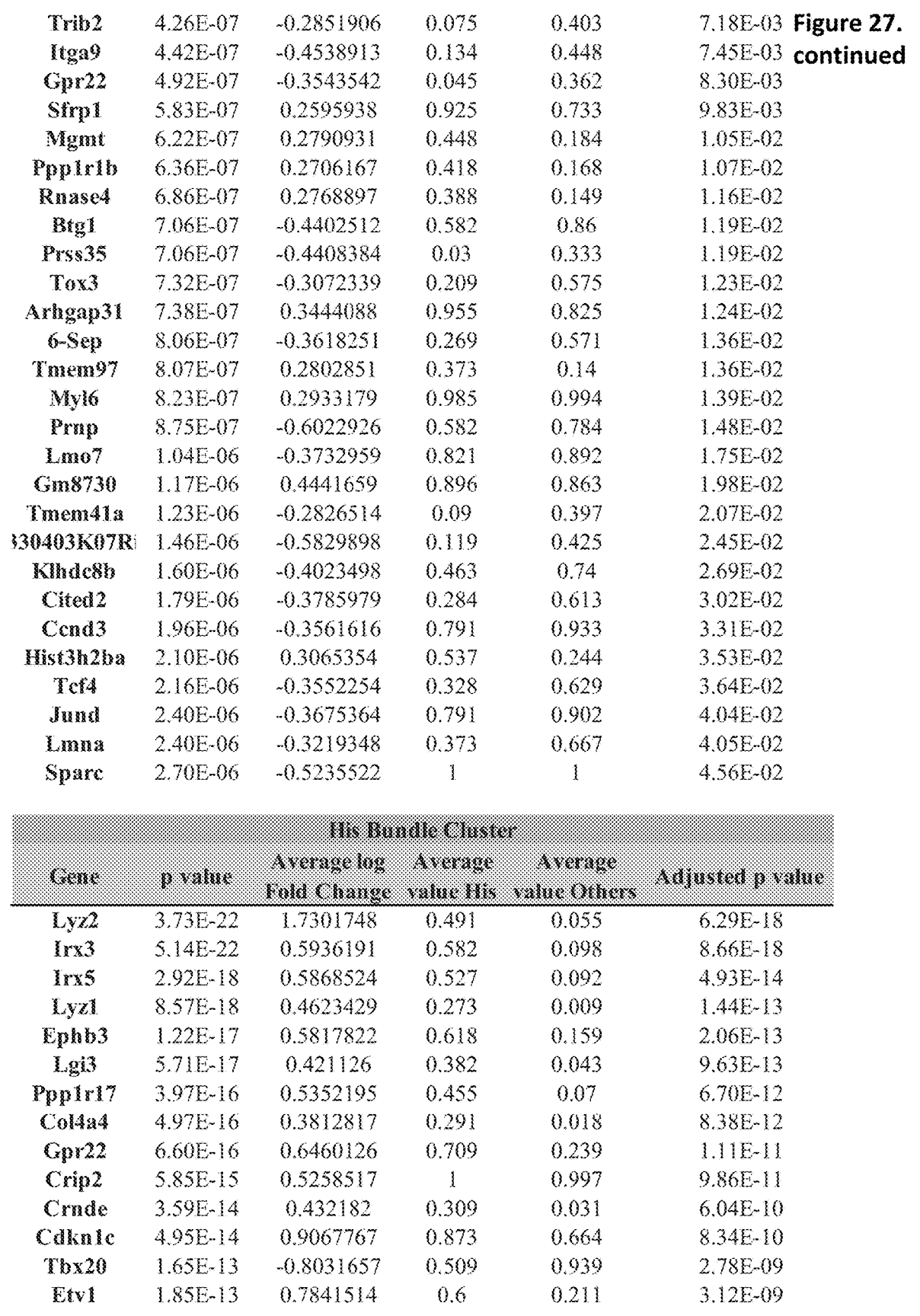

| Trib2 | 4.26E-07 | -0.2851906 | 0.075 | 0.403 | 7.18E-03 |
| Itga9 | 4.42E-07 | -0.4538913 | 0.134 | 0.448 | 7.45E-03 |
| Gpr22 | 4.92E-07 | -0.3543542 | 0.045 | 0.362 | 8.30E-03 |
| Sfrp1 | 5.83E-07 | 0.2595938 | 0.925 | 0.733 | 9.83E-03 |
| Mgmt | 6.22E-07 | 0.2790931 | 0.448 | 0.184 | 1.05E-02 |
| Ppp1r1b | 6.36E-07 | 0.2706167 | 0.418 | 0.168 | 1.07E-02 |
| Rnase4 | 6.86E-07 | 0.2768897 | 0.388 | 0.149 | 1.16E-02 |
| Btg1 | 7.06E-07 | -0.4402512 | 0.582 | 0.86 | 1.19E-02 |
| Prss35 | 7.06E-07 | -0.4408384 | 0.03 | 0.333 | 1.19E-02 |
| Tox3 | 7.32E-07 | -0.3072339 | 0.209 | 0.575 | 1.23E-02 |
| Arhgap31 | 7.38E-07 | 0.3444088 | 0.955 | 0.825 | 1.24E-02 |
| 6-Sep | 8.06E-07 | -0.3618251 | 0.269 | 0.571 | 1.36E-02 |
| Tmem97 | 8.07E-07 | 0.2802851 | 0.373 | 0.14 | 1.36E-02 |
| Myl6 | 8.23E-07 | 0.2933179 | 0.985 | 0.994 | 1.39E-02 |
| Prnp | 8.75E-07 | -0.6022926 | 0.582 | 0.784 | 1.48E-02 |
| Lmo7 | 1.04E-06 | -0.3732959 | 0.821 | 0.892 | 1.75E-02 |
| Gm8730 | 1.17E-06 | 0.4441659 | 0.896 | 0.863 | 1.98E-02 |
| Tmem41a | 1.23E-06 | -0.2826514 | 0.09 | 0.397 | 2.07E-02 |
| ?30403K07R? | 1.46E-06 | -0.5829898 | 0.119 | 0.425 | 2.45E-02 |
| Klhdc8b | 1.60E-06 | -0.4023498 | 0.463 | 0.74 | 2.69E-02 |
| Cited2 | 1.79E-06 | -0.3785979 | 0.284 | 0.613 | 3.02E-02 |
| Ccnd3 | 1.96E-06 | -0.3561616 | 0.791 | 0.933 | 3.31E-02 |
| Hist3h2ba | 2.10E-06 | 0.3065354 | 0.537 | 0.244 | 3.53E-02 |
| Tcf4 | 2.16E-06 | -0.3552254 | 0.328 | 0.629 | 3.64E-02 |
| Jund | 2.40E-06 | -0.3675364 | 0.791 | 0.902 | 4.04E-02 |
| Lmna | 2.40E-06 | -0.3219348 | 0.373 | 0.667 | 4.05E-02 |
| Sparc | 2.70E-06 | -0.5235522 | 1 | 1 | 4.56E-02 |

Figure 27. continued

| His Bundle Cluster | | | | | |
|---|---|---|---|---|---|
| Gene | p value | Average log Fold Change | Average value His | Average value Others | Adjusted p value |
| Lyz2 | 3.73E-22 | 1.7301748 | 0.491 | 0.055 | 6.29E-18 |
| Irx3 | 5.14E-22 | 0.5936191 | 0.582 | 0.098 | 8.66E-18 |
| Irx5 | 2.92E-18 | 0.5868524 | 0.527 | 0.092 | 4.93E-14 |
| Lyz1 | 8.57E-18 | 0.4623429 | 0.273 | 0.009 | 1.44E-13 |
| Ephb3 | 1.22E-17 | 0.5817822 | 0.618 | 0.159 | 2.06E-13 |
| Lgi3 | 5.71E-17 | 0.421126 | 0.382 | 0.043 | 9.63E-13 |
| Ppp1r17 | 3.97E-16 | 0.5352195 | 0.455 | 0.07 | 6.70E-12 |
| Col4a4 | 4.97E-16 | 0.3812817 | 0.291 | 0.018 | 8.38E-12 |
| Gpr22 | 6.60E-16 | 0.6460126 | 0.709 | 0.239 | 1.11E-11 |
| Crip2 | 5.85E-15 | 0.5258517 | 1 | 0.997 | 9.86E-11 |
| Crnde | 3.59E-14 | 0.432182 | 0.309 | 0.031 | 6.04E-10 |
| Cdkn1c | 4.95E-14 | 0.9067767 | 0.873 | 0.664 | 8.34E-10 |
| Tbx20 | 1.65E-13 | -0.8031657 | 0.509 | 0.939 | 2.78E-09 |
| Etv1 | 1.85E-13 | 0.7841514 | 0.6 | 0.211 | 3.12E-09 |

| | | | | | |
|---|---|---|---|---|---|
| Vcan | 3.14E-13 | 0.8110563 | 0.745 | 0.352 | 5.29E-09 |
| Rtn2 | 4.06E-13 | 0.4940046 | 0.709 | 0.287 | 6.84E-09 |
| Ankrd63 | 4.87E-13 | 0.3161492 | 0.327 | 0.043 | 8.20E-09 |
| Atp1b1 | 7.82E-13 | 0.7602711 | 1 | 0.997 | 1.32E-08 |
| Alcam | 1.62E-12 | 0.784239 | 0.618 | 0.251 | 2.73E-08 |
| Cpne5 | 1.71E-12 | 0.7599924 | 0.8 | 0.367 | 2.88E-08 |
| Meg3 | 2.29E-12 | 0.9733785 | 0.836 | 0.526 | 3.87E-08 |
| Mpped2 | 4.79E-12 | 0.7260421 | 0.691 | 0.336 | 8.07E-08 |
| Sparc | 5.04E-12 | 0.5945862 | 1 | 1 | 8.50E-08 |
| Pam | 6.65E-12 | -0.9140712 | 0.8 | 0.979 | 1.12E-07 |
| Acaa2 | 1.01E-11 | -0.6658188 | 0.582 | 0.933 | 1.70E-07 |
| Pgam2 | 1.33E-11 | -0.6559928 | 0.964 | 1 | 2.24E-07 |
| Hn1 | 1.36E-11 | -0.6563004 | 0.727 | 0.963 | 2.30E-07 |
| Igf2 | 2.00E-11 | -0.8127299 | 0.491 | 0.881 | 3.37E-07 |
| Rbm3 | 2.18E-11 | -0.5601991 | 0.818 | 0.942 | 3.68E-07 |
| P23-455C13 | 2.54E-11 | 0.6337484 | 1 | 0.905 | 4.28E-07 |
| Kcne1 | 6.06E-11 | 0.8828247 | 0.909 | 0.737 | 1.02E-06 |
| 330403K07R | 6.33E-11 | 0.6541098 | 0.709 | 0.315 | 1.07E-06 |
| Robo1 | 6.36E-11 | 0.6791809 | 0.545 | 0.205 | 1.07E-06 |
| Slco3a1 | 7.54E-11 | 0.5347741 | 0.582 | 0.229 | 1.27E-06 |
| Tsc22d3 | 1.05E-10 | 0.6899873 | 0.909 | 0.734 | 1.77E-06 |
| Ccnd3 | 2.29E-10 | 0.4720896 | 0.964 | 0.899 | 3.86E-06 |
| Aldh1b1 | 3.00E-10 | -0.5550353 | 0.164 | 0.667 | 5.06E-06 |
| Myl7 | 3.21E-10 | -2.5648543 | 0.818 | 0.966 | 5.40E-06 |
| Fitm1 | 3.38E-10 | 0.5797444 | 0.945 | 0.737 | 5.70E-06 |
| Sln | 3.58E-10 | -2.9976226 | 0.036 | 0.498 | 6.03E-06 |
| 930011G23R | 4.65E-10 | 0.3908132 | 0.436 | 0.116 | 7.84E-06 |
| Klhdc8b | 9.16E-10 | 0.5483164 | 0.873 | 0.661 | 1.54E-05 |
| Cdo1 | 9.43E-10 | 0.6042711 | 0.436 | 0.119 | 1.59E-05 |
| Ybx1 | 1.06E-09 | -0.4151491 | 0.982 | 1 | 1.78E-05 |
| Cd81 | 1.16E-09 | 0.357852 | 1 | 0.988 | 1.95E-05 |
| Myl4 | 1.23E-09 | -1.0027838 | 0.964 | 0.991 | 2.07E-05 |
| Ccdc184 | 1.33E-09 | 0.3805051 | 0.364 | 0.086 | 2.24E-05 |
| Rps12 | 1.40E-09 | -0.3970636 | 0.982 | 0.997 | 2.37E-05 |
| Hspe1 | 1.91E-09 | -0.4399961 | 0.927 | 0.985 | 3.21E-05 |
| Fgf9 | 2.01E-09 | 0.3563738 | 0.455 | 0.144 | 3.40E-05 |
| Pln | 2.05E-09 | 0.5246783 | 1 | 0.945 | 3.45E-05 |
| Ankrd1 | 2.91E-09 | -1.0325897 | 0.709 | 0.939 | 4.90E-05 |
| Nkx2-5 | 3.02E-09 | 0.5090407 | 0.945 | 0.905 | 5.10E-05 |
| Rpsa | 5.08E-09 | -0.4091467 | 1 | 0.997 | 8.57E-05 |
| Nrtn | 6.54E-09 | 0.542298 | 0.818 | 0.563 | 1.10E-04 |
| Stk39 | 8.68E-09 | -0.4707466 | 0.236 | 0.67 | 1.46E-04 |
| Myom2 | 9.61E-09 | -0.5268658 | 0.018 | 0.437 | 1.62E-04 |
| Myl6 | 1.17E-08 | -0.4670575 | 0.964 | 0.997 | 1.97E-04 |
| Sema3c | 1.66E-08 | 0.5214986 | 0.491 | 0.199 | 2.80E-04 |

**Figure 27.
continued**

| | | | | | |
|---|---|---|---|---|---|
| Ndufa4 | 2.12E-08 | -0.2774358 | 1 | 1 | 3.58E-04 |
| Myh7 | 2.43E-08 | 0.4986866 | 1 | 0.972 | 4.10E-04 |
| Cav1 | 2.85E-08 | -0.7841692 | 0.091 | 0.477 | 4.81E-04 |
| Slit2 | 2.93E-08 | 0.6933785 | 0.291 | 0.064 | 4.95E-04 |
| Abracl | 2.94E-08 | -0.4699812 | 0.709 | 0.924 | 4.96E-04 |
| Dpysl3 | 3.51E-08 | 0.486556 | 0.964 | 0.859 | 5.91E-04 |
| Atp5g3 | 4.58E-08 | -0.3344018 | 1 | 0.997 | 7.72E-04 |
| Vcl | 6.02E-08 | -0.4181759 | 0.291 | 0.716 | 1.01E-03 |
| Fbxl22 | 6.74E-08 | -0.6214695 | 0.691 | 0.893 | 1.14E-03 |
| Reep5 | 7.83E-08 | -0.4301287 | 0.836 | 0.969 | 1.32E-03 |
| Lpl | 9.39E-08 | 0.441685 | 0.982 | 0.933 | 1.58E-03 |
| Ehd4 | 9.42E-08 | -0.408034 | 0.418 | 0.832 | 1.59E-03 |
| Hspa9 | 9.45E-08 | -0.3984044 | 0.836 | 0.911 | 1.59E-03 |
| Gtsf1 | 1.15E-07 | 0.357727 | 0.345 | 0.098 | 1.94E-03 |
| Ppia | 1.38E-07 | -0.2970593 | 1 | 0.997 | 2.33E-03 |
| Bex1 | 1.43E-07 | -0.5605149 | 0.727 | 0.878 | 2.41E-03 |
| Adgrb2 | 1.65E-07 | 0.3123676 | 0.309 | 0.076 | 2.78E-03 |
| Gsg1l | 1.80E-07 | 0.3347888 | 0.545 | 0.226 | 3.04E-03 |
| Eid1 | 1.83E-07 | 0.3890018 | 0.927 | 0.856 | 3.09E-03 |
| Gng2 | 2.50E-07 | -0.4073301 | 0.109 | 0.514 | 4.21E-03 |
| Atp1a2 | 2.59E-07 | 0.4167959 | 0.709 | 0.453 | 4.36E-03 |
| Tmem108 | 2.93E-07 | 0.4042161 | 0.545 | 0.275 | 4.94E-03 |
| Parm1 | 3.30E-07 | 0.3603669 | 0.855 | 0.667 | 5.57E-03 |
| Rpl22l1 | 3.72E-07 | -0.4024543 | 0.909 | 1 | 6.27E-03 |
| Dctpp1 | 4.24E-07 | -0.4047986 | 0.327 | 0.697 | 7.15E-03 |
| Atp6v1g1 | 5.90E-07 | 0.310664 | 0.927 | 0.966 | 9.94E-03 |
| Atp5g1 | 6.40E-07 | -0.2841032 | 1 | 1 | 1.08E-02 |
| Plpp3 | 7.21E-07 | -0.3934442 | 0.018 | 0.358 | 1.22E-02 |
| Apobec2 | 8.71E-07 | 0.4204209 | 0.945 | 0.911 | 1.47E-02 |
| Igfbp5 | 9.65E-07 | 0.2818951 | 0.927 | 0.602 | 1.63E-02 |
| Dusp26 | 1.02E-06 | 0.2756954 | 0.382 | 0.135 | 1.72E-02 |
| Adamtsl2 | 1.02E-06 | 0.3554117 | 0.545 | 0.266 | 1.73E-02 |
| Ndufb8 | 1.05E-06 | -0.3113876 | 0.982 | 0.997 | 1.77E-02 |
| Stmn1 | 1.09E-06 | -0.5551575 | 0.618 | 0.844 | 1.84E-02 |
| Aif1l | 1.23E-06 | -0.3388382 | 0.036 | 0.385 | 2.07E-02 |
| H19 | 1.32E-06 | -1.0291989 | 0.545 | 0.823 | 2.22E-02 |
| Irx2 | 1.32E-06 | 0.3810258 | 0.273 | 0.07 | 2.23E-02 |
| Id2 | 1.86E-06 | 0.4408082 | 0.927 | 0.789 | 3.13E-02 |
| Mef2c | 1.89E-06 | -0.3954639 | 0.4 | 0.719 | 3.19E-02 |
| Gal | 1.95E-06 | 0.7074839 | 0.273 | 0.067 | 3.29E-02 |
| Tcap | 2.26E-06 | 0.3642867 | 0.982 | 0.914 | 3.81E-02 |
| Atp2a2 | 2.29E-06 | -0.5375797 | 0.982 | 0.988 | 3.86E-02 |
| Cycs | 2.32E-06 | -0.3076662 | 0.982 | 0.997 | 3.91E-02 |
| Tpm2 | 2.43E-06 | -0.3526558 | 0.255 | 0.615 | 4.10E-02 |
| Eef1a2 | 2.53E-06 | 0.3795597 | 0.945 | 0.85 | 4.27E-02 |

Figure 27.
continued

| Gene | | | | | |
|---|---|---|---|---|---|
| Hey2 | 2.64E-06 | -0.3096538 | 0.018 | 0.343 | 4.44E-02 |
| Tomm5 | 2.66E-06 | -0.3627125 | 0.673 | 0.92 | 4.48E-02 |
| Cnn2 | 2.73E-06 | -0.390524 | 0.364 | 0.725 | 4.61E-02 |
| Scarb2 | 2.79E-06 | 0.3880955 | 0.709 | 0.477 | 4.70E-02 |
| Mpc1 | 2.88E-06 | -0.356602 | 0.855 | 0.927 | 4.86E-02 |

Figure 27. continued

| cAVN Cluster | | | | | |
|---|---|---|---|---|---|
| Gene | p value | Average log Fold Change | Average value cAVN | Average value Others | Adjusted p value |
| Vsnl1 | 1.14E-32 | 1.175144 | 0.884 | 0.139 | 1.92E-28 |
| Acvr1c | 1.33E-23 | 0.4746629 | 0.419 | 0.021 | 2.24E-19 |
| Igfbp5 | 2.21E-21 | 1.6782009 | 1 | 0.605 | 3.72E-17 |
| Slc22a1 | 5.43E-21 | 1.4823286 | 1 | 0.475 | 9.15E-17 |
| Gcgr | 8.21E-21 | 0.4477034 | 0.488 | 0.044 | 1.38E-16 |
| Sln | 1.11E-20 | 1.3737116 | 1 | 0.36 | 1.87E-16 |
| Shox2 | 1.89E-20 | 0.8835155 | 0.465 | 0.041 | 3.19E-16 |
| Cav1 | 3.22E-20 | 0.9189318 | 1 | 0.348 | 5.43E-16 |
| Gnao1 | 5.34E-20 | 0.8779989 | 0.907 | 0.327 | 9.00E-16 |
| Cacna2d2 | 8.33E-18 | 0.8149896 | 0.953 | 0.357 | 1.40E-13 |
| Bmp2 | 2.50E-16 | 1.0941716 | 0.791 | 0.26 | 4.21E-12 |
| Myl2 | 4.41E-16 | -3.054083 | 0.791 | 0.956 | 7.43E-12 |
| Myh6 | 4.88E-16 | 1.0425535 | 1 | 0.926 | 8.23E-12 |
| Shisa2 | 7.39E-16 | 0.6314404 | 0.744 | 0.198 | 1.25E-11 |
| Ryr3 | 9.98E-16 | 0.7374212 | 0.605 | 0.133 | 1.68E-11 |
| Alox8 | 1.70E-15 | 0.2761323 | 0.349 | 0.029 | 2.86E-11 |
| Nr2f2 | 2.52E-15 | 0.5519646 | 0.651 | 0.15 | 4.25E-11 |
| Myl3 | 7.31E-15 | -2.0108644 | 0.721 | 0.932 | 1.23E-10 |
| Myh7 | 8.11E-15 | -1.6225707 | 0.884 | 0.988 | 1.37E-10 |
| Rxfp1 | 1.74E-14 | 0.7526562 | 0.814 | 0.316 | 2.93E-10 |
| Myl1 | 2.07E-14 | 1.099674 | 0.907 | 0.413 | 3.50E-10 |
| Ank1 | 1.08E-13 | 0.746443 | 0.86 | 0.375 | 1.83E-09 |
| Myl4 | 1.15E-13 | 0.7616141 | 1 | 0.985 | 1.93E-09 |
| Perp | 4.46E-13 | 0.6676102 | 0.977 | 0.891 | 7.51E-09 |
| Mlf1 | 5.63E-13 | 0.5883125 | 1 | 0.941 | 9.48E-09 |
| Kcnj5 | 6.80E-13 | 0.6354128 | 0.837 | 0.381 | 1.15E-08 |
| Nr2f1 | 1.21E-12 | 0.698744 | 0.535 | 0.124 | 2.04E-08 |
| Myl7 | 1.31E-12 | 1.0260965 | 1 | 0.938 | 2.20E-08 |
| Mybph1 | 2.06E-12 | 0.5612728 | 0.744 | 0.206 | 3.48E-08 |
| Atp2a2 | 2.58E-12 | 0.7461198 | 0.977 | 0.988 | 4.34E-08 |
| Plppr5 | 4.35E-12 | 0.4399312 | 0.581 | 0.153 | 7.33E-08 |
| Pln | 5.08E-12 | -1.3186806 | 0.837 | 0.968 | 8.56E-08 |
| Npnt | 1.18E-11 | 0.2646823 | 0.442 | 0.08 | 1.99E-07 |
| Tbx5 | 3.18E-11 | 0.5683876 | 0.884 | 0.422 | 5.36E-07 |
| Rbpms | 3.68E-11 | 0.6149034 | 0.977 | 0.979 | 6.20E-07 |

| | | | | | |
|---|---|---|---|---|---|
| Cdc14b | 6.82E-11 | 0.5553599 | 0.744 | 0.342 | 1.15E-06 |
| Cpne5 | 6.86E-11 | 0.6617855 | 0.814 | 0.381 | 1.16E-06 |
| Lgals1 | 7.39E-11 | -0.8766889 | 0.767 | 0.938 | 1.24E-06 |
| Rgs12 | 9.03E-11 | 0.4929957 | 0.86 | 0.428 | 1.52E-06 |
| Myl9 | 1.16E-10 | 0.6179796 | 1 | 0.991 | 1.95E-06 |
| Cox6a2 | 1.40E-10 | 0.4597618 | 1 | 0.979 | 2.35E-06 |
| Adm | 1.51E-10 | 0.5329761 | 0.465 | 0.106 | 2.54E-06 |
| Hs6st2 | 3.17E-10 | 0.2820555 | 0.465 | 0.106 | 5.34E-06 |
| Slitrk5 | 3.89E-10 | 0.5411167 | 0.628 | 0.233 | 6.55E-06 |
| Smpx | 5.31E-10 | -0.979032 | 0.814 | 0.95 | 8.95E-06 |
| Smyd2 | 5.69E-10 | -0.6643872 | 0.023 | 0.56 | 9.60E-06 |
| Kcnj3 | 5.88E-10 | 0.454784 | 0.628 | 0.201 | 9.91E-06 |
| Tbx3 | 6.46E-10 | 0.4358131 | 0.605 | 0.186 | 1.09E-05 |
| Ier5 | 9.34E-10 | 0.4136664 | 0.721 | 0.307 | 1.57E-05 |
| Crip1 | 9.80E-10 | -1.027975 | 0.512 | 0.808 | 1.65E-05 |
| Tmem178 | 1.03E-09 | 0.270766 | 0.372 | 0.071 | 1.74E-05 |
| Maged2 | 1.14E-09 | 0.5551748 | 0.93 | 0.696 | 1.92E-05 |
| Aspscr1 | 1.25E-09 | 0.750755 | 0.907 | 0.743 | 2.10E-05 |
| Enpep | 1.66E-09 | 0.3985962 | 0.512 | 0.147 | 2.80E-05 |
| Kdr | 1.73E-09 | 0.3476425 | 0.512 | 0.136 | 2.92E-05 |
| Slc39a8 | 2.01E-09 | 0.3903998 | 0.512 | 0.142 | 3.40E-05 |
| Nid2 | 2.05E-09 | 0.4372986 | 0.744 | 0.372 | 3.45E-05 |
| Hcfc1r1 | 2.17E-09 | -0.5736625 | 0.907 | 0.988 | 3.66E-05 |
| Rpl18a | 2.53E-09 | -0.3568114 | 1 | 1 | 4.26E-05 |
| Plpp3 | 2.66E-09 | 0.5486384 | 0.651 | 0.265 | 4.48E-05 |
| Serf2 | 3.49E-09 | -0.347181 | 1 | 1 | 5.88E-05 |
| Ncald | 3.81E-09 | 0.301405 | 0.488 | 0.13 | 6.42E-05 |
| Hcn4 | 5.22E-09 | 0.2683556 | 0.326 | 0.059 | 8.80E-05 |
| Epha4 | 5.95E-09 | 0.5197977 | 0.814 | 0.386 | 1.00E-04 |
| Drap1 | 1.46E-08 | 0.5332056 | 0.93 | 0.823 | 2.45E-04 |
| Smim1 | 2.27E-08 | 0.3386601 | 0.628 | 0.227 | 3.83E-04 |
| Rgs6 | 3.15E-08 | 0.4239399 | 0.791 | 0.392 | 5.31E-04 |
| Meis2 | 3.70E-08 | -0.6228079 | 0.116 | 0.555 | 6.23E-04 |
| Negr1 | 3.79E-08 | 0.3347849 | 0.279 | 0.05 | 6.38E-04 |
| Gyg | 3.81E-08 | -0.6825423 | 0.93 | 0.976 | 6.43E-04 |
| Atp1a1 | 3.94E-08 | 0.4518373 | 1 | 0.976 | 6.64E-04 |
| Lrrc10 | 4.13E-08 | -0.5356365 | 0.093 | 0.537 | 6.97E-04 |
| Kif1b | 4.59E-08 | 0.5089581 | 0.907 | 0.749 | 7.74E-04 |
| Tmem132c | 6.41E-08 | 0.2757278 | 0.302 | 0.059 | 1.08E-03 |
| Zwint | 6.47E-08 | 0.4265039 | 0.884 | 0.708 | 1.09E-03 |
| Mb | 6.70E-08 | -1.1497203 | 0.302 | 0.652 | 1.13E-03 |
| Fras1 | 7.71E-08 | 0.4163772 | 0.698 | 0.327 | 1.30E-03 |
| Fam162a | 7.78E-08 | -0.6078514 | 0.86 | 0.953 | 1.31E-03 |
| Dok7 | 8.16E-08 | 0.2791486 | 0.488 | 0.153 | 1.38E-03 |
| Mpped2 | 1.07E-07 | -0.5581046 | 0 | 0.437 | 1.80E-03 |

**Figure 27.
continued**

| | | | | | |
|---|---|---|---|---|---|
| Map1b | 1.16E-07 | 0.5234587 | 0.93 | 0.773 | 1.95E-03 |
| Zbtb20 | 1.16E-07 | 0.4963818 | 1 | 0.912 | 1.96E-03 |
| Ccnd2 | 1.69E-07 | 0.5410358 | 0.907 | 0.823 | 2.86E-03 |
| Gja1 | 1.99E-07 | -0.7684293 | 0.023 | 0.445 | 3.36E-03 |
| Rps11 | 2.44E-07 | -0.2710573 | 1 | 1 | 4.12E-03 |
| S100a11 | 3.03E-07 | -0.584032 | 0.605 | 0.855 | 5.10E-03 |
| Arhgap31 | 3.06E-07 | 0.4489469 | 0.953 | 0.835 | 5.16E-03 |
| Cacna1h | 3.38E-07 | 0.2973294 | 0.558 | 0.212 | 5.70E-03 |
| Obscn | 3.57E-07 | 0.4694857 | 0.93 | 0.767 | 6.02E-03 |
| Ctsc | 3.91E-07 | 0.3166944 | 0.512 | 0.189 | 6.59E-03 |
| Lamb1 | 4.49E-07 | 0.3902204 | 0.814 | 0.549 | 7.57E-03 |
| Rpl39 | 5.50E-07 | -0.264744 | 1 | 0.997 | 9.26E-03 |
| Hopx | 5.52E-07 | -0.6604384 | 0.605 | 0.823 | 9.30E-03 |
| 6-Sep | 5.98E-07 | -0.4417045 | 0.163 | 0.563 | 1.01E-02 |
| Spon1 | 6.15E-07 | 0.4597405 | 0.721 | 0.41 | 1.04E-02 |
| Pdlim1 | 6.63E-07 | -0.4484693 | 0.047 | 0.442 | 1.12E-02 |
| Rd3 | 7.22E-07 | 0.3274752 | 0.512 | 0.165 | 1.22E-02 |
| Adam33 | 7.30E-07 | 0.394375 | 0.488 | 0.18 | 1.23E-02 |
| Nppb | 7.35E-07 | -1.2447869 | 0.023 | 0.416 | 1.24E-02 |
| Fth1 | 8.58E-07 | -0.2656438 | 1 | 1 | 1.45E-02 |
| H19 | 9.59E-07 | -1.2839859 | 0.628 | 0.802 | 1.62E-02 |
| Furin | 1.01E-06 | 0.39098 | 0.814 | 0.549 | 1.69E-02 |
| Ociad2 | 1.05E-06 | 0.4202399 | 0.581 | 0.251 | 1.77E-02 |
| Itga6 | 1.27E-06 | 0.3490107 | 0.512 | 0.192 | 2.14E-02 |
| Ndst1 | 1.56E-06 | 0.2576012 | 0.372 | 0.118 | 2.63E-02 |
| Ntm | 1.73E-06 | 0.4223268 | 0.791 | 0.425 | 2.92E-02 |
| Sdpr | 1.94E-06 | -0.4581867 | 0.302 | 0.717 | 3.26E-02 |
| Lbh | 2.02E-06 | -0.5403712 | 0.581 | 0.808 | 3.41E-02 |
| Erbb2 | 2.35E-06 | 0.307879 | 0.605 | 0.298 | 3.96E-02 |
| Ccdc141 | 2.40E-06 | 0.4645845 | 0.86 | 0.794 | 4.04E-02 |
| Grb10 | 2.45E-06 | -0.4165277 | 0.953 | 0.988 | 4.13E-02 |
| Spata13 | 2.47E-06 | 0.2646945 | 0.442 | 0.153 | 4.17E-02 |
| Id2 | 2.73E-06 | 0.5607362 | 1 | 0.785 | 4.60E-02 |
| Tbc1d16 | 2.78E-06 | 0.3263835 | 0.698 | 0.339 | 4.68E-02 |
| Tmsb4x | 2.93E-06 | -0.5318925 | 1 | 1 | 4.95E-02 |
| Rgs10 | 2.95E-06 | 0.2909865 | 0.372 | 0.109 | 4.97E-02 |

| | | | NAVR Cluster | | |
|---|---|---|---|---|---|
| Gene | p value | Average log Fold Change | Average value NAVR | Average value Others | Adjusted p value |
| Ntsr1 | 5.79E-49 | 1.0625731 | 0.879 | 0.04 | 9.75E-45 |
| Gnb3 | 2.24E-44 | 1.1018451 | 0.818 | 0.04 | 3.78E-40 |
| Pitx2 | 4.00E-27 | 1.4099434 | 0.879 | 0.16 | 6.73E-23 |
| Asic4 | 6.45E-23 | 0.3813035 | 0.273 | 0 | 1.09E-18 |

Figure 27. continued

| | | | | | |
|---|---|---|---|---|---|
| Susd3 | 1.53E-20 | 0.3895496 | 0.273 | 0.003 | 2.57E-16 |
| Adamts8 | 1.92E-18 | 0.7813483 | 0.727 | 0.146 | 3.24E-14 |
| Ramp1 | 9.42E-17 | 1.1761862 | 1 | 0.868 | 1.59E-12 |
| Tnnt1 | 1.51E-16 | 1.6031979 | 1 | 0.676 | 2.55E-12 |
| Fabp5 | 4.39E-16 | 3.1771475 | 0.879 | 0.453 | 7.41E-12 |
| Rd3 | 1.06E-14 | 0.6985349 | 0.667 | 0.16 | 1.78E-10 |
| Fabp4 | 3.41E-14 | 2.2474851 | 0.697 | 0.212 | 5.74E-10 |
| Ntm | 3.64E-14 | 0.940547 | 0.909 | 0.424 | 6.13E-10 |
| Cacna1d | 1.17E-13 | 0.5169003 | 0.576 | 0.115 | 1.98E-09 |
| Adk | 2.65E-13 | 1.062923 | 0.939 | 0.711 | 4.46E-09 |
| Chil1 | 4.39E-13 | 0.429362 | 0.333 | 0.032 | 7.40E-09 |
| Myl3 | 1.62E-12 | -2.2865426 | 0.667 | 0.931 | 2.73E-08 |
| Itgb8 | 4.10E-12 | 0.6745185 | 0.576 | 0.14 | 6.92E-08 |
| Lta4h | 8.33E-12 | 0.7785772 | 0.879 | 0.53 | 1.40E-07 |
| Prss35 | 9.36E-12 | 0.7323157 | 0.727 | 0.238 | 1.58E-07 |
| Dapk2 | 9.62E-12 | 0.4326224 | 0.515 | 0.103 | 1.62E-07 |
| Adgrl3 | 1.08E-11 | 0.5156412 | 0.455 | 0.083 | 1.81E-07 |
| Smpx | 1.29E-11 | -1.25864 | 0.758 | 0.951 | 2.17E-07 |
| Gal | 2.16E-11 | 1.3813672 | 0.424 | 0.066 | 3.63E-07 |
| Itm2c | 2.69E-11 | 0.6538902 | 0.939 | 0.587 | 4.54E-07 |
| Hopx | 2.96E-11 | -1.0511993 | 0.364 | 0.84 | 4.98E-07 |
| Sfrp1 | 2.97E-11 | 1.0165988 | 0.939 | 0.751 | 5.01E-07 |
| Sdk2 | 3.04E-11 | 0.3387273 | 0.364 | 0.049 | 5.13E-07 |
| Prss23 | 5.81E-11 | 0.6900275 | 0.697 | 0.258 | 9.79E-07 |
| Ptgds | 9.98E-11 | -0.8938858 | 0.03 | 0.673 | 1.68E-06 |
| Kdr | 1.21E-10 | 0.6647145 | 0.545 | 0.143 | 2.05E-06 |
| Smim1 | 1.44E-10 | 0.8111529 | 0.667 | 0.235 | 2.42E-06 |
| Mob1b | 2.98E-10 | 0.7231204 | 0.879 | 0.682 | 5.02E-06 |
| Casq2 | 3.74E-10 | 0.7451957 | 1 | 0.957 | 6.30E-06 |
| Crip1 | 4.62E-10 | -1.1793718 | 0.364 | 0.814 | 7.78E-06 |
| Casq1 | 6.74E-10 | -1.3062033 | 0.242 | 0.762 | 1.14E-05 |
| F11r | 6.79E-10 | 0.591001 | 0.636 | 0.232 | 1.14E-05 |
| Spon1 | 1.21E-09 | 0.7800559 | 0.788 | 0.413 | 2.05E-05 |
| Tuba1a | 1.25E-09 | 0.7631574 | 1 | 0.957 | 2.10E-05 |
| Htra1 | 1.35E-09 | 0.8070165 | 0.909 | 0.599 | 2.28E-05 |
| Cacna2d2 | 1.47E-09 | 0.6415485 | 0.879 | 0.381 | 2.47E-05 |
| Atp1a1 | 2.01E-09 | 0.6145318 | 1 | 0.977 | 3.38E-05 |
| Gdi2 | 2.38E-09 | 0.5120468 | 0.97 | 0.908 | 4.01E-05 |
| Tpt1 | 2.56E-09 | -0.4180245 | 1 | 1 | 4.32E-05 |
| Arhgap31 | 2.58E-09 | 0.7078721 | 0.939 | 0.84 | 4.34E-05 |
| Gde1 | 2.74E-09 | 0.631107 | 0.909 | 0.639 | 4.63E-05 |
| Morf4l1 | 3.67E-09 | 0.3906223 | 1 | 0.991 | 6.19E-05 |
| Map1lc3a | 3.98E-09 | 0.508214 | 1 | 0.989 | 6.71E-05 |
| Shisa4 | 5.66E-09 | 0.5108952 | 0.697 | 0.284 | 9.55E-05 |
| Mb | 7.89E-09 | -1.2863535 | 0.121 | 0.659 | 1.33E-04 |

Figure 27. continued

| | | | | | |
|---|---|---|---|---|---|
| mt-Nd1 | 1.20E-08 | -0.5691453 | 1 | 1 | 2.02E-04 |
| Tmem176b | 1.25E-08 | 0.6601553 | 0.909 | 0.828 | 2.10E-04 |
| Bmp2 | 1.32E-08 | 0.562167 | 0.727 | 0.281 | 2.22E-04 |
| Oxr1 | 1.74E-08 | 0.5362965 | 0.697 | 0.37 | 2.94E-04 |
| Fitm1 | 1.83E-08 | 0.6774734 | 0.939 | 0.751 | 3.09E-04 |
| Sh3kbp1 | 3.63E-08 | -0.6724071 | 0.121 | 0.622 | 6.12E-04 |
| Tbx5 | 3.63E-08 | 0.6575881 | 0.818 | 0.441 | 6.12E-04 |
| Rps4x | 3.71E-08 | -0.3560252 | 1 | 0.994 | 6.26E-04 |
| Mif | 4.87E-08 | -0.6308366 | 1 | 0.986 | 8.20E-04 |
| mt-Co2 | 4.87E-08 | -0.5580932 | 1 | 0.997 | 8.20E-04 |
| Dhrs7 | 5.34E-08 | 0.8505514 | 0.758 | 0.527 | 9.01E-04 |
| Igfbp5 | 5.98E-08 | 0.5640643 | 0.939 | 0.622 | 1.01E-03 |
| mt-Nd2 | 7.51E-08 | -0.503074 | 1 | 1 | 1.26E-03 |
| Prmt7 | 8.40E-08 | 0.9128108 | 0.636 | 0.287 | 1.42E-03 |
| Zfp36l1 | 8.78E-08 | 0.505524 | 1 | 0.877 | 1.48E-03 |
| Cobl | 8.90E-08 | 0.5560602 | 0.667 | 0.335 | 1.50E-03 |
| Myl2 | 9.65E-08 | -2.166828 | 0.818 | 0.948 | 1.63E-03 |
| Capn6 | 1.02E-07 | 0.5838199 | 0.576 | 0.238 | 1.71E-03 |
| Yap1 | 1.06E-07 | 0.4683274 | 0.818 | 0.51 | 1.78E-03 |
| 6-Sep | 1.09E-07 | -0.5244763 | 0.03 | 0.564 | 1.83E-03 |
| mt-Cytb | 1.42E-07 | -0.4357191 | 1 | 1 | 2.39E-03 |
| Cox8b | 1.44E-07 | -0.7527239 | 0.667 | 0.934 | 2.43E-03 |
| Klhl41 | 1.45E-07 | 0.4478906 | 0.455 | 0.135 | 2.44E-03 |
| Ccnd3 | 1.56E-07 | 0.5205129 | 0.97 | 0.903 | 2.63E-03 |
| Wwtr1 | 1.62E-07 | -0.4340681 | 0 | 0.507 | 2.74E-03 |
| Gpr37 | 1.67E-07 | 0.2910699 | 0.303 | 0.054 | 2.81E-03 |
| Ptp4a3 | 1.80E-07 | 0.5575614 | 0.939 | 0.834 | 3.03E-03 |
| mt-Atp6 | 1.92E-07 | -0.4899402 | 1 | 1 | 3.23E-03 |
| Rspo3 | 2.18E-07 | 0.813306 | 0.636 | 0.244 | 3.68E-03 |
| Rpl32 | 2.35E-07 | -0.3758571 | 1 | 1 | 3.96E-03 |
| Myl7 | 2.50E-07 | 0.7868903 | 1 | 0.94 | 4.21E-03 |
| Btg2 | 2.67E-07 | 0.7623417 | 0.727 | 0.43 | 4.51E-03 |
| Hspa1a | 3.04E-07 | 0.7593062 | 0.576 | 0.215 | 5.13E-03 |
| Slitrk5 | 3.87E-07 | 0.4657066 | 0.606 | 0.246 | 6.52E-03 |
| Peg3 | 4.98E-07 | 0.5086372 | 0.848 | 0.59 | 8.39E-03 |
| Mrvi1 | 6.09E-07 | 0.3476641 | 0.333 | 0.074 | 1.03E-02 |
| Ckm | 7.52E-07 | -0.6405144 | 0.788 | 0.997 | 1.27E-02 |
| Pdcd5 | 8.15E-07 | 0.3822281 | 1 | 0.971 | 1.37E-02 |
| Acta2 | 8.26E-07 | -1.0473999 | 0.242 | 0.708 | 1.39E-02 |
| Apoe | 8.97E-07 | -0.7421229 | 0.242 | 0.673 | 1.51E-02 |
| Smtnl2 | 9.13E-07 | 0.5894352 | 0.758 | 0.464 | 1.54E-02 |
| Ktn1 | 9.20E-07 | 0.4101852 | 0.909 | 0.808 | 1.55E-02 |
| Gpx3 | 9.25E-07 | 0.6561459 | 1 | 0.963 | 1.56E-02 |
| 190002N15R | 9.56E-07 | 0.4632891 | 0.727 | 0.404 | 1.61E-02 |
| mt-Nd4 | 1.13E-06 | -0.4549501 | 1 | 1 | 1.91E-02 |

Figure 27. continued

| | | | | | |
|---|---|---|---|---|---|
| Jun | 1.17E-06 | 0.6776398 | 0.788 | 0.542 | 1.97E-02 |
| Ckb | 1.22E-06 | -0.6000558 | 0.333 | 0.745 | 2.05E-02 |
| Pln | 1.29E-06 | -1.0813709 | 0.939 | 0.954 | 2.18E-02 |
| Ackr3 | 1.34E-06 | 0.3403082 | 0.303 | 0.066 | 2.26E-02 |
| Zfp36 | 1.35E-06 | 0.4788462 | 0.485 | 0.186 | 2.27E-02 |
| Pirt | 1.41E-06 | 0.4540991 | 0.606 | 0.261 | 2.38E-02 |
| Dbi | 1.42E-06 | -0.4976817 | 0.909 | 0.986 | 2.40E-02 |
| Sh3gl3 | 1.47E-06 | 0.3689213 | 0.333 | 0.08 | 2.48E-02 |
| Acaa2 | 1.50E-06 | 0.4637565 | 1 | 0.871 | 2.52E-02 |
| Sfrp5 | 1.51E-06 | 0.4543175 | 0.303 | 0.066 | 2.54E-02 |
| Art3 | 1.61E-06 | 0.6219405 | 0.576 | 0.264 | 2.72E-02 |
| Tcap | 1.62E-06 | 0.8195002 | 0.97 | 0.92 | 2.73E-02 |
| Sparc | 1.75E-06 | 0.5292517 | 1 | 1 | 2.96E-02 |
| Cystm1 | 1.80E-06 | -0.4936091 | 0.121 | 0.596 | 3.03E-02 |
| Adra1b | 1.87E-06 | 0.4562065 | 0.485 | 0.178 | 3.15E-02 |
| Lmod2 | 1.87E-06 | 0.4390572 | 0.909 | 0.636 | 3.16E-02 |
| Gyg | 1.97E-06 | -0.7056698 | 0.848 | 0.983 | 3.31E-02 |
| Cpne5 | 2.31E-06 | 0.5139619 | 0.788 | 0.395 | 3.89E-02 |
| Fbxl22 | 2.44E-06 | -0.7330088 | 0.515 | 0.897 | 4.11E-02 |
| Ddah1 | 2.51E-06 | -0.4186004 | 0.03 | 0.467 | 4.24E-02 |
| Me3 | 2.52E-06 | 0.3129255 | 0.455 | 0.158 | 4.25E-02 |
| Trdn | 3.29E-06 | 0.518044 | 1 | 0.943 | 5.55E-02 |
| Il13ra1 | 3.31E-06 | 0.4630762 | 0.606 | 0.312 | 5.58E-02 |
| Ctsl | 3.41E-06 | 0.5238114 | 0.939 | 0.885 | 5.75E-02 |
| Slc22a17 | 3.45E-06 | 0.4272585 | 0.667 | 0.375 | 5.81E-02 |
| Hcfc1r1 | 3.53E-06 | -0.444641 | 0.97 | 0.98 | 5.95E-02 |
| Tmem176a | 3.67E-06 | 0.5145031 | 0.727 | 0.461 | 6.19E-02 |
| Brk1 | 3.94E-06 | 0.4356458 | 0.909 | 0.883 | 6.65E-02 |
| Trabd2b | 4.03E-06 | 0.5569198 | 0.515 | 0.223 | 6.79E-02 |
| Plxdc2 | 4.30E-06 | 0.391922 | 0.455 | 0.158 | 7.25E-02 |
| Cited1 | 4.45E-06 | -0.7599554 | 0.303 | 0.699 | 7.50E-02 |
| mt-Co3 | 4.64E-06 | -0.3777383 | 1 | 1 | 7.82E-02 |
| Raly | 4.65E-06 | 0.4710591 | 0.909 | 0.848 | 7.83E-02 |
| Rgs10 | 4.70E-06 | 0.3446253 | 0.394 | 0.115 | 7.91E-02 |
| Myoz2 | 5.35E-06 | -0.5503169 | 0.758 | 0.948 | 9.02E-02 |
| Spop | 5.74E-06 | 0.408885 | 0.788 | 0.656 | 9.67E-02 |

**Figure 27.
continued**

Online Table VII: Differentially Expressed Genes in Cluster 13 of Zone III.    Figure 28.

| Gene | p value | Average log Fold Change | Average value Cluster 13 | Average value Other Clusters | Adjusted p value |
|---|---|---|---|---|---|
| Dcpp1 | 2.22E-308 | 2.7503009 | 0.274 | 0.003 | 2.22E-308 |
| Cacna2d2 | 2.22E-308 | 1.2147351 | 0.457 | 0.006 | 2.22E-308 |
| Crnde | 2.22E-308 | 0.9383849 | 0.509 | 0.022 | 2.22E-308 |
| Cpne5 | 2.22E-308 | 0.6793414 | 0.389 | 0.004 | 2.22E-308 |
| Slc16a12 | 2.22E-308 | 0.6351618 | 0.331 | 0.006 | 2.22E-308 |
| Nsg2 | 2.22E-308 | 0.537721 | 0.269 | 0.001 | 2.22E-308 |
| Bmp10 | 2.15E-304 | 0.9878821 | 0.423 | 0.015 | 6.03E-300 |
| Sema3c | 2.83E-276 | 0.7290903 | 0.451 | 0.02 | 7.92E-272 |
| Myl1 | 3.29E-276 | 1.261849 | 0.629 | 0.043 | 9.21E-272 |
| Gm15543 | 2.81E-255 | 1.176617 | 0.543 | 0.034 | 7.88E-251 |
| Irx5 | 1.43E-196 | 0.6117243 | 0.491 | 0.036 | 4.01E-192 |
| Adamtsl2 | 2.28E-196 | 0.3423443 | 0.251 | 0.008 | 6.39E-192 |
| Slc22a1 | 2.68E-189 | 0.6732325 | 0.32 | 0.014 | 7.50E-185 |
| Sema3a | 2.67E-188 | 0.5824507 | 0.32 | 0.015 | 7.49E-184 |
| Gja5 | 4.16E-188 | 0.9724381 | 0.531 | 0.044 | 1.17E-183 |
| Adgrb2 | 1.01E-185 | 0.3694906 | 0.263 | 0.009 | 2.83E-181 |
| Stard10 | 6.46E-178 | 0.7351767 | 0.446 | 0.032 | 1.81E-173 |
| Slco3a1 | 2.15E-161 | 0.8521804 | 0.503 | 0.048 | 6.02E-157 |
| Lyz2 | 2.92E-153 | 0.3079107 | 0.383 | 0.027 | 8.19E-149 |
| Ankrd63 | 5.80E-144 | 0.4440687 | 0.377 | 0.028 | 1.62E-139 |
| Spock2 | 4.13E-129 | 0.4141307 | 0.291 | 0.018 | 1.16E-124 |
| Mgp | 1.67E-127 | 1.3988914 | 0.72 | 0.124 | 4.69E-123 |
| Irx3 | 6.75E-124 | 0.508814 | 0.406 | 0.039 | 1.89E-119 |
| Ephb3 | 1.67E-119 | 0.5154093 | 0.394 | 0.038 | 4.68E-115 |
| Sdc4 | 8.67E-118 | 0.6871758 | 0.56 | 0.078 | 2.43E-113 |
| Ntm | 2.26E-114 | 0.6135754 | 0.44 | 0.05 | 6.32E-110 |
| Etv1 | 2.38E-109 | 0.8931675 | 0.629 | 0.113 | 6.67E-105 |
| Dbh | 4.55E-109 | 0.3450327 | 0.297 | 0.023 | 1.27E-104 |
| Igfbp5 | 3.96E-105 | 0.9575551 | 0.697 | 0.14 | 1.11E-100 |
| Slc6a6 | 4.25E-104 | 1.0200692 | 0.709 | 0.151 | 1.19E-99 |
| Vcan | 5.41E-101 | 1.0411418 | 0.766 | 0.184 | 1.51E-96 |
| Irx2 | 1.42E-98 | 0.7077895 | 0.549 | 0.092 | 3.98E-94 |
| Scn5a | 1.72E-90 | 0.7602381 | 0.663 | 0.145 | 4.81E-86 |
| Clu | 2.03E-90 | 0.9885256 | 0.6 | 0.119 | 5.68E-86 |
| Rgs6 | 2.22E-86 | 0.3505099 | 0.331 | 0.036 | 6.22E-82 |
| Trabd2b | 7.57E-86 | 0.3783752 | 0.28 | 0.026 | 2.12E-81 |
| Nppa | 9.80E-82 | 2.346775 | 0.783 | 0.242 | 2.74E-77 |
| Mpped2 | 2.40E-80 | 0.9434391 | 0.777 | 0.236 | 6.72E-76 |
| Gpx3 | 2.48E-79 | 1.6510324 | 0.949 | 0.557 | 6.94E-75 |
| Corin | 9.64E-78 | 1.104568 | 0.737 | 0.235 | 2.70E-73 |

| | | | | | |
|---|---|---|---|---|---|
| Epha4 | 3.30E-72 | 0.5747562 | 0.44 | 0.076 | 9.25E-68 |
| Slit2 | 9.17E-67 | 0.694685 | 0.343 | 0.05 | 2.57E-62 |
| Cst3 | 5.84E-66 | 1.0854267 | 0.994 | 0.813 | 1.64E-61 |
| Wif1 | 3.94E-65 | 0.5305266 | 0.44 | 0.082 | 1.10E-60 |
| Irx1 | 7.78E-65 | 0.3588275 | 0.354 | 0.054 | 2.18E-60 |
| Kcnk3 | 5.61E-63 | 0.6385524 | 0.571 | 0.143 | 1.57E-58 |
| Tsc22d3 | 1.37E-62 | 1.0746414 | 0.943 | 0.524 | 3.83E-58 |
| Ramp1 | 4.23E-62 | 1.0413544 | 0.834 | 0.339 | 1.18E-57 |
| Sulf2 | 1.85E-61 | 0.889616 | 0.857 | 0.374 | 5.18E-57 |
| Fbxo32 | 2.57E-59 | 0.5737561 | 0.537 | 0.135 | 7.20E-55 |
| Alcam | 1.96E-58 | 0.4230022 | 0.446 | 0.091 | 5.48E-54 |
| Fbn2 | 3.10E-58 | 0.788644 | 0.829 | 0.357 | 8.68E-54 |
| Prrx2 | 5.87E-57 | 0.5140432 | 0.48 | 0.11 | 1.64E-52 |
| Sorcs2 | 7.95E-56 | 0.275344 | 0.28 | 0.039 | 2.23E-51 |
| Ppp1r3b | 3.60E-54 | 0.561056 | 0.623 | 0.192 | 1.01E-49 |
| P23-455C13 | 9.83E-54 | 0.8546625 | 0.909 | 0.46 | 2.75E-49 |
| Atp1b1 | 1.42E-52 | 0.8764827 | 0.977 | 0.647 | 3.97E-48 |
| Rpsa | 3.01E-52 | -0.7413267 | 0.983 | 0.988 | 8.44E-48 |
| Kif26b | 4.36E-52 | 0.5687558 | 0.554 | 0.158 | 1.22E-47 |
| Wisp1 | 7.84E-52 | 0.6515965 | 0.52 | 0.141 | 2.20E-47 |
| Atp1a1 | 2.73E-51 | 0.815434 | 0.966 | 0.696 | 7.63E-47 |
| Hfe2 | 5.39E-49 | 0.3020887 | 0.326 | 0.058 | 1.51E-44 |
| Casq2 | 2.13E-48 | 0.8014827 | 0.983 | 0.659 | 5.96E-44 |
| Fgf1 | 1.38E-46 | 0.3798938 | 0.343 | 0.068 | 3.87E-42 |
| Parm1 | 1.53E-46 | 0.6077837 | 0.669 | 0.253 | 4.28E-42 |
| 32451O06R | 1.77E-45 | 0.4973268 | 0.457 | 0.12 | 4.94E-41 |
| Fxyd1 | 3.08E-45 | 0.7219351 | 1 | 0.801 | 8.62E-41 |
| Tgm2 | 9.58E-45 | 0.6910174 | 0.891 | 0.502 | 2.68E-40 |
| Rpl18a | 1.05E-44 | -0.6470523 | 1 | 0.996 | 2.95E-40 |
| Bcam | 1.61E-44 | 0.684354 | 0.926 | 0.596 | 4.51E-40 |
| Tesc | 4.74E-44 | 0.6107968 | 0.497 | 0.143 | 1.33E-39 |
| Id2 | 8.88E-44 | 0.5819657 | 0.617 | 0.205 | 2.49E-39 |
| Rps8 | 1.40E-43 | -0.6035439 | 1 | 0.997 | 3.91E-39 |
| Eid1 | 1.46E-43 | 0.7579637 | 0.909 | 0.586 | 4.09E-39 |
| Igf2r | 2.09E-42 | 0.7494384 | 0.971 | 0.678 | 5.84E-38 |
| Cdkn1a | 9.75E-42 | 0.5413395 | 0.531 | 0.167 | 2.73E-37 |
| Adamts19 | 1.70E-41 | 0.3006822 | 0.28 | 0.051 | 4.75E-37 |
| Fam174b | 2.46E-41 | 0.4300852 | 0.509 | 0.151 | 6.89E-37 |
| Trdn | 1.96E-40 | 0.6974518 | 0.954 | 0.62 | 5.48E-36 |
| Ank1 | 6.03E-40 | 0.6407661 | 0.48 | 0.15 | 1.69E-35 |
| Rpl3 | 2.02E-39 | -0.5804933 | 1 | 0.996 | 5.66E-35 |
| Trim11 | 3.51E-39 | 0.3710972 | 0.371 | 0.09 | 9.83E-35 |
| Rpl7 | 5.72E-39 | -0.7133694 | 1 | 0.991 | 1.60E-34 |
| Rpl2 | 1.69E-38 | -0.643954 | 0.966 | 0.975 | 4.74E-34 |
| Nav2 | 2.09E-38 | 0.6505376 | 0.749 | 0.364 | 5.86E-34 |

Figure 28. continued

| | | | | | |
|---|---|---|---|---|---|
| Rpl32 | 3.16E-38 | -0.5801253 | 1 | 0.997 | 8.86E-34 |
| Lrrc10 | 3.38E-38 | 0.6282398 | 0.64 | 0.245 | 9.46E-34 |
| Rpl28 | 6.67E-38 | -0.5670153 | 0.994 | 0.992 | 1.87E-33 |
| Cited1 | 2.81E-37 | 0.9383696 | 0.88 | 0.555 | 7.87E-33 |
| Rabgap1l | 3.90E-37 | 0.518099 | 0.617 | 0.242 | 1.09E-32 |
| Rps12 | 1.68E-36 | -0.715284 | 0.971 | 0.986 | 4.69E-32 |
| Tcap | 2.55E-36 | 0.6920188 | 0.931 | 0.578 | 7.13E-32 |
| Rps15a | 4.09E-36 | -0.5300687 | 1 | 0.996 | 1.15E-31 |
| Rps13 | 4.93E-36 | -0.5326987 | 0.989 | 0.991 | 1.38E-31 |
| Cxcl12 | 5.83E-36 | 0.7647908 | 0.48 | 0.157 | 1.63E-31 |
| Rplp2 | 1.06E-35 | -0.4523022 | 1 | 0.997 | 2.98E-31 |
| Col4a5 | 2.29E-35 | 0.4743142 | 0.611 | 0.243 | 6.42E-31 |
| Rps25 | 2.52E-35 | -0.473452 | 0.994 | 0.993 | 7.06E-31 |
| Rps3a1 | 4.00E-35 | -0.5202091 | 1 | 0.992 | 1.12E-30 |
| Rps19 | 6.03E-35 | -0.7036452 | 0.989 | 0.993 | 1.69E-30 |
| Kif13a | 2.78E-34 | 0.5175387 | 0.634 | 0.272 | 7.80E-30 |
| Itgb5 | 4.28E-34 | 0.5001319 | 0.549 | 0.203 | 1.20E-29 |
| Pdzrn3 | 5.17E-34 | 0.4507606 | 0.589 | 0.232 | 1.45E-29 |
| Hcfc1r1 | 9.22E-34 | 0.5696057 | 0.994 | 0.852 | 2.58E-29 |
| Sparc | 1.07E-33 | 0.2830219 | 1 | 0.82 | 3.00E-29 |
| Rpl4 | 1.21E-33 | -0.6598996 | 0.943 | 0.977 | 3.39E-29 |
| Rps4x | 2.02E-33 | -0.4986655 | 1 | 0.992 | 5.67E-29 |
| Fgl2 | 4.45E-33 | 0.4332562 | 0.463 | 0.153 | 1.24E-28 |
| Gpr22 | 5.10E-33 | 0.4414115 | 0.44 | 0.137 | 1.43E-28 |
| Rps15 | 6.19E-33 | -0.4965856 | 0.994 | 0.994 | 1.73E-28 |
| Hrc | 6.23E-33 | 0.5759108 | 0.651 | 0.293 | 1.74E-28 |
| Rpl23 | 1.97E-32 | -0.4541293 | 1 | 0.998 | 5.53E-28 |
| Mgst3 | 2.12E-32 | 0.6189196 | 0.92 | 0.674 | 5.93E-28 |
| Slc22a17 | 2.53E-32 | 0.3499469 | 0.394 | 0.114 | 7.09E-28 |
| Lamb2 | 2.79E-32 | 0.4449029 | 0.503 | 0.18 | 7.80E-28 |
| Htra1 | 3.44E-32 | 0.2801799 | 0.309 | 0.073 | 9.64E-28 |
| Rpl8 | 3.49E-32 | -0.5405756 | 0.994 | 0.988 | 9.76E-28 |
| Klhdc8b | 6.84E-32 | 0.5064998 | 0.68 | 0.311 | 1.92E-27 |
| Gipr | 7.14E-32 | 0.2845983 | 0.331 | 0.082 | 2.00E-27 |
| Serinc1 | 1.91E-31 | 0.5177085 | 0.874 | 0.555 | 5.36E-27 |
| Hif1a | 3.61E-31 | 0.4946859 | 0.84 | 0.503 | 1.01E-26 |
| Rps27a | 4.75E-31 | -0.5117135 | 1 | 0.995 | 1.33E-26 |
| mt-Nd4 | 4.80E-31 | 0.4659996 | 0.989 | 0.988 | 1.34E-26 |
| 90002N15R | 5.33E-31 | 0.4970563 | 0.549 | 0.22 | 1.49E-26 |
| Rbm3 | 8.70E-31 | -0.6545106 | 0.726 | 0.902 | 2.44E-26 |
| Rps3 | 2.92E-30 | -0.5442187 | 0.994 | 0.989 | 8.16E-26 |
| Rps24 | 6.17E-30 | -0.518818 | 1 | 0.993 | 1.73E-25 |
| Rpl14 | 7.22E-30 | -0.5259679 | 1 | 0.993 | 2.02E-25 |
| Rps16 | 9.46E-30 | -0.5256038 | 1 | 0.994 | 2.65E-25 |
| Rpl27a | 1.40E-29 | -0.4782878 | 0.989 | 0.995 | 3.92E-25 |

Figure 28. continued

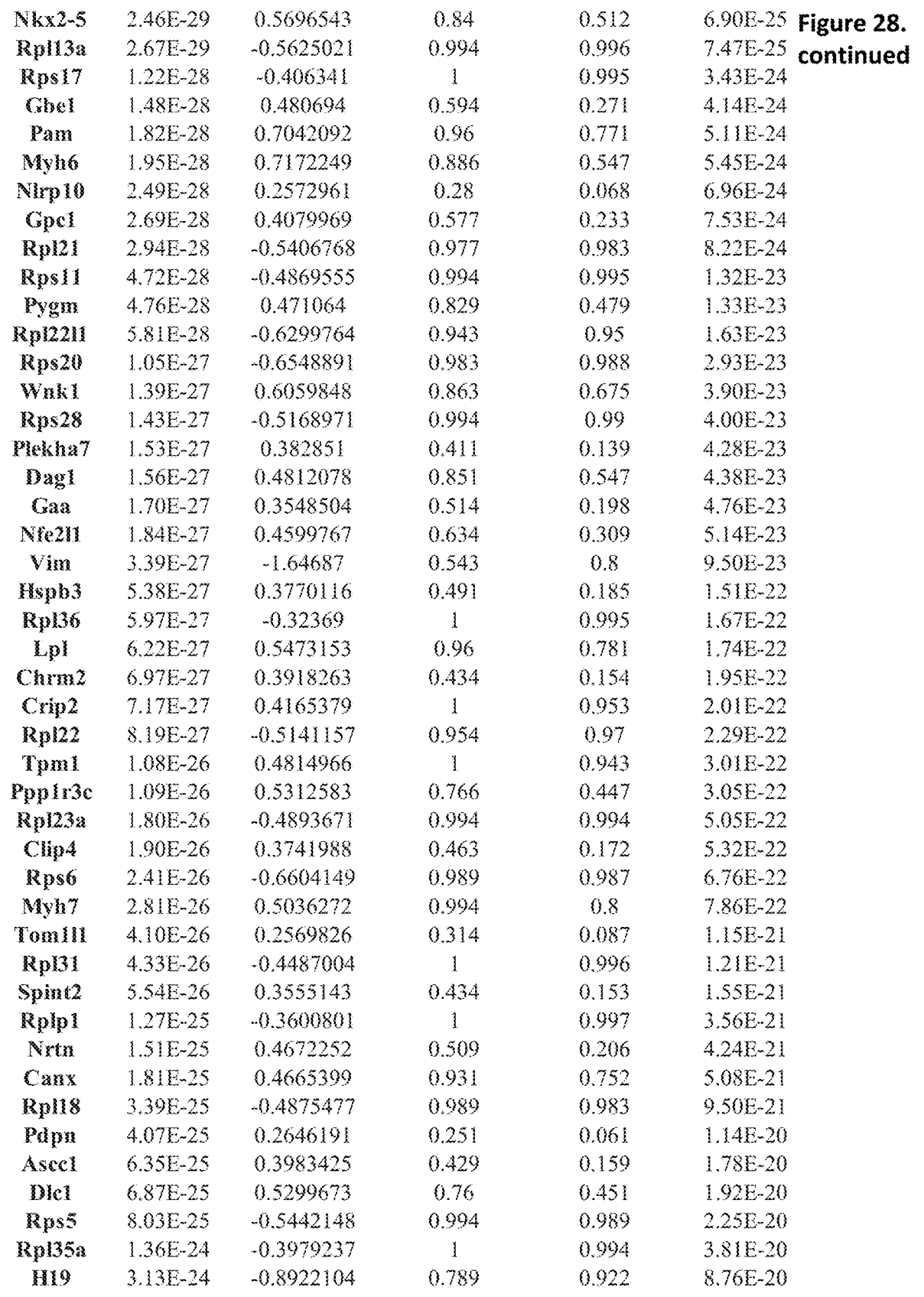

| | | | | | |
|---|---|---|---|---|---|
| Nkx2-5 | 2.46E-29 | 0.5696543 | 0.84 | 0.512 | 6.90E-25 |
| Rpl13a | 2.67E-29 | -0.5625021 | 0.994 | 0.996 | 7.47E-25 |
| Rps17 | 1.22E-28 | -0.406341 | 1 | 0.995 | 3.43E-24 |
| Gbe1 | 1.48E-28 | 0.480694 | 0.594 | 0.271 | 4.14E-24 |
| Pam | 1.82E-28 | 0.7042092 | 0.96 | 0.771 | 5.11E-24 |
| Myh6 | 1.95E-28 | 0.7172249 | 0.886 | 0.547 | 5.45E-24 |
| Nlrp10 | 2.49E-28 | 0.2572961 | 0.28 | 0.068 | 6.96E-24 |
| Gpc1 | 2.69E-28 | 0.4079969 | 0.577 | 0.233 | 7.53E-24 |
| Rpl21 | 2.94E-28 | -0.5406768 | 0.977 | 0.983 | 8.22E-24 |
| Rps11 | 4.72E-28 | -0.4869555 | 0.994 | 0.995 | 1.32E-23 |
| Pygm | 4.76E-28 | 0.471064 | 0.829 | 0.479 | 1.33E-23 |
| Rpl22l1 | 5.81E-28 | -0.6299764 | 0.943 | 0.95 | 1.63E-23 |
| Rps20 | 1.05E-27 | -0.6548891 | 0.983 | 0.988 | 2.93E-23 |
| Wnk1 | 1.39E-27 | 0.6059848 | 0.863 | 0.675 | 3.90E-23 |
| Rps28 | 1.43E-27 | -0.5168971 | 0.994 | 0.99 | 4.00E-23 |
| Plekha7 | 1.53E-27 | 0.382851 | 0.411 | 0.139 | 4.28E-23 |
| Dag1 | 1.56E-27 | 0.4812078 | 0.851 | 0.547 | 4.38E-23 |
| Gaa | 1.70E-27 | 0.3548504 | 0.514 | 0.198 | 4.76E-23 |
| Nfe2l1 | 1.84E-27 | 0.4599767 | 0.634 | 0.309 | 5.14E-23 |
| Vim | 3.39E-27 | -1.64687 | 0.543 | 0.8 | 9.50E-23 |
| Hspb3 | 5.38E-27 | 0.3770116 | 0.491 | 0.185 | 1.51E-22 |
| Rpl36 | 5.97E-27 | -0.32369 | 1 | 0.995 | 1.67E-22 |
| Lpl | 6.22E-27 | 0.5473153 | 0.96 | 0.781 | 1.74E-22 |
| Chrm2 | 6.97E-27 | 0.3918263 | 0.434 | 0.154 | 1.95E-22 |
| Crip2 | 7.17E-27 | 0.4165379 | 1 | 0.953 | 2.01E-22 |
| Rpl22 | 8.19E-27 | -0.5141157 | 0.954 | 0.97 | 2.29E-22 |
| Tpm1 | 1.08E-26 | 0.4814966 | 1 | 0.943 | 3.01E-22 |
| Ppp1r3c | 1.09E-26 | 0.5312583 | 0.766 | 0.447 | 3.05E-22 |
| Rpl23a | 1.80E-26 | -0.4893671 | 0.994 | 0.994 | 5.05E-22 |
| Clip4 | 1.90E-26 | 0.3741988 | 0.463 | 0.172 | 5.32E-22 |
| Rps6 | 2.41E-26 | -0.6604149 | 0.989 | 0.987 | 6.76E-22 |
| Myh7 | 2.81E-26 | 0.5036272 | 0.994 | 0.8 | 7.86E-22 |
| Tom1l1 | 4.10E-26 | 0.2569826 | 0.314 | 0.087 | 1.15E-21 |
| Rpl31 | 4.33E-26 | -0.4487004 | 1 | 0.996 | 1.21E-21 |
| Spint2 | 5.54E-26 | 0.3555143 | 0.434 | 0.153 | 1.55E-21 |
| Rplp1 | 1.27E-25 | -0.3600801 | 1 | 0.997 | 3.56E-21 |
| Nrtn | 1.51E-25 | 0.4672252 | 0.509 | 0.206 | 4.24E-21 |
| Canx | 1.81E-25 | 0.4665399 | 0.931 | 0.752 | 5.08E-21 |
| Rpl18 | 3.39E-25 | -0.4875477 | 0.989 | 0.983 | 9.50E-21 |
| Pdpn | 4.07E-25 | 0.2646191 | 0.251 | 0.061 | 1.14E-20 |
| Ascc1 | 6.35E-25 | 0.3983425 | 0.429 | 0.159 | 1.78E-20 |
| Dlc1 | 6.87E-25 | 0.5299673 | 0.76 | 0.451 | 1.92E-20 |
| Rps5 | 8.03E-25 | -0.5442148 | 0.994 | 0.989 | 2.25E-20 |
| Rpl35a | 1.36E-24 | -0.3979237 | 1 | 0.994 | 3.81E-20 |
| H19 | 3.13E-24 | -0.8922104 | 0.789 | 0.922 | 8.76E-20 |

Figure 28. continued

| | | | | | |
|---|---|---|---|---|---|
| Stox2 | 4.15E-24 | 0.3352746 | 0.417 | 0.154 | 1.16E-19 |
| Csrp3 | 4.16E-24 | 0.5396841 | 1 | 0.797 | 1.16E-19 |
| Myl7 | 5.97E-24 | 1.0942075 | 0.771 | 0.518 | 1.67E-19 |
| Mt3 | 6.38E-24 | 0.5089666 | 0.577 | 0.271 | 1.79E-19 |
| Dpysl3 | 8.81E-24 | 0.5303403 | 0.777 | 0.493 | 2.47E-19 |
| Inafm2 | 9.26E-24 | 0.3029167 | 0.377 | 0.129 | 2.59E-19 |
| Rplp0 | 1.00E-23 | -0.5282757 | 0.977 | 0.982 | 2.81E-19 |
| Fry | 1.14E-23 | 0.4421469 | 0.606 | 0.296 | 3.18E-19 |
| Cryab | 1.35E-23 | 0.4207486 | 1 | 0.788 | 3.77E-19 |
| Rpl19 | 1.75E-23 | -0.4207254 | 1 | 0.993 | 4.89E-19 |
| Gnb2l1 | 2.31E-23 | -0.4998532 | 0.966 | 0.959 | 6.48E-19 |
| Pygb | 2.37E-23 | 0.4288323 | 0.823 | 0.505 | 6.62E-19 |
| Cox6a2 | 2.95E-23 | 0.4465472 | 1 | 0.78 | 8.25E-19 |
| Cdh13 | 3.34E-23 | 0.4516005 | 0.611 | 0.31 | 9.34E-19 |
| Rxfp1 | 4.37E-23 | 0.2613396 | 0.286 | 0.081 | 1.22E-18 |
| Itm2b | 5.09E-23 | 0.6158803 | 0.943 | 0.768 | 1.42E-18 |
| Npm1 | 5.37E-23 | -0.5184158 | 0.954 | 0.947 | 1.50E-18 |
| Plxna4 | 5.49E-23 | 0.2568517 | 0.286 | 0.081 | 1.54E-18 |
| Rps7 | 5.79E-23 | -0.5234785 | 1 | 0.986 | 1.62E-18 |
| Rps29 | 6.18E-23 | -0.3397167 | 1 | 0.999 | 1.73E-18 |
| Rpl6 | 1.05E-22 | -0.4956822 | 1 | 0.986 | 2.94E-18 |
| Obscn | 1.51E-22 | 0.4860287 | 0.863 | 0.588 | 4.22E-18 |
| Mb | 1.84E-22 | -1.2133979 | 0.669 | 0.754 | 5.16E-18 |
| Apobec2 | 2.04E-22 | 0.4240528 | 0.92 | 0.628 | 5.70E-18 |
| Lpgat1 | 2.06E-22 | 0.4746933 | 0.629 | 0.339 | 5.75E-18 |
| Pabpc1 | 2.79E-22 | -0.5745745 | 0.697 | 0.852 | 7.82E-18 |
| Ldb3 | 6.01E-22 | 0.4269546 | 0.983 | 0.695 | 1.68E-17 |
| Rpl9 | 7.99E-22 | -0.4126775 | 0.983 | 0.985 | 2.24E-17 |
| Synpo2l | 8.13E-22 | 0.4197439 | 0.891 | 0.575 | 2.28E-17 |
| Rps18 | 9.27E-22 | -0.4622633 | 1 | 0.985 | 2.59E-17 |
| Fstl1 | 1.14E-21 | 0.3423308 | 0.891 | 0.668 | 3.19E-17 |
| Txlnb | 1.21E-21 | 0.3721966 | 0.531 | 0.244 | 3.39E-17 |
| Ppp1r1a | 1.56E-21 | 0.4251993 | 0.697 | 0.381 | 4.38E-17 |
| Hopx | 2.63E-21 | 0.4977989 | 0.943 | 0.704 | 7.37E-17 |
| Crip1 | 3.08E-21 | 0.4800743 | 0.857 | 0.585 | 8.62E-17 |
| Furin | 3.89E-21 | 0.3163056 | 0.429 | 0.172 | 1.09E-16 |
| mt-Cytb | 4.01E-21 | 0.3388173 | 0.994 | 0.996 | 1.12E-16 |
| Hmgb1 | 6.57E-21 | -0.6680984 | 0.869 | 0.89 | 1.84E-16 |
| Rpl10a | 6.81E-21 | -0.4483876 | 1 | 0.989 | 1.91E-16 |
| Rps2 | 7.64E-21 | -0.4390619 | 0.977 | 0.977 | 2.14E-16 |
| Hmgb2 | 8.35E-21 | -1.3289424 | 0.411 | 0.651 | 2.34E-16 |
| Nudt3 | 8.75E-21 | 0.4757696 | 0.674 | 0.402 | 2.45E-16 |
| Arl5a | 9.01E-21 | 0.4190389 | 0.68 | 0.401 | 2.52E-16 |
| Map1lc3a | 1.03E-20 | 0.3613699 | 0.977 | 0.853 | 2.89E-16 |
| Rtn2 | 1.09E-20 | 0.3053204 | 0.366 | 0.13 | 3.04E-16 |

Figure 28. continued

| | | | | | |
|---|---|---|---|---|---|
| Selm | 1.10E-20 | 0.4383227 | 0.806 | 0.508 | 3.08E-16 |
| Rpl35 | 1.51E-20 | -0.4487778 | 0.983 | 0.968 | 4.24E-16 |
| Rpl30 | 2.84E-20 | -0.4418405 | 0.977 | 0.976 | 7.95E-16 |
| Atp9a | 3.84E-20 | 0.2721684 | 0.274 | 0.084 | 1.08E-15 |
| Phtf2 | 5.28E-20 | 0.3238952 | 0.514 | 0.238 | 1.48E-15 |
| Serinc3 | 5.69E-20 | 0.405121 | 0.817 | 0.557 | 1.59E-15 |
| Asph | 6.96E-20 | 0.4230642 | 0.8 | 0.545 | 1.95E-15 |
| Sgca | 7.06E-20 | 0.2727495 | 0.394 | 0.147 | 1.98E-15 |
| Rpl11 | 7.41E-20 | -0.4436652 | 1 | 0.99 | 2.07E-15 |
| Hn1 | 8.15E-20 | -0.5396882 | 0.714 | 0.876 | 2.28E-15 |
| Tmx4 | 8.16E-20 | 0.3845749 | 0.56 | 0.282 | 2.29E-15 |
| Tspan2 | 8.63E-20 | 0.2956577 | 0.371 | 0.143 | 2.42E-15 |
| Hspa5 | 1.05E-19 | 0.50674 | 0.891 | 0.709 | 2.94E-15 |
| Rpl37 | 1.47E-19 | -0.3927781 | 1 | 0.996 | 4.12E-15 |
| Yap1 | 1.63E-19 | 0.3144956 | 0.486 | 0.224 | 4.55E-15 |
| Mef2d | 1.75E-19 | 0.3978016 | 0.554 | 0.285 | 4.89E-15 |
| Cpe | 2.16E-19 | 0.3508034 | 0.76 | 0.458 | 6.05E-15 |
| Fitm1 | 2.38E-19 | 0.4475189 | 0.669 | 0.383 | 6.67E-15 |
| Stmn1 | 2.44E-19 | -0.7006871 | 0.451 | 0.703 | 6.84E-15 |
| Unc5b | 5.12E-19 | 0.2577643 | 0.383 | 0.142 | 1.43E-14 |
| Mtus1 | 6.34E-19 | 0.3868116 | 0.789 | 0.524 | 1.78E-14 |
| Ezr | 7.26E-19 | 0.4428566 | 0.669 | 0.397 | 2.03E-14 |
| Smyd1 | 9.69E-19 | 0.4113779 | 0.766 | 0.477 | 2.71E-14 |
| Tmsb4x | 1.03E-18 | -0.8222975 | 0.994 | 0.993 | 2.89E-14 |
| Rpl7 | 1.33E-18 | -0.4156527 | 0.983 | 0.985 | 3.73E-14 |
| Pbxip1 | 1.42E-18 | 0.3700744 | 0.617 | 0.331 | 3.98E-14 |
| Ppia | 1.45E-18 | -0.3197717 | 1 | 0.996 | 4.05E-14 |
| Sobp | 1.48E-18 | 0.2610564 | 0.343 | 0.125 | 4.14E-14 |
| Eif4a2 | 1.68E-18 | 0.3634449 | 0.897 | 0.672 | 4.69E-14 |
| Ranbp1 | 1.68E-18 | -0.5345288 | 0.737 | 0.84 | 4.70E-14 |
| Mllt3 | 1.81E-18 | 0.312493 | 0.36 | 0.139 | 5.06E-14 |
| H2afz | 1.87E-18 | -0.9903371 | 0.897 | 0.893 | 5.24E-14 |
| Sspn | 1.93E-18 | 0.355201 | 0.771 | 0.471 | 5.41E-14 |
| Ndrg4 | 2.08E-18 | 0.4188086 | 0.737 | 0.466 | 5.82E-14 |
| Dab2ip | 2.39E-18 | 0.275408 | 0.394 | 0.162 | 6.69E-14 |
| App | 2.99E-18 | 0.4428845 | 0.737 | 0.495 | 8.36E-14 |
| Ccnd2 | 3.31E-18 | 0.3844682 | 0.823 | 0.557 | 9.26E-14 |
| Grn | 3.34E-18 | 0.3211146 | 0.646 | 0.369 | 9.35E-14 |
| Lifr | 3.41E-18 | 0.2921734 | 0.389 | 0.162 | 9.54E-14 |
| Kcng2 | 3.84E-18 | 0.3758592 | 0.623 | 0.347 | 1.07E-13 |
| Tmod1 | 3.95E-18 | 0.3769417 | 0.943 | 0.644 | 1.11E-13 |
| Mylk3 | 4.25E-18 | 0.3850366 | 0.771 | 0.473 | 1.19E-13 |
| Rps26 | 4.31E-18 | -0.4060817 | 0.994 | 0.991 | 1.21E-13 |
| Ppp1r14c | 4.74E-18 | 0.3891585 | 0.943 | 0.675 | 1.33E-13 |
| Erh | 4.88E-18 | -0.4612405 | 0.817 | 0.877 | 1.37E-13 |

Figure 28. continued

| | | | | | |
|---|---|---|---|---|---|
| Itgav | 5.16E-18 | 0.2704438 | 0.309 | 0.106 | 1.45E-13 |
| Lrrc4b | 6.40E-18 | 0.2704298 | 0.36 | 0.139 | 1.79E-13 |
| Nebl | 6.96E-18 | 0.3231528 | 0.92 | 0.585 | 1.95E-13 |
| Mef2a | 1.07E-17 | 0.363767 | 0.903 | 0.715 | 3.00E-13 |
| Rps9 | 1.08E-17 | -0.3622238 | 1 | 0.993 | 3.04E-13 |
| Agl | 1.25E-17 | 0.3855149 | 0.829 | 0.552 | 3.51E-13 |
| Rpl7a | 1.43E-17 | -0.3898996 | 0.983 | 0.974 | 4.00E-13 |
| Slc38a10 | 1.46E-17 | 0.3436349 | 0.451 | 0.205 | 4.08E-13 |
| Rpl36a | 1.49E-17 | -0.4430108 | 0.989 | 0.989 | 4.16E-13 |
| Raph1 | 1.66E-17 | -0.5689189 | 0.234 | 0.543 | 4.65E-13 |
| Pdlim7 | 1.71E-17 | 0.4345936 | 0.669 | 0.418 | 4.80E-13 |
| Rpl3 | 1.72E-17 | -0.4502641 | 0.989 | 0.977 | 4.83E-13 |
| Lamp2 | 1.73E-17 | 0.3570952 | 0.72 | 0.477 | 4.83E-13 |
| Rpl10 | 1.79E-17 | -0.447522 | 0.983 | 0.983 | 5.00E-13 |
| Atp1a2 | 2.29E-17 | 0.3275545 | 0.474 | 0.218 | 6.40E-13 |
| Rpl26 | 2.32E-17 | -0.3604566 | 0.989 | 0.98 | 6.49E-13 |
| mt-Nd5 | 2.81E-17 | 0.3731281 | 0.989 | 0.907 | 7.88E-13 |
| Hspb2 | 3.49E-17 | 0.379105 | 0.88 | 0.583 | 9.78E-13 |
| Rpl37a | 3.80E-17 | -0.3487449 | 1 | 0.998 | 1.06E-12 |
| Tfpi | 4.14E-17 | 0.3696027 | 0.646 | 0.376 | 1.16E-12 |
| Adgrl1 | 4.29E-17 | 0.2619009 | 0.343 | 0.133 | 1.20E-12 |
| Chsy1 | 4.58E-17 | 0.3328973 | 0.417 | 0.188 | 1.28E-12 |
| Hipk3 | 5.65E-17 | 0.3529336 | 0.817 | 0.574 | 1.58E-12 |
| Gmpr | 7.46E-17 | 0.3575195 | 0.68 | 0.41 | 2.09E-12 |
| Rpl5 | 8.14E-17 | -0.3472984 | 0.983 | 0.957 | 2.28E-12 |
| Kctd12 | 1.18E-16 | 0.3360535 | 0.389 | 0.168 | 3.30E-12 |
| Pfn2 | 1.20E-16 | 0.3247962 | 0.463 | 0.222 | 3.36E-12 |
| Nptn | 1.35E-16 | 0.3350681 | 0.617 | 0.376 | 3.79E-12 |
| 00094K13R | 1.50E-16 | -0.5834724 | 0.554 | 0.749 | 4.21E-12 |
| Ran | 1.70E-16 | -0.5425101 | 0.834 | 0.87 | 4.75E-12 |
| Cbx6 | 1.98E-16 | 0.3392232 | 0.6 | 0.339 | 5.55E-12 |
| Dsg2 | 2.21E-16 | 0.2520092 | 0.303 | 0.109 | 6.19E-12 |
| Asb11 | 2.22E-16 | 0.262315 | 0.526 | 0.252 | 6.20E-12 |
| Hif3a | 3.16E-16 | 0.2535847 | 0.406 | 0.175 | 8.85E-12 |
| Nfat5 | 4.09E-16 | 0.3339166 | 0.566 | 0.313 | 1.15E-11 |
| Cks2 | 4.10E-16 | -1.1140521 | 0.137 | 0.427 | 1.15E-11 |
| Pcdh7 | 5.10E-16 | 0.4058152 | 0.771 | 0.508 | 1.43E-11 |
| Rpl24 | 5.38E-16 | -0.294837 | 1 | 0.994 | 1.51E-11 |
| Tulp4 | 5.56E-16 | 0.3028133 | 0.48 | 0.241 | 1.56E-11 |
| Ybx1 | 5.87E-16 | -0.3170325 | 0.977 | 0.972 | 1.64E-11 |
| Ypel5 | 7.46E-16 | 0.3091786 | 0.434 | 0.211 | 2.09E-11 |
| Snrpf | 9.95E-16 | -0.4331047 | 0.617 | 0.798 | 2.78E-11 |
| Srl | 1.15E-15 | 0.3445666 | 0.863 | 0.609 | 3.21E-11 |
| Perp | 1.33E-15 | 0.3551612 | 0.777 | 0.505 | 3.72E-11 |
| Ndufa3 | 1.59E-15 | 0.2600268 | 0.989 | 0.921 | 4.46E-11 |

Figure 28. continued

| | | | | | |
|---|---|---|---|---|---|
| Zbtb20 | 1.62E-15 | 0.4234446 | 0.783 | 0.553 | 4.53E-11 |
| Ctsd | 1.67E-15 | 0.3318341 | 0.829 | 0.59 | 4.68E-11 |
| Tspan3 | 1.88E-15 | 0.3750026 | 0.794 | 0.6 | 5.26E-11 |
| Psap | 2.10E-15 | 0.282835 | 0.823 | 0.63 | 5.88E-11 |
| Tmem161a | 2.30E-15 | 0.2650984 | 0.469 | 0.222 | 6.45E-11 |
| Gm10709 | 2.58E-15 | -0.4323045 | 0.886 | 0.913 | 7.22E-11 |
| Tmem176a | 2.78E-15 | 0.3154046 | 0.434 | 0.202 | 7.79E-11 |
| Ube2c | 3.10E-15 | -0.9926039 | 0.074 | 0.355 | 8.68E-11 |
| Cdh2 | 3.71E-15 | 0.3308384 | 0.914 | 0.656 | 1.04E-10 |
| Fau | 3.79E-15 | -0.3977636 | 1 | 0.989 | 1.06E-10 |
| Myl6 | 3.82E-15 | -0.4808311 | 0.949 | 0.941 | 1.07E-10 |
| Eef1b2 | 4.29E-15 | -0.4561914 | 0.903 | 0.914 | 1.20E-10 |
| Mid2 | 5.09E-15 | 0.2626141 | 0.309 | 0.125 | 1.43E-10 |
| Kcne1 | 5.83E-15 | 0.6687247 | 0.657 | 0.42 | 1.63E-10 |
| Hspe1 | 5.88E-15 | -0.3365067 | 0.914 | 0.938 | 1.65E-10 |
| mt-Nd4l | 7.25E-15 | 0.3072979 | 0.943 | 0.802 | 2.03E-10 |
| Ndufa13 | 7.94E-15 | 0.2748324 | 1 | 0.943 | 2.22E-10 |
| Tmem38a | 9.72E-15 | 0.3359644 | 0.663 | 0.395 | 2.72E-10 |
| 10417H13R | 9.91E-15 | -0.7725474 | 0.051 | 0.321 | 2.77E-10 |
| Eef1g | 1.16E-14 | -0.4463199 | 0.931 | 0.934 | 3.25E-10 |
| Inppl1 | 1.21E-14 | 0.274245 | 0.486 | 0.253 | 3.39E-10 |
| Pja2 | 1.31E-14 | 0.3248823 | 0.714 | 0.486 | 3.68E-10 |
| Pmp22 | 1.43E-14 | 0.2642902 | 0.434 | 0.202 | 4.00E-10 |
| Rpl34 | 1.48E-14 | -0.4094471 | 0.994 | 0.986 | 4.15E-10 |
| Cers4 | 1.65E-14 | 0.3303319 | 0.571 | 0.332 | 4.62E-10 |
| Ppp2r3a | 1.70E-14 | 0.361463 | 0.794 | 0.584 | 4.77E-10 |
| Ccdc141 | 2.02E-14 | 0.313356 | 0.806 | 0.495 | 5.66E-10 |
| Rpl15 | 2.34E-14 | -0.4087437 | 0.88 | 0.904 | 6.56E-10 |
| Fndc3b | 3.10E-14 | 0.2944895 | 0.457 | 0.237 | 8.67E-10 |
| Pdpk1 | 3.53E-14 | 0.2694224 | 0.474 | 0.247 | 9.87E-10 |
| Txnip | 3.59E-14 | 0.3347321 | 0.571 | 0.334 | 1.00E-09 |
| Dsp | 3.86E-14 | 0.3438148 | 0.857 | 0.608 | 1.08E-09 |
| Mest | 4.18E-14 | 0.5872964 | 0.811 | 0.665 | 1.17E-09 |
| Casq1 | 4.23E-14 | 0.451701 | 0.406 | 0.193 | 1.18E-09 |
| Lamp1 | 4.35E-14 | 0.3273835 | 0.834 | 0.694 | 1.22E-09 |
| Fuca2 | 6.06E-14 | 0.320256 | 0.446 | 0.219 | 1.70E-09 |
| Cux1 | 6.21E-14 | 0.3054652 | 0.663 | 0.412 | 1.74E-09 |
| Azin1 | 6.88E-14 | 0.3101139 | 0.823 | 0.574 | 1.93E-09 |
| Sh3bgr | 7.46E-14 | 0.3399041 | 0.983 | 0.736 | 2.09E-09 |
| Gm10260 | 9.00E-14 | -0.4357688 | 0.771 | 0.853 | 2.52E-09 |
| Fabp5 | 1.17E-13 | -1.8882414 | 0.194 | 0.435 | 3.28E-09 |
| Emilin2 | 1.35E-13 | 0.2668543 | 0.4 | 0.187 | 3.77E-09 |
| Myl9 | 1.43E-13 | 0.4123183 | 0.954 | 0.747 | 4.00E-09 |
| Cd81 | 1.50E-13 | 0.2523384 | 0.994 | 0.891 | 4.19E-09 |
| mt-Nd3 | 1.56E-13 | 0.281676 | 1 | 0.942 | 4.38E-09 |

Figure 28.
continued

| | | | | | |
|---|---|---|---|---|---|
| Plekhb2 | 1.61E-13 | 0.267836 | 0.377 | 0.176 | 4.50E-09 |
| Pgam1 | 1.98E-13 | 0.3252637 | 0.96 | 0.838 | 5.53E-09 |
| Hnrnpf | 2.13E-13 | -0.4181919 | 0.754 | 0.81 | 5.97E-09 |
| Akap11 | 2.56E-13 | 0.279098 | 0.417 | 0.207 | 7.17E-09 |
| Btf3 | 2.58E-13 | -0.3424989 | 0.92 | 0.929 | 7.23E-09 |
| Hey2 | 2.74E-13 | -0.3918131 | 0.097 | 0.371 | 7.68E-09 |
| Ptgfrn | 2.81E-13 | 0.2765695 | 0.617 | 0.367 | 7.87E-09 |
| Tuba1b | 2.86E-13 | -0.7286424 | 0.857 | 0.862 | 8.01E-09 |
| Dnajb11 | 3.26E-13 | 0.252439 | 0.543 | 0.305 | 9.12E-09 |
| Hnrnpa1 | 3.34E-13 | -0.357372 | 0.886 | 0.914 | 9.36E-09 |
| Ncam1 | 4.08E-13 | 0.3077221 | 0.691 | 0.436 | 1.14E-08 |
| Fam162a | 4.10E-13 | -0.4259144 | 0.851 | 0.896 | 1.15E-08 |
| Anapc13 | 4.45E-13 | 0.2502374 | 0.971 | 0.854 | 1.25E-08 |
| Bmp7 | 5.46E-13 | 0.2862371 | 0.554 | 0.314 | 1.53E-08 |
| Alpk2 | 5.56E-13 | 0.2821512 | 0.451 | 0.23 | 1.56E-08 |
| Myl4 | 5.65E-13 | 0.401771 | 0.926 | 0.754 | 1.58E-08 |
| Tpm4 | 5.84E-13 | -0.9019954 | 0.091 | 0.339 | 1.63E-08 |
| Pank1 | 6.14E-13 | 0.3039093 | 0.474 | 0.259 | 1.72E-08 |
| Birc5 | 6.24E-13 | -0.7852565 | 0.08 | 0.326 | 1.75E-08 |
| Scd2 | 6.66E-13 | 0.293896 | 0.937 | 0.762 | 1.87E-08 |
| Cenpa | 6.87E-13 | -0.799125 | 0.091 | 0.345 | 1.92E-08 |
| Ndufv3 | 7.17E-13 | 0.2602761 | 1 | 0.917 | 2.01E-08 |
| Ndufaf5 | 8.46E-13 | 0.2753754 | 0.44 | 0.231 | 2.37E-08 |
| Fgf13 | 8.51E-13 | 0.2879407 | 0.589 | 0.337 | 2.38E-08 |
| Scarb2 | 8.87E-13 | 0.3016937 | 0.423 | 0.223 | 2.48E-08 |
| mt-Co1 | 9.37E-13 | 0.3023183 | 0.994 | 0.986 | 2.62E-08 |
| Pcp4l1 | 1.02E-12 | 0.3107112 | 0.383 | 0.183 | 2.85E-08 |
| Dmd | 1.15E-12 | 0.259902 | 0.56 | 0.319 | 3.22E-08 |
| Tubb5 | 1.22E-12 | -0.6880503 | 0.903 | 0.892 | 3.42E-08 |
| Hspg2 | 1.23E-12 | 0.259424 | 0.634 | 0.381 | 3.44E-08 |
| Tmed7 | 1.24E-12 | 0.2968909 | 0.646 | 0.416 | 3.48E-08 |
| Adprhl1 | 1.25E-12 | 0.3595177 | 0.789 | 0.551 | 3.50E-08 |
| Actg1 | 1.41E-12 | -1.3259865 | 0.703 | 0.805 | 3.94E-08 |
| Tmem30a | 1.68E-12 | 0.2878538 | 0.657 | 0.435 | 4.71E-08 |
| Pmepa1 | 1.72E-12 | 0.265379 | 0.343 | 0.156 | 4.81E-08 |
| Marcks | 1.76E-12 | -0.7077283 | 0.36 | 0.575 | 4.94E-08 |
| Pdgfa | 1.86E-12 | 0.268814 | 0.623 | 0.376 | 5.21E-08 |
| Rps10 | 2.06E-12 | -0.3097541 | 0.989 | 0.986 | 5.78E-08 |
| Cacna2d1 | 2.24E-12 | 0.2506851 | 0.48 | 0.26 | 6.27E-08 |
| Smc4 | 2.48E-12 | -0.6297725 | 0.177 | 0.418 | 6.95E-08 |
| Cand2 | 2.72E-12 | 0.2638699 | 0.417 | 0.209 | 7.61E-08 |
| Bri3 | 2.76E-12 | 0.2706225 | 0.96 | 0.854 | 7.73E-08 |
| Ddr1 | 2.83E-12 | 0.277628 | 0.503 | 0.28 | 7.93E-08 |
| Sgcg | 2.98E-12 | 0.2529262 | 0.331 | 0.148 | 8.35E-08 |
| Rpl41 | 2.99E-12 | -0.2588267 | 1 | 0.999 | 8.38E-08 |

Figure 28. continued

| | | | | | |
|---|---|---|---|---|---|
| Tshz1 | 3.20E-12 | 0.3141296 | 0.36 | 0.178 | 8.97E-08 |
| Pink1 | 3.51E-12 | 0.2862133 | 0.509 | 0.293 | 9.83E-08 |
| H3f3b | 3.59E-12 | -0.7349754 | 0.857 | 0.873 | 1.01E-07 |
| Antxr2 | 4.07E-12 | 0.3060701 | 0.571 | 0.345 | 1.14E-07 |
| Tusc3 | 4.22E-12 | 0.3104428 | 0.497 | 0.295 | 1.18E-07 |
| Dnmt3a | 4.30E-12 | 0.3064546 | 0.606 | 0.388 | 1.20E-07 |
| Cdca8 | 4.55E-12 | -0.505999 | 0.034 | 0.267 | 1.27E-07 |
| Snrpn | 4.88E-12 | 0.2769099 | 0.383 | 0.195 | 1.37E-07 |
| Strn3 | 4.96E-12 | 0.3108949 | 0.72 | 0.509 | 1.39E-07 |
| Hk1 | 5.15E-12 | 0.299106 | 0.749 | 0.537 | 1.44E-07 |
| Sfrp1 | 5.18E-12 | 0.4692883 | 0.583 | 0.384 | 1.45E-07 |
| Tns1 | 5.70E-12 | 0.285626 | 0.783 | 0.544 | 1.60E-07 |
| Ndufa1 | 6.05E-12 | 0.2951866 | 0.977 | 0.872 | 1.69E-07 |
| Ccna2 | 6.33E-12 | -0.6200228 | 0.04 | 0.266 | 1.77E-07 |
| Rrm2 | 6.55E-12 | -0.6175107 | 0.069 | 0.302 | 1.83E-07 |
| Srsf3 | 8.55E-12 | -0.4080562 | 0.749 | 0.837 | 2.39E-07 |
| Ntn1 | 9.02E-12 | 0.3510247 | 0.446 | 0.239 | 2.52E-07 |
| Smim14 | 1.02E-11 | 0.2526122 | 0.691 | 0.482 | 2.87E-07 |
| Hmgn1 | 1.14E-11 | -0.4560132 | 0.8 | 0.858 | 3.20E-07 |
| Pkm | 1.32E-11 | 0.2613395 | 0.989 | 0.911 | 3.71E-07 |
| Hmgn2 | 1.33E-11 | -0.4930222 | 0.554 | 0.696 | 3.72E-07 |
| Mif | 1.38E-11 | -0.3322984 | 0.966 | 0.965 | 3.87E-07 |
| Calr | 1.45E-11 | 0.3455916 | 0.914 | 0.736 | 4.06E-07 |
| Gas6 | 1.51E-11 | 0.299475 | 0.674 | 0.459 | 4.24E-07 |
| Mef2c | 1.69E-11 | -0.4306155 | 0.314 | 0.563 | 4.74E-07 |
| Naca | 1.86E-11 | -0.3493694 | 0.966 | 0.956 | 5.22E-07 |
| Eef1a2 | 2.24E-11 | 0.3125118 | 0.737 | 0.497 | 6.26E-07 |
| Cenpm | 2.35E-11 | -0.3174617 | 0.04 | 0.266 | 6.58E-07 |
| Peg3 | 2.48E-11 | 0.2962979 | 0.709 | 0.493 | 6.95E-07 |
| Prkar1a | 2.83E-11 | 0.3042463 | 0.891 | 0.771 | 7.93E-07 |
| Camk2d | 3.01E-11 | 0.2882387 | 0.863 | 0.701 | 8.44E-07 |
| Ccnb2 | 3.09E-11 | -0.4495288 | 0.034 | 0.251 | 8.65E-07 |
| Txn1 | 3.17E-11 | -0.4033593 | 0.794 | 0.866 | 8.87E-07 |
| Tagln2 | 3.96E-11 | -1.2068249 | 0.097 | 0.311 | 1.11E-06 |
| Tmsb10 | 4.34E-11 | -0.5759543 | 0.96 | 0.969 | 1.21E-06 |
| Trp53inp2 | 4.62E-11 | 0.2736347 | 0.657 | 0.444 | 1.29E-06 |
| Enah | 4.77E-11 | 0.2771088 | 0.749 | 0.504 | 1.34E-06 |
| Cenpf | 5.02E-11 | -0.6903493 | 0.04 | 0.254 | 1.41E-06 |
| Rps23 | 5.04E-11 | -0.3887467 | 1 | 0.996 | 1.41E-06 |
| Snrpe | 5.13E-11 | -0.3311066 | 0.794 | 0.858 | 1.44E-06 |
| Cdca3 | 5.26E-11 | -0.4106103 | 0.04 | 0.258 | 1.47E-06 |
| Mark3 | 5.48E-11 | 0.2726782 | 0.469 | 0.274 | 1.54E-06 |
| Herc3 | 6.37E-11 | 0.2619164 | 0.469 | 0.259 | 1.78E-06 |
| Adam10 | 6.44E-11 | 0.2747661 | 0.52 | 0.314 | 1.80E-06 |
| Gm42418 | 6.76E-11 | 0.3952136 | 0.669 | 0.491 | 1.89E-06 |

Figure 28. continued

| | | | | | |
|---|---|---|---|---|---|
| Maged1 | 6.79E-11 | 0.2846642 | 0.731 | 0.539 | 1.90E-06 |
| Pfn1 | 7.96E-11 | -0.3507072 | 0.994 | 0.967 | 2.23E-06 |
| Camta1 | 8.00E-11 | 0.2599706 | 0.846 | 0.647 | 2.24E-06 |
| Lockd | 8.14E-11 | -0.3910385 | 0.069 | 0.298 | 2.28E-06 |
| Hes6 | 8.60E-11 | 0.2809915 | 0.486 | 0.286 | 2.41E-06 |
| Cenpw | 9.60E-11 | -0.3785283 | 0.097 | 0.328 | 2.69E-06 |
| Higd2a | 1.00E-10 | 0.2555031 | 0.943 | 0.825 | 2.81E-06 |
| Gsta4 | 1.09E-10 | 0.2857892 | 0.497 | 0.293 | 3.05E-06 |
| Dpysl2 | 1.12E-10 | 0.3268047 | 0.56 | 0.347 | 3.15E-06 |
| Rcan2 | 1.20E-10 | 0.2674329 | 0.663 | 0.431 | 3.35E-06 |
| Gmnn | 1.27E-10 | -0.3844237 | 0.143 | 0.372 | 3.55E-06 |
| Rps14 | 1.43E-10 | -0.3087329 | 1 | 0.996 | 3.99E-06 |
| Prelid1 | 1.46E-10 | -0.3862352 | 0.663 | 0.754 | 4.10E-06 |
| Yae1d1 | 1.67E-10 | 0.2790106 | 0.509 | 0.311 | 4.67E-06 |
| Purb | 1.72E-10 | 0.2729059 | 0.76 | 0.564 | 4.83E-06 |
| Hspb7 | 1.73E-10 | 0.2844629 | 0.994 | 0.753 | 4.83E-06 |
| Eef1a1 | 1.83E-10 | -0.2575863 | 1 | 0.998 | 5.13E-06 |
| Pmf1 | 1.90E-10 | -0.3226644 | 0.103 | 0.325 | 5.31E-06 |
| Ccnd3 | 2.01E-10 | 0.2663754 | 0.903 | 0.731 | 5.64E-06 |
| Rpl27 | 2.04E-10 | -0.3056761 | 0.954 | 0.947 | 5.71E-06 |
| Rps12-ps3 | 2.10E-10 | -0.4209261 | 0.463 | 0.657 | 5.88E-06 |
| Rps21 | 2.25E-10 | -0.3087823 | 0.994 | 0.978 | 6.29E-06 |
| Nme1 | 2.39E-10 | -0.353692 | 0.617 | 0.758 | 6.68E-06 |
| C1qbp | 3.34E-10 | -0.3545319 | 0.634 | 0.759 | 9.36E-06 |
| Fxr1 | 4.39E-10 | 0.2671758 | 0.777 | 0.573 | 1.23E-05 |
| Idh2 | 4.70E-10 | 0.2594245 | 1 | 0.905 | 1.32E-05 |
| Itm2a | 5.27E-10 | -0.2786949 | 0.543 | 0.3 | 1.48E-05 |
| Cks1b | 5.94E-10 | -0.519718 | 0.337 | 0.523 | 1.66E-05 |
| Arpc1b | 6.03E-10 | -0.8018603 | 0.126 | 0.327 | 1.69E-05 |
| Ube3a | 6.30E-10 | 0.2605492 | 0.857 | 0.669 | 1.76E-05 |
| Ttn | 6.33E-10 | 0.3109818 | 0.989 | 0.731 | 1.77E-05 |
| Rasl11b | 7.12E-10 | 0.2582683 | 0.406 | 0.228 | 1.99E-05 |
| Hnrnpab | 7.51E-10 | -0.3411918 | 0.714 | 0.791 | 2.10E-05 |
| Abracl | 7.63E-10 | -0.3484899 | 0.697 | 0.794 | 2.14E-05 |
| Zak | 8.29E-10 | 0.2690023 | 0.829 | 0.597 | 2.32E-05 |
| Rps27 | 8.63E-10 | -0.3418728 | 1 | 0.993 | 2.42E-05 |
| Ankrd1 | 8.96E-10 | 0.6181879 | 0.72 | 0.544 | 2.51E-05 |
| Rnf207 | 1.03E-09 | 0.264827 | 0.497 | 0.31 | 2.88E-05 |
| Ppp1r1b | 1.03E-09 | -0.3161889 | 0.08 | 0.293 | 2.89E-05 |
| Lmnb1 | 1.07E-09 | -0.3820811 | 0.171 | 0.383 | 3.00E-05 |
| Flnc | 1.18E-09 | 0.26284 | 0.697 | 0.491 | 3.29E-05 |
| Tnnt2 | 1.68E-09 | 0.2786876 | 1 | 0.886 | 4.72E-05 |
| Prdx1 | 1.70E-09 | -0.2786784 | 0.966 | 0.935 | 4.77E-05 |
| Sumo2 | 1.76E-09 | -0.2718694 | 0.92 | 0.926 | 4.93E-05 |
| Mt1 | 2.66E-09 | -0.4313692 | 0.749 | 0.788 | 7.45E-05 |

**Figure 28.
continued**

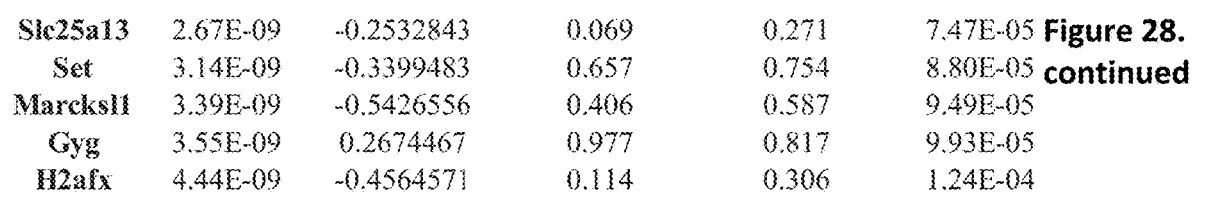

| | | | | | |
|---|---|---|---|---|---|
| Slc25a13 | 2.67E-09 | -0.2532843 | 0.069 | 0.271 | 7.47E-05 |
| Set | 3.14E-09 | -0.3399483 | 0.657 | 0.754 | 8.80E-05 |
| Marcksl1 | 3.39E-09 | -0.5426556 | 0.406 | 0.587 | 9.49E-05 |
| Gyg | 3.55E-09 | 0.2674467 | 0.977 | 0.817 | 9.93E-05 |
| H2afx | 4.44E-09 | -0.4564571 | 0.114 | 0.306 | 1.24E-04 |

Figure 28. continued

| Gene | p value | Average log Fold Change | Average value Standard PF | Average value Transitional PF | Adjusted p value |
|---|---|---|---|---|---|
| Cacna2d2 | 9.78E-23 | 1.5020046 | 0.917 | 0.217 | 2.74E-18 |
| Mgp | 1.30E-22 | 1.7413662 | 0.983 | 0.583 | 3.65E-18 |
| Crnde | 4.20E-21 | 1.2389077 | 0.9 | 0.304 | 1.18E-16 |
| Nsg2 | 1.24E-20 | 1.0208815 | 0.7 | 0.043 | 3.47E-16 |
| Gm15543 | 1.82E-19 | 1.3493768 | 0.917 | 0.348 | 5.10E-15 |
| Myl1 | 5.27E-18 | 1.1835439 | 0.95 | 0.461 | 1.48E-13 |
| Slco3a1 | 3.78E-17 | 0.9827074 | 0.85 | 0.322 | 1.06E-12 |
| Gja5 | 7.01E-17 | 1.1016894 | 0.883 | 0.348 | 1.96E-12 |
| Itm2b | 7.21E-17 | 1.0069434 | 0.983 | 0.922 | 2.02E-12 |
| Sbk2 | 7.30E-17 | 0.7950252 | 0.567 | 0.026 | 2.04E-12 |
| Tmem163 | 7.29E-16 | 0.6800148 | 0.5 | 0.009 | 2.04E-11 |
| Stard10 | 1.38E-15 | 1.0132101 | 0.8 | 0.261 | 3.86E-11 |
| Igfbp5 | 4.36E-15 | 1.0406347 | 0.933 | 0.574 | 1.22E-10 |
| Ramp1 | 2.25E-14 | 0.9626509 | 0.967 | 0.765 | 6.29E-10 |
| Cpne5 | 3.80E-14 | 0.7982547 | 0.767 | 0.191 | 1.06E-09 |
| Slit2 | 3.90E-14 | 1.076859 | 0.7 | 0.157 | 1.09E-09 |
| Dcpp1 | 1.62E-13 | 3.2427699 | 0.6 | 0.104 | 4.54E-09 |
| Tsc22d3 | 3.77E-13 | 0.7721066 | 1 | 0.913 | 1.05E-08 |
| Fhl2 | 3.85E-13 | -0.9884016 | 0.4 | 0.852 | 1.08E-08 |
| Ank1 | 4.56E-13 | 0.8557534 | 0.8 | 0.313 | 1.28E-08 |
| Art1 | 6.26E-13 | 0.5338408 | 0.483 | 0.035 | 1.75E-08 |
| Ankrd1 | 1.12E-12 | -1.5259038 | 0.417 | 0.878 | 3.13E-08 |
| Gata6 | 1.22E-12 | -0.775104 | 0.05 | 0.626 | 3.41E-08 |
| Spock2 | 1.95E-12 | 0.6517306 | 0.617 | 0.122 | 5.47E-08 |
| Tesc | 2.01E-12 | 0.8613869 | 0.8 | 0.339 | 5.63E-08 |
| Nppb | 5.62E-12 | -1.4205696 | 0.117 | 0.678 | 1.57E-07 |
| Sema3c | 9.88E-12 | 0.7841296 | 0.75 | 0.296 | 2.77E-07 |
| Gpx3 | 6.01E-11 | 0.9238563 | 0.933 | 0.957 | 1.68E-06 |
| Pmp22 | 7.63E-11 | 0.5723879 | 0.733 | 0.278 | 2.14E-06 |
| Sparcl1 | 9.29E-11 | 0.788139 | 0.65 | 0.191 | 2.60E-06 |
| Bmp2 | 1.40E-10 | 0.544123 | 0.35 | 0.009 | 3.92E-06 |
| Dbi | 2.07E-10 | 0.4614424 | 1 | 0.991 | 5.79E-06 |
| Sema3a | 2.56E-10 | 0.8431505 | 0.6 | 0.174 | 7.18E-06 |
| Fabp3 | 2.64E-10 | -0.6477596 | 0.933 | 0.974 | 7.39E-06 |
| Cited1 | 3.03E-10 | 0.8795259 | 0.967 | 0.835 | 8.49E-06 |
| Slit3 | 5.02E-10 | 0.3846581 | 0.333 | 0.009 | 1.40E-05 |
| Dcpp2 | 5.98E-10 | 1.5262984 | 0.383 | 0.035 | 1.67E-05 |
| Slc22a1 | 6.94E-10 | 0.8813106 | 0.617 | 0.165 | 1.94E-05 |
| Ptges | 8.82E-10 | 0.5353973 | 0.367 | 0.026 | 2.47E-05 |

Online Table VIII: Differentially Expressed Genes in Two Subclusters of Cluster 13.

Figure 29.

| | | | | | |
|---|---|---|---|---|---|
| Cdkn1a | 9.76E-10 | 0.5338788 | 0.85 | 0.365 | 2.73E-05 |
| Txnip | 1.18E-09 | 0.5742133 | 0.85 | 0.426 | 3.30E-05 |
| Sorbs2 | 1.43E-09 | -0.6254688 | 0.85 | 0.974 | 4.00E-05 |
| Mgst3 | 2.02E-09 | 0.4797265 | 0.983 | 0.887 | 5.66E-05 |
| Cst3 | 2.75E-09 | 0.5651454 | 1 | 0.991 | 7.70E-05 |
| Corin | 4.60E-09 | 0.700234 | 0.9 | 0.652 | 1.29E-04 |
| Ivns1abp | 6.10E-09 | -0.6435162 | 0.517 | 0.809 | 1.71E-04 |
| Tbx20 | 6.12E-09 | -0.6813026 | 0.183 | 0.643 | 1.71E-04 |
| Sparc | 7.93E-09 | 0.4873088 | 1 | 1 | 2.22E-04 |
| Acta2 | 7.98E-09 | -1.1822977 | 0.333 | 0.739 | 2.23E-04 |
| Sdc4 | 9.47E-09 | 0.673311 | 0.817 | 0.426 | 2.65E-04 |
| Mif | 1.09E-08 | -0.5804576 | 0.933 | 0.983 | 3.04E-04 |
| Sorcs2 | 1.09E-08 | 0.4325905 | 0.533 | 0.148 | 3.06E-04 |
| Rpl39 | 1.33E-08 | -0.3024069 | 1 | 1 | 3.73E-04 |
| Rpl38 | 1.43E-08 | -0.3297776 | 1 | 1 | 4.02E-04 |
| Epha4 | 1.48E-08 | 0.659153 | 0.717 | 0.296 | 4.14E-04 |
| Trim11 | 1.68E-08 | 0.5212449 | 0.65 | 0.226 | 4.72E-04 |
| Sulf2 | 1.73E-08 | 0.6017632 | 0.933 | 0.817 | 4.86E-04 |
| Kif13a | 1.74E-08 | 0.5104516 | 0.833 | 0.53 | 4.88E-04 |
| Lxn | 1.84E-08 | 0.5201064 | 0.467 | 0.104 | 5.14E-04 |
| Bves | 2.08E-08 | -0.6703869 | 0.283 | 0.661 | 5.82E-04 |
| Atp2a2 | 2.28E-08 | -0.5130573 | 0.95 | 0.991 | 6.39E-04 |
| Igsf1 | 2.34E-08 | 0.3654904 | 0.3 | 0.017 | 6.54E-04 |
| Igf2 | 2.99E-08 | -0.6472284 | 0.633 | 0.896 | 8.38E-04 |
| Ptp4a2 | 3.29E-08 | 0.5485927 | 0.95 | 0.861 | 9.22E-04 |
| Lamb3 | 3.53E-08 | 0.4888921 | 0.45 | 0.087 | 9.88E-04 |
| H19 | 4.26E-08 | -1.0773475 | 0.683 | 0.843 | 1.19E-03 |
| Dcpp3 | 4.93E-08 | 0.9474818 | 0.267 | 0.009 | 1.38E-03 |
| Rps17 | 5.93E-08 | -0.3310117 | 1 | 1 | 1.66E-03 |
| Tgm2 | 6.46E-08 | 0.4853854 | 0.95 | 0.861 | 1.81E-03 |
| Fam162a | 7.67E-08 | -0.5958635 | 0.75 | 0.904 | 2.15E-03 |
| Meg3 | 8.74E-08 | 0.7286597 | 0.8 | 0.487 | 2.45E-03 |
| Dlc1 | 9.71E-08 | 0.5353325 | 0.9 | 0.687 | 2.72E-03 |
| Adgrb2 | 1.06E-07 | 0.4705899 | 0.5 | 0.139 | 2.96E-03 |
| Paip2 | 1.37E-07 | 0.4145833 | 0.95 | 0.817 | 3.84E-03 |
| Atp1a1 | 1.62E-07 | 0.4554128 | 0.967 | 0.965 | 4.53E-03 |
| Oxct1 | 1.77E-07 | -0.5523441 | 0.417 | 0.765 | 4.94E-03 |
| Map1b | 1.85E-07 | 0.3906838 | 0.783 | 0.443 | 5.17E-03 |
| Lyz2 | 2.01E-07 | 0.8439976 | 0.633 | 0.252 | 5.61E-03 |
| Popdc2 | 2.99E-07 | -0.5252035 | 0.433 | 0.748 | 8.39E-03 |
| Rpsa | 3.12E-07 | -0.4673454 | 0.967 | 0.991 | 8.74E-03 |
| Angpt1 | 3.22E-07 | 0.7999435 | 0.35 | 0.061 | 9.01E-03 |
| Hn1 | 3.91E-07 | -0.5871371 | 0.583 | 0.783 | 1.09E-02 |
| Cox6a2 | 4.14E-07 | 0.3210532 | 1 | 1 | 1.16E-02 |
| Rps8 | 4.21E-07 | -0.3288291 | 1 | 1 | 1.18E-02 |

Figure 29.
continued

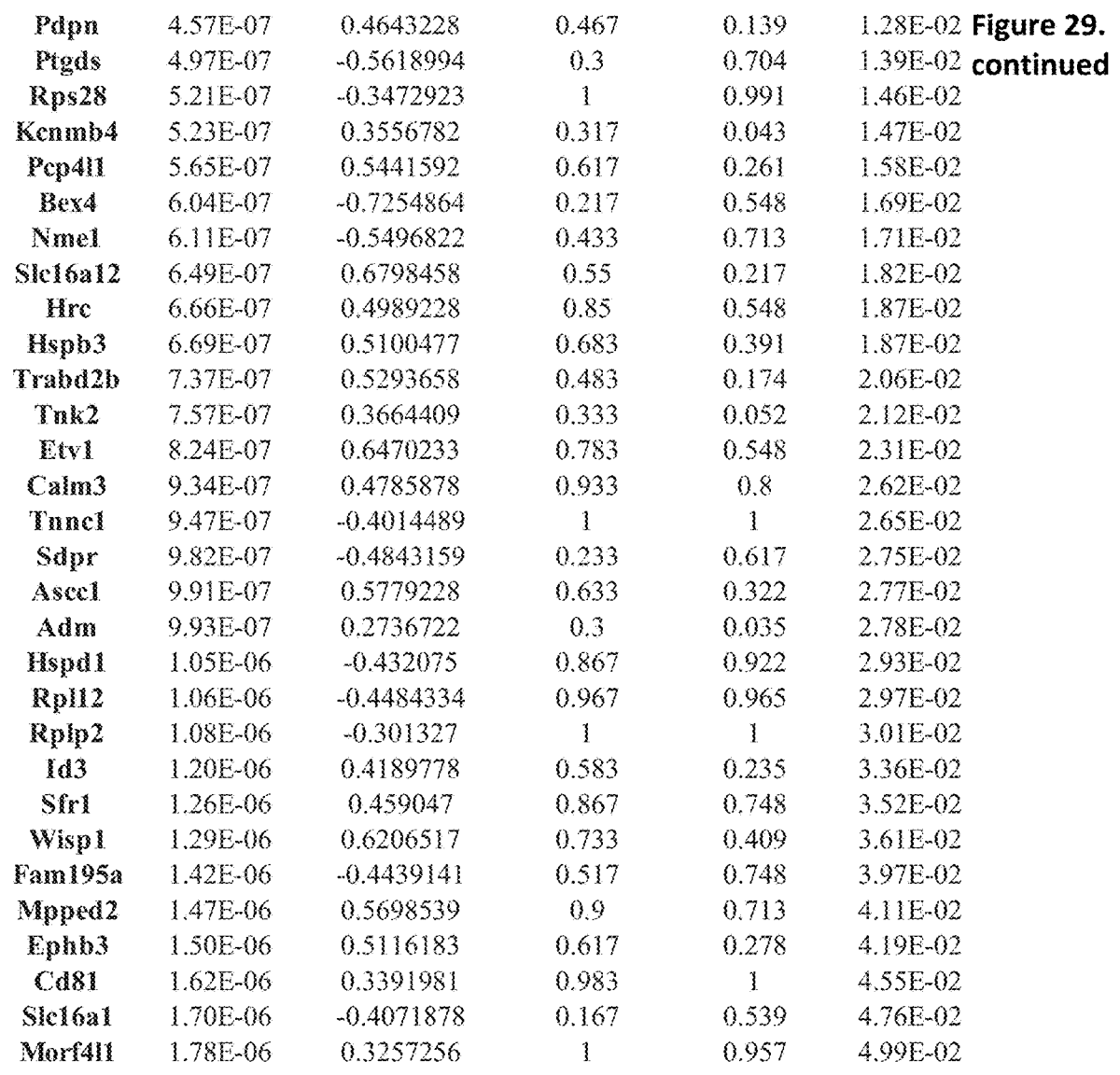

| | | | | | |
|---|---|---|---|---|---|
| Pdpn | 4.57E-07 | 0.4643228 | 0.467 | 0.139 | 1.28E-02 |
| Ptgds | 4.97E-07 | -0.5618994 | 0.3 | 0.704 | 1.39E-02 |
| Rps28 | 5.21E-07 | -0.3472923 | 1 | 0.991 | 1.46E-02 |
| Kcnmb4 | 5.23E-07 | 0.3556782 | 0.317 | 0.043 | 1.47E-02 |
| Pcp4l1 | 5.65E-07 | 0.5441592 | 0.617 | 0.261 | 1.58E-02 |
| Bex4 | 6.04E-07 | -0.7254864 | 0.217 | 0.548 | 1.69E-02 |
| Nme1 | 6.11E-07 | -0.5496822 | 0.433 | 0.713 | 1.71E-02 |
| Slc16a12 | 6.49E-07 | 0.6798458 | 0.55 | 0.217 | 1.82E-02 |
| Hrc | 6.66E-07 | 0.4989228 | 0.85 | 0.548 | 1.87E-02 |
| Hspb3 | 6.69E-07 | 0.5100477 | 0.683 | 0.391 | 1.87E-02 |
| Trabd2b | 7.37E-07 | 0.5293658 | 0.483 | 0.174 | 2.06E-02 |
| Tnk2 | 7.57E-07 | 0.3664409 | 0.333 | 0.052 | 2.12E-02 |
| Etv1 | 8.24E-07 | 0.6470233 | 0.783 | 0.548 | 2.31E-02 |
| Calm3 | 9.34E-07 | 0.4785878 | 0.933 | 0.8 | 2.62E-02 |
| Tnnc1 | 9.47E-07 | -0.4014489 | 1 | 1 | 2.65E-02 |
| Sdpr | 9.82E-07 | -0.4843159 | 0.233 | 0.617 | 2.75E-02 |
| Ascc1 | 9.91E-07 | 0.5779228 | 0.633 | 0.322 | 2.77E-02 |
| Adm | 9.93E-07 | 0.2736722 | 0.3 | 0.035 | 2.78E-02 |
| Hspd1 | 1.05E-06 | -0.432075 | 0.867 | 0.922 | 2.93E-02 |
| Rpl12 | 1.06E-06 | -0.4484334 | 0.967 | 0.965 | 2.97E-02 |
| Rplp2 | 1.08E-06 | -0.301327 | 1 | 1 | 3.01E-02 |
| Id3 | 1.20E-06 | 0.4189778 | 0.583 | 0.235 | 3.36E-02 |
| Sfr1 | 1.26E-06 | 0.459047 | 0.867 | 0.748 | 3.52E-02 |
| Wisp1 | 1.29E-06 | 0.6206517 | 0.733 | 0.409 | 3.61E-02 |
| Fam195a | 1.42E-06 | -0.4439141 | 0.517 | 0.748 | 3.97E-02 |
| Mpped2 | 1.47E-06 | 0.5698539 | 0.9 | 0.713 | 4.11E-02 |
| Ephb3 | 1.50E-06 | 0.5116183 | 0.617 | 0.278 | 4.19E-02 |
| Cd81 | 1.62E-06 | 0.3391981 | 0.983 | 1 | 4.55E-02 |
| Slc16a1 | 1.70E-06 | -0.4071878 | 0.167 | 0.539 | 4.76E-02 |
| Morf4l1 | 1.78E-06 | 0.3257256 | 1 | 0.957 | 4.99E-02 |

Figure 29. continued

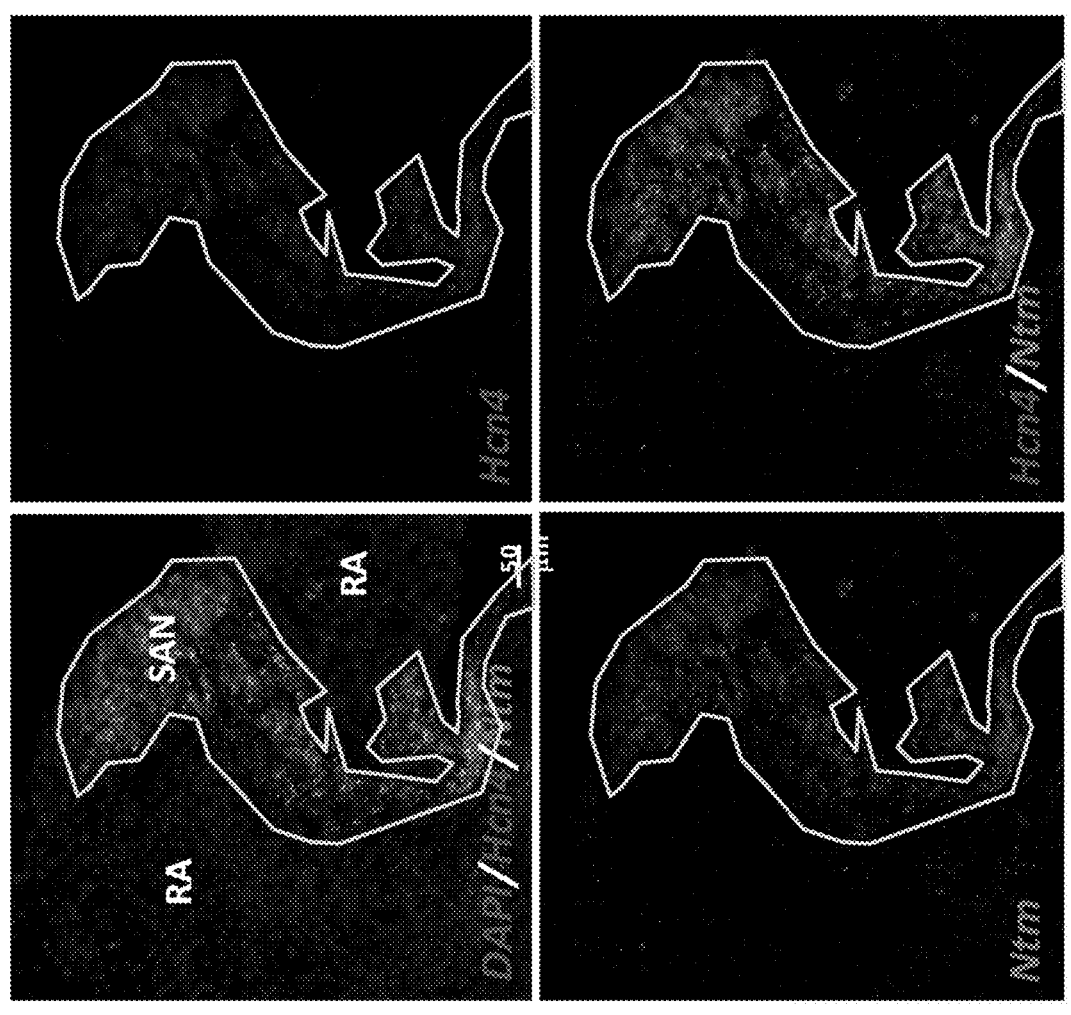
Figure 30. Ntm is Enriched in the Cardiac Conduction System of the Mouse Heart.

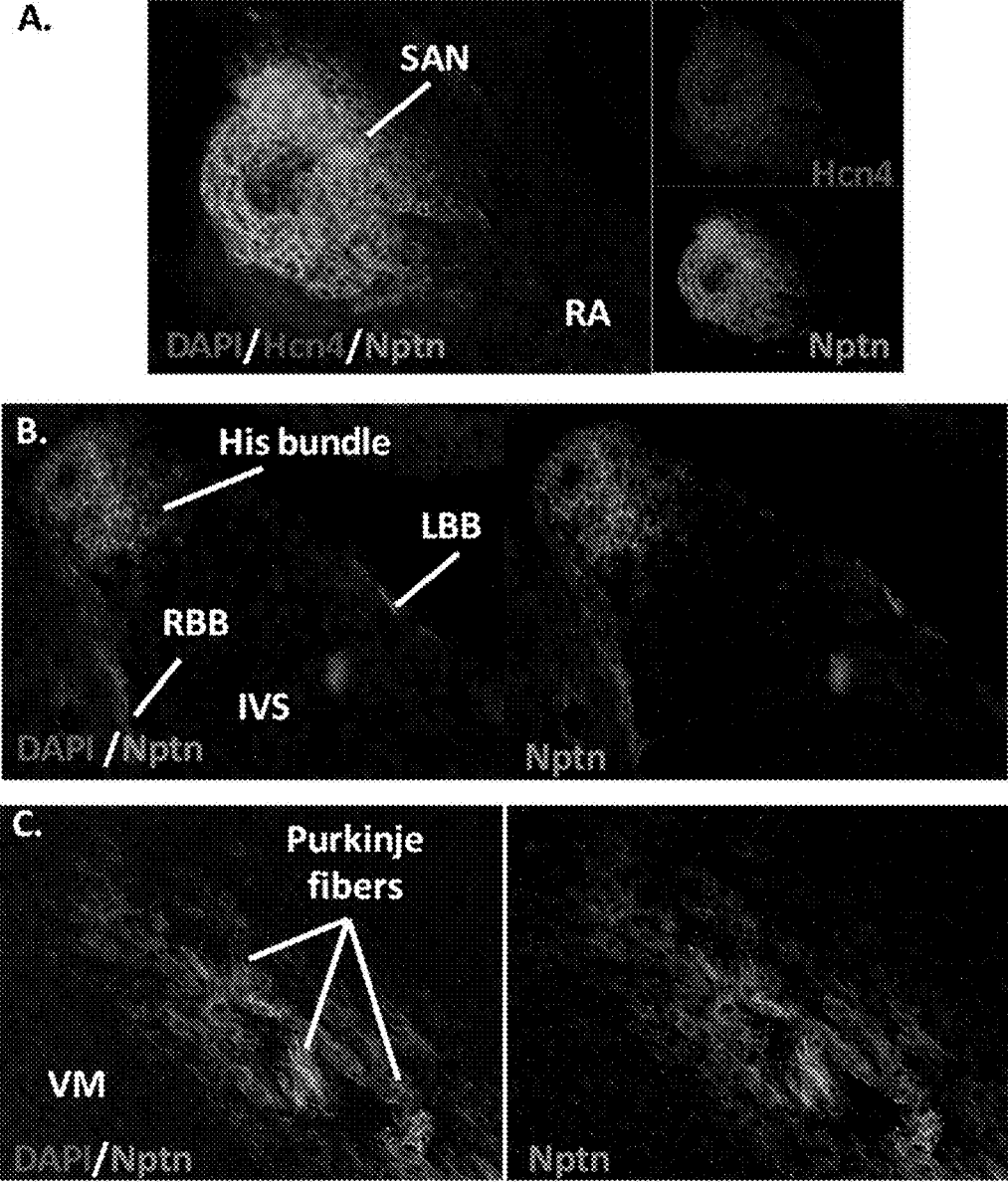
Figure 31. Nptn is Enriched in the Cardiac Conduction System of the Mouse Heart.

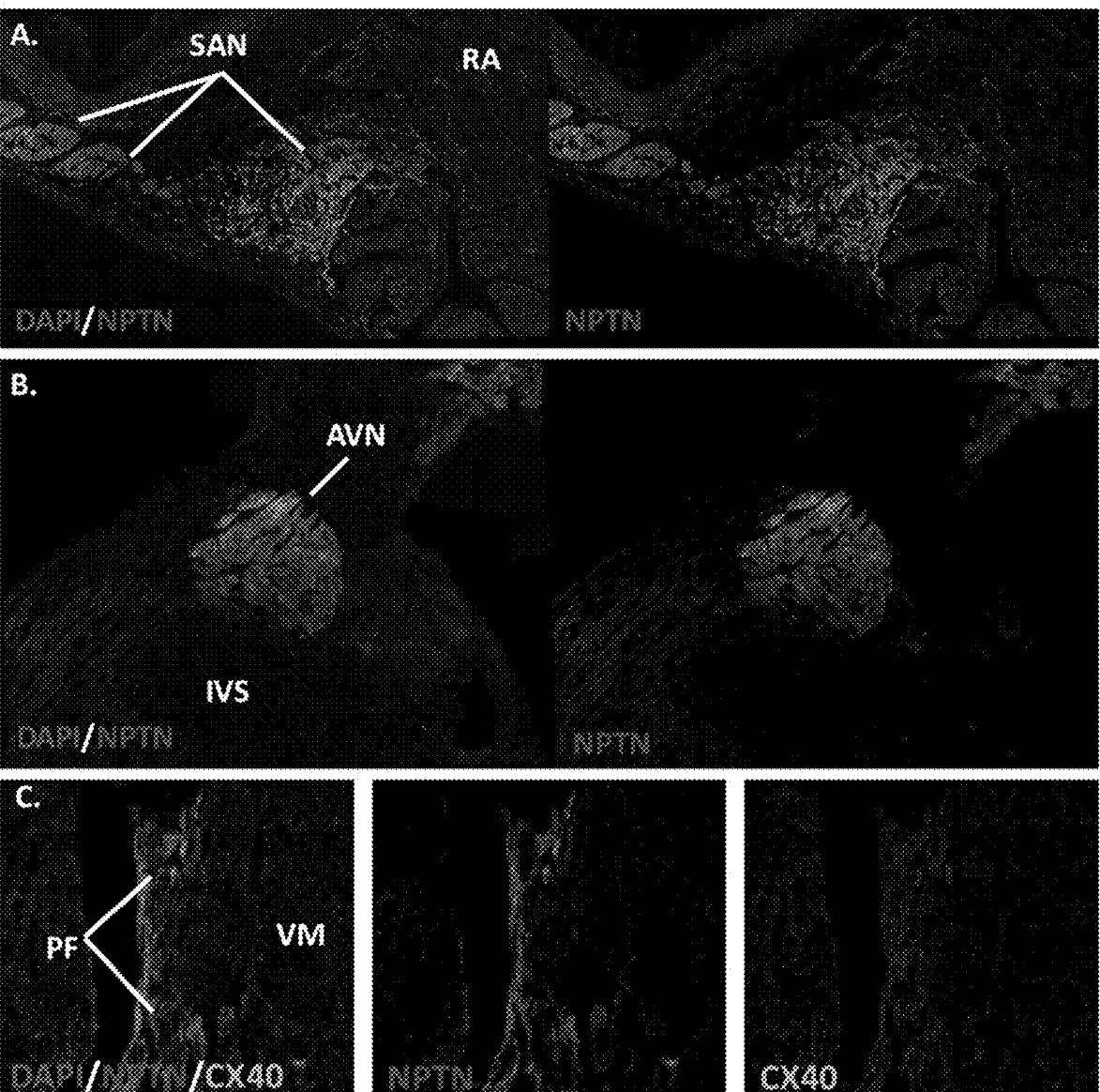
Figure 32. NPTN is Enriched in the Cardiac Conduction System of the Human Heart.

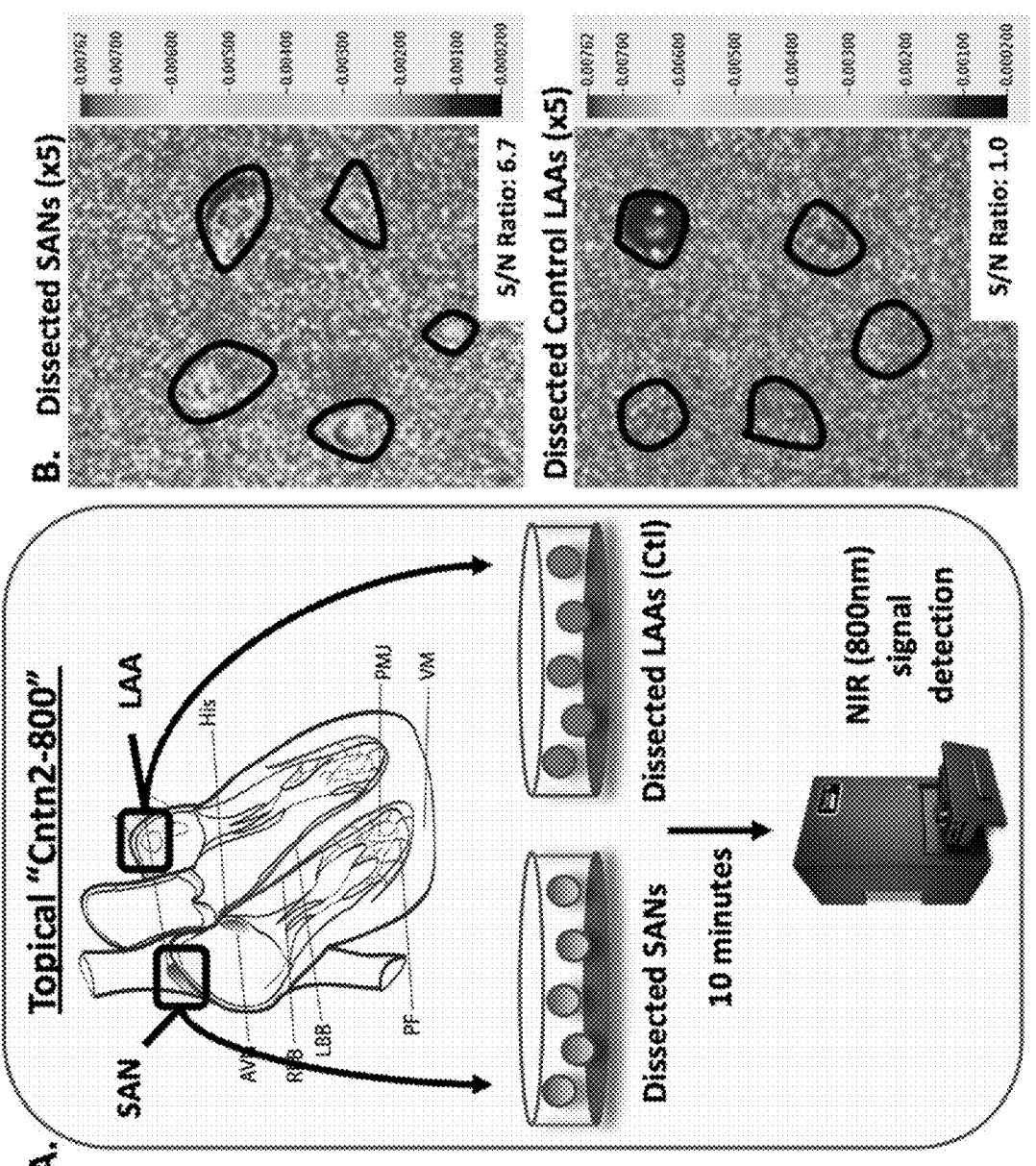
Figure 33. Topical Application of Cntn2-800 Labels Murine SAN Tissue.

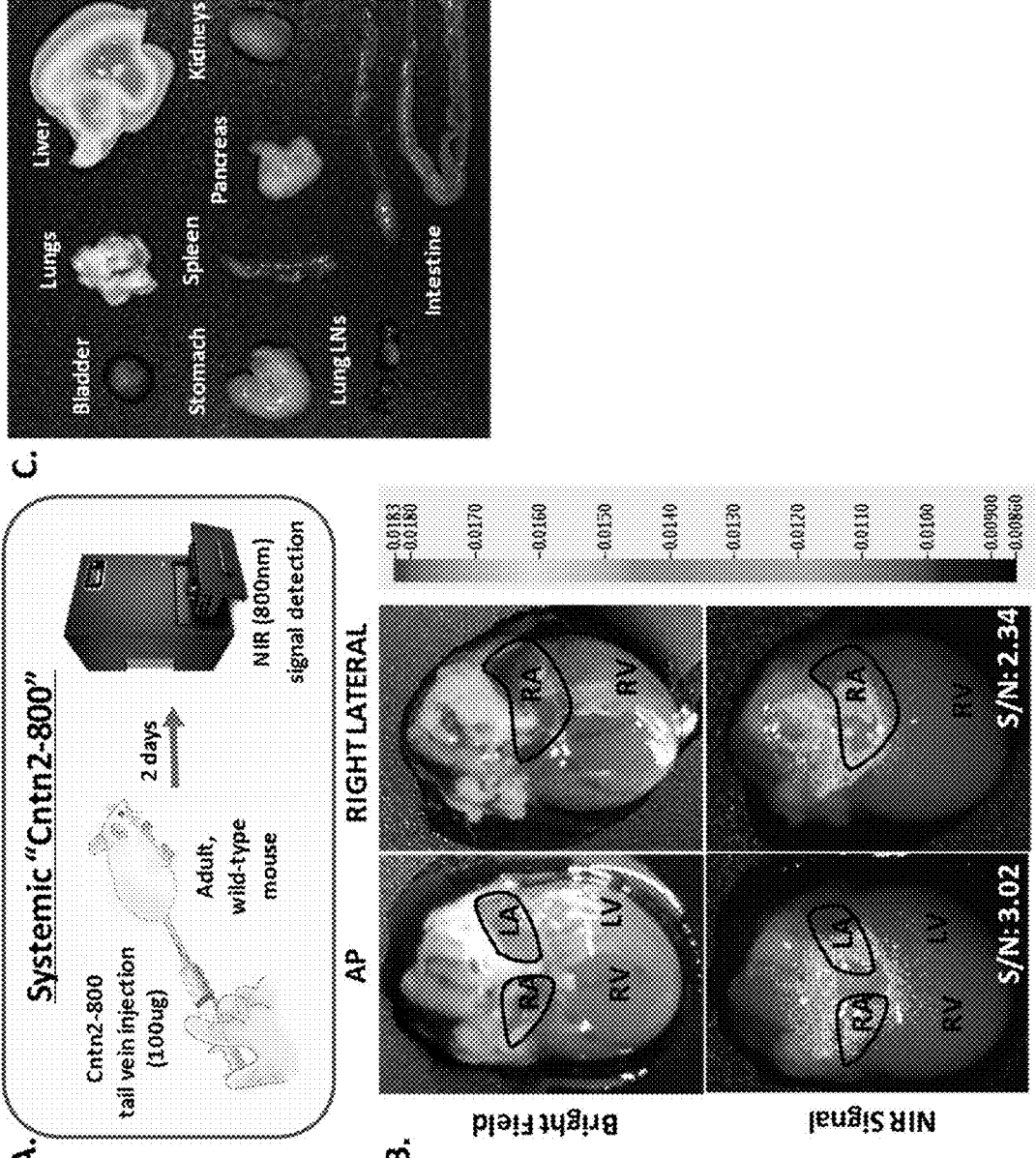
Figure 34. Systemic Injection of Cntn2-800 in Mice Labels the CCS *In Vivo.*

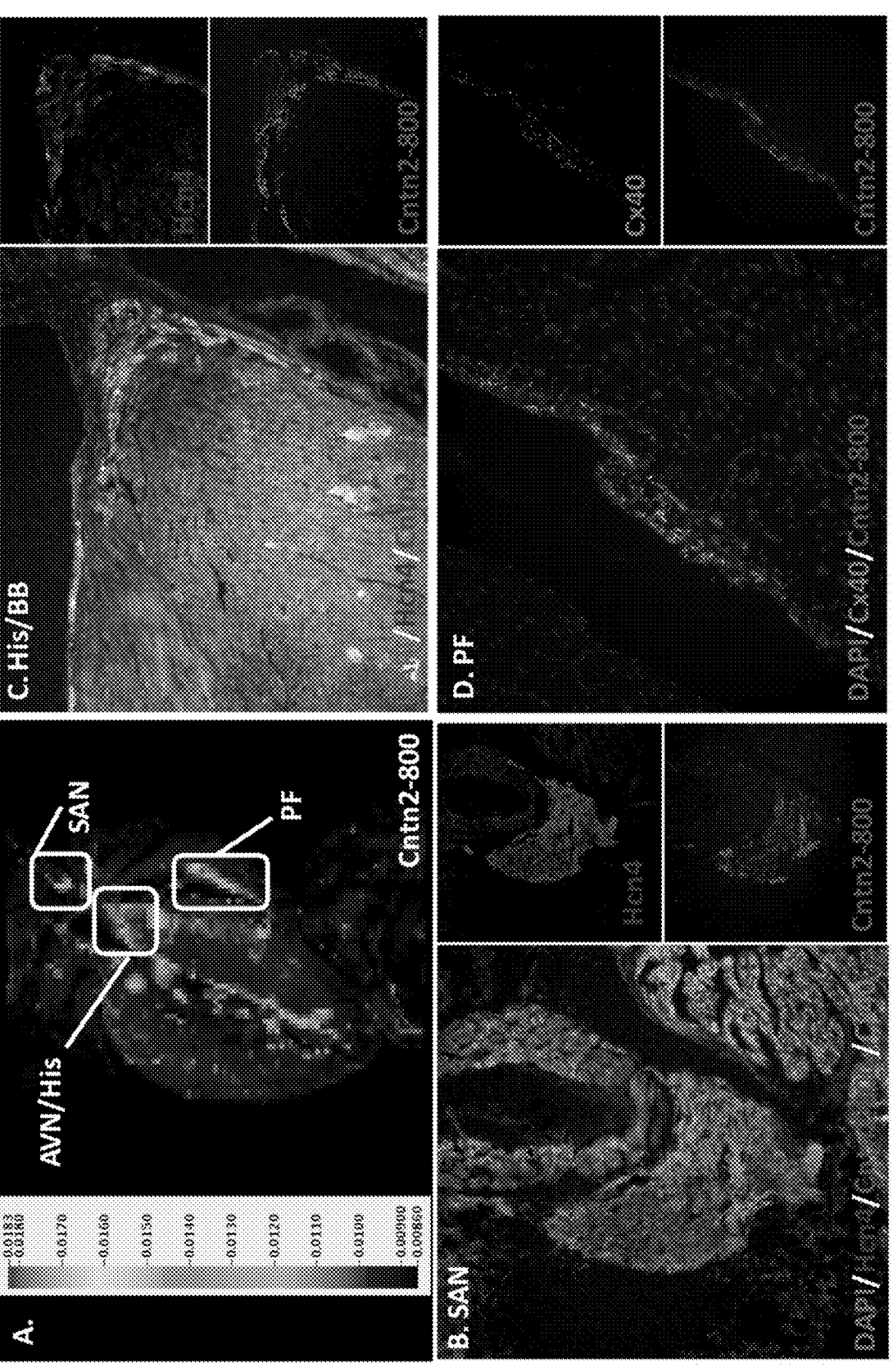
Figure 35. Cntn2-800 Specifically Labels All CCS Components Following Systemic Delivery.

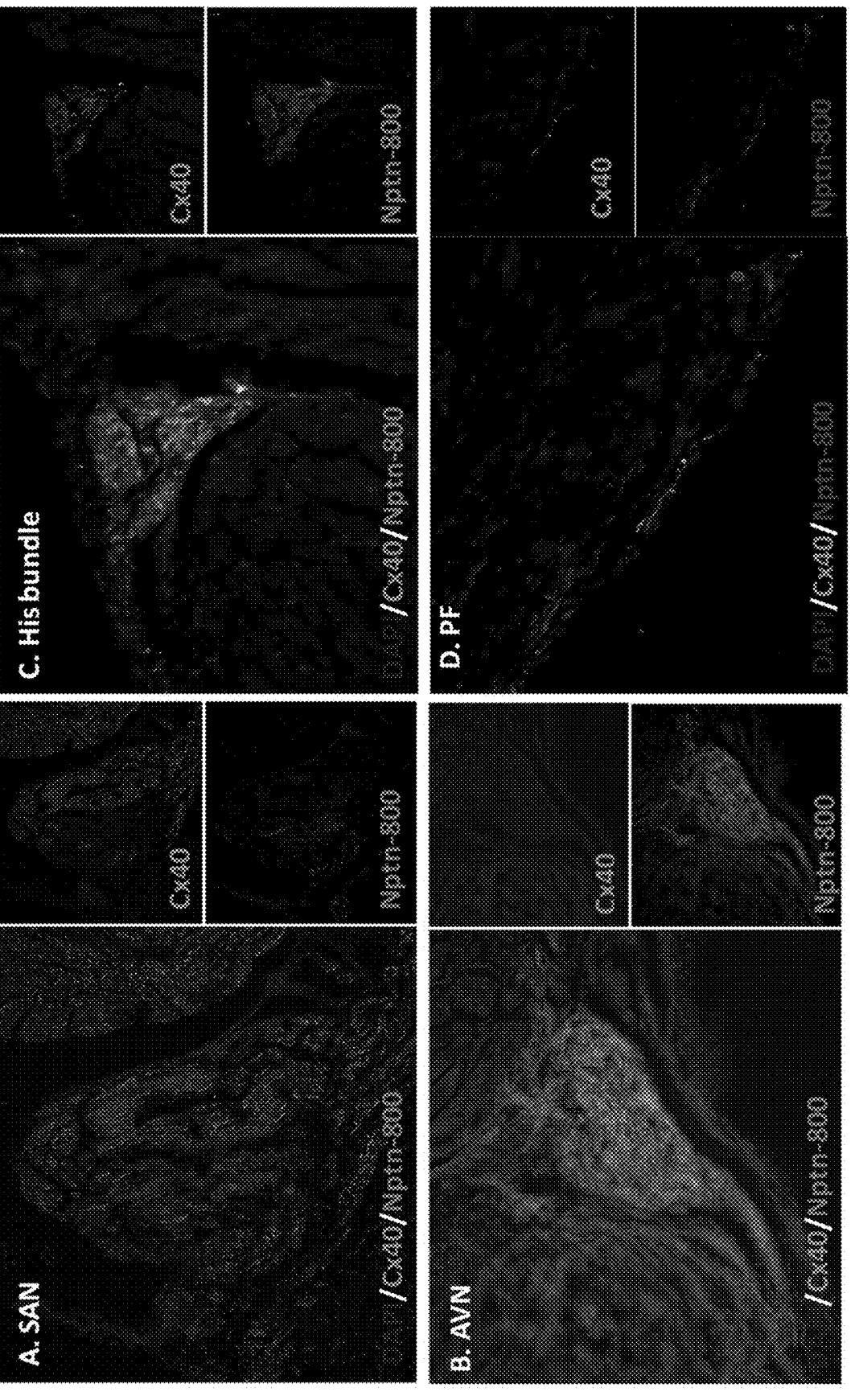
Figure 36. Nptn-800 Labels all CCS Components Following Systemic Delivery.

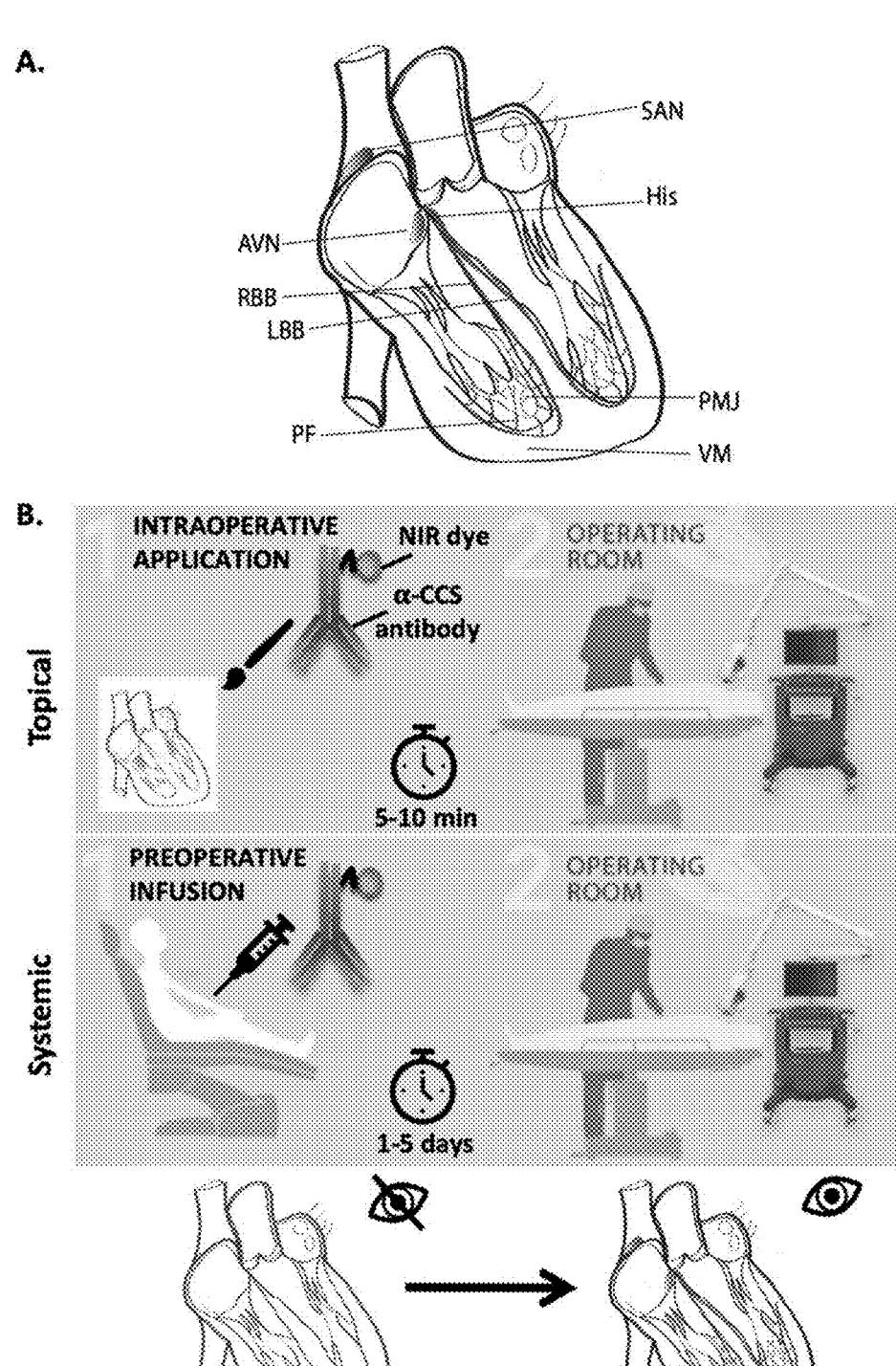
Figure 37. Novel Optical Imaging Agents Used to Visualize the Cardiac Conduction System (CCS) Intraoperatively in Real-Time.

MOLECULAR TOOLS TO VISUALIZE AND TARGET THE CARDIAC CONDUCTION SYSTEM (CCS)

CROSS-REFERENCE TO RELATED APPLICATIONS

This application is a U.S. national stage application of PCT application PCT/US2020/040965 with the international filing date of Jul. 7, 2020 which claims the benefit of priority from U.S. provisional application 62/871,551 filed on Jul. 8, 2019 and U.S. provisional application 62/950,428 filed on Dec. 19, 2019, the combined disclosure of all these applications is herein incorporated by reference.

STATEMENT OF GOVERNMENT INTEREST

This invention was made with Government support under contract LM012179 awarded by the National Institutes of Health. The Government has certain rights in the invention.

TECHNICAL FIELD

The invention relates to imaging reagents for the cardiac conduction system (CCS) cells and compositions and methods for delivering therapeutic agents to the CCS cells. The invention further relates to compositions and methods visualizing the CCS cells in vivo in real time, including in a subject undergoing a cardiothoracic surgery or other cardiac intervention. In further aspect, the invention relates to compositions and methods for isolation, purification, analyses and/or transplantation of the CCS cells, including pluripotent stem cell (hiPSC)-derived or human embryonic stem cell (hESC)-derived CCS cells.

BACKGROUND

The cardiac conduction system (CCS) is made up of specialized heart cells that establish the rhythmic beating of the heart through coordinated contraction of its chambers. The cardiac conduction system (CCS) is comprised of distinct components including the sinoatrial node (SAN), atrioventricular node (AVN), His bundle (HIS), bundle branches (BB) and Purkinje fibers (PF). The CCS is essential for the formation and normal function of the heart and disturbance to the CCS can result in severe clinical manifestations including arrhythmias, decreased cardiac output and even sudden death. Despite an essential role for the CCS in heart development and function, the CCS has remained difficult to study due to inherent obstacles including small cell numbers, large cell type heterogeneity, complex anatomy and difficulty in isolation.

Each component of the CCS consists of unique cardiac cell types with their own physiologic and electrochemical properties.[4] Further, the CCS components each have significant intracomponent cell type heterogeneity.[5] The most clinically relevant example of this heterogeneity has been the discovery of "transitional cells", that exist in each CCS component and provide a cellular bridge to the surrounding working myocardium.[6-10] They are hypothesized to play a role in facilitating the spread of depolarization, providing a high resistance barrier as well as amplifying the current before passing it on to the surrounding myocardium.[9] Transitional cells have been implicated in several important clinical disorders including sinus node dysfunction, heart block and even ventricular fibrillation. However, they remain poorly understood due to challenges in their identification, isolation and, ultimately, molecular characterization.

Currently, the limited number of distinct molecular markers that are known for the different CCS cell types present a number of challenges for additional investigation into their specification, patterning and function. While individual factors have been examined thus far, these studies have been performed at tissue but not at single-cell resolution.[12-14] Specific hurdles to better understanding the molecular signature of the CCS cells have included: 1) low total number of conduction cells in the heart; 2) complex three-dimensional anatomy of the CCS; 3) inability to isolate these cells from the surrounding working myocardium; and 4) the aforementioned significant inter- and intra-component cell type heterogeneity.[1] While prior studies have assessed gene expression within individual components of the CCS using sophisticated techniques such as microdissection, laser capture or even fluorescence-activated cell sorting[12-21], these analyses are unable to discern cell type heterogeneity due to bulk tissue analysis and/or a reliance on transgenic fluorescent reporter models.

The CCS is essential for the normal formation and function of the heart, and injury to the CCS can result in heart block, arrhythmias, decreased cardiac output and even sudden death. Congenital heart disease remains the most common birth defect, affecting roughly 1 in 100 infants, with a significant fraction requiring corrective heart surgery. Iatrogenic surgical damage to the CCS remains a significant complication in both congenital heart disease (CHD) and adult cardiac surgeries. This is due in part to an inability to visualize, and thus, avoid damaging the surrounding CCS by inadvertent incision or suture placement.

Accidental intraoperative injury to the cardiac conduction system (CCS) complicates roughly 1-3% of all congenital heart disease surgeries and an even higher percentage of the ~106,000 adult heart valve surgeries performed in the United States alone.

Postoperative heart block and other forms of intraoperative CCS damage remain significant causes of morbidity, increased cost, decreased long-term survival and often the life-long need for mechanical pacemakers. Similarly, many adult cardiac surgeries (including mitral and aortic valve replacements, myomectomy in hypertrophic cardiomyopathy, etc.) are plagued with an even higher risk (~8-25%) given their proximity to the conduction system. Current standard of care in both pediatric and adult intracardiac surgeries remains the use of anatomical landmarks to essentially guess the approximate location of the CCS, otherwise indistinguishable from the surrounding heart muscle. To date, there exists no intraoperative method for surgeons to detect the cardiac conduction system, which surrounds many key surgical targets (septal defects, valve disorders, etc.) in congenital heart surgeries, resulting in a significant risk for damage.

This occurs in part due to an inability to visualize the cardiac conduction system, and thus, avoid damaging the surrounding CCS by inadvertent incision or suture placement. Optical imaging agents have been successfully generated for the intraoperative detection of various cancers in order to improve the precision of tumor resection, however this tool has never been applied to the heart. In fact, to our knowledge, no method has ever been described to visualize substructures within the heart in real-time.

To date, there exists no molecular method to detect the cardiac conduction system in vivo. Intraoperative injury to the CCS results in increased healthcare costs and remains a significant cause of morbidity and mortality. Furthermore, there has been no strategy to directly target the CCS with small molecules or RNA/DNA for altering the behavior of CCS cells specifically.

SUMMARY

This disclosure addresses at least some of these unmet needs in the art.

In one aspect, the present disclosure provides an antibody comprising an antigen binding site which recognizes selectively and binds specifically to the CCS cell surface marker displayed at the outer surface of the CCS cell membrane of the CCS cell. The antibodies include those which recognize selectively and bind specifically the CCS cell surface markers such as a protein, an extracellular domain, or a fragment, or a variant or an epitope encoded by a gene listed in Table 1 or any human homologue thereof. The antibodies include antibodies which recognize selectively and bind specifically Neurotrimin Neuroplastin, Contactin 2, or any fragment or variant thereof displayed at the outer surface of the CCS cell membrane of the CCS cell. The antibodies include a diabody, scFv, Fab or $F(ab)_2$. In some embodiments, the antibody is a polyclonal antibody, monoclonal antibody, a single-chain antibody, a chimeric antibody, or a humanized monoclonal antibody.

In another aspect, the present disclosure provides a composition comprising the antibody according to this disclosure and one or more excipients. The compositions include those formulated for oral, topical, local or systemic delivery to a patient. The compositions may comprise water, a buffer, a solvent, a carrier, a bulking agent and/or a filler.

In another aspect, the present disclosure provides a method of treating a subject, the method comprising administering to the subject one or more compositions of this disclosure comprising one or more antibodies according to this disclosure.

In further aspect, the present disclosure provides an imaging and/or diagnostic reagent comprising an antibody conjugated to one or more detection agents, the imaging and/or diagnostic reagent capable of binding to a cell of the cardiac conductions system (CCS), and wherein the antibody has a binding affinity to a CCS cell surface marker displayed at the outer surface of the CCS cell membrane of the CCS cell. The imaging and/or diagnostic reagents include those, wherein the detection agent is one or more of the following: an imaging dye comprising a chromophore, a fluorophore, a tag, a radioactive isotope, a small molecule, a biomolecule, and/or a nanoparticle. The imaging and/or diagnostic reagents include those, wherein the detection agent comprises a biocompatible near-infrared fluorophore. The imaging and/or diagnostic also include those, wherein the CCS cell surface marker is a protein, an extracellular domain, or a fragment, or a variant or an epitope encoded by a gene listed in Table 1 or any human homologue thereof. Particularly preferred imaging and/or diagnostic reagents include those, wherein the antibody is specific to Neurotrimin, Neuroplastin, Contactin 2, or any fragment or variant thereof displayed at the outer surface of the CCS cell membrane of the CCS cell. In any of the imaging and/or diagnostic reagents according to this disclosure, the antibody may be a diabody, scFv, Fab or $F(ab)_2$. In some of the imaging and/or diagnostic reagents of this disclosure, the antibody may be a polyclonal antibody, monoclonal antibody, a single-chain antibody, a chimeric antibody, or a humanized monoclonal antibody. The imaging and/or diagnostic reagents of this disclosure include those, wherein the antibody is conjugated directly to the detection agent. The imaging and/or diagnostic reagents of this disclosure include those, wherein the antibody is conjugated to the detection agent indirectly via a linker or a carrier.

In yet another aspect, the present disclosure provides a composition comprising one or more excipients and the imaging and/or diagnostic reagent according to this disclosure. The composition may be formulated for oral, topical, local or systemic delivery. The composition may comprise from 0.1 wt % to 99.9 wt % of the CCS imaging and/or diagnostic reagent and from 0.1 wt % to 99.9 wt % of the one or more excipients.

In a further aspect, this disclosure provides a method for visualizing the CCS in a subject, the method comprising administering to the subject one or more of the following: the imaging and/or diagnostic reagent according to this disclosure, and/or the composition comprising the imaging and/or diagnostic reagent according to this disclosure. The methods may further comprise detecting the CCS in the subject in real time. The methods include those, wherein the detecting comprises one of more of the following: ultrasound, computed tomography, illuminating with a scope the CCS of the subject under UV, visible, and/or infrared light; and/or directly shining the UV, visible, and/or infrared light at the CCS of the subject. The methods include those, wherein the method further comprises capturing images of the CCS in real time with camera. The methods include those, wherein the subject is undergoing a cardiothoracic surgery or a catheter procedure.

In yet another aspect, the present disclosure provides a method for preparing the imaging and/or diagnostic reagent of this disclosure, the method comprises linking an antibody specific for the CCS cell surface marker to the detection agent.

In yet another aspect, the present disclosure provides a therapeutic product comprising an antibody conjugated to one or more therapeutic drugs, the therapeutic product being capable of binding to a cell of the cardiac conductions system (CCS), and wherein the antibody has a binding affinity to a CCS cell surface marker displayed at the outer surface of the CCS cell membrane. The therapeutic products include those, wherein the CCS cell surface marker is a protein, an extracellular domain, or a fragment, or a variant or an epitope encoded by a gene listed in Table 1 or any human homologue thereof. Preferred therapeutic products include those, wherein the antibody is specific to Neurotrimin, Neuroplastin, Contactin 2, or any fragment or variant thereof displayed at the outer surface of the CCS cell membrane of the CCS cell. The therapeutic products also include those, wherein the antibody is a diabody, scFv, Fab or $F(ab)_2$. In some of the therapeutic products, the antibody may be a polyclonal antibody, monoclonal antibody, a single-chain antibody, a chimeric antibody, or a humanized monoclonal antibody. In some therapeutic products, the antibody is conjugated directly to the therapeutic drug. In some therapeutic products, the therapeutic drug may be encapsulated, and the antibody is displayed at the outer surface of the capsule. In some therapeutic products, the therapeutic drug may be encapsulated in a liposome. The therapeutic products include those, wherein the therapeutic drug is a small molecule or a biomolecule. The therapeutic products include those, wherein the therapeutic drug digoxin, a calcium channel blocker, a beta blocker, an anti-arrhythmic drug, or RNA or DNA that can silence or activate at least one biologic function of the CCS cell. The therapeutic products include those, wherein the therapeutic drug is an antiarrhythmics drug, an CCS agonist drug, and/or an anti-inflammatory drug. The therapeutic products include those, wherein the therapeutic drug is diltiazem, verapamil, metoprolol, carvedilol, atenolol, digoxin, adenosine, dipyridamole, diphtheria toxin A, methotrexate, doxorubicin, isoproterenol, epinephrine, glucocorticoid, cyclosporin A or tacrolimus.

In yet another aspect, the present disclosure provides compositions comprising one or more excipients and one or more therapeutic products according to this disclosure. The excipient may comprise water, a buffer and/or any other solvent and/or carrier, e.g. a liposome. The compositions include those, wherein the composition is formulated for oral, topical, systemic or local administration. Some of the compositions may comprise from 0.1 wt % to 99.9 wt % of the therapeutic product and from 0.1 wt % to 99.9 wt % of the one or more excipients.

In yet another aspect, the present disclosure provides a method of treating a patient in need for treatment of the CCS related disorder or disease, the method comprising administering to the patient one or more compositions according to this disclosure. The methods include those, wherein the patient is treated for one of the following diseases: cardiac arrhythmia, accelerated heart rhythm, heart block, or atrial or ventricular fibrillation. The methods include those, wherein the patient is administered from 0.05 mg to about 100 mg of the therapeutic drug per one kilogram of the body weight.

In another aspect, the present disclosure provides a method for separation of a CCS cell from a mixture of cells, the method comprising:

contacting the mixture of cells with an antibody comprising an antigen binding site which recognizes selectively and binds specifically to the CCS cell surface marker displayed at the outer surface of the CCS cell membrane of the CCS cell; and separating CCS cells bound to the antibody from the mixture.

In this method, the antibody may be conjugated to a detection agent. In some embodiments of the method, the antibody may be bound to a solid support and/or magnetic beads. In some embodiments of the method, the separation may comprise one or more of the following: centrifugation and FACS sorting. In the method, the CCS cells may be human-induced pluripotent stem cell (hiPSC)-derived, human embryonic stem cell (hESC)-derived conduction cells and/or conduction cells derived from living mammalian heart tissue.

In yet another embodiment, the present disclosure provides a method for producing a recombinant CCS cell from a human-induced pluripotent stem cell or a human-embryonic stem cell, the method comprising differentiating a population of the human-induced pluripotent stem cell or the human-embryonic stem cell into the CCS cells, and reacting the population with an antibody comprising an antigen binding site which recognizes selectively and binds specifically to the CCS cell surface marker displayed at the outer surface of the CCS cell membrane of the CCS cell.

BRIEF DESCRIPTION OF THE DRAWINGS

FIG. 1. Single-Cell Isolation and Expression Profiling of Murine Cardiac Conduction System Components. (A) Schematic representation of experimental design and workflow. Wild-type, embryonic day 16.5 (E16.5) CD1 mouse hearts were harvested and three zones of microdissection were isolated based on anatomical landmarks and entailed: Zone I—Sinoatrial node (SAN) region, Zone II—Atrioventricular node (AVN)/His region and Zone III—Bundle branch (BB)/ Purkinje fiber (PF) region. A minimum of 6 embryonic hearts were pooled per zone. Tissues were digested into a single cell (SC) suspension, isolated via oil droplets, mRNA labelled with cell-specific barcodes, made into a library and subsequently sequenced, all using the commercial droplet-based cell capture platform from 10× Genomics®. Data was then aligned with gene expression quantified followed by a series quality control (QC) steps as well as differential gene expression and subcluster analysis. (B) (Left) Table listing the number of cells isolated from each Zone and total number of cells evaluated. (Right) t-SNE plot of all cells combined with representative cell types identified by cluster. CCS, cardiac conduction system. CM, cardiomyocyte. LBB, left bundle branch. PMJ, Purkinje-myocyte junction. RBC, red blood cell. RBB, right bundle branch. scRNA-seq, single-cell RNA sequencing. SMC, smooth muscle cell. VM, ventricular myocardium. WBC, white blood cell.

FIG. 2. scRNA-seq Analysis of Zone I Revealed a Bona Fide Sino-Atrial Node (SAN) Cell Cluster. (A) Cluster cell numbers and t-SNE plot for Zone I cells. (B) Heatmap of differentially expressed genes for each cluster of cells. (C) Cardiomyocyte (Actn2+) and Nodal (Hcn4+, Isl1+, Shox2+, Tbx3+) signatures visualized by ViolinPlots (top) and FeaturePlots (bottom). (D) Table highlighting differentially expressed genes in Cluster 9. Avg log FC, average log fold change. (E) Gene ontology (GO) functional cluster analysis of all enriched genes for Cluster 9. (F) Immunofluorescence staining of postnatal day 4 (P4) (n=8) wild-type murine cardiac tissue sections showing a SAN with colocalization of Hcn4 (green) and Igfbp5 (red) protein. Nuclei stained with DAPI (blue). RA, right atrial myocardium.

FIG. 3. Analysis of Cluster 9 Revealed Unique SAN Subtypes. (A) t-SNE plot of Cluster 9 cells demonstrated two distinct subclusters consistent with compact SA nodal cells (cSAN) (Hcn4$^{hi}$/Gja5$^{neg}$/Gjc1$^+$) and Transitional cells (Tz) (Hcn4$^{low/neg}$ Gja5$^+$/Gjc1$^+$). (B) Expression heatmap of established SAN and atrial CM genes for each subcluster of cells. (C) ViolinPlots (top) and FeaturePlots (bottom) for key cSAN and Tz markers. (D) Table highlighting differentially expressed genes between cSAN and Tz subclusters. Avg log FC, average log fold change. (E) Gene expression enrichment for Smoc2 within Cluster 9 and the cSAN cluster as compared to all Zone I cells and the Tz cluster, respectively. Smoc2 gene expression within Cluster 9 visualized by ViolinPlot (top) and Featureplot (bottom). (F) Fluorescent RNA in situ hybridization targeting Hcn4 (red punctae) and Smoc2 (green punctae) mRNA within postnatal day 0 (P0) (n=3), wild-type mice. Compact SA node (cSAN), transitional (Tz) and surrounding right atrial (RA) cells. DAPI (blue). Solid line depicting cSAN cells (Hcn4$^{hi}$/Smoc2$^+$) and dashed line showing Tz cells (Hcn4$^{low/neg}$/Smoc2$^+$). Beyond these borders are right atrial cardiomyocytes (RA) (Hcn4$^{neg}$/Smoc2$^{neg}$). (G) Immunofluorescent staining of P0 (n=5) wild-type murine cardiac tissue sections showing a cSAN with expression of Smoc2 protein (red) and negative staining for Cx40 (green). A transitional cell population of cells (Smoc2$^+$/Cx40$^{low}$) emerging from the cSAN is demarcated by dashed border. Surrounding tissue is the RA (Smoc2$^{neg}$/Cx40$^+$).

FIG. 4. Identification of an AVN/His Cell Cluster Within Zone II. (A) Cluster cell numbers and t-SNE plot of Zone II cells. (B) Heatmap of differentially expressed genes by cell cluster. (C) Cardiomyocyte (Actn2$^+$) and AVN (Hcn4$^+$, Cacna2d2$^+$, Cacna1g$^+$) gene signatures visualized by ViolinPlots (top) and FeaturePlots (bottom). (D) Table highlighting differentially expressed genes in Cluster 4. Avg log FC, average log fold change. (E) Gene ontology (GO) functional cluster analysis of all enriched genes for Cluster 4. (F) Cpne5 and Smoc2 gene expression within Zone II cells as illustrated by ViolinPlots. Cpne5 expression is enriched within Cluster 4 while Smoc2 is not. (G) The same postnatal day 12 (P12) heart co-immunostained for Cpne5 and Smoc2 protein (white); insets show a Cpne5$^+$ (solid white arrow) but Smoc2$^{neg}$ (empty white arrow) AVN. Red arrows, internodal tracks; blue arrows, right AV ring bundle; yellow arrows, left AV ring bundle. (H) FISH targeting Hcn4 (red punctae) and Cpne5 (green punctae) mRNA within a E16.5 (n=3), wild-type mouse heart section showing the His bundle giving rise to the left bundle branch (LBB) (both Hcn4$^+$/Cpne5$^+$) and surrounding ventricular cells of the IVS (Hcn4$^{neg}$/Cpne5$^{neg}$).

FIG. 5. Analysis of Cluster 4 in Zone II Unveiled Distinct AVN and Transitional Cell Subtypes. (A) Cells from the putative AVN/His cluster (Cluster 4 in Zone II) were selected for further analysis. t-SNE plot of Cluster 4 cells demonstrated six distinct subclusters. (B) Illustration of AV nodal region subdomains by transcriptional profiling (adapted from Aanhaanen et al. 2010).[6] (C) Heatmap, (D) ViolinPlots and (E) FeaturePlots demonstrating typical nodal, transitional and ventricular CM gene expression signatures for each subcluster of cells. ATZ, Atrial Transitional Zone; cAVN, compact AVN; His, His bundle; NAVR, nodal AV ring; TAVR, transitional AV ring; VTZ, ventricular transitional zone; VM, ventricular cardiomyocytes.

FIG. 6. An Immature Purkinje Fiber (PF) Cell Cluster was Detected Within Zone III. (A) Cluster cell numbers and t-SNE plot of Zone III cells. (B) Heatmap of differentially expressed genes for each cluster of cells. (C) Cardiomyocyte (Actn2$^+$) and PF (Gja5$^+$, Scn5a$^+$, Irx3$^+$ and Cacna2d2$^+$) gene signatures visualized by ViolinPlots (top) and FeaturePlots (bottom). (D) Gene ontology (GO) functional cluster analysis of all enriched genes for Cluster 13. (E) Table highlighting differentially expressed genes in Cluster 13. Avg log FC, average log fold change. (F) Cpne5 gene expression within Zone III cells illustrated by ViolinPlot (left) and FeaturePlot (right). (G) Immunofluorescence staining of an E16.5 (n=6) wild-type murine cardiac tissue section showing Cpne5 (white) of the immature PF network.

FIG. 7. Analysis of Cluster 13 in Zone III Identified Unique Immature PF and Transitional PF Cell Subtypes. (A) t-SNE plot demonstrated two distinct subclusters within Cluster 13, consistent with a standard immature PF cluster ("PF") and a transitional PF cluster ("Tz"). (B) Expression heatmap of known PF and ventricular cardiomyocyte genes within the standard PF and Tz clusters. (C) Table highlighting differentially expressed genes between the two subclusters, represented by (D) ViolinPlots (top) and FeaturePlots (bottom). Avg log FC, average log fold change. (E) Illustration of the Purkinje-myocyte junction (PMJ) consisting of standard PF (blue), ventricular CMs (gray) and transitional PFs (red) bridging the two (adapted from Tranum-Jensen et al. 1991).[9] Summary of enriched (green) and downregulated (red) genes for each cell subtype based on scRNAseq data presented here. (F) Gene expression enrichment table for Ntm between Cluster 13 and standard PF subcluster as compared to the rest of Zone III cells and Tz subcluster, respectively. Ntm gene expression demonstrated in Zone III (upper panels) and within Cluster 13 (lower panels) as visualized by ViolinPlot (left) and Featureplot (right). (G) Fluorescent RNA in situ hybridization targeting Hcn4 (red punctae) and Ntm (green punctae) mRNA expression within immature PFs and transitional PF cells within a P0 mouse heart section (n=3). DAPI (blue). Solid line depicting standard immature PF cells (Hcn4$^+$/Ntm$^+$) and dashed line showing Tz cells (Hcn4$^{low/neg}$/Ntm$^+$). Beyond these borders are ventricular myocardial cells (Hcn4$^{neg}$/Ntm$^{neg}$). Larger brightly-stained objects (examples noted by white arrows) in both red and green channels represent autofluorescence from red blood cells (yellow in merge photos). True RNAscope fluorescent in situ hybridization signal is represented by small punctae in either green (Ntm) or red (Hcn4).

FIG. 8. Optical Clearing and 3D Volumetric Analyses Delineate the Architecture of the Entire CCS and SA Nodal Substructure Within Intact Murine Hearts. (A) Schematic representation of workflow for iDISCO+ clearing of intact embryonic and postnatal mouse hearts and visualization using light sheet microscopy. At least 10 biological replicates were used for each immunolabelling. (B) A wild-type whole heart from an E16.5 mouse embryo is shown at four angles of view (0, 90, 180 and 270 degrees) at 0.63× magnification. Top and bottom rows are the same optically cleared heart using iDISCO+ where, in the top row, background fluorescence has been saturated to provide a representation of the opacified heart. Bottom row demonstrates the same tissue-cleared heart, showing Igfbp5 immunostaining which marks the cardiac conduction system in its entirety. (C) iDISCO+ cleared wild-type, intact SAN (6.3× magnification) from E16.5 murine heart co-immunolabeled for Hcn4 (red) and Rgs6 (green) protein. SAN shown at three angles of view (0, 90, ~225 degrees). (D) Merge image (Hcn4 in red, Rgs6 in green) with two major transitional sinoatrial conduction pathways (SACPs) outlined (Hcn4$^{neg}$/Rgs6$^+$). Purple SACP: from SAN body directed rightward; Black SACP: from the SAN head directed inferiorly and leftward. A third Hcn4+ SACP is also marked by Rgs6 and emerges inferiorly from the tail of the SAN to give rise to the internodal tracks (blue line) not seen here but visible in panel 8B. Ant, Anterior. AVN, atrioventricular node. His, His bundle. INT, internodal tracks. LA/RA, left or right atrium. LAVRB, left AV ring bundle. LBB/RBB, left of right bundle branch. LV/RV, left or right ventricle. PF, Purkinje fiber. Post, Posterior. RAVRB, right AV ring bundle. SAN, sinoatrial node.

FIG. 9. Transcriptional Landscape of the Cardiac Conduction System. A summary of differential gene expression, both established and novel per the scRNA-seq findings of this study, within all components of the CCS including the sino-atrial node (SAN), atrioventricular node/His bundle (AVN/His) and Purkinje fiber (PF) regions. Asterisk (*) highlights genes with different expression as compared to parental cell type within the hierarchy. AM, atrial myocardium, ATZ, Atrial Transitional Zone; cAVN, compact AVN; NAVR, nodal AV ring; TAVR, transitional AV ring; VTZ, ventricular transitional zone; VM, ventricular cardiomyocytes.

FIG. 10. GO/KEGG Term Enrichment Analyses of Zone I Non-Cardiomyocyte Lineages. Pathway enrichment analysis on all non-cardiomyocyte clusters of Zone I. Statistically significant gene ontologies were consistent with suspected cluster identities based on differential gene expression including fibroblasts (Clusters 2, 5, 6, 11), endocardial/endothelial cells (Clusters 4, 7, 13), white blood cells (Cluster 8), epicardial cells (Cluster 10) and neuronal cells (Cluster 14). Dot size is proportional to the number of deferentially expression genes within a given pathway; the color is proportional to the significance (FDR adjusted p-value).

FIG. 11. Comparison of SAN Gene Enrichment in Bulk vs. scRNA Sequencing. (A) Table modified from Vedantham et al. 2015[20] listing the 30 most significant differentially expressed sinoatrial node (SAN) genes. RNA sequencing data from this prior study was generated from SAN tissue (vs. right atrial (RA) myocardium) isolated by laser capture microdissection on unfixed, unstained cryosections from flash-frozen Hcn4-GFP (green-fluorescent protein) transgenic mouse hearts harvested at embryonic day 14.5 (E14.5). Right side of table shows the corresponding cluster enrichment of highlighted genes from the current study's RNA-seq data within Zone I of E16.5 mice. Genes highlighted in green represent known SAN genes. Genes highlighted in red represent examples of enrichment due to suspected contaminant cells as listed. Gm15415 encodes a predicted long non-coding RNA that was not detected within our dataset under its current name. CM, cardiomyocyte. (B) Gene expression enrichment across all 15 clusters within Zone I. Cluster 9 (C9) represents the putative SA nodal cluster, while other atrial cardiomyocyte clusters include C0, C1, C3, C12, C15. Additional clusters, based on their respective gene expression profiles, include fibroblasts (Clusters 2, 5, 6, 11), endocardial/endothelial cells (Clusters 4, 7, 13), epicardial cells (Cluster 10), white blood cells (Cluster 8) and neuronal cells (Cluster 14).

FIG. 12. Comparison of SAN Gene Enrichment in Tbx3-Sorted vs. scRNA Sequencing. (A) Table modified from Van Eif et al. 2019[21] listing the reported top 16 differentially expressed sinoatrial node (SAN) genes in sorted Tbx3-Venus[+] cells versus Katushka+ cells from embryonic day 17.5 (E17.5) mice. Right side of table shows the corresponding cluster enrichment of highlighted genes from the current study's RNA-seq data within Zone I of E16.5 mice. Genes highlighted in green represent known SAN genes. Genes highlighted in red represent examples of enrichment due to suspected contaminant cells as listed. (B) Gene expression enrichment across all 15 clusters within Zone I. Cluster 9 (C9) represents the putative SA nodal cluster, while other atrial cardiomyocyte clusters include C0, C1, C3, C12, C15. Additional clusters, based on their respective gene expression profiles, include fibroblasts (Clusters 2, 5, 6, 11), endocardial/endothelial cells (Clusters 4, 7, 13), epicardial cells (Cluster 10), white blood cells (Cluster 8) and neuronal cells (Cluster 14).

FIG. 13. Igfbp5 is Expressed Within the Compact SAN and Transitional Cells but Not Within the SAN Artery. Immunofluorescent staining (n=5) of a postnatal day 12 (P12) wild-type murine cardiac tissue sections showing a compact SAN (cSAN) (outlined by solid line), transitional cells (Tz) (dashed line) populations and SAN artery (SAN Art.) labelled by Cx40 (green). Igfbp5 (red). RA, right atrial myocardium.

FIG. 14. Igfbp5, Cpne5, Smoc2, Rgs6 and Ntm are Enriched in the Compact SAN and Transitional Cells of the Mouse Heart. Immunofluorescent staining of wild-type murine cardiac tissue sections showing the compact SAN (cSAN) (outlined by solid line) and transitional cell (Tz) (dashed line) populations. (A) Igfbp5 (red), Cx40 (green) and Hcn4 (blue); E14.5 heart (n=5). (B) Cpne5 (red) and Hcn4 (blue); E16.5 heart. (n=6) (C) Smoc2 (red) and Cx40 (green); P0 heart. (D) Rgs6 (red) and Hcn4 (blue); E16.5 heart. (n=6) (E) Fluorescent RNA in situ hybridization targeting Hcn4 (red punctae) and Ntm (green punctae) mRNA expression within P0 mouse heart sections (n=3). DAPI (blue). RA, right atrial myocardium; SAN Art., SAN artery.

FIG. 15. Expression of Igfbp5, Cpne5, Rgs6 and Ntm Within cSAN and Transitional Cell Subclusters of Cluster 9. Expression of each gene represented by ViolinPlot (top) and FeaturePlot (bottom) within the compact SAN (cSAN) and transitional cell (Tz) subclusters of Cluster 9 from Zone I.

FIG. 16. Analysis of Hcn4+ Cells in Zone I Reveal Compact SAN Subtypes Consistent with Head and Tail Regions. (A) Diagram detailing workflow and cell numbers for Hcn4 positive and negative cardiomyocytes (CM) isolated for further analysis from the total number of cells within Zone I. (B) t-SNE plot of 127 Hcn4[+] cardiomyocytes (Hcn4[+]/Actn2[+]) revealed two distinct cell subpopulations consistent with SA nodal "Head" and "Tail" cells. (C) General CM signature (Tnni3[+]) demonstrating that both clusters are indeed CMs. (D) Illustration of known functional SAN subdomains including the "Head" ($Hcn4^{hi}$/$Shox2^+$/$Tbx18^+$/$Nkx2\text{-}5^-$) and "Tail" ($Hcn4^{low}$/$Shox2^+$/$Tbx18^-$/$Nkx2\text{-}5^+$) cells with representative enriched (green) and repressed (red) genes. (E) Gene signature of SAN Head vs Tail gene expression visualized by ViolinPlots (left) and FeaturePlots (right).

FIG. 17. Igfbp5, Rgs6 and Ntm are Enriched in the Murine AVN. Immunofluorescent staining of wild-type murine cardiac tissue sections showing the AVN. (A) Igfbp5 (red) and Cx40 (green); P4 heart (n=4). Four panels showing progressively more anterior sections (A.1-A.4). Inset showing an enlarged area of AVN region. Note the AVN ($Igfbp5^+$/$Cx40^{neg}$) gives rise to the His bundle ($Igfbp5^+$/$Cx40^+$) as the sections move anteriorly. Gene expression visualized by ViolinPlots showing enrichment in Cluster 4 (AVN Cluster). White arrow, AVN; purple arrow, His bundle; red arrows, internodal tracks; blue arrows, right AV ring bundle; yellow arrows, left AV ring bundle. (B) Rgs6 (white) with inset showing AVN; E16.5 heart (n=6). Gene expression visualized by ViolinPlots showing enrichment in Cluster 4 (AVN Cluster). (C) DAPI stain (white) of a P0, wild-type heart with the AVN and surrounding cardiac structures labelled. LA, left atrium; LV, left ventricle; MV, mitral valve. Ntm gene expression visualized by ViolinPlots showing enrichment in Cluster 4 (AVN Cluster). (D) Magnification of the boxed AVN region in subpanel C with fluorescent RNA in situ hybridization targeting Hcn4 (red punctae) and Ntm (teal punctae) mRNA; DAPI in blue. (n=3) AVN, surrounding internodal tracks (INT) (above) and ventricular cardiomyocytes (below) of the interventricular septum (IVS) are labeled. Solid lines demarcating the AVN. Larger brightly-stained objects (examples noted by white arrows) in both red and green channels represent autofluorescence from red blood cells (yellow in merge photos). True fluorescent in situ hybridization signal is represented by small punctae in either green (Ntm) or red (Hcn4).

FIG. 18. Cpne5 Expression in Cluster 4 Cell Subtypes. Cpne5 expression represented by ViolinPlot (left) and FeaturePlot (right).

FIG. 19. Igfbp5 and Cpne5 Are Expressed in the Ventricular Conduction System. (A) Anti-Igfbp5 immunofluorescence stain (white) within E16.5, wild-type mouse heart. (n=8) All ventricular conduction system components labelled. (B) Fluorescent RNA in situ hybridization (n=3) demonstrating overlap of Hcn4 (red punctae) and Cpne5 (green punctae) expression within the Purkinje fibers of a P0 wild-type mouse heart. DAPI (blue). Solid line depicting standard immature PF cells (Hcn4[+]/Cpne5[+]) and dashed line showing Tz cells ($Hcn4^{low/neg}$/Cpne5[+]). Beyond these borders are ventricular myocardial (VM) cells ($Hcn4^{neg}$/$Cpne5^{neg}$). His, His bundle; LBB, left bundle branch; PF, Purkinje fiber; RBB, right bundle branch; Tz, Transitional cells.

FIG. 20. Igfbp5 is Enriched Within the Entire Cardiac Conduction System. (A) Fold enrichment of Igfbp5 expression within Cluster 9 in Zone I ("SAN" Cluster), Cluster 4 in Zone II ("AVN/His" Cluster) and Cluster 13 in Zone III ("PF" Cluster) as compared to all other cells within each respective zone. (B) E16.5 wild-type mouse heart (above) with corresponding two-dimensional z-projections (below) from indicated z-planes. Igfbp5 expression shown in white with conduction system components labelled. (n=10) (C) iDISCO+ with immunostaining for Cx40/Gja5 (green) and Igfbp5 (red) protein. Note the reciprocal labelling of SAN tissue (Igfbp5, red) versus the surrounding atrial working myocardium (Cx40, green). (n=4) AVN, atrioventricular node. His, His bundle. INT, internodal tracks. LBB/RBB, left of right bundle branch. PF, Purkinje fiber. SAN, sinoatrial node.

FIG. 21. Optical Clearing and 3D Volumetric Analyses Illustrate Transitional Cell Populations Exiting the SAN. (A) iDISCO+ cleared wild-type SAN (6.3× magnification) co-immunolabeled for Hcn4 (red) and Smoc2 (green) protein from a postnatal day 12 (P12) heart. SAN shown at three angles of view (0, 90, ~225 degrees). Merge image (Hcn4 in red, Smoc2 in green) with two major transitional sinoatrial conduction pathways (SACPs) outlined (Hcn4$^{neg}$/Smoc2$^{+}$). Purple SACP: from SAN body directed rightward; Black SACP: from the SAN head directed inferiorly and leftward. A third Hcn4+ SACP is also marked by Smoc2 and emerges inferiorly from the tail of the SAN to give rise to the internodal tracks (blue line), not shown here. (B-C) Immunolabeling of Igfbp5 (B) and Cpne5 (C) (both purple) within the SANs of P0 and P12 murine hearts, respectively. Similar SACP pathways are outlined as above.

FIG. 22 depicts online table IA.
FIG. 23 depicts online table IIA.
FIG. 24 depicts online table IIIA.
FIG. 25 depicts online table IVA.
FIG. 26 depicts online table VA.
FIG. 27 depicts online table VIA.
FIG. 28 depicts online table VIIA.
FIG. 29 depicts online table VIIIA.

FIG. 30. Ntm is Enriched in the Cardiac Conduction System of the Mouse Heart. Immunofluorescent staining of wild-type murine cardiac tissue sections showing the sinoatrial node (SAN) (outlined by solid line). Fluorescent RNA in situ hybridization targeting Hcn4 (red punctae) and Ntm (green punctae) mRNA expression within P0 mouse heart sections. DAPI (blue). RA, right atrial myocardium.

FIG. 31. Nptn is Enriched in the Cardiac Conduction System of the Mouse Heart. Immunofluorescent staining of wild-type murine, embryonic day 16.5 cardiac tissue sections showing (A) the sinoatrial node (SAN) as evidenced by anti-Hcn4 staining (red); (B) His bundle, right bundle branch (RBB) and left bundle branch (LBB); and (c) Purkinje fibers. Anti-Nptn staining against the Np65 isoform (cyan). DAPI (blue). RA, right atrial myocardium; IVS, interventricular septum; VM, ventricular myocardium.

FIG. 32. NPTN is Enriched in the Cardiac Conduction System of the Human Heart. Immunofluorescent staining of cardiac tissue sections from a 11 month old human heart showing (A) the sinoatrial node (SAN); (B) atrioventricular node (AVN); and (c) Purkinje fibers (PF) co-stained with connexin 40 (CX40). Anti-Nptn staining against the NP55 isoform (A) or Np65 isoform (B-C) (cyan). DAPI (blue). RA, right atrial myocardium; IVS, interventricular septum; VM, ventricular myocardium.

FIG. 33. Topical Application of Cntn2-800 Labels Murine SAN Tissue. (A) Experimental workflow. (B) Five dissected sinoatrial nodes (SANs) (Top) and five control left atrial appendages (LAAs) (Bottom). Near infrared (NIR) signal demonstrating robust signal to noise ratios (S/N Ratio) within isolated SANs but with only background signal within the control LAAs, which lack conduction tissue (Blue→Red=Lowest→Highest signal).

FIG. 34. Systemic Injection of Cntn2-800 in Mice Labels the CCS In Vivo. (A) Experimental work flow. (B) Whole mouse heart from a mouse injected 2 days prior with Cntn2-800, in anterior-posterior (AP) and right lateral views. Top: Brightfield. Bottom: Near infrared (NIR) signal demonstrating labelling of the presumptive CCS (Blue→Red=Lowest→Highest signal). (C) Whole-body biodistribution of other tissue types, showing expected clearance within the liver, bladder and kidneys. LA, left atrium; LV, left ventricle; RA, right atrium; RV, right ventricle; S/N, signal to noise ratio.

FIG. 35. Cntn2-800 Specifically Labels All CCS Components Following Systemic Delivery. (A) Heart section from adult mouse injected 2 days prior with Cntn2-800. Near infrared signal demonstrating labelling of the CCS (Blue→Red=Lowest→Highest). (B-D) Magnified images of the CCS components labelled with Cntn2-800 (Purple) and co-stained with anti-Hcn4 (Red, SAN/AVN/His) or anti-Cx40 (Green, PF), known markers of the CCS. DAPI (Blue, nuclei). AVN, atrioventricular node; BB, bundle branches; His, His bundle; PF, Purkinje fibers; SAN, sinoatrial node.

FIG. 36. Nptn-800 Labels all CCS Components Following Systemic Delivery. Heart sections from adult mouse injected 2 days prior with Nptn-800. (A) SAN showing reciprocal Nptn-800 staining (red) with Cx40 staining (cyan), the latter labeling the surrounding atrial working myocardium. (B) AVN labeled with Nptn-800 (red) and consistently lacking Cx40 expression (cyan). (C) His bundle and (D) Purkinje fibers co-stained with Cx40 (cyan) and Nptn-800 signal (red). Nptn-800 signal amplified using an anti-sheep 555 nm secondary antibody following tissue fixation. DAPI (Blue, nuclei).

FIG. 37. Novel Optical Imaging Agents Used to Visualize the Cardiac Conduction System (CCS) Intraoperatively in Real-Time. (A) Anatomy of the CCS (purple). Heart muscle tissue (gray). (B) Conceptual diagram of optical imaging agents used to detect the CCS intraoperatively consisting of an CCS-specific antibody conjugated to a near infrared (NIR) dye. The diagnostic agent is either topically applied to the heart tissue intraoperatively or systemically injected into the patient prior to the planned intracardiac surgery. Conduction system is then detectable in real-time and displayed on a video screen for the surgeon to avoid injury to the CCS. LA, left atrium; LV, left ventricle; RA, right atrium; RV, right ventricle.

DETAILED DESCRIPTION

In one aspect, this disclosure relates to a theranostic tool for visualizing in real time and/or targeting of the cardiac conduction system (CCS) in order to help prevent CCS damage due to surgical or catheter-based procedures or to target the CCS cells for therapeutic effects in patients with arrhythmia such as accelerated heart rhythm, heart block, or atrial or ventricular fibrillation.

In one embodiment, this disclosure provides reagents, compositions and methods with an antibody which binds CCS cells. The antibody, which in this disclosure may be a functional antibody fragment, is specific to an epitope which is present and unmasked in the extracellular domain of a CCS cell surface marker when the CCS cell surface marker is displayed at the outer surface of the CCS cell membrane. The antigen-binding site in the antibody recognizes selectively and binds specifically to the CCS cell surface marker displayed at the outer surface of the CCS cell membrane of the CCS cell.

This disclosure also provides compositions which comprise one or more of the CCS cell-specific antibodies and one or more excipients which may be pharmaceutically acceptable excipients. The excipients may be water, a buffer and/or any other solvent, a filler, a bulking agent, and/or carrier. The compositions also include those with one or more excipients for oral, topical, local or systemic, e.g. intravenous (IV) injection, administration to a patient. These compositions may comprise from 0.1 wt % to 99.9 wt % of the CCS cell specific antibody and from 0.1 wt % to 99.9 wt % of the one or more excipients.

The present disclosure provides a CCS imaging and/or diagnostic reagent which comprises, consists essentially of, or consists of an antibody being conjugated to one or more detection agents, and the CCS imaging and/or diagnostic reagent capable of binding to a cell of the cardiac conductions system (CCS), and wherein the antibody has a binding affinity to a CCS cell surface marker displayed at the outer surface of the CCS cell membrane. The detection agent may be an imaging dye comprising a chromophore, a fluorophore, a tag, a radioactive isotope, a small molecule, a biomolecule, and/or a nanoparticle.

Any of the CCS imaging and/or diagnostic reagents in this disclosure may be also referred as "an optical imaging agent."

This disclosure also provides compositions which comprise, consist essentially of, or consist of the CCS imaging and/or diagnostic reagent and one or more pharmaceutically acceptable excipients which may be water, a buffer and/or any other solvent, a filler, a bulking agent, and/or carrier. The compositions also include those in which the CCS imaging and/or diagnostic reagent is formulated with one or more excipients for oral, topical, local or systemic, e.g. intravenous (IV) injection, administration to a patient. These compositions may comprise from 0.1 wt % to 99.9 wt % of the CCS imaging and/or diagnostic reagent and from 0.1 wt % to 99.9 wt % of the one or more excipients.

The disclosure also provides methods which comprise visualizing the CCS in real time in a subject by administering to the subject one or more compositions of this disclosure which comprise the CCS imaging and/or diagnostic reagent of this disclosure. These methods include cardiothoracic surgeries and catheter procedures. The routes of administration for the compositions in these methods include oral, topical, local or systemic. After the composition is administered to the subject, the CCS imaging and/or diagnostic reagent binds to CCS cells. The CCS in the subject is then visualized in real time with the detection agent which is bound to the CCS cells via the antibody to which the detection agent is conjugated. Thus, the CCS can be monitored in real time during diagnostic and/or surgical procedures. In these methods, detection may comprise illuminating the CCS with UV, visible, and/or infrared light with a scope and/or by directly shining the light at the CCS if this is an open-heart surgery. Detection may also comprise an ultrasound and computed tomography if the CCS is examined in connection with diagnostic tests which may include neonatal tests. The detection may further comprise capturing images of the CCS with a camera in real time and further storing the images of the CCS in a computer system, if necessary, and optionally transmitting the images to at least one remote location.

In further aspect, the present disclosure provides methods for treating a patient. The methods include cardiothoracic surgeries, e.g. on open heart surgery, and catheter procedures. In the methods, the subject's CCS is visualized in real time as described above during the surgery and/or catheter procedure.

The disclosure also provides methods for preparing the CCS imaging and/or diagnostic reagents (optical imaging agents). These methods include linking the detection agent, e.g. an imaging dye, such as for example a biocompatible NIR dye to an antibody specific for the CCS cell surface marker. Once conjugated the final dye:protein ratio can be in the range 1:1000 to 1000:1.

In another aspect, the present disclosure provides a CCS therapeutic product which comprises, consists essentially of, or consists of an antibody being conjugated to one or more therapeutic drugs, and the CCS therapeutic product being capable of binding to a cell of the cardiac conductions system (CCS), and wherein the antibody has a binding affinity to a CCS cell surface marker displayed at the outer surface of the CCS cell membrane.

This disclosure also provides compositions which comprise, consist essentially of, or consist of the therapeutic product and one or more excipients which may include water, a buffer and/or any other solvent and/or carrier, e.g. a liposome. The compositions also include those in which the therapeutic product is formulated with one or more excipients for oral, topically, systemic, e.g. intravenous (IV) injection, or local administration to a patient. These compositions may comprise from 0.1 wt % to 99.9 wt % of the therapeutic product and from 0.1 wt % to 99.9 wt % of the one or more excipients.

The disclosure also provides treatment methods which comprise administering to a subject one or more compositions of this disclosure which comprise the therapeutic product. The treatment methods include those for treating cardiac arrhythmia in a subject or any other the CCS related disorders and/or diseases, including accelerated heart rhythm, heart block, or atrial or ventricular fibrillation.

In present visualization/diagnostic and/or treatment methods, the compositions according to this disclosure may be administered orally, topically, locally or systemically to a subject in any suitable amount, as may be needed. Typically, from about 0.05 mg to about 100 mg of an active ingredient (the therapeutic drug) per one kilogram of the body weight may be administered. The dosages may be adjusted as needed, depending on various factors, including the subject's weight, his/her metabolic response to the medication and a route of administration.

In further embodiments, this disclosure provides methods for direct identification and/or purification/sorting of conduction cells from a mixture of cells. These methods can be performed with a mixture of cells comprising human-induced pluripotent stem cell (hiPSC)-derived conduction cells, human embryonic stem cell (hESC)-derived conduction cells or conduction cells derived from the living mammalian heart tissue. These methods include isolation of conduction cells, purification of conduction cells, analyses of conduction cells and/or harvesting of conduction cells for transplantation. The methods comprise contacting a mixture of cells with one or more of the CCS cell surface marker specific antibodies of this disclosure. The antibody binds selectively to conduction (CCS) cells in the mixture. The antibody/conduction cell complexes can then be separated from other cells in the mixture by a number of different procedures. For example, the antibody may be bound to a magnetic bead and/or to a solid support. The antibody may be conjugated to one or more detection agent which may be a fluorescent dye and/or some other dye which permits FACS sorting of the CCS cells and separation of the conduction cells from other cells in a sample.

In this disclosure, the CCS cell surface markers include any proteins, protein fragments, protein epitopes, protein domains, protein variants or other molecules which are selectively displayed at the outer cell membrane surface of one or more CCS cells and/or which are otherwise selectively localized or co-localized within the cardiac conduction system, including one or more of the sinoatrial node (SAN), the atrioventricular node (AVN), the HIS bundle (HIS), the bundle branches (BB), and/or the Purkinje fibers (PF).

In this disclosure, the "selectively displayed surface marker" means that a particular protein or at least one of its domains or a particular protein variant or other molecule is preferentially detected as associated with the outer surface of the cell membrane of one or more the CCS cells, while the same marker is detected only at a lesser level, if at all, in working myocardium. The detection methods include, but are not limited to, a tissue immunostaining and/or in situ hybridization which detects gene expression and/or single-cell RNA-sequencing (scRNAseq).

In this disclosure, "displayed at the outer surface of the cell membrane of one or more CCS cells" include trans-membrane proteins with extracellular domains, e.g. cell surface receptors and trans-membrane channels, as well peripheral membrane proteins or variants located in the outer layer of the lipid bilayer or any other proteins or at least some of their domains which associate directly or indirectly with the outer surface of the CCS cell membrane, e.g. adhesion molecules and proteins which are anchored to the outer surface of the cell membrane by post-translational modifications and/or via interaction with other proteins and/or molecules.

The CCS cells include cells which make up any of the CCS components: the SAN, the AVN, the HIS bundle, the bundle branches (BB) and/or the Purkinje fibers (PF).

The term "protein" can be used in this disclosure to refer to a full polypeptide as well as any peptide and/or a protein domain, or any protein fragment, e.g. epitope which may be a conformation of several amino acids displayed at the cell membrane surface of the CCS cell. The term "protein" further includes modified proteins, e.g. glycoproteins, and peptides.

Table 1 provides a list of mouse genes for preferred CCS cell surface markers enriched within at least one component of the cardiac conduction system. Table 1 includes differentially expressed genes enriched within at least one major component of the CCS as compared to the working myocardium. Analyses performed on single-cell RNA-sequencing (scRNAseq) dataset from microdissected CCS tissue of wild-type, embryonic day 16.5 (E16.5) mouse hearts. Avg log FC, average log fold change; Adj p value, adjusted p value.

TABLE 1

Enriched Cell Surface Markers Within Each Component of the Cardiac Conduction
Enriched Cell Surface Markers Within Each Component of the Cardiac Conduction System.

| | SAN | | | AVN | | | PF | |
|---|---|---|---|---|---|---|---|---|
| Gene | Avg log FC | Adjusted p value | Gene | Avg log FC | Adjusted p value | Gene | Avg log FC | Adjusted p value |
| Cacna2d2 | 1.3371584 | 2.56E−166 | Cacna2d2 | 0.880363 | 2.22E−308 | Cacna2d2 | 1.2147351 | 2.22E−308 |
| Ntm | 0.7120715 | 6.07E−60 | Slc22a1 | 1.717583 | 2.22E−308 | Slc16a12 | 0.6351618 | 2.22E−308 |
| Pcdh17 | 0.6543139 | 4.87E−50 | Ramp1 | 1.018729 | 7.20E−126 | Slc22a1 | 0.6732325 | 7.50E−185 |
| Slc24a2 | 0.3389513 | 2.05E−46 | Pirt | 0.298884 | 1.17E−111 | Gja5 | 0.9724381 | 1.17E−183 |
| Clic5 | 0.5008894 | 6.19E−42 | Kcnj5 | 0.420015 | 4.33E−102 | Adgrb2 | 0.3694906 | 2.83E−181 |
| Adora1 | 0.4566276 | 1.16E−34 | Ntm | 0.554708 | 1.20E−101 | Ephb3 | 0.5154093 | 4.68E−115 |
| Dbh | 0.3592005 | 2.42E−34 | Cacna1g | 0.385195 | 9.57E−96 | Sdc4 | 0.6871758 | 2.43E−113 |
| Mfsd6 | 0.3805107 | 1.51E−32 | Fras1 | 0.353021 | 2.87E−90 | Ntm | 0.6135754 | 6.32E−110 |
| Tenm4 | 0.5079904 | 1.05E−29 | Parm1 | 0.508829 | 4.05E−89 | Slc6a6 | 1.0200692 | 1.19E−99 |
| Cacna1h | 0.3634994 | 1.42E−29 | Epha4 | 0.452814 | 1.02E−81 | Scn5a | 0.7602381 | 4.81E−86 |
| Nptn | 0.5822915 | 2.92E−27 | Rxfp1 | 0.378436 | 4.84E−77 | Trabd2b | 0.3783752 | 2.12E−81 |
| Atp1b2 | 0.4038063 | 1.09E−26 | Adora1 | 0.276241 | 7.23E−76 | Epha4 | 0.5747562 | 9.25E−68 |
| Gria1 | 0.3850788 | 2.49E−26 | Kcne1 | 0.982113 | 3.59E−75 | Kcnk3 | 0.6385524 | 1.57E−58 |
| Trabd2b | 0.5260834 | 4.61E−26 | Tmem51 | 0.366699 | 8.58E−71 | Fbxo32 | 0.5737561 | 7.20E−55 |
| Lrrn2 | 0.39467 | 4.21E−24 | Chrm2 | 0.318351 | 5.02E−70 | Alcam | 0.4230022 | 5.48E−54 |
| Pirt | 0.3752498 | 1.71E−23 | Gpc1 | 0.419522 | 8.14E−69 | Hfe2 | 0.3020887 | 1.51E−44 |
| Cacna1d | 0.2848937 | 3.76E−23 | Slitrk5 | 0.273086 | 2.16E−60 | Parm1 | 0.6077837 | 4.28E−42 |
| Adam33 | 0.4427006 | 8.91E−22 | Kcnk3 | 0.305829 | 9.97E−56 | Fam174b | 0.4300852 | 6.89E−37 |
| Kcnh2 | 0.3694565 | 1.35E−21 | Ddr1 | 0.344363 | 1.08E−54 | Itgb5 | 0.5001319 | 1.20E−29 |
| Efnb2 | 0.3121067 | 1.30E−19 | Furin | 0.356964 | 1.74E−54 | Gpr22 | 0.4414115 | 1.43E−28 |
| Enpp1 | 0.2675914 | 4.77E−18 | Kcng2 | 0.323374 | 9.10E−50 | Slc22a17 | 0.3499469 | 7.09E−28 |
| Fn1 | −1.2785734 | 6.38E−18 | Jph2 | 0.344274 | 1.34E−46 | Gipr | 0.2845983 | 2.00E−27 |
| Slc03a1 | 0.3695732 | 4.17E−16 | Cxadr | 0.302512 | 3.20E−46 | Nlrp10 | 0.2572961 | 6.96E−24 |
| Atp1a2 | 0.4128887 | 1.11E−15 | Vldlr | 0.392485 | 7.22E−43 | Gpc1 | 0.4079969 | 7.53E−24 |
| Lrrc4b | 0.2939199 | 2.64E−14 | Cdh13 | 0.362823 | 1.27E−39 | Chrm2 | 0.3918263 | 1.95E−22 |
| Sec61b | −0.6433686 | 7.65E−14 | Tmem38a | 0.288973 | 3.40E−38 | Spint2 | 0.3555143 | 1.55E−21 |
| Shi5a4 | 0.318808 | 1.04E−13 | Slc22a17 | 0.270187 | 1.29E−37 | Pdpn | 0.2646191 | 1.14E−20 |
| Smim5 | 0.3743883 | 1.27E−13 | Ifitm2 | −0.91783 | 3.19E−37 | Inafm2 | 0.3029167 | 2.59E−19 |
| Sort1 | 0.3296642 | 1.62E−10 | Slc2a1 | 0.282417 | 3.73E−35 | Rxfp1 | 0.2613396 | 1.22E−18 |
| Cacnb2 | 0.2897371 | 4.40E−10 | Ramp2 | −1.30726 | 7.46E−35 | Plxna4 | 0.2568517 | 1.54E−18 |
| Plppr5 | 0.3054754 | 1.59E−09 | Itga9 | 0.30395 | 1.44E−34 | Atp9a | 0.2721684 | 1.08E−15 |
| Ltbp4 | −0.4408858 | 2.42E−08 | Smim5 | 0.265722 | 1.79E−33 | Sgca | 0.2727495 | 1.98E−15 |
| Cotl1 | −0.4337112 | 2.82E−06 | Atp1a2 | 0.304016 | 3.52E−33 | Tspan2 | 0.2956577 | 2.42E−15 |
| Eng | −0.6765922 | 6.61E−06 | Tmx4 | 0.328454 | 2.85E−31 | Unc5b | 0.2577643 | 1.43E−14 |
| Arl6ip1 | −0.6683399 | 1.27E−04 | Emp1 | −0.65498 | 8.24E−26 | Dab2ip | 0.275408 | 6.69E−14 |
| Plpp1 | −0.2796226 | 3.55E−04 | Arhgef7 | 0.2528 | 5.18E−23 | Lifr | 0.2921734 | 9.54E−14 |
| Magi3 | 0.2580286 | 5.00E−04 | Cd34 | −0.76766 | 1.42E−22 | Itgav | 0.2704438 | 1.45E−13 |

TABLE 1-continued

Enriched Cell Surface Markers Within Each Component of the Cardiac Conduction
Enriched Cell Surface Markers Within Each Component of the Cardiac Conduction System.

| SAN | | | AVN | | | PF | | |
|---|---|---|---|---|---|---|---|---|
| Gene | Avg log FC | Adjusted p value | Gene | Avg log FC | Adjusted p value | Gene | Avg log FC | Adjusted p value |
| Mfge8 | −0.2723024 | 2.74E−03 | Tm4sf1 | −0.93752 | 2.97E−21 | Lrrc4b | 0.2704298 | 1.79E−13 |
| Fuca1 | −0.2525502 | 5.40E−03 | Eng | −0.63906 | 1.18E−20 | Slc38a10 | 0.3436349 | 4.08E−13 |
| | | | Fxyd6 | −0.86538 | 9.24E−14 | Atp1a2 | 0.3275545 | 6.40E−13 |
| | | | Lsp1 | −0.6191 | 2.34E−13 | Nptn | 0.3350681 | 3.79E−12 |
| | | | | | | Kctd12 | 0.3360535 | 3.30E−12 |
| | | | | | | Dsg2 | 0.2520092 | 6.19E−12 |
| | | | | | | Tmem161a | 0.2650984 | 6.45E−11 |
| | | | | | | Tmem176a | 0.3154046 | 7.79E−11 |
| | | | | | | Fndc3b | 0.2944895 | 8.67E−10 |
| | | | | | | Pdpk1 | 0.2694224 | 9.87E−10 |
| | | | | | | Cacna2d1 | 0.2506851 | 6.27E−08 |
| | | | | | | Sgcg | 0.2529262 | 8.35E−08 |

In this disclosure, any human gene homologues to at least one gene listed in table 1 encode a preferred CCS cell surface marker of this disclosure. Accordingly, the preferred CCS cell surface markers include any proteins or their extracellular domains or fragments or variants or epitopes encoded by any of human gene homologues of the genes listed in table 1.

The most preferred CCS cell surface markers according to this disclosure include Neurotrimin and any of Neurotrimin-derived epitopes, its alternatively spliced variants or any peptide produced from an alternative transcript, or any fragments of Neurotrimin, e.g. any peptide derived from Neurotrimin and/or its postranslationally modified forms, e.g. Neurotrimin to which glycosylphosphatidylinositol is attached, as well as any mutated isoform of Neurotrimin or its fragment as may be found in a human disorder or a disease. In humans, Neurotrimin is a protein encoded by the NTM gene.

The most preferred CCS cell surface markers also include Neuroplastin and any Neuroplastin-derived epitopes and Contactin 2 and any Contactin 2-derived epitopes, and any of their alternatively spliced variants or a peptide produced from an alternative transcript, or any fragments, e.g. peptides, and/or postranslationally modified forms, as well as any mutated isoform of Neuroplastin or its fragment or Contactin 2 or its fragment as may be found a human disorder or a disease. Neuroplastin is a protein encoded by the NPTN gene in humans. Contactin 2 is a protein encoded by the CNTN2 gene in humans.

In this disclosure, the term "antibody" is understood broadly. For a detailed description of "an antibody," a person of skill is referred to "Cellular and Molecular Immunology, the 9th Edition" by Drs. A. Abbas, A. Lichtman and S. Pillal; published by Elsevier. Antibodies include immunoglobulins: Ig A, IgD, IgE, IgG and IgM or any combinations. In this disclosure, "antibody" may refer to a functional antibody fragment. The "functional" means that the fragment has a specific affinity an epitope. Examples of suitable functional antibody fragments include, but are not limited to, a diabody, scFv, Fab and F(ab)₂. The antibody may be a recombinant antibody which obtained by screening a phage display library or by any other recombinant technology or a monoclonal antibody obtained from a cell hybridoma or a polyclonal antibody produced in a rabbit, goat, horse, chicken or any other species. The antibodies and antibody fragments may be at least partially or fully humanized. The antibodies include polyclonal, monoclonal, single-chain, and chimeric antibodies. Humanized monoclonal antibodies and their functional fragments are preferred.

In this disclosure, the term "an antibody or a functional antibody fragment has a binding affinity to a CCS cell surface marker" means that the antibody or the functional antibody fragment has a $K_d$ to an epitope derived from the CCS cell surface marker in the range from $10^{-6}$ M to $10^{-12}$ M. A person of skill will immediately recognize that "$K_d$" stands for the equilibrium dissociation constant between an antibody and its epitope. In order to determine $K_d$, a person of skill can follow a protocol disclosed in "Antibodies: a laboratory manual, Second Edition," edited by E. Greenfield, 2014 or any other similar laboratory manuals generally available to a person of skill.

Particularly preferred antibodies or antibody fragments include those with $K_d$ to such an epitope in the range from $10^{-9}$ M to $10^{-12}$ M.

The term "epitope" in this disclosure means an antigenic determinant which is a contiguous or non-contiguous peptide conformation present in the extra-cellular portion of the CCS cell surface marker.

In this disclosure, the reagents, therapeutic products and compositions include those in which an antibody or a functional antibody fragment is conjugated directly or indirectly to a detection agent and/or a therapeutic drug.

"Conjugated directly" means that one or more moieties, e.g. an imaging dye, is covalently attached (linked) or non-covalently attached (linked) to the antibody or the functional antibody fragment.

"Conjugated indirectly" means that the moiety, e.g. a drug (small organic molecule or a biomolecule) or a dye, is attached to the antibody via a linker and or the drug or the dye is encapsulated in a carrier, e.g. a liposome or some other time of a carrier and/or shell, and the antibody is displayed at the carrier and targets the carrier (along with the drug and/or dye) to the CCS cells.

The term "linker" refers to any molecule, e.g. a short peptide or any other group of atoms or a chemical molecule which is positioned between the antibody and the drug and/or dye. The linker is linked with at least one of its atoms or residues to the antibody. The linker is also linked with at least one of its atoms or residues to the drug and/or dye. Accordingly, the linker links the antibody and the drug and/or the detection agent together.

The "detection agents" of this disclosure include radioactive isotopes, nanoparticles, biotin, tags, e.g. the histidine tag, or imaging agents. A great variety of imaging agents is currently available. Preferred imaging agents in this disclosure include contrast agents and MRI dyes which are typically used in clinical procedures. Particularly preferred imaging agents include those with biocompatible NIR (near-infrared) fluorophore.

Through the standard NHS ester chemistry (NHS ester reactive group provides the functionality for labeling primary and secondary amines, such as lysine residues in proteins), or maleimide chemistry (functionality for labeling molecules that contain free sulfhydryl (—SH) groups, such as cysteine residues in proteins), or other forms of conjugation chemistry, the antibodies or the functional antibody fragments of this disclosure may be covalently or non-covalently conjugated to any standard dyes of the visible and non-visible spectrums (e.g. fluorescein, 488, FITC, 555, Cy3, Cy5, Cy5.5, 598, 640, 680, 780, 800, zw800, indocyanine green, 900 and newly designed and ultrapurified fluorescent probe-antibody conjugates with fluorescence emissions in the NIR-II region 1,000-1,700 nm). Similarly, additional conjugates of therapeutic and diagnostic use include contrast agents (CT and MRI), radiotracers, quantum dots and/or nanoparticles.

Particularly preferred imaging dyes for the reagents and compositions of this disclosure include LiCor IRDye 800CW which are near-infrared fluorescent dyes available from LiCor BioSciences U.S.

Particularly preferred reagents of this disclosure include an anti-Contactin 2 (which can be abbreviated in this disclosure as anti-Cntn2) antibody, an anti-Neurotrimin (which can be abbreviated in this disclosure as anti-NTM) antibody and/or an anti-Neuroplastin antibody (anti-NPTN) conjugated with a detection agent which comprises a biocompatible NIR (near-infrared) fluorophore which can be an NIR dye with broad absorption spectrum (778 nm) and emission (795 nm). In the conjugates, the preferred dye:protein ratio is 1.5-2.

Some of the compositions and therapeutic products of this disclosure may comprise one or more therapeutic drugs and the antibody or the functional antibody fragment specific to the CCS cell surface marker or its fragment. In some embodiments, the antibody or the functional antibody fragment is conjugated covalently or non-covalently. In other embodiments, to the therapeutic drug may be encapsulated into a carrier, e.g. a liposome or some other membrane, and the antibody or the functional antibody fragment is displayed at the surface of the carrier in order to deliver the encapsulated drug selectively to the CCS cells in a subject. Some of the compositions and therapeutic products of this disclosure may comprise the antibody or the functional antibody fragment specific to the CCS cell surface marker or its fragment and one or more therapeutic drugs, wherein the therapeutic drug comprises a biomolecule or a small molecule. Suitable biomolecules include DNA or an RNA molecule which alter expression and/or function of one or more genes and/or proteins in the CCS cell. Suitable RNA or DNA molecules include those that can silence or activate the biology activity of the CCS cell.

For CCS therapeutic applications, the antibodies targeting CCS-specific proteins may be conjugated with small molecule drugs such as digoxin, calcium channel blocker, beta blocker, or anti-arrhythmic drugs or RNA or DNA that can silence or activate at least one biologic function of the CCS cell.

Some of the compositions and the therapeutic products of this disclosure may comprise one or more of the following drugs: antiarrhythmics, CCS agonists, or anti-inflammatories. Suitable antiarrhythmics include, but are not limited to, Class I drugs which block voltage-gated Na channels, Class II drugs which are β-Blockers, Class III drugs which prolong the action potential, usually via K+ channel blockade, or Class IV drugs which are Ca2+ antagonists. The following drugs are non-non-liming examples of suitable antiarrhythmics: Procainamide, Quinidine, Disopyramide, Lidocaine, phenytoin, tocainide, mexiletine, Flecainide, encainide, propafenone, moricizine, Atenolol, acebutolol, metoprolol, nadolol, propranolol, NAPA, Amiodarone, Sotalol, Ibutilide, Amlodipine, diltiazem, felodipine, isradipine, nicardipine, nifedipine, nisoldipine, verapamil, sodium/potassium/ATPase blocker (e.g. digoxin), and adenosine receptor blocker (e.g. adenosine, dipyridamole). CCS agonists include: beta 1 agonists: (e.g. dobutamine); beta 2 agonists: (e.g. salmeterol, terbutaline); and non-selective beta agonists: (e.g. isoproterenol, epinephrine). Antiinflammatories include NSAIDs (e.g. ibuprofen, naproxen), preferential and selective COX2 inhibitors, corticosteroids (e.g. prednisone, methyl-prednisone), conventional DMARDs (e.g. methotrexate, leflunomide, sulfasalazine, hydroxychloroquine) and biologic DMARDs (e.g. Adalimumab, Etanercept, Infliximab, Rituximab, Abatacept).

Particularly preferred therapeutic drugs include: calcium channel blockers (e.g. diltiazem, verapamil), beta adrenergic blockers (e.g. metoprolol, carvediolol, atenolol), sodium/potassium/ATPase blockers (e.g. digoxin), adenosine receptor blockers (e.g. adenosine, dipyridamole), cytotoxic agents (e.g. diphtheria toxin A, methotrexate, doxorubicin), adrenergic agonists (e.g. isoproterenol, epinephrine) and anti-inflammatory (e.g. glucocorticoids, cyclosporin A, tacrolimus).

For application as CCS imaging agents in real-time, the antibody conjugated to an imaging dye such IRDye800CW can be given to a patient either topically or by intravenous or intracoronary systemic delivery. The administration of this composition delivers the imaging dye to the CCS and the CCS can be then monitored in real time during a cardiac surgery with one or more devices typically used to detect the imaging dye. Visualizing and monitoring the CCS in real time during the cardiac surgery leads to prevention of iatrogenic damage to the conduction system during both congenital and adult heart surgeries.

The real-time visualization methods for the CCS help with preventing injuries to the CCS. The CCS injuries can result in heart block, arrhythmias, decreased cardiac output, and even sudden death. Iatrogenic damage to the CCS remains a significant surgical complication in both congenital heart disease (CHD) and adult cardiac surgeries. This is due in part to an inability to visualize and, thus, avoid damaging the surrounding CCS by inadvertent incision or suture placement. In the current era, postoperative heart block alone, secondary to accidental surgical damage of the atrioventricular node, complicates roughly 1-3% of all CHD surgeries. Postoperative heart block and other forms of intraoperative CCS damage remain a significant cause of morbidity, increased cost, decreased long-term survival and often the life-long need for mechanical pacemakers.

The present visualization methods for the CCS in real time can be helpful in conjunction with various adult cardiac surgeries, including mitral and aortic valve replacements, myomectomy in hypertrophic cardiomyopathy. The ability to visualize and monitor the CCS in real time provides a significant technical contribution to the current standard of care in both pediatric and adult intracardiac surgeries which currently entails the use of anatomical landmarks to guess the approximate location of the CCS, otherwise indistinguishable from the surrounding heart muscle.

The disclosed herewith compositions and methods can directly target the CCS structure in order to therapeutically modify the behavior of these cells. For example, the atrial-ventricular node (AVN) is the key structure that regulate the ventricular heart rate during atrial arrhythmia such as atrial fibrillation, a major disease order in aging population with significant healthcare expenditure. The ability to direct target the AVN to provide it with drugs that would reduce its ability to conduct electrical activity from the atria during atrial fibrillation represents a major advantage over the current use of drugs that blocks AVN which has also blood pressure lowering effects when that patients are usually hypotensive. In addition, there is emerging data to support the origin of ventricular fibrillation from the Purkinje fiber network. Being able to target the Purkinfe fiber structure of the CCS with antibodies directly binding and delivery therapeutic agents to the Purkinje cells provides a major improvement in comparison with non-specific effects of anti-arrhythmic drugs that are currently being used.

The present disclosure uncovers a number of highly novel, conduction-specific cell surface markers by profiling genes that are expressed in different CCS structure (e.g. pacemaker/SAN, AVN, Purkinje fibers) at single-cell resolution as shown in table 1 and other tables submitted in this disclosure.

This disclosure further provides novel diagnostic tools for imaging the CCS with an antibody and near infrared dye (IRDye800CW) for the real-time, intraoperative visualization of the CCS with the purpose of preventing iatrogenic damage to the conduction system during both congenital and adult heart surgeries.

Further applications for the antibody-imaging agent method include other modes of imaging such as MRI or CT. For example, the near infrared dye may be replaced with other molecules (e.g. iron tag, magnetic beads, etc.) that can be detected by MRI, CT, or intracardiac catheters, etc.).

The reagents, compositions and methods of this disclosure may also be used for the direct identification and sorting of human-induced pluripotent stem cell (hiPSC)-derived or human embryonic stem cell (hESC)-derived conduction cells or conduction cells derived from living mammalian heart tissue for the purpose of isolation, purification, analyses and/or harvesting for transplantation. Additionally, isolated hiPSC-derived conduction cells or human embryonic stem cell (hESC)-derived conduction cells or conduction cells derived from living mammalian heart tissue using our agents and method may also be used for high-throughput drug screening of conduction cells for either agonistic or adverse effects.

The agent and method may also be adapted by replacing the near infrared dye with other therapeutic molecules (eg. drugs, small molecules, DNA or RNA) by direct conjugation or liposomal packaging for direct delivery of therapeutics to the cardiac conduction system.

Importantly, many of the CCS cell surface markers are known to be expressed within some other cell types, including neurons and certain types of cancer such as glioblastoma and breast cancer, providing additional valuable targets in the prevention of surgical damage (peripheral neurons) as well as in detection of certain cancers.

The optic imaging agents that may be used for CCS imaging or therapy may be based on commercially acquired antibodies. For example, anti-Cntn2 Goat Polyclonal antibody—AF4439 or anti-NPTN Goat Polyclonal antibody—AF5360 can be used in studies in mice. Other commercially available anti-human antibodies can be also used.

An antibody can be generated against an epitope derived from the CCS surface marker by using any of the techniques generally known to a person of skill.

For imaging applications, these antibodies can be covalently conjugated to a benign, near-infrared (NIR) dye (IRDye800CW, Li-cor #929-70020) using company specifications. IRDye800CW is a NIR imaging probe with broad absorption (778 nm) and emission (794 nm) peaks that is nontoxic to rodents and currently used in human clinical imaging trials. Once conjugated, the final dye:protein ratio can be approximately 1.5-2.

The invention will now be described in further detail with the following non-liming examples.

Further aspects of this disclosure include recombinant DNA or RNA constructs, e.g. plasmids, which express one or more antibodies or one or more epitopes of this disclosure. Further aspects of this disclosure also include recombinant cells which comprise recombinant DNA or RNA molecules which express one or more antibodies, or one or more epitopes described in this disclosure.

Example 1. Methods for Studies in Examples 2-10

Mice: Wild-type, timed pregnant CD1 mice were acquired from Jackson Laboratory (Sacramento, CA). Embryonic pups or postnatal mice at indicated ages were used in accordance with the Institutional Animal Care and Use Committee of Stanford University. Both female and male mice were used for all experiment types described at a 1:1 ratio.

Tissue isolation and single-cell sequencing using the 10× Genomics® platform: Single cells were isolated and analyzed using the droplet-based platform by 10× Genomics, Inc per recommended company guidelines. Single cells were prepared following the protocol from 10× Genomics, Inc (Pleasanton, CA). Briefly, embryonic day 16.5 (E16.5), wild-type CD1 mouse hearts were harvested and three zones of microdissection were isolated based on anatomical landmarks and entailed: Zone I—Sinoatrial node (SAN) region (SVC/right atrial junction), Zone II—Atrioventricular node (AVN)/His region (crux of heart) and Zone III—Bundle branch (BB)/Purkinje fiber (PF) region (luminal side of ventricles). Specifically, Zone II was dissected as a large area at the crux of the heart from the base of the interatrial septum (including the triangle of Koch) to below the plane of the mitral annulus, from the posterior-most aspect of the heart to the anterior-most. Tissues from a total of six different embryos were pooled for each zone of dissection. Use of E16.5 hearts for analysis was influenced by: 1. size restriction associated with cell capture within microfluidic channels of the Chromium™ platform from 10× Genomics; and 2. the opportunity to investigate the genetic program required not only for the function but also for the embryonic development of the CCS. The libraries were sequenced using Illumina HiSeq 4000.

Bioinformatics analysis: The Droplet platform data was de-multiplexed and mapped to mouse genome MM10 using CellRanger from 10× Genomics with default parameters. Cell filter, data normalization, and unsupervised analysis were carried out in Seurat version 2 per their recommended steps (Butler et al., 2018; Macosko et al., 2015). Significance is presented as an "adjusted p-value", which is based on the Bonferroni correction using all features in the dataset. Briefly, the cells were filtered by their gene number and UMI number. The threshold we used for gene number is 500 to 60,000, and UMI number is 1,000 to 5 million. Next, we used the LogNormalize function to normalize gene expression in each cell. Specifically, we calculated the expression value of genes by following this formula: log $\{$(each gene expression level/total gene expression value)*10,000$\}$. The Y-axis of all ViolinPlots indicates this normalized gene expression. Average log fold change (avg_log FC) described in all data provided (Online Tables II-VII) represents the log fold-change of the average expression between the two groups. To remove the unwanted sources of variations, we scaled the data with the "vars.to.regress" parameter based on the number of UMIs, percentage of ribosome genes, and Rn45s expression value. Furthermore, we found all the variable genes and used them to perform principal component analysis (PCA). Within all the PCs, we used the top 10 PCs to do clustering and tSNE analysis. In the tSNE analysis, we set the seed.use as 10 and perplexity as 30. Finally, we used the FindAllMarker function to identify the genes differentially expressing in the cell clusters. To be detected, the genes have to express in at least 25% of cells in one of the two comparing clusters and the differential expression level also should be higher than 25%. Finally, Gene Ontology (GO) Expression Analysis was performed using the DAVID Bioinformatics Resources 6.8, NIAID/NIH (https://david.ncifcrf.gov/summary.jsp). GO/KEGG term enrichment analyses were performed using geneAnswers R package with hypergeometric test. Statistically significant cardiac-related terms with at least 2 genes were used for each gene list.

Immunofluorescence: Immunofluorescence staining was carried out by following a previous protocol with minor modifications[24].

Primary antibodies used included: Anti-mouse Igfbp5 Goat Polyclonal Antibody (R&D systems/Fisher Scientific: AF578) at 1:100 dilution; Anti-mouse Connexin 40 Rabbit Polyclonal antibody (Alpha Diagnostics, Cx40-A) at 1:100 dilution; Anti-mouse Hcn4 Rat Monoclonal [SHG 1E5] antibody (Abcam, ab32675) at 1:75 dilution. The following secondaries were used at a 1:500 dilution: Donkey anti-goat IgG Alexa Fluor 555 (Invitrogen, A-21432), Chicken anti-Rabbit IgG Alexa Fluor 488 (Invitrogen, A-21441), Donkey anti-Rabbit IgG Alexa Fluor 647 (Invitrogen, A-31573) and Chicken anti-Rat IgG AlexaFluor 488 (Invitrogen A-21470). All images were taken with Axioimager microscope at Neuroscience Microscope Service (NMS) facility at Stanford University. Negative controls for immunostaining included the use of primaries or secondary antibodies alone. A minimum of 4 biological (different hearts) and 4 technical (different slides/heart) replicates were used for each antibody staining.

iDISCO+: For detailed protocol, please see https://idisco.info/idisco-protocol/. Protocol was followed strictly with primary and secondary incubation periods lasting 2 days each. The following primary antibodies were used: Anti-mouse Igfbp5 Goat Polyclonal Antibody (R&D systems/Fisher Scientific: AF578) at 1:200 dilution (total 1.4 mL/embryo); Anti-mouse Cx40 Rabbit Polyclonal antibody (Alpha Diagnostics, Cx40-A) at 1:200 dilution (total 1.4 mL/embryo); Anti-mouse Hcn4 Rat Monoclonal [SHG 1E5] antibody (Abcam, ab32675) at 1:200 dilution (total 1.4 mL/embryo). The following secondaries were used at a 1:700 dilution: Donkey anti-goat IgG Alexa Fluor 555 (Invitrogen, A-21432), Donkey anti-Rabbit IgG Alexa Fluor 647 (Invitrogen, A-31573) and Chicken anti-Rat IgG AlexaFluor 647 (Invitrogen A-21472). At least one day after clearing, iDISCO+ samples were imaged on a light sheet microscope (Ultramicroscope II, LaVision Biotec) equipped with a sCMOS camera (Andor Neo) and a 2×/0.5 NA objective lens (MVPLAPO 2×) equipped with a 6 mm working distance dipping cap. Version v285 of the Imspector Microscope controller software was used. We imaged using 488-nm, 561-nm, and 640-nm lasers. The samples were scanned with a step-size of 3 μm using the continuous light-sheet scanning method. A minimum of 8 biological (different hearts) replicates were used for each immunolabelling within optically cleared hearts.

RNAscope in situ hybridization: RNAscope® Multiplex Fluorescent v2 (Cat. #323100) was used per manufacturer suggested protocol. The following murine probes were used: Mm-Hcn4-C2—421271-C2, Mm-Smoc2-C1—Cat No. 318541, Mm-Rgs6-C1—Cat No. 521211, Mm-Rgs6-C1—Cat No. 521211, Mm-Cpne5-C3—Cat No. 496711-C3 and Mm-Ntm-C1—Cat No. 489111. All images were taken with Axioimager microscope at Neuroscience Microscope Service (NMS) facility at Stanford University. A minimum of 3 biological (different hearts) and 4 technical (different slides/heart) replicates were used for each in situ hybridization.

Accession Numbers: All scRNA-seq raw data have been deposited into the NCBI/GEO database under accession number GEO: GSE132658.

Example 2. Single-Cell Isolation and Expression Profiling of Cardiac Conduction Cells In order to obtain the transcriptional profiles of individual cardiac conduction cells, wild-type, embryonic day 16.5 (E16.5) mouse hearts (n=6 per zone) were harvested and three zones of microdissection were isolated based on anatomical landmarks (FIG. 1A). These three zones included the SAN region (Zone I), the AVN/His region (Zone II) and the BB/PF region (Zone III). Our designed workflow then entailed tissue digestion and single-cell capture on a microfluidic panel, automated reverse transcription, barcoding, library generation, and high-throughput sequencing and bioinformatics analysis (FIG. 1A). We acquired high quality samples from each zone, collecting 5,919 cells from Zone I, 5,625 cells from Zone II and 10,918 from Zone III (FIG. 1B). Unsupervised dimensionality reduction of the scRNA-seq data by t-Distributed Stochastic Neighbor Embedding (t-SNE)[25] from each zone, or all zones combined, demonstrated expected clusters of the major cell types contained within the E16.5 heart including fibroblasts, endocardial, epicardial, endothelial and smooth muscle cells in addition to cardiomyocytes (FIG. 1B, FIG. 11, FIG. 22 (Online Table I)). Interestingly, when we analyzed genes that were previously reported to be differentially expressed in the SAN using the most stringent bulk RNA sequencing approaches to date[20] (e.g., transgenic reporter plus laser capture microdissection), we found a significant portion (25%) of these genes to be enriched in other cell types such as endothelial cells and fibroblasts rather than SAN cells (FIG. 11), demonstrating the power and specificity of the single cell transcriptomic approach. Similarly, more recent efforts[21] using cell sorting and knock-in Tbx3 reporter mice to perform transcriptome analysis of the SAN showed similar issues of contamination (FIG. 12). When compared to our dataset, 12 of the top 16 (75%) reported SAN-enriched genes from E17.5 mice appear to be enriched within non-conduction cell clusters including fibroblasts (Clusters 2, 5, 6, 11; eg. Tnxb), endothelial (Cluster 13; eg. Tgfbl), endocardial (Clusters 4 and 7; eg. Sox18) and/or neuronal (Cluster 14; eg. Ngfr) rather than the Hcn4+/Shox2+/Tbx3+ SAN cluster (Cluster 9).

Example 3. Identification of a Bona Fide Sinoatrial Node (SAN) Cell Cluster within Zone I Zone I cells underwent unsupervised clustering by t-SNE (FIG. 2A), and gene enrichment analysis (FIG. 2B) revealed six cardiomyocyte clusters (Tnnt2$^+$/Actn2$^+$ double positive) (Clusters 0, 1, 3, 9, 12, 15) (FIG. 2A-B). To identify the cell cluster(s) containing putative SAN cells, we assessed for the expression of established SAN markers including Hcn4, Isl1, Shox2, and Tbx3[5,26,27] in addition to a cardiomyocyte signature. Only one (Cluster 9) of all sixteen clusters showed significant enrichment of nodal markers (FIG. 2C-D). Further, gene ontology (GO) functional cluster analysis of all enriched genes for Cluster 9 revealed multiple statistically significant GO terms associated with not only cardiac development but also heart rate regulation and SAN development and function (FIG. 2E). Finally, in addition to the enrichment of established nodal genes, our analysis revealed a host of significant novel genes not previously involved in SAN development or function (FIG. 23 (Online Table II)), including Igfbp5 (Insulin growth factor binding protein 5) which showed the greatest amount of enrichment (2.12 avg log FC, adjusted p value=2.63×10$^{-126}$). Immunostaining of murine heart sections confirmed expression of Igfbp5 protein within the compact SA node (cSAN) but not in the surrounding atrial working myocardium (FIG. 2F) nor additional cardiac cell types such as the SAN artery (FIG. 13). Igfbp5 gene expression was also enriched within Clusters 4 (endocardial) and 10 (epicardial) (FIG. 2B); however, protein expression could not be detected within these additional cell populations by immunofluorescence (data not shown). Other novel genes found to be significantly enriched within Cluster 9 included Smoc2 (SPARC-related modular calcium-binding protein 2; 1.69 avg log FC, adjusted p=5.2×10$^{-164}$), Ntm (Neurotrimin; 0.75 avg log FC, adjusted p value=4.97× 10$^{-81}$), and Cpne5 (Copine 5; 0.57 avg log FC, adjusted p value=2.90×10$^{-37}$) as well as the previously identified Rgs6 (regulator of G-protein signaling type 6; 0.6 avg log FC; adjusted p value=2.92×10$^{-61}$) (FIG. 2D).[28] Interestingly, Smoc2 was also recently reported by the Christoffels group as a new SAN marker.[21] We subsequently validated these genes by either immunostaining or FISH, showing their enrichment within the SAN as compared to the surrounding atrial myocardium (FIG. 14).

Example 4. Analysis of Cluster 9 in Zone I Reveals Unique Compact SAN and Transitional Cell Subtypes To further evaluate SAN cell type heterogeneity, Cluster 9 was isolated as an independent Seurat object and unbiased subcluster analysis was then performed (FIG. 3A).[29] Two distinct subclusters were identified within Cluster 9, both showing high expression of Actn2 consistent with cardiomyocyte identities (FIG. 3B-C). One cluster (named "cSAN" for compact SAN) showed high levels of established SAN markers including Hcn4, Hcn1, Gjc1, Isl1, Shox2, Tbx3 and Tbx18, with low or no expression of known atrial cardiomyocyte gene markers Gja5 (Cx40), Scn5a and Nkx2-5, consistent with isolation of compact SAN cells (FIG. 3C-D). Conversely, while the second cluster (named "Tz" for transitional cells) expressed these same nodal markers, they were expressed at lower levels. Additionally, the Tz cluster was reciprocally enriched for atrial cardiomyocyte markers consistent with the isolation of a hybrid or transitional SAN cell population (FIG. 3D).[2,7,8,30,31] Differential gene expression was assessed between the cSAN and Tz cell clusters (FIG. 24 (Online Table III)). Notably, Smoc2 was found to be present in both the cSAN and Tz subclusters (FIG. 3E). Consistently, high resolution fluorescent in situ hybridization (RNAscope) and co-immunostaining analyses of wild-type murine heart sections of the SAN region further validated these results. Clear subpopulations of cells entailing: 1) cSAN cells (Hcn4$^+$/Smoc2$^+$/Cx40$^{neg}$); 2) Tz cells (Hcn4$^{low/neg}$/Smoc2$^+$/Cx40$^{low}$); and 3) atrial cardiomyocytes (Hcn4$^{neg}$/Smoc2$^{neg}$/Cx40$^+$) (FIG. 3F-G). Additional novel SAN markers, including Igfbp5, Cpne5, Rgs6 and Ntm, were also found to be expressed in both the cSAN and transitional cell subpopulations (FIG. 15) and validated by immunostaining or FISH (FIG. 14).

In order to further investigate possible subdomains within the cSAN, cardiomyocytes (CMs) expressing the nodal gene Hcn4 (Hcn4$^+$/Actn2$^+$ double positive) were next isolated in silico. Notably, two distinct clusters emerged consistent with previously recognized "Head" and "Tail" subdomains within the cSAN (FIG. 16A).[5,8] While both clusters were expectedly enriched for the nodal markers Hcn4 and Shox2, the "Head" cluster showed increased Tbx18 and decreased Nkx2-5 expression as per prior reports (FIG. 16B).[2,31] Conversely, the "Tail" cluster reciprocally showed downregulation of Tbx18 and upregulation of Nkx2-5.[2,5,31] These subclusters represent highly distinct cell populations consistent with the previously recognized functional subdomains of the SAN. Comparison of these two subpopulations have revealed a host of significant, differentially expressed genes not previously reported (FIG. 25 (Online Table IV)).

Example 5. Identification of an Atrioventricular Node (AVN)/His Cluster in Zone II Unbiased clustering of Zone II single cells by t-SNE revealed 14 total clusters of which five (Clusters 0, 3, 4, 5, 7) represented cardiomyocyte clusters by gene expression analysis (FIG. 4A). Only one (Cluster 4) showed enrichment of established AVN/His markers including Hcn4, Kcne1, Cacna2d2 and Cacna1g[6,26,32-35] consistent with isolation of a legitimate AVN/His cluster (FIG. 4C-D). GO functional clustering analysis of all significantly enriched genes in Cluster 4 also revealed several significant GO terms associated with cardiac development and regulation of heart rate in addition to Bundle of His development (FIG. 4E). Finally, Cluster 4 showed highly significant enrichment of several novel genes not previously reported in AVN/His cells (FIG. 26 (Online Table V)), including Cpne5 (0.73 avg log FC, adjusted p value<2.22×10$^{-308}$) but not the SAN-enriched gene, Smoc2 (FIG. 4D, 4F). Consistent with this scRNA-seq data, immunostaining within murine heart sections confirmed robust and specific signal within the AVN for Cpne5 but not Smoc2 (FIG. 4G). Of note, while our scRNA-seq data showed that Smoc2 was mildly enriched within Clusters 2, 8, 11 (Fibroblasts) and Cluster 13 (Epicardial) within Zone II (FIG. 4F), Smoc2 could not be detected by immunofluorescence within these cell types (data not shown).

Single-cell FISH analysis of Cpne5 expression additionally confirmed robust and specific signal within the His bundle but not the surrounding ventricular myocardium (FIG. 4H). Additionally, most of the other novel genes found to be enriched within the SAN cluster were also present within the AVN/His cluster including Igfbp5 (1.19 avg log FC, p=1.49×10$^{-120}$), Rgs6 (0.39 avg log FC; p=9.75×10$^{-53}$)

and Ntm (0.55 avg log FC, p=$1.20\times10^{-101}$). Consistently, expression of Igfbp5, Rgs6 and Ntm were all detected within the murine AV node (FIG. 17).

Example 6. Analysis of Cluster 4 in Zone H Unveiled Distinct AVN, his Bundle and Transitional Cell Subtypes Prior studies have described at least four distinct cell subtypes within the AVN/His region through detailed immunofluorescence and electrophysiologic analyses, including the compact AVN (cAVN), nodal AV Ring (NAVR) and His bundle[32,36] as well as transitional cell types such as the transitional AV ring (TAVR).[6,33,37]

In order to evaluate for transcriptional heterogeneity within the AVN/His region and their relationship to these previously reported cell subtypes, we focused on Cluster 4 from Zone II and performed a subcluster analysis (FIG. 5A-B). Six distinct subclusters were identified and these show consistency with previously reported gene profiles[6] including: 1) cAVN (Hcn4$^{hi}$/Tbx3$^{hi}$/Kcne1$^{hi}$/Gjc1$^{+}$/Gja1$^{neg}$/Gja5$^{neg}$ Scn5a$^{neg}$/Cacna2d2$^{+}$); 2) NAVR (Tbx3$^{+}$/Kcne1$^{+}$/Gjc1$^{+}$/Gja1$^{neg}$/Gja5$^{neg}$/Scn5a$^{neg}$/Cacna2d2$^{+}$); 3) His bundle (Hcn4$^{+}$/Tbx3$^{+}$/Kcne$^{hi}$/Gjc1$^{+}$/Gja1$^{neg}$/Gja5$^{+}$/Etv1$^{+}$/Scn5a$^{+}$/Cacna2d2$^{+}$); and 4) TAVR (Hcn4$^{neg}$/Tbx3$^{low/neg}$/Kcne1$^{+}$/Gjc1$^{+}$/Gja1$^{+}$/Gja5$^{neg}$/Scn5a$^{+}$/Cacna2d2$^{low}$). Two additional, distinct transitional cell types were isolated which we have termed: 5) Atrial Transitional Zone (ATZ) (Myh6$^{hi}$/Tbx3$^{low/neg}$/Kcne1$^{low}$/Gjc1$^{+}$/Gja5a$^{hi}$/Cacna2d2$^{+}$); and 6) Ventricular Transitional Zone (VTZ) (Myl2$^{hi}$/Myh7$^{hi}$/Tbx3$^{low/neg}$/Kcne1$^{hi}$/Gjc1$^{+}$/Gja1$^{+}$/Gja5$^{neg}$/Cacna2d2$^{low}$) based on their atrial/nodal and ventricular/nodal hybrid expression signatures, respectively (FIG. 5C-E). Differential gene expression between each cell cluster revealed a number of genes that are significantly different in their expression level, further refining their unique signatures (FIG. 27 (Online Table VI)). When assessing Cpne5 gene expression within the AVN cell subtypes, it was found to be enriched in all of the Hcn4 positive cell populations, including the cAVN and His bundle cells (FIG. 18). Consistently, in situ hybridization revealed perfect co-localization of Cpne5 mRNA expression with Hcn4 expression (FIG. 411).

Example 7. Identification of an Immature Purkinje Fiber (PF) Cell Cluster in Zone III Unsupervised clustering of Zone III cells by t-SNE revealed 15 distinct clusters, nine of which (Clusters 0, 1, 2, 3, 6, 7, 8, 10, 13) were ventricular cardiomyocytes based on their gene signatures (FIG. 6A-B). Of all clusters, only one (Cluster 13) demonstrated significant enrichment of the ventricular conduction system genes Gja5 (Cx40), Scn5a, Irx3 and Cacna2d2 among others (FIG. 6C).[17,26,38-40] Given the isolation of putative Purkinje fiber cells within Cluster 13 of Zone III occurs at embryonic day 16.5 these cells are considered to be "immature" Purkinje fiber cells.

The concordant expression of these known PF genes, however, strongly supports the identification of Cluster 13 as a bona fide PF cluster. Further, GO term analysis of all significantly enriched genes within Cluster 13 revealed functional categories such as heart development, regulation of heart rate and cardiac conduction (FIG. 6D). Enrichment of several novel genes were detected within this PF cluster (FIG. 28 (Online Table VII)) including Igfbp5 (0.96 avg log FC, adjusted p value=$1.11\times10^{-00}$), Cpne5 (0.68 avg log FC, adjusted p value<$2.22\times10^{-308}$) and Ntm (0.61 avg log FC, adjusted p value=$6.32\times10^{-110}$) (FIG. 6E, 6F). FISH and immunostaining of murine heart sections confirmed highly specific expression of these genes within the ventricular conduction system including the bundle branches and Purkinje fiber network as compared to the surrounding ventricular working myocardium (FIG. 6G and FIG. 19).

Example 8. Analysis of Cluster 13 in Zone III Identified Distinct PF and Transitional PF Cell Subtypes To further evaluate subpopulations of cells within Cluster 13, subcluster analysis was performed. Two distinct cell clusters were detected, representing standard Purkinje fibers (PF) as well as transitional PF cells (Tz), both known to exist at the Purkinje-myocyte junction (FIG. 7A-B).[9,10,41,42] Consistent with these prior reports, the standard PFs were enriched for Gja5 (Cx40), Etv1, Cacna2d2 and Sema3a while the transitional PF cells expressed these distal conduction genes at lower levels as well as the conduction marker Gjc1. Conversely, Tz PF cells were enriched for the ventricular myocardial gap junction gene Gja1 (Cx43) (FIG. 7D-E). Several novel genes were noted to be significantly enriched within the Tz PF cells that were largely found to be expressed within the ventricular myocardium as well, consistent with a transitional or hybrid phenotype (FIG. 29 (Online Table VIII).

Overall, Cluster 13 showed significant upregulation of many genes not previously associated with ventricular conduction cells including Ntm.[43] Interestingly, upon subcluster analysis, Ntm was found to be expressed in both standard and transitional PF cell types, with a trend towards enrichment within the standard PF subcluster (0.53 avg log FC, adjusted p=$1.22\times10^{-01}$) (FIG. 7F). Consistently, FISH of wild-type murine heart sections of the ventricular conduction region reinforced these in silico results, showing cell subpopulations including 1) standard immature Purkinje fiber cells (Hcn4$^{+}$/Ntm$^{hi}$); 2) transitional PF cells (Hcn4$^{neg}$/Ntm$^{low}$); and 3) ventricular cardiomyocytes (Hcn4$^{neg}$/Ntm$^{neg}$) (FIG. 7G). Cpne5 expression was similarly detected within transitional PF cells in addition to standard PF cells (FIG. 19).

Example 9. Optical Clearing and 3D Volumetric Analyses Delineate the Architecture of the Entire CCS and SA Nodal Substructure within Intact Murine Hearts Comparative gene analysis of all conduction cardiomyocytes throughout the CCS (SAN=Zone I Cluster 9; AVN/His=Zone II Cluster 4; BB/PF=Zone III Cluster 13) as compared to all other cell types revealed multiple enriched genes including Igfbp5, Cpne5, Rgs6 and Ntm (FIG. 23 (Online Table II), FIG. 26 (online Table V) and FIG. 28 (online table VII). For example, the expression of Igfbp5 was dramatically increased in all conduction clusters including the SAN (Cluster 9, Zone I=2.12 avg log FC, adjusted p value=$2.63\times10^{-126}$), AVN/His (Cluster 4, Zone II=1.19 avg log FC, adjusted p value=$1.49\times10^{-120}$) and BB/PF (Cluster 13, Zone III=0.96 avg log FC, adjusted p value=$1.11\times10^{-100}$) (FIG. 20A). Given the challenges of visualizing the complex three-dimensional anatomy of the CCS, whole-mount immunostaining and 3D imaging was undertaken using tissue clearing (iDISCO+)[44] and light sheet microscopy with volume rendering on intact wild-type mouse hearts (FIG. 8A). Consistent with the enrichment of Igfbp5 expression within the conduction system by scRNA-seq, anti-Igfbp5 protein signal was detected within the entire CCS, including SAN, AVN, His, bundle branches and Purkinje fiber network (FIG. 8B). Igfbp5 was also detected within connecting tracts between these major CCS components including the internodal tracts and right and left atrioventricular ring bundles (FIG. 8B, FIG. 20). Similarly, Cpne5, another novel marker, was shown to mark the entirety of the CCS in 3D.

In order to further evaluate the transitional and compact SAN subpopulations uncovered in our transcriptome analyses, iDISCO+ cleared wild-type hearts were co-immunolabeled for Hcn4 and Rgs6, one of the novel CCS markers we uncovered in this study (FIG. 8C-D). At least 2 distinct transitional sinoatrial conduction pathways (SACPs) (Hcn4$^{neg}$/Rgs6$^+$) exiting the SA node were visualized including one from SAN body directed rightward towards the crista terminalis and another from the SAN head directed inferiorly and leftward (FIG. 8C-D). Additionally, a third Hcn4$^+$/Rgs6$^+$ pathway emerged from the tail to give rise to the internodal tracts (FIG. 8D). These transitional SACPs were faithful across multiple timepoints examined (E16.5 through P12) and, consistent with the aforementioned 2D data (FIG. 3, FIG. 14), also labelled by other novel markers including Smoc2, Igfbp5 and Cpne5 protein (FIG. 21).

Example 10. Discussion of Studies from Examples 1-9

While the cardiac conduction system remains a crucial element to heart development and function, progress in our understanding of its intricate cellular and molecular landscape remains incomplete.[5] Significant limitations within the field have included: 1) low conduction cell numbers within the heart; 2) intra- and intercomponent cell type heterogeneity; 3) challenges in conduction cell isolation; and 4) complexity of the three-dimensional anatomy of the CCS. As a result, our molecular understanding of the conduction system of the heart has largely originated from painstaking evaluation of the overlapping expression of a handful of known markers within each component, including ion channels (Hcn4, Cacna2d2), transcription factors (Isl1, Tbx3, Tbx5, Tbx18) and gap junction genes (Gjc1/Cx45, Gja5 Cx40), with only a limited number of unique and validated conduction-specific markers (Hcn4, Contactin 2).[18,45] Further, bulk RNA sequencing approaches are plagued by non-CCS cell contamination (FIG. 11) even when coupled with cell-sorting strategies using historical SAN reporter genes such as Tbx3 (FIG. 12).

Single-cell RNA sequencing (scRNA-seq) allows for global gene expression analysis at single-cell resolution and thereby circumvents many of the aforementioned hurdles including small cell numbers, complex and variable anatomy as well as distortion of unique transcriptional profiles by cell type heterogeneity or contamination from non-conduction cell types. The inventors performed scRNA-seq on over 22,000 cells from wild-type, developing mouse hearts, successfully capturing all components of the CCS including previously unattainable conduction cell subtypes including transitional cells.

Using unsupervised weighted gene co-expression network analysis[22,23], the inventors discovered sets of uniquely expressed genes within the entire conduction system, individual CCS components as well as conduction cell subtypes. Validation of both established and novel markers derived from our scRNA-seq data was performed at single-cell resolution using fluorescence RNA in situ hybridization (RNAscope). Additionally, whole-mount immunostaining and volume imaging using iDISCO+ (immunolabeling-enabled three-dimensional imaging of solvent-cleared organs) and light sheet microscopy was utilized to visualize, three-dimensionally, the entire conduction system in intact whole hearts.

Overall, these studies represent the first step in the deconvolution of the molecular and cellular identity of the cardiac conduction system at single-cell resolution, resulting in the discovery and validation of a host of new conduction-specific genes and an unprecedented profiling of previously elusive conduction cell subtypes. This molecular analysis of individual cells in the CCS provides a new foundation for future efforts to understand the functional role of this anatomically complex cellular network and to improve our ability to diagnose and treat diseases of the conduction system in utero and during adulthood.

In this disclosure, the inventors have employed microdissection coupled with single-cell isolation and RNA sequencing in order to overcome the aforementioned technical hurdles. Specifically, the inventors have successfully isolated cell types representing the entirety of the cardiac conduction system including rare CCS subtypes for deep sampling in order to assess differential genome-wide expression. Our analyses have uncovered a host of novel conduction markers as well as unique molecular signatures of the various CCS cell subtypes not previously attainable to provide the foundation for a molecular blueprint of the conduction system (FIG. 9). Further, high-resolution in situ hybridization (RNAscope) and volume-rendering whole-mount immunofluorescence with iDISCO+ tissue clearing have provided platforms for gene expression validation both at single-cell resolution and in complex three-dimensional space within the intact murine heart.

The SAN, the primary pacemaker of the heart, has long been recognized as a multicomponent structure containing functional subdomains, including "Head" and "Tail" regions.[5] The Head represents the leading pacemaker region; however, this can shift ("wandering pacemaker") to the tail in response to various stimuli both physiologic and extrinsic.[30,46] These distinct but partially redundant subdomains have even been suggested to provide important "fail-safes" to prevent from rhythm failure[47] further arguing for additional insight into these poorly defined structures.[48] Additionally, in between the compact SAN and surrounding working atrial myocardium, the existence of transitional cells have also been recognized by electron microscopy and patch clamp experiments.[1,49] They are suspected to facilitate the spread of depolarization and may play a crucial clinical role (e.g., sinus node exit block); however, the molecular and cellular identity of these cell types remains virtually unknown.[5] By combining microdissection with scRNA-seq, we have demonstrated the isolation of not only a bona fide SAN cell cluster (Cluster 9 from Zone I) (FIG. 2) but unique SAN cell subtypes including Head and Tail cells within the compact node (FIG. 14) and transitional SAN cells (FIG. 3), thereby allowing differential gene expression analysis at unprecedented resolution (FIG. 24 (Online Table IIIA) and FIG. 25 (Online Table IVA)). As a result, a host of novel SAN genes were uncovered including Igfbp5, Cpne5, Rgs6, Ntm and Smoc2. Interestingly, Smoc2, a gene previously associated with endothelial cell proliferation and migration and angiogenesis in non-cardiac tissues[50], was enriched in the compact SAN, transitional SAN and internodal cell populations but excluded from the rest of the CCS. Finally, enrichment of Rgs6 within the SAN is consistent with prior reports demonstrating Rgs6 as a necessary modulator of parasympathetic innervation in the heart[28] and implicated in resting heart rate variability in humans by GWAS.[51]

Homozygous Rgs6 knockout mice demonstrated exaggerated bradycardia in response to carbachol and significantly enhanced the effect of carbachol on inhibition of spontaneous SAN cell action potential firing.[28]

Interestingly, all of these novel SAN markers were also present within the transitional SAN cell population, providing some of the first unique markers for this previously elusive cell type. Further, high-resolution, 3D studies using iDISCO+ have provided insight into SA nodal architecture, detailing the exact locations of these transitional cells (Hcn4$^{low/neg}$/Igfbp5$^+$/Cpne5$^+$/Rgs6$^+$/Smoc2$^+$) in at least 2 clear transitional SAN conduction pathways (SACPs) (FIG. 8, FIG. 21). These findings are remarkably consistent with prior activation mapping research of the SAN and surrounding atria in canines and humans showing at least 2 SACPs exiting the SAN in similar locations.[8,14,52,53] These electrophysiological studies demonstrated that SACPs not only allow for direct activation of the surrounding atrial tissue but also play an important role in protecting the SAN against overdrive activation during atrial arrhythmias.[53] Further studies are now needed to understand a possible role for these other novel genes uncovered within the conduction system, in particular the transitional SAN cell population.

The AVN remains critical to the CCS in transmitting and delaying the electrical impulses generated by the SAN, thereby allowing the ventricles to be filled before their contraction is initiated.[33] Unfortunately, due to its complex anatomy, buried within the crux of the heart, and significant cell type heterogeneity, the AVN has remained a challenge to define molecularly. Our study has not only demonstrated successful isolation of AVN cells but also uncovered a host of novel AVN-specific genes and represents the first genome-wide analysis of the AVN region at single-cell resolution (FIG. 4A-D). Notably, one of the most significantly enriched genes within the original AVN cluster (Cluster 4, Zone II) was Cpne5 (FIG. 4D), a member of the copine calcium-dependent, phospholipid-binding family of proteins thought to possibly play a role in membrane trafficking.[54] While its true function remains unknown, Cpne5, along with its paralog Cpne8, have been associated with heart rate variability in humans by GWAS.[55] Unsupervised analysis of the AVN cluster additionally unveiled six subclusters representing previously suspected AVN subtypes.[6,33,37] With our ability to identify these AVN subtypes we are well-positioned to resolve the unique molecular signature of each cell type (FIG. 5, FIG. 27 (Online Table VIA)) and begin to understand the factors intrinsic in establishing their function and, possibly, development.

The distal portion of the conduction system, including the bundle branches and Purkinje fibers, allow for the rapid transmission of electrical impulses throughout the ventricular myocardium thereby allowing for their coordinated contraction.[4] Within Zone III ventricular cells, a legitimate immature Purkinje fiber cluster was detected (Cluster 13) (FIG. 6A-E). Differential gene expression analysis of this cluster revealed a host of novel genes including Igfbp5, Cpne5 and Ntm. Neurotrimin (Ntm), a member of the IgLON immunoglobulin domain-containing cell adhesion molecules[43] was found to be significantly enriched in ventricular conduction cells by scRNA-seq data (FIG. 7F) and validated by FISH (FIG. 7G). Ntm, not previously associated with the CCS, was found to be expressed within all components of the CCS (FIG. 7, FIGS. 14 and 16).

To date, while a unified description of Purkinje fiber subtypes is lacking within the literature, several groups have concretely showed at least two distinct cell types in the distal portions of the CCS by electron microscopy and functional patch clamp analysis: 1) standard PF cells[56] and 2) transitional PF cells—broader cells that serve as an intermediate layer between the PF and the working cardiomyocytes.[9,41] Poised at the Purkinje-myocyte junction, these transitional PF cells are hypothesized to play a role in facilitating the spread of depolarization, providing a high resistance barrier, shielding the Purkinje system from electrotonic loading, as well as amplifying the current before passing it on to the surrounding myocardium.[9] Clinically, Purkinje fiber and transitional PF cells are believed to be particularly vulnerable for the development of serious and even life-threatening tachyarrhythmias including bundle branch or fascicular re-entry and polymorphic ventricular tachycardia/fibrillation (VT/VF).[11] Upon subcluster analysis of Cluster 13, two distinct populations were isolated that suggest their identities as standard PFs and transitional PFs (FIG. 7A-E), identified by at least two novel markers including Ntm (FIG. 7G) and Cpne5 (FIG. 19). To our knowledge, these finding represent the first transcriptomic characterization of these cell subtypes and provides a unique opportunity for uncovering new molecular markers and key regulators for standard and transitional PFs.

Finally, in addition to providing insight into the rare conduction cell subtypes of each CCS component, our analyses have also allowed for the systematic discovery of a host of genes enriched throughout the entire conduction system including Igfbp5, Cpne5 and Ntm. Our dataset has also allowed for the discovery of conduction genes enriched within specific CCS components such as Smoc2 that was found to be specifically enriched within the SAN and internodal tracts but notably absent from the AVN. Further studies are currently underway to validate additional conduction-specific genes as well as employing CRISPR-Cas9 technology in order to generate systemic knockdowns of top candidates for the assessment of their possible functional roles in CCS development and/or function. Altogether, our study represents the first comprehensive assessment of transcriptional profiles from the entire CCS at single-cell resolution (FIG. 9) and provides bioinformatics tools to facilitate future efforts in conduction cell identification, isolation, characterization in the context of development and disease and to improve our ability to diagnose and treat diseases of the conduction system in utero and during adulthood.

Example 11. Methods for Studies in Examples 12-14

Mice: Wild-type, timed pregnant CD1 mice were acquired from Jackson Laboratory (Sacramento, CA). Postnatal mice at indicated ages were used in accordance with the Institutional Animal Care and Use Committee of Stanford University. Both female and male mice were used for all experiment types described at a 1:1 ratio.

Human CCS Tissue: Human cardiac conduction system tissue samples were acquired from the Stanford University Department of Pathology tissue bank and were appropriately de-identified.

Bioinformatics Analysis: The Droplet platform data was de-multiplexed and mapped to mouse genome MM10 using CellRanger from 10× Genomics with default parameters. Cell filter, data normalization, and unsupervised analysis were carried out in Seurat version 2 per their recommended steps[10,11]. Significance is presented as an "adjusted p-value", which is based on the Bonferroni correction using all features in the dataset. Briefly, the cells were filtered by their gene number and UMI number. The threshold we used for gene number is 500 to 60,000, and UMI number is 1,000 to 5 million. Next, we used the LogNormalize function to normalize gene expression in each cell. Specifically, we calculated the expression value of genes by following this formula: log {(each gene expression level/total gene expression value)*10,000}. Average log fold change (avg_log FC) described in all data provided represents the log fold-change of the average expression between the two groups. To remove the unwanted sources of variations, we scaled the data with the "vars.to.regress" parameter based on the number of UMIs, percentage of ribosome genes, and Rn45s expression value. Furthermore, we found all the variable genes and used them to perform principal component analysis (PCA). Within all the PCs, we used the top 10 PCs to do clustering and tSNE analysis. In the tSNE analysis, we set the seed.use as 10 and perplexity as 30. Finally, we used the FindAllMarker function to identify the genes differentially expressing in the cell clusters. To be detected, the genes have to express in at least 25% of cells in one of the two comparing clusters and the differential expression level also should be higher than 25%.

Description of Optical Imaging Agents:

The generated optical imaging agents consist of commercially acquired antibodies (1. anti-Cntn2 Goat Polyclonal antibody—AF4439; and 2. anti-NPTN Goat Polyclonal antibody—AF5360) that have been covalently conjugated to a benign, near-infrared (NIR) dye (IRDye800CW, Li-cor #929-70020) using company specifications. IRDye800CW is a NIR imaging probe with broad absorption (778 nm) and emission (794 nm) peaks that is nontoxic to rodents[12] and currently used in human clinical imaging trials[13]. Once conjugated, the final dye:protein ratio was approximately 1.5-2. Conjugated agents and solubilized non-peptide probes were stored at 4° C., in the dark.

Delivery of Optical Imaging Agents and Imaging:

For topical application, sinoatrial nodes (conduction tissue) and left atrial appendage (control tissue) were dissected from adult, CD1 mouse hearts using standard anatomical landmarks. These tissues were then incubated for 10 minutes with 100 ug of Cntn2-800, diluted in 1 mL of HBSS (+Ca/+Mg) (Gibco, 14025-134) prior to brief washing in fresh HBSS and imaging using the closed-field (Pearl Impulse, LI-COR, Lincoln, NE) fluorescence imaging (FLI) device.

Closed-field fluorescence images were analyzed with ImageStudio (LI-COR) by calculating mean fluorescence intensity (MFI) within a tailored region of interest (ROI). The ROI was hand drawn around the sinoatrial nodal (SAN) tissue to quantify conduction tissue MFI. To assess background MFI, an ROI was created on the left atrial appendage (LAA). The conduction-to-background MFI ratio (TBR) was assessed for each mouse to evaluate the temporal effect on the fluorescence contrast produced by each agent.

For systemic application, adult, CD1 mice were administered 100 ug of either Nptn-800 or Cntn2-800, diluted in 100 ul of PBS, by tail-vein injection under inhaled sedation. Surface electrocardiograms were taken prior to injection and daily until euthanasia after 48 hours. On day 2 post-injection, the heart, along with all other organs were then harvested using the closed-field (Pearl Impulse, LI-COR, Lincoln, NE) fluorescence imaging (FLI) device. Subsequently, each heart was processed for immunofluorescence as detailed below.

Immunofluorescence: Immunofluorescence staining was carried out by following a previous protocol with minor modifications[4]. Briefly, injected adult CD1 mice were isolated by dissection, washed in HBSS (+Ca/+Mg) (Gibco, 14025-134) prior to fixation overnight in 4% paraformaldehyde (Fisher, 50-980-487) at 4° C. Hearts were then washed in PBS for 15 min three times prior to incubation in 30% sucrose in PBS overnight at 4° C. and then embedded in Tissue-Plus OCT (Fisher, 23-730-571). The embryos were cut as cryosections of 10 μM thickness and stored at −80° C. The sections were dried for 1 hour prior to use, rehydrated in PBS, washed three times in PBST (PBS+0.1% Triton X100) and then blocked (PBST+0.5% Bovine serum albumin) for 1 hour at room temperature. Following this, the sections were incubated with primary antibodies diluted in blocking solution overnight at 4° C. in humid chambers. Primary antibodies used included: Anti-mouse Connexin 40 Rabbit Polyclonal antibody (Alpha Diagnostics, Cx40-A) at 1:100 dilution; Anti-mouse Hcn4 Rat Monoclonal [SHG 1E5] antibody (Abcam, ab32675) at 1:75 dilution.

On the second day, after washing three times with PBST, the sections were incubated with secondary antibody for 2 hours at room temperature. The following secondaries were used at a 1:500 dilution: Donkey anti-goat IgG Alexa Fluor 555 (Invitrogen, A-21432), Chicken anti-Rabbit IgG Alexa Fluor 488 (Invitrogen, A-21441), Donkey anti-Rabbit IgG Alexa Fluor 647 (Invitrogen, A-31573) and Chicken anti-Rat IgG AlexaFluor 488 (Invitrogen A-21470). After additional washing with PBS for 5 minutes three times, the sections were mounted with mounting media containing DAPI (Vector Laboratories, H-1200). All images were taken with Axioimager microscope at Neuroscience Microscope Service (NMS) facility at Stanford University. Negative controls for immunostaining included the use of primaries or secondary antibodies alone. A minimum of 4 biological (different hearts) and 4 technical (different slides/heart) replicates were used for each antibody staining.

Example 12. Single-Cell RNA-Sequencing of Murine Cardiac Conduction System Reveal Novel Conduction Cell-Specific Surface Markers The Analysis of examples 1-9 of the comprehensive single-cell RNA-sequencing (scRNAseq) data of the murine cardiac conduction system revealed a host of novel cell surface genes enriched within the cardiac conduction system (CCS) not previously reported (Table 1). Specifically, the inventors found genes encoding cell surface proteins enriched throughout the entire conduction system as well as component-specific markers within the sinoatrial node, atrioventricular node and/or Purkinje fiber network.

In order to validate these findings, the inventors next assessed some of these candidates, including Neurotrimin (Ntm) and Neuroplastinin (Nptn) by fluorescent in situ hybridization (FISH) and immunostaining of murine heart sections (FIGS. 30 and 31). These studies confirmed highly specific expression of these cell surface genes within the murine cardiac conduction system as compared to the surrounding working myocardium. Further, immunostaining of human heart tissue confirmed the specificity of NPTN within all components of the human CCS (FIG. 32).

Example 13. Cntn-800—an Optical Imaging Agent for the In Vivo Visualization of the Cardiac Conduction System In order to visualize the CCS in real-time, the inventors generated optical imaging tools similar to those that have been successfully generated for the detection of various cancers intraoperatively to improve the precision of tumor resection. First, the inventors created "Cntn2-800" consisting of a polyclonal antibody (R&D Systems, AF4439)

directed against Contactin-2, a known cell surface protein expressed specifically within the CCS of mammals including mice and humans[15,16], and a near infrared dye (IRDye800CW, Li-cor #929-70020) commonly used in human clinical imaging.

The inventors first evaluated the ability of Cntn2-800 to label the conduction system by topical application (FIG. 33). Adult murine sinoatrial nodes (SANs) and control heart tissue (left atrial appendages) were isolated and incubated with Cntn2-800 for 10 minutes prior to visualization using a closed-field near infrared (NIR) system (Pearl, Li-cor, Lincoln, NE) (FIG. 33A). Results demonstrated robust detection of the SAN conduction tissue as compared to the control heart tissue (FIG. 31B).

Next, the inventors assessed the efficacy of Cntn2-800 binding to the CCS in mice by systemic delivery (FIG. 34A). Following intravenous tail vein injection of Cntn2-800 in wild-type mice, whole hearts were isolated after 48 hours and imaged under the closed NIR camera system. These results showed high intensity signal localized specifically to the CCS within intact hearts (FIG. 34B). The inventors additionally assessed the biodistribution of Cntn2-800 in other organs and identified it expectedly within the liver, bladder and kidneys similar to prior reports of clearance of other optical imaging agents in these organs[17] (FIG. 34C). No signal was detected within the brain tissue despite the presence of neurons expressing Cntn2[18], consistent with the exclusion of the Cntn2-800 by an intact blood-brain barrier. The NIR signal in whole heart was later confirmed to be exclusive to the CCS by serial sections of the heart and co-staining with well-known protein markers of the CCS, Hcn4 and Cx40 (FIG. 35).

Example 14. Nptn-800—an Optical Imaging Agent for the In Vivo Visualization of the Cardiac Conduction System Similar to Cntn2-800, Nptn-800 consists of a polyclonal antibody directed against our novel CCS-specific cell surface marker Neuroplastin and the same NIR dye. As above, the assessed the efficacy of Nptn-800 binding to the CCS in mice by systemic delivery. Following intravenous tail vein injections of Nptn-800 in wild-type mice, whole hearts were isolated after 48 hours and imaged using the closed NIR camera system. These results showed high intensity signal localized specifically to all components of the CCS by serial sections of the heart and co-staining with well-known protein markers of the CCS (FIG. 36). The biodistribution of Nptn-800 was similar to Cntn2-800 (FIG. 34B) and, again, was excluded from the brain tissue consistent with an intact blood-brain barrier.

Example 15. Discussion of Studies from Examples 11-14

Congenital heart disease remains the most common birth defect worldwide, with a significant fraction requiring corrective heart surgery[19]. During cardiothoracic surgery, inadvertent damage to the conduction system, which surrounds many key surgical targets (septal defects, valve disorders, etc.), can result in a host of irreversible, life-threatening arrhythmias (heart block, pacemaker dysfunction). Iatrogenic injury to the CCS is in part due to an inability to visualize the conduction system and remains a significant source of morbidity and mortality in both pediatric[6] and adult heart surgeries[20] alike.

In order to address this unmet medical need, the inventors first assessed differential genome-wide expression at single cell resolution of the entire CCS in order to uncover a host of conduction-specific cell surface markers not previously associated with the conduction system (Table 1). In doing so, the inventors have discovered novel extracellular markers that can be used to molecularly distinguish the CCS from the rest of the working myocardium. Further, high-resolution in situ hybridization (RNAscope) and immunofluorescence was employed to validate the specificity of this gene expression within two of these candidates in both mouse and human hearts (FIGS. 30-32). Similar to the longstanding efforts utilizing unique cell surface makers to distinguish the various hematopoetic lineages[21,22], the inventors believe these conduction-specific gene signatures can be coupled with powerful techniques, such as flow cytometry, for the effective identification, isolation and electrophysiologic characterization of the entire CCS as well as its many clinically-relevant but poorly understood subtypes[23-25].

The inventors capitalized on these surface markers in order to generate novel, fluorescent, antibody-based diagnostic tools for the real-time visualization of the CCS (FIG. 37), a similar strategy employed for fluorescence-guided oncologic surgery to improve tumor resection. Using both known (Cntn2)[15] and newly discovered (Nptn) cell-surface makers of the CCS, the inventors have successfully created optical imaging agents (Cntn2-800 and Nptn-800, respectively) with high sensitivity and specificity for labeling the entirety of the CCS within mice by both topical and systemic application. This study is believed to represent the first evidence of real-time, in vivo, labeling of any cardiac component. Additional studies within larger animal models are clearly needed to further assess these tools, specifically regarding the degree of resolution and signal intensity in larger, more dense hearts. Reassuringly, however, both human CNTN2[26] and NPTN are known to be expressed specifically within the human CCS, remaining viable targets for translational opportunities currently being pursued.

Integration of optical imaging diagnostic tools into the surgical management of cardiothoracic surgery has the potential to dramatically improve adverse outcomes in both pediatric and adult intracardiac surgeries. Specifically, the inventors envision that the identification of the CCS through direct, intraoperative visualization by surgeons will minimize the risk of iatrogenic damage, thereby improving hospital costs and length of stay as well as overall morbidity and mortality.

REFERENCES

1. Vedantham V. New Approaches to Biological Pacemakers: Links to Sinoatrial Node Development. *Trends Mol Med.* 2015; 21:749-761.
2. Christoffels V M, Smits G J, Kispert A, Moorman A F M. Development of the pacemaker tissues of the heart. *Circ Res.* 2010; 106:240-254.
3. CDC. Research|Congenital Heart Defects|NCBDDD|CDC [Internet]. Centers for Disease Control and Prevention. 2018 [cited 2018 Sep. 26]; Available from: https://www.cdc.gov/ncbddd/heartdefects/research.html
4. Peretto G, Durante A, Limite L R, Cianflone D. Postoperative arrhythmias after cardiac surgery: incidence, risk factors, and therapeutic management. *Cardiol Res Pract.* 2014; 2014:615987.
5. Karyofillis P, Kostopoulou A, Thomopoulou S, Habibi M, Livanis E, Karavolias G, Voudris V. Conduction abnormalities after transcatheter aortic valve implantation. *J Geriatr Cardiol.* 2018; 15:105-112.

6. Bonatti V, Agnetti A, Squarcia U. Early and late postoperative complete heart block in pediatric patients submitted to open-heart surgery for congenital heart disease. *Pediatr Med Chir.* 1998; 20:181-186.

7. Gross G J, Chiu C C, Hamilton R M, Kirsh J A, Stephenson E A. Natural history of postoperative heart block in congenital heart disease: implications for pacing intervention. *Heart Rhythm.* 2006; 3:601-604.

8. Cho Y H, Quintana E, Schaff H V, Nishimura R A, Dearani J A, Abel M D, Ommen S. Residual and recurrent gradients after septal myectomy for hypertrophic cardiomyopathy-mechanisms of obstruction and outcomes of reoperation. *J Thorac Cardiovasc Surg.* 2014; 148:909-915; discussion 915-916.

9. Harmsen S, Teraphongphom N, Tweedle M F, Basilion J P, Rosenthal E L. Optical Surgical Navigation for Precision in Tumor Resections. *Mol Imaging Biol.* 2017; 19:357-362.

10. Butler A, Hoffman P, Smibert P, Papalexi E, Satija R. Integrating single-cell transcriptomic data across different conditions, technologies, and species. *Nat Biotechnol.* 2018; 36:411-420.

11. Macosko E Z, Basu A, Satija R, Nemesh J, Shekhar K, Goldman M, Tirosh I, Bialas A R, Kamitaki N, Martersteck E M, Trombetta J J, Weitz D A, Sanes J R, Shalek A K, Regev A, McCarroll S A. Highly Parallel Genome-wide Expression Profiling of Individual Cells Using Nanoliter Droplets. *Cell.* 2015; 161:1202-1214.

12. Marshall M V, Draney D, Sevick-Muraca E M, Olive D M. Single-Dose Intravenous Toxicity Study of IRDye 800CW in Sprague-Dawley Rats. *Mol Imaging Biol.* 2010; 12:583-594.

13. Rosenthal E L, Warram J M, de Boer E, Chung T K, Korb M L, Brandwein-Gensler M, Strong T V, Schmalbach C E, Morlandt A B, Agarwal G, Hartman Y E, Carroll W R, Richman J S, Clemons L K, Nabell L M, Zinn K R. Safety and Tumor Specificity of Cetuximab-IRDye800 for Surgical Navigation in Head and Neck Cancer. *Clin Cancer Res.* 2015; 21:3658-3666.

14. Goodyer W R, Gu X, Liu Y, Bottino R, Crabtree G R, Kim S K. Neonatal β cell development in mice and humans is regulated by calcineurin/NFAT. *Dev Cell.* 2012; 23:21-34.

15. Pallante B A, Giovannone S, Fang-Yu L, Zhang J, Liu N, Kang G, Dun W, Boyden P A, Fishman G I. Contactin-2 expression in the cardiac Purkinje fiber network. *Circ Arrhythm Electrophysiol.* 2010; 3:186-194.

16. Shekhar A, Lin X, Liu F-Y, Zhang J, Mo H, Bastarache L, Denny J C, Cox N J, Delmar M, Roden D M, Fishman G I, Park D S. Transcription factor ETV1 is essential for rapid conduction in the heart. *J Clin Invest.* 126:4444-4459.

17. Prince A C, Moore L S, Tipirneni K E, Ramesh T, Limdi M A, Bevans S L, Walsh E M, Greene B, Rosenthal E L, Warram J M. Evaluation of optical imaging agents in a fluorescence-guided surgical model of head and neck cancer. *Surg Oncol.* 2018; 27:225-230.

18. Fukamauchi F, Aihara O, Wang Y J, Akasaka K, Takeda Y, Horie M, Kawano H, Sudo K, Asano M, Watanabe K, Iwakura Y. TAG-1-deficient mice have marked elevation of adenosine A1 receptors in the hippocampus. *Biochem Biophys Res Commun.* 2001; 281:220-226.

19. Hoffman J I. The global burden of congenital heart disease. Cardiovasc J Afr. 2013; 24:141-145.

20. Socie P, Nicot F, Baudinaud P, Estagnasie P, Brusset A, Squara P, Nguyen L S. Frequency of Recovery from Complete Atrioventricular Block After Cardiac Surgery. *American Journal of Cardiology.* 2017; 120: 1841-1846.

21. Ng D, Johnston J J, Teer J K, Singh L N, Peller L C, Wynter J S, Lewis K L, Cooper D N, Stenson P D, Mullikin J C, Biesecker L G, NIH Intramural Sequencing Center (NISC) Comparative Sequencing Program. Interpreting secondary cardiac disease variants in an exome cohort. *Circ Cardiovasc Genet.* 2013; 6:337-346.

22. Spangrude G J, Heimfeld S, Weissman I L. Purification and characterization of mouse hematopoietic stem cells. *Science.* 1988; 241:58-62.

23. Csepe T A, Zhao J, Hansen B J, Li N, Sul L V, Lim P, Wang Y, Simonetti O P, Kilic A, Mohler P J, Janssen P M L, Fedorov V V. Human sinoatrial node structure: 3D microanatomy of sinoatrial conduction pathways. *Progress in Biophysics and Molecular Biology.* 2016; 120:164-178.

24. Aanhaanen W T J, Mommersteeg M T M, Norden J, Wakker V, de Gier-de Vries C, Anderson R H, Kispert A, Moorman A F M, Christoffels V M. Developmental Origin, Growth, and Three-Dimensional Architecture of the Atrioventricular Conduction Axis of the Mouse Heart. *Circulation Research.* 2010; 107:728-736.

25. Tranum-Jensen J, Wilde A A, Vermeulen J T, Janse M J. Morphology of electrophysiologically identified junctions between Purkinje fibers and ventricular muscle in rabbit and pig hearts. *Circulation Research.* 1991; 69:429-437.

26. Shekhar A, Lin X, Liu F-Y, Zhang J, Mo H, Bastarache L, Denny J C, Cox N J, Delmar M, Roden D M, Fishman G I, Park D S. Transcription factor ETV1 is essential for rapid conduction in the heart. *J Clin Invest.* 2016; 126:4444-4459.

What is claimed is:

1. A method for visualizing in real time cardiac conduction system (CCS) in a subject undergoing cardiothoracic surgery or catheter procedure, the method comprising:

a) administering topically, intravenously or intracoronary or by preoperative infusion to the subject a composition comprising one or more excipients and an antibody conjugated directly to a detection agent which comprises a fluorophore, wherein the antibody has a specific binding affinity to Neurotrimin, Neuroplastin or Contactin 2 displayed on a CCS cell, and wherein subsequent to the administration, the antibody conjugate binds to the CCS cell; and b) illuminating the subject's heart and thereby visualizing the bound antibody conjugate in the subject while the subject is undergoing the cardiothoracic surgery or catheter procedure.

2. The method of claim 1, wherein the method further comprises capturing images of the CCS in real time with camera.

3. The method of claim 1, wherein the composition comprises from 0.1 wt % to 99.9 wt % of the antibody conjugate and from 0.1 wt % to 99.9 wt % of the one or more excipients.

4. The method of claim 1, wherein the fluorophore is a biocompatible near-infrared (NIR) fluorophore.

5. The method of claim 1, wherein the subject's heart is illuminated with infrared light.

6. The method of claim 1, wherein the subject's heart is illuminated with a scope placed into the subject.

7. The method of claim 1, wherein the antibody is conjugated covalently to the detection agent.

* * * * *